(12) United States Patent
Igawa et al.

(10) Patent No.: US 12,371,485 B2
(45) Date of Patent: Jul. 29, 2025

(54) ANTIGEN-BINDING MOLECULE INDUCING IMMUNE RESPONSE TO TARGET ANTIGEN

(71) Applicant: Chugai Seiyaku Kabushiki Kaisha, Tokyo (JP)

(72) Inventors: Tomoyuki Igawa, Shizuoka (JP); Atsuhiko Maeda, Shizuoka (JP); Kenta Haraya, Shizuoka (JP); Tatsuhiko Tachibana, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 600 days.

(21) Appl. No.: 16/717,064

(22) Filed: Dec. 17, 2019

(65) Prior Publication Data

US 2020/0115447 A1 Apr. 16, 2020

Related U.S. Application Data

(62) Division of application No. 14/347,448, filed as application No. PCT/JP2012/075043 on Sep. 28, 2012, now Pat. No. 10,556,949.

(30) Foreign Application Priority Data

Sep. 30, 2011 (JP) ................................ 2011-216958

(51) Int. Cl.
*C07K 16/28* (2006.01)
*A61K 39/00* (2006.01)

(52) U.S. Cl.
CPC ............ *C07K 16/28* (2013.01); *C07K 16/283* (2013.01); *A61K 2039/505* (2013.01); *C07K 2317/52* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,277,375 B1 | 8/2001 | Ward | |
| 6,602,684 B1 | 8/2003 | Umana et al. | |
| 6,737,056 B1 | 5/2004 | Presta | |
| 8,568,726 B2 | 10/2013 | Beaumont et al. | |
| 9,029,515 B2 | 5/2015 | Pons et al. | |
| 10,011,858 B2* | 7/2018 | Igawa | A61P 35/00 |
| 10,556,949 B2* | 2/2020 | Igawa | C07K 16/28 |
| 10,618,965 B2* | 4/2020 | Igawa | A61P 3/10 |
| 11,124,576 B2* | 9/2021 | Igawa | C07K 16/303 |
| 11,142,587 B2* | 10/2021 | Igawa | G01N 33/53 |
| 11,168,344 B2* | 11/2021 | Igawa | A61P 35/00 |
| 11,718,678 B2* | 8/2023 | Igawa | A61P 31/04 435/69.6 |
| 11,827,699 B2* | 11/2023 | Igawa | A61P 31/04 |
| 2006/0067930 A1 | 3/2006 | Adams et al. | |
| 2006/0141456 A1 | 6/2006 | Edwards et al. | |
| 2006/0173170 A1* | 8/2006 | Chamberlain | C07K 16/2878 530/387.3 |
| 2007/0111281 A1 | 5/2007 | Sondermann et al. | |
| 2007/0148164 A1 | 6/2007 | Farrington et al. | |
| 2008/0089892 A1 | 4/2008 | Allan et al. | |
| 2008/0181887 A1* | 7/2008 | Dall-Acqua | C07K 16/1027 424/133.1 |
| 2009/0215991 A1 | 8/2009 | Lazar et al. | |
| 2010/0098730 A1* | 4/2010 | Lowman | C07K 16/32 424/278.1 |
| 2010/0330076 A1 | 12/2010 | Georgiou et al. | |
| 2011/0111406 A1* | 5/2011 | Igawa | C07K 16/248 435/69.6 |
| 2012/0009188 A1 | 1/2012 | Behrens et al. | |
| 2013/0011866 A1 | 1/2013 | Igawa et al. | |
| 2013/0131319 A1 | 5/2013 | Igawa et al. | |
| 2013/0303396 A1 | 11/2013 | Igawa et al. | |

(Continued)

FOREIGN PATENT DOCUMENTS

| | | |
|---|---|---|
| CN | 1997667 | 7/2007 |
| CN | 101291954 | 10/2008 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Chalaris et al., "The soluble Interleukin 6 receptor: Generation and role in inflammation and cancer," Eur J Cell Biol, Jun.-Jul. 2011, 90(6-7):484-494. doi: 10.1016/j.ejcb.2010.10.007. Epub Dec. 8, 2010. PMID: 21145125.
Elvin et al., Sequences of Proteins of Immunological Interest, 1991, Table of Contents, p. iv, pp. 661, 662, 671.
Ober et al., "Differences in promiscuity for antibody-FcRn interactions across species: implications for therapeutic antibodies," Int Immunol, Dec. 2001, 13(12):1551-1559.
Adams et al., "Monoclonal antibody therapy of cancer," Nat Biotechnol, Sep. 2005, 23(9):1147-57.

(Continued)

*Primary Examiner* — Phuong Huynh
(74) *Attorney, Agent, or Firm* — Fish & Richardson P.C.

(57) ABSTRACT

The present inventors have discovered that in living organisms that have received an antigen-binding molecule containing an antigen-binding domain whose binding activity to an antigen changes depending on ion concentration conditions and containing an FcRn-binding domain having FcRn-binding activity in a neutral pH range, immune responses to the antigen are induced. Furthermore, the present inventors have discovered that in living organisms that have received an antigen-binding molecule containing an antigen-binding domain whose binding activity to an antigen changes depending on ion concentration conditions and containing an FcRn-binding domain having FcRn-binding activity in a neutral pH range, immune responses to the antigen are induced, and also the antigen-binding molecule has cytotoxicity or antiproliferative action against cancer cells, foreign biological species, or such that express the antigen to which the antigen-binding molecule binds.

22 Claims, 37 Drawing Sheets

Specification includes a Sequence Listing.

(56) References Cited

U.S. PATENT DOCUMENTS

| | | |
|---|---|---|
| 2014/0105889 A1 | 4/2014 | Igawa et al. |
| 2014/0234340 A1 | 8/2014 | Igawa et al. |
| 2014/0255398 A1 | 9/2014 | Igawa et al. |
| 2014/0271617 A1 | 9/2014 | Igawa et al. |
| 2014/0335089 A1 | 11/2014 | Igawa et al. |
| 2014/0363428 A1 | 12/2014 | Igawa et al. |
| 2015/0056182 A1 | 2/2015 | Igawa et al. |
| 2015/0166654 A1 | 6/2015 | Igawa et al. |
| 2015/0353630 A1 | 12/2015 | Igawa et al. |
| 2016/0176954 A1 | 6/2016 | Ruike et al. |
| 2016/0200807 A1 | 7/2016 | Ruike et al. |
| 2016/0229908 A1 | 8/2016 | Igawa et al. |

FOREIGN PATENT DOCUMENTS

| | | | |
|---|---|---|---|
| CN | 101589057 | 11/2009 | |
| CN | 101679966 | 3/2010 | |
| CN | 102056946 | 5/2011 | |
| CN | 102245208 | 11/2011 | |
| EP | 2 119 780 A | 11/2009 | |
| EP | 2 275 443 | 1/2011 | |
| EP | 2 752 200 A | 7/2014 | |
| JP | 2008-505174 | 2/2008 | |
| MX | 366968 | 8/2019 | |
| RU | 2318829 | 3/2008 | |
| WO | WO 00/42072 | 7/2000 | |
| WO | WO 2004/039826 | 5/2004 | |
| WO | WO 2005/110474 | 11/2005 | |
| WO | WO 2006/019447 | 2/2006 | |
| WO | WO 2006/130834 | 12/2006 | |
| WO | WO 2007/031875 | 3/2007 | |
| WO | WO 2008/043822 | 4/2008 | |
| WO | WO 2009/125825 | 10/2009 | |
| WO | WO-2009125825 A1 * | 10/2009 | ............ A61K 39/12 |
| WO | WO 2009/139822 | 11/2009 | |
| WO | WO 2010/045193 | 4/2010 | |
| WO | WO 2010/058860 | 5/2010 | |
| WO | WO 2010/085682 | 7/2010 | |
| WO | WO 2010/088444 | 8/2010 | |
| WO | WO 2011/122011 | 10/2011 | |
| WO | WO-2011122011 A2 * | 10/2011 | ............ A61K 38/17 |
| WO | WO 2012/073992 | 6/2012 | |
| WO | WO 2016/000813 | 1/2016 | |

OTHER PUBLICATIONS

Bonvin et al., "De novo isolation of antibodies with pH-dependent binding properties," mAbs, Mar./Apr. 2015, 7(2):294-302.

Borrok et al., "pH-dependent binding engineering reveals an FcRn affinity threshold that governs IgG recycling," J Biol Chem, Feb. 13, 2015, 290(7):4282-90. doi: 10.1074/jbc.M114.603712. Epub Dec. 23, 2014.

Bronte et al., "IL-2 enhances the function of recombinant poxvirus-based vaccines in the treatment of established pulmonary metastases," J Immunol, May 15, 1995, 154(10):5282-92.

Cartron et al., "Therapeutic activity of humanized anti-CD20 monoclonal antibody and polymorphism in IgG Fc receptor FcγRIIIa gene," Blood, Feb. 1, 2002, 99(3):754-8.

Chaparro-Riggers et al., "Increasing serum half-life and extending cholesterol lowering in vivo by engineering antibody with pH-sensitive binding to PCSK9," J Biol Chem, Mar. 30, 2012, 287(14):11090-7. doi: 10.1074/jbc.M111.319764. Epub Jan. 31, 2012.

Chen et al., "Enhancement and destruction of antibody function by somatic mutation: unequal occurrence is controlled by V gene combinatorial associations," EMBO J, Jun. 15, 1995, 14(12):2784-94.

Clark, "IgG effector mechanisms," Chem Immunol, 1997, 65:88-110.

Clynes et al., "Fc receptors are required in passive and active immunity to melanoma," Proc Natl Acad Sci USA, Jan. 1998, 95(2):652-6.

Clynes et al., "Inhibitory Fc receptors modulate in vivo cytotoxicity against tumor targets," Nat Med, Apr. 2000, 6(4):443-6.

Dall'Acqua et al., "Properties of human IgG1s engineered for enhanced binding to the neonatal Fc receptor (FcRn)," J Biol Chem, Aug. 18, 2006, 281(33):23514-24. Epub Jun. 21, 2006.

Dall'Acqua et al., "Increasing the affinity of a human IgG1 for the neonatal Fc receptor: biological consequences," J Immunol, Nov. 1, 2002, 169(9):5171-80.

De Felice et al., "Formation of amyloid aggregates from human lysozyme and its disease-associated variants using hydrostatic pressure," FASEB J, Jul. 2004, 18(10):1099-101. (dol:10.1096/fj.03-1072fje; PMID 15155566).

Deng et al., "Pharmacokinetics of humanized monoclonal anti-tumor necrosis factor-{alpha} antibody and its neonatal Fc receptor variants in mice and cynomolgus monkeys," Drug Metab Dispos, Apr. 2010, 38(4):600-5. doi: 10.1124/dmd.109.031310. Epub Jan. 13, 2010.

Devanaboyina et al., "The effect of pH dependence of antibody-antigen interactions on subcellular trafficking dynamics," mAbs, Nov.-Dec. 2013, 5(6):851-9. doi: 10.4161/mabs.26389.

Dufner et al., "Harnessing phage and ribosome display for antibody optimization," Trends Biotechnol, Nov. 2006, 24(11):523-9.

Fukuzawa et al., "Long lasting neutralization of C5 by SKY59, a novel recycling antibody, is a potential therapy for complement-mediated diseases," Sci Reports 7, Apr. 24, 2017, 1080:1-12.

Greenwood et al., "Structural motifs involved in human IgG antibody effector functions," Eur J Immunol, May 1993, 23(5):1098-104.

Horton et al., "Potent in vitro and in vivo activity of an Fc-engineered anti-CD19 monoclonal antibody against lymphoma and leukemia," Cancer Res, Oct. 1, 2008, 68(19):8049-57.

Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.

Igawa et al., "Engineered monoclonal antibody with novel antigen-sweeping activity in vivo," PLoS One, May 7, 2013, 8(5):e63236. doi: 10.1371/journal.pone.0063236. Print 2013.

Igawa et al., "Antibody recycling by engineered pH-dependent antigen binding improves the duration of antigen neutralization," Nat Biotechnol, Nov. 2010, 28(11):1203-7.

Igawa et al., "Reduced elimination of IgG antibodies by engineering the variable region," Protein Eng Des Sel, Feb. 15, 2010, 23(5):385-92.

Igawa et al., "Sweeping antibody as a novel therapeutic antibody modality capable of eliminating soluble antigens from circulation," Immunol Rev, Mar. 2016, 270(1): 132-151.

Janeway et al., Chapter 3 "Structure of the Antibody Molecule and Immunoglobulin Genes," Immunobiology, The Immune System in Health and Disease, 3rd Edition, 1997, Garland Publishing Inc., pp. 3:1-3:11.

Jefferis et al., "Interaction sites on human IgG—Fc for FcγR: current Models," Immunol Lett, Jun. 2002, 82(1-2):57-65.

Kussie et al., "A single engineered amino acid substitution changes antibody fine specificity," J Immunol, Jan. 1, 1994, 152(1):146-52.

Lazar et al., "Engineered antibody Fc variants with enhanced effector function," Proc Natl Acad Sci USA, Mar. 14, 2006, 103(11):4005-10.

Mi et al., "Targeting the neonatal fc receptor for antigen delivery using engineered fc fragments," J Immunol, Dec. 1, 2008, 181(11):7550-61.

Morgan et al., "The N-terminal end of the CH2 domain of chimeric human IgG1 anti-HLA-DR is necessary for C1q, Fc gamma RI and Fc gamma RIII binding," Immunology, Oct. 1995, 86(2):319-24.

Nimmerjahn et al., "Divergent immunoglobulin g subclass activity through selective Fc receptor binding," Science, Dec. 2, 2005, 310(5753):1510-2.

Ober et al., "Exocytosis of IgG as mediated by the receptor, FcRn: an analysis at the single-molecule level," Proc Natl Acad Sci USA, Jul. 27, 2004, 101(30):11076-81. Epub Jul. 16, 2004.

Oettgen et al., Chapter 6 "The History of Cancer Immunotherapy," Biological Therapy of Cancer, 1991, pp. 87-119.

(56) References Cited

OTHER PUBLICATIONS

Park et al., "The therapeutic effect of anti-HER2/neu antibody depends on both innate and adaptive immunity," Cancer Cell, Aug. 17, 2010, 18(2):160-70.
Pavlou et al., "The therapeutic antibodies market to 2008," Eur J Pharm Biopharm, Apr. 2005, 59(3):389-396.
Petkova et al., "Enhanced half-life of genetically engineered human IgG1 antibodies in a humanized FcRn mouse model: potential application in humorally mediated autoimmune disease," Int Immunol, Dec. 2006, 18(12):1759-69.
Raghavan et al., "Analysis of the pH dependence of the neonatal Fc receptor/immunoglobulin G interaction using antibody and receptor variants," Biochemistry, Nov. 14, 1995, 34(45):14649-57.
Reichert et al., "Monoclonal antibody successes in the clinic," Nat Biotechnol, Sep. 2005, 23(9):1073-78.
Reverberi et al., "Factors affecting the antigen-antibody reaction," Blood Transfus, Nov. 2007, 5(4):227-40. doi: 10.2450/2007.0047-07.
Roitt et al., "Antibody Structure and Function," Immunology, Moscow, Mir, 2000, pp. 110-111 (in Russian, with what is believed to be a published English equivalent of those pages).
Rudikoff et al., "Single amino acid substitution altering antigen-binding specificity," Proc Natl Acad Sci USA, Mar. 1982, 79(6):1979-83.
Schuster et al., "Signaling of human ciliary neurotrophic factor (CNTF) revisited. The interleukin-6 receptor can serve as an alpha-receptor for CTNF," J Biol Chem, Mar. 14, 2003, 278(11):9528-35.
Seda et al., "B-cell receptor signalling and its crosstalk with other pathways in normal and malignant cells," Eur J Haematol, Mar. 2015, 94(3):193-205. doi: 10.1111/ejh.12427. Epub Sep. 13, 2014.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-73. Epub Nov. 8, 2002.
Singer et al., "The Genetic Molecules," Genes & Genomes, Moscow, Mir, 1998, vol. 1, pp. 63-64 (in Russian, with what is believed to be a published English equivalent of those pages).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol, Feb. 15, 2010, 184(4):1968-76.
Tanabe et al., "Characterization of the Monoclonal Antibodies against Human Protein C Specific for Calcium Ion-induced Conformers," Japanese Journal of Thrombosis and Hemostasis, 1992, 3(1):29-35.
Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).
Taylor et al., "Augmented HER-2 specific immunity during treatment with trastuzumab and chemotherapy," Clin Cancer Res, Sep. 1, 2007, 13(17):5133-43.
Tsuji et al., "Antibody-targeted NY-ESO-1 to mannose receptor or DEC-205 in vitro elicits dual human CD8+ and CD4+ T cell responses with broad antigen specificity," J Immunol, Jan. 15, 2011, 186(2):1218-27. Epub Dec. 13, 2010.
Vaccaro et al., "Engineering the Fc region of immunoglobulin G to modulate in vivo antibody levels," Nat Biotechnol, Oct. 2005, 23(10):1283-8. Epub Sep. 25, 2005.
Wang et al., "Monoclonal antibodies with identical Fc sequences can bind to FcRn differentially with pharmacokinetic consequences," Drug Metab Dispos, Sep. 2011, 39(9):1469-77. doi: 10.1124/dmd.111.039453. Epub May 24, 2011.
Wolf et al., "BiTEs: bispecific antibody constructs with unique anti-tumor activity," Drug Discov Today, Sep. 15, 2005, 10(18):1237-44.
Wu et al., "Humanization of a murine monoclonal antibody by simultaneous optimization of framework and CDR residues," J Mol Biol, Nov. 19, 1999, 294(1):151-62.

Yeung et al., "Engineering human IgG1 affinity to human neonatal Fc receptor: impact of affinity improvement on pharmacokinetics in primates," J Immunol, Jun. 15, 2009, 182(12):7663-71. doi: 10.4049/jimmunol.0804182.
Yu et al., "Interaction between bevacizumab and murine VEGF-A: a reassessment," Invest Ophthalmol Vis Sci, Feb. 2008, 49(2):522-7.
Zalevsky et al., "The impact of Fc engineering on an anti-CD19 antibody: increased Fcγ receptor affinity enhances B-cell clearing in nonhuman primates," Blood, Apr. 16, 2009, 113(16):3735-43. Epub Dec. 24, 2008.
Zalevsky et al., "Enhanced antibody half-life improves in vivo activity," Nat Biotechnol, Feb. 2010, 28(2):157-9.
Zatloukal et al., "Somatic gene therapy for cancer: the utility of transferrinfection in generating 'tumor vaccines'," Gene, Dec. 15, 1993, 135(1-2):199-207.
International Search Report for App. Ser. No. PCT/JP2012/075403, mailed Nov. 27, 2012, 4 pages.
International Preliminary Report on Patentability for App. Ser. No. PCT/JP2012/075403, dated Apr. 1, 2014, 9 pages.
USPTO Restriction Requirement in U.S. Appl. No. 14/347,034, dated Dec. 18, 2014, 9 pages.
Fish & Richardson P.C., Reply to Restriction Requirement dated Dec. 18, 2014 in U.S. Appl. No. 14/347,034, filed Mar. 18, 2015, 2 pages.
USPTO Non-Final Office Action in U.S. Appl. No. 14/347,034, dated Apr. 16, 2015, 9 pages.
USPTO Interview Summary in U.S. Appl. No. 14/347,034, dated Aug. 17, 2015, 3 pages.
Fish & Richardson P.C., Reply to Non-Final Office Action dated Apr. 16, 2015 in U.S. Appl. No. 14/347,034, filed Sep. 16, 2015, 28 pages.
USPTO Final Office Action in U.S. Appl. No. 14/347,034, dated Oct. 16, 2015, 5 pages.
Fish & Richardson P.C., Reply to Final Office Action dated Oct. 16, 2015 in U.S. Appl. No. 14/347,034, filed Jan. 13, 2016, 28 pages.
USPTO Notice of Allowance in U.S. Appl. No. 14/347,034, dated Feb. 17, 2016, 6 pages.
USPTO Notice of Allowance in U.S. Appl. No. 14/347,034, dated Jun. 3, 2016, 5 pages.
USPTO Notice of Allowance in U.S. Appl. No. 14/347,034, dated Sep. 22, 2016, 9 pages.
USPTO Non-Final Office Action in U.S. Appl. No. 14/347,034, dated May 25, 2017, 16 pages.
USPTO Non-Final Office Action in U.S. Appl. No. 14/347,034, dated Jan. 8, 2018, 15 pages.
Non-Final Office Action for U.S. Appl. No. 15/230,904, dated May 25, 2017, 9 pages.
Non-Final Office Action for U.S. Appl. No. 15/230,904, dated Jan. 8, 2018, 16 pages.
USPTO Restriction Requirement in U.S. Appl. No. 14/347,187, dated Jan. 26, 2017, 9 pages.
USPTO Non-Final Office Action in U.S. Appl. No. 14/347,187, dated Jun. 14, 2017, 23 pages.
Fish & Richardson P.C., Reply to Non-Final Office Action dated Jun. 14, 2017, in U.S. Appl. No. 14/347,187, filed Oct. 16, 2017, 36 pages.
USPTO Final Office Action in U.S. Appl. No. 14/347,187, dated Jan. 19, 2018, 24 pages.
USPTO Applicant-Initiated Interview Summary in U.S. Appl. No. 14/347,187, dated Jul. 10, 2018, 3 pages.
USPTO Non-Final Office Action in U.S. Appl. No. 14/347,187, dated Sep. 4, 2018, 22 pages.
USPTO Notice of Allowance in U.S. Appl. No. 14/347,187, dated Jan. 7, 2019, 13 pages.
USPTO Non-Final Office Action in U.S. Appl. No. 16/028,140, dated Jul. 9, 2019, 95 pages.
Kim et al., "Kinetics of FcRn-mediated recycling of IgG and albumin in human: pathophysiology and therapeutic implications using a simplified mechanism-based model," Clin Immunol, Feb. 2007, 122(2):146-155. doi: 10.1016/j.clim.2006.09.001. Epub Oct. 13, 2006.

(56) References Cited

OTHER PUBLICATIONS

Fish & Richardson P.C., Reply to Restriction Requirement in U.S. Appl. No. 14/347,448, filed Mar. 21, 2016, 13 pages.
Fish & Richardson P.C., Amendment and Reply to Action of May 26, 2016 in U.S. Appl. No. 14/347,448, filed Nov. 28, 2016, 27 pages.
Fish & Richardson P.C., Amendment and Reply to Action of Feb. 21, 2017 in U.S. Appl. No. 14/347,448, filed Aug. 18, 2017, 46 pages.
Fish & Richardson P.C., Reply to Restriction Requirement in U.S. Appl. No. 14/347,448, filed Feb. 22, 2018, 3 pages.
Fish & Richardson P.C., Amendment and Reply to Non-Final Action of Mar. 9, 2018 in U.S. Appl. No. 14/347,448, filed Sep. 5, 2018, 41 pages.
Fish & Richardson P.C., Amendment and Reply to Final Office Action of Nov. 13, 2018 in U.S. Appl. No. 14/347,448, filed May 10, 2019, 19 pages.
USPTO Restriction Requirement in U.S. Appl. No. 14/347,448, dated Dec. 21, 2015, 8 pages.
USPTO Non-Final Office Action in U.S. Appl. No. 14/347,448, dated May 26, 2016, 54 pages.
USPTO Final Office Action in U.S. Appl. No. 14/347,448, dated Feb. 21, 2017, 45 pages.
USPTO Interview Summary in U.S. Appl. No. 14/347,448, dated Aug. 16, 2017, 4 pages.
USPTO Restriction Requirement in U.S. Appl. No. 14/347,448, dated Nov. 24, 2017, 13 pages.
USPTO Non-Final Office Action in U.S. Appl. No. 14/347,448, dated Mar. 9, 2018, 32 pages.
USPTO Final Office Action in U.S. Appl. No. 14/347,448, dated Nov. 13, 2018, 29 pages.
USPTO Notice of Allowance in U.S. Appl. No. 14/347,448, dated Sep. 26, 2019, 12 pages.
Min et al., "Anti-CD20 Monoclonal Antibody RTX Enhances Radiosensitivity of Lymphoma Cells," Journal of Experimental Hematology, 2010, 18(3):660-665 (with English translation).
Qiu, "scFv antibodies binding to FcRn pH-dependently enable to prolong serum half-life of therapeutic protein," Ph.D. Dissertation Submitted to School of Pharmacy, Shanghai Jiao Tong University, May 2016 (with English translation).
Vaughn et al., "Structural basis of pH-dependent antibody binding by the neonatal Fc receptor," Structure, Jan. 15, 1998;6(1):63-73.
Wang et al., "Advance on Production and Application of Humanized Antibody," Letters in Biotechnology, 2007, 18(4):683-687 (with English translation).
Yang et al., "Maximizing in vivo target clearance by design of pH-dependent target binding antibodies with altered affinity to FcRn," mAbs, Oct. 2017, 9(7):1105-1117. doi: 10.1080/19420862.2017.1359455. Epub Aug. 8, 2017.

\* cited by examiner (i)

Ca²⁺
2mM

Interaction

Ca²⁺
3μM

Repulsion (ii)

pH7.4
Ca²⁺
2mM

Interaction pH6.0
Ca²⁺
3μM

Repulsion (i) Crystal structure in the presence of calcium ion (ii) Crystal structure in the absence of calcium ion

ANTIGEN-BINDING MOLECULE INDUCING IMMUNE RESPONSE TO TARGET ANTIGEN

CROSS-REFERENCE TO RELATED APPLICATIONS

This application is a divisional of U.S. application Ser. No. 14/347,448, filed on Mar. 26, 2014 (now U.S. Pat. No. 10,556,949), which is the National Stage of International Application Serial No. PCT/JP2012/075043, filed on Sep. 28, 2012, which claims the benefit of Japanese Application Serial No. 2011-216958, filed on Sep. 30, 2011.

TECHNICAL FIELD

The present invention provides pharmaceutical compositions comprising as an active ingredient an antigen-binding molecule that induces an immune response to a target antigen, or therapeutic methods that use the pharmaceutical compositions. The present invention also provides pharmaceutical compositions comprising as an active ingredient, an antigen-binding molecule that induces the above-mentioned immune response and also has cytotoxicity (cytotoxic activity) or antiproliferative action (cell proliferation inhibitory activity) against cells expressing a target antigen, or therapeutic methods that use the pharmaceutical compositions.

BACKGROUND ART

To date, attempts have been made to develop a number of therapeutic vaccines directed to tumor cells. This is because it is considered that there are qualitative or quantitative differences between tumor cells and normal cells that may be recognized by the immune system of a living organism, and the immune system stimulated by active and specific sensitization by vaccines utilizing such differences (neoepitopes) can recognize and eliminate tumor cells.

To bring about such anti-tumor response, at least two conditions may have to be met. Firstly, the tumor cells must express an antigen that does not appear in normal cells, or express an antigen to such an extent that normal cells and tumor cells can be distinguished solely in a qualitative manner. Secondly, the immune system must be activated by vaccines or such in order to react with the antigen of interest. A major obstacle in tumor immunotherapy is considered to be that the immunogenicity of tumors is particularly weak in humans.

In recent years, tumor-related and tumor-specific antigens including such neoepitopes that may constitute targets to be attacked by the immune system have been discovered. Nonetheless, the immune system cannot eliminate tumors expressing such neoepitopes, and this may be due to insufficient immune response to these neoepitopes, rather than due to the absence of neoepitopes.

Two general strategies have been developed for the purpose of cell-based cancer immunotherapies. One of them is adoptive immunotherapy where tumor-reactive T lymphocytes expanded in vitro are reintroduced into a patient, and the other is active immunotherapy which uses tumor cells to induce systemic tumor response by triggering new or stronger immune response to a tumor antigen.

Tumor vaccines based on active immunotherapy have been prepared by various methods. To induce immune response to a tumor antigen, irradiated tumor cells mixed with an immune-stimulating adjuvant such as *Bacillus* Calmette Guerin (BCG) (Non-Patent Document 1), tumor cells genetically modified to produce, for example, cytokines (Non-Patent Document 2), and alienated autologous tumor cells (Non-Patent Document 3) have been prepared. However, the immunogenicity of the tumor cells is low, and this is considered to be due to the quantity of the tumor antigen, not the quality.

On the other hand, antibodies are known to induce humoral immune responses (production of antibodies against an antigen) and cellular immune responses (production of CD8-positive T cells against an antigen) to antigens by cross-presenting bound antigens to antigen-presenting cells, and it has been reported that administration of an antibody can induce acquired immunity to an antigen (Non-Patent Document 4). Recently, for the anti-tumor effect by an anti-HER2 antibody, it has been shown in an in vivo mouse model that acquired immunity to the HER2 antigen induced by administration of the antibody plays a more important role than the direct ADCC of the administered antibody (Non-Patent Document 5). In fact, in clinical use of Herceptin, which is an IgG1 subclass antibody drug against HER2, acquired immunity was induced by Herceptin administration, and humoral immune response to HER2 was observed (Non-Patent Document 6). Since patients in whom Herceptin administration was effective particularly showed an increased anti-HER2 antibody titer, induction of acquired immunity by Herceptin administration was considered to play an important role in the anti-tumor effect.

Antibodies are highly stable in blood and have few side effects, and are therefore drawing attention as pharmaceuticals (Non-Patent Documents 7 and 8). Many studies have been carried out so far on antibody-dependent cellular cytotoxicity (hereinafter denoted as ADCC) and complement-dependent cytotoxicity (hereinafter denoted as CDC), which are effector functions of IgG class antibodies. It has been reported that in the human IgG class, antibodies of the IgG1 subclass have the highest ADCC activity and CDC activity (Non-Patent Document 9). Furthermore, antibody-dependent cell-mediated phagocytosis (ADCP), which is phagocytosis of target cells mediated by IgG class antibodies, is also suggested to be one of the antibody effector functions (Non-Patent Documents 10 and 11). Since IgG1 subclass antibodies can exert these effector functions against tumors, IgG1 subclass antibodies are used for most antibody pharmaceuticals against cancer antigens.

In order for IgG antibodies to mediate ADCC and ADCP activities, the Fc region of the IgG antibodies must bind to antibody receptors (hereinafter denoted as FcγR) that are present on the surface of effector cells such as killer cells, natural killer cells, and activated macrophages. In humans, isoforms FcγRIa, FcγRIIa, FcγRIIb, FcγRIIIa, and FcγRIIIb have been reported as members of the FcγR protein family, and their respective allotypes have been reported as well (Non-Patent Document 12).

Enhancement of cytotoxic effector functions such as ADCC and ADCP has been drawing attention as a promising means for enhancing the antitumor effects of anticancer antibodies. Importance of FcγR-mediated effector functions aimed for antitumor effects of antibodies has been reported using mouse models (Non-Patent Documents 13 and 14). Furthermore, it was observed that clinical effects in humans correlated with the high-affinity polymorphic allotype (V158) and the low-affinity polymorphic allotype (F158) of FcγRIIIa (Non-Patent Document 15). These reports suggest that antibodies with an Fc region optimized for binding to a specific FcγR mediates stronger effector functions, and thereby exert more effective antitumor effects. The balance between the affinity of antibodies against the activating receptors including FcγRIa, FcγRIIa, FcγRIIIa, and FcγRIIIb, and the inhibitory receptors including FcγRIIb is an important factor in optimizing antibody effector functions. Enhancing the affinity to activating receptors may give antibodies a property to mediate stronger effector functions (Non-Patent Document 16), and therefore has been reported in various reports to date as an antibody engineering technique for improving or enhancing the antitumor activity of antibody pharmaceuticals against cancer antigens.

Regarding binding between the Fc region and FcγR, several amino acid residues in the antibody hinge region and the CH2 domain, and a sugar chain added to Asn at position 297 (EU numbering) bound to the CH2 domain have been shown as being important (Non-Patent Documents 9, 17, and 18). Focusing on this binding site, studies have so far been carried out on mutants of the Fc region having various FcγR binding properties, and Fc region mutants with higher affinity to activating FcγR have been obtained (Patent Documents 1 and 2). For example, Lazar et al. have succeeded in increasing the binding of human IgG1 to human FcγRIIIa (V158) by approximately 370 fold by substituting Ser at position 239, Ala at position 330, and Ile at position 332 (EU numbering) of human IgG1 with Asn, Leu, and Glu, respectively (Non-Patent Document 19 and Patent Document 2). The ratio of binding to FcγRIIIa and FcγRIIb (A/I ratio) for this mutant was approximately 9-fold that of the wild type. Furthermore, Shinkawa et al. have succeeded in increasing the binding to FcγRIIIa up to approximately 100 fold by removing fucose from the sugar chain added to Asn at position 297 (EU numbering) (Non-Patent Document 20). These methods can greatly improve the ADCC activity of human IgG1 compared to that of naturally-occurring human IgG1.

While there are many reports, as described above, on methods for enhancing ADCC by antibody engineering, no reports have been made to date on antibody engineering techniques for enhancing or improving induction of acquired immunity by antibody administration. There is a report on methods for inducing acquired immunity against a cancer antigen, in which a cancer antigen against which acquired immunity is desired to be induced is fused with an antibody that binds to a high-mannose receptor or DEC-205 expressed on antigen presenting cells, thereby promoting incorporation and presentation of the cancer antigen by antigen presenting cells (Non-Patent Document 21). However, in these methods the target of antibody binding is not a cancer antigen as in the case of the above-mentioned anti-HER2 antibody. That is, since these methods induce acquired immunity against a cancer antigen fused to the antibody itself, the antibody itself cannot bind to the cancer antigen, and has the disadvantage of not being able to exhibit direct action on the cancer antigen. Furthermore, since this method induces acquired immunity not only against the cancer antigen fused to the antibody but also against the antibody itself used for targeting antigen-presenting cells, anti-drug antibodies will emerge and this leads to weakening of the effects. Therefore, this method may not be preferable for therapeutic purposes.

According to the above, while it is desirable to induce acquired immunity to a target antigen by administering an antigen-binding molecule having binding activity to the target antigen, there has been no reports on engineering techniques for improving or enhancing acquired immunity by such methods.

PRIOR ART DOCUMENTS

Patent Documents

[Patent Document 1] WO2000/042072
[Patent Document 2] WO2006/019447

Non-Patent Documents

[Non-patent Document 1] Oettgen, H. F., and Old, L. J., The history of cancer immunotherapy, Biological Therapy of Cancer (1991) 87-119 DeVita et al. ed.

[Non-patent Document 2] Zatloukal K, Schmidt W, Cotten M, Wagner E, Stingl G, Birnstiel M L., Somatic gene therapy for cancer: the utility of transferrinfection in generating 'tumor vaccines', Gene (1993) 135, 199-207

[Non-patent Document 3] Bronte V, Tsung K, Rao J B, Chen P W, Wang M, Rosenberg S A, Restifo N P., IL-2 enhances the function of recombinant poxvirus-based vaccines in the treatment of established pulmonary metastases, J. Immunol. (1995) 154, 5282-5292

[Non-patent Document 4] Adams G P, Weiner L M., Monoclonal antibody therapy of cancer, Nat. Biotechnol. (2005) 23, 1147-1157

[Non-patent Document 5] Park S, Jiang Z, Mortenson E D, Deng L, Radkevich-Brown O, Yang X, Sattar H, Wang Y, Brown N K, Greene M, Liu Y, Tang J, Wang S, Fu Y X., The therapeutic effect of anti-HER2/neu antibody depends on both innate and adaptive immunity, Cancer Cell (2010) 18, 160-170 (2010)

[Non-patent Document 6] Taylor C, Hershman D, Shah N, Suciu-Foca N, Petrylak D P, Taub R, Vandat L, Cheng B, Pegram M, Knutson K L, Clynes R. Augmented HER-2 specific immunity during treatment with trastuzumab and chemotherapy, Clin. Cancer Res, (2007) 13, 5133-43

[Non-patent Document 7] anice M Reichert, Clark J Rosensweig, Laura B Faden & Matthew C Dewitz, Monoclonal antibody successes in the clinic, Nat. Biotechnol. (2005) 23, 1073-1078

[Non-patent Document 8] avlou A K, Belsey M J., The therapeutic antibodies market to 2008, Eur. J. Pharm. Biopharm. (2005) 59(3), 389-396

[Non-patent Document 9] Clark, M., Antibody Engineering IgG Effector Mechanisms, Chemical Immunology (1997), 65, 88-110

[Non-patent Document 10] Horton H M, Bernett M J, Pong E, Peipp M, Karki S, Chu S Y, Richards J O, Vostiar I, Joyce P F, Repp R, Desjarlais J R, Zhukovsky E A., Potent in vitro and in vivo activity of an Fc-engineered anti-CD19 monoclonal antibody against lymphoma and leukemia, Cancer Res. (2008) 68, 8049-8057

[Non-patent Document 11] Zalevsky J, Leung I W, Karki S, Chu S Y, Zhukovsky E A, Desjarlais J R, Carmichael D F, Lawrence C E., The impact of Fc engineering on an anti-CD19 antibody: increased Fcγ receptor affinity enhances B-cell clearing in nonhuman primates, Blood (2009) 113, 3735-3743

[Non-patent Document 12] Jefferis R, Lund J., Interaction sites on human IgG-Fc for FcgammaR: current models, Immunol. Lett. (2002) 82, 57-65

[Non-patent Document 13] Clynes, R., Yoshizumi, T., Moroi, Y, Houghton, A. N., and Ravetch, J. V., Fc Receptors are required for passive and active immunity to melanoma, Proc. Natl. Acad. Sci. U.S.A (1998) 95, 652-656

[Non-patent Document 14] Clynes R A, Towers T L, Presta L C; Ravetch J V., Inhibitory Fc receptors modulate in vivo cytoxicity against tumor targets, Nat. Med. (2000) 6, 443-446

[Non-patent Document 15] Cartron G, Dacheux L, Salles G, Solal-Celigny P, Bardos P, Colombat P, Watier H., Therapeutic activity of humanized anti-CD20 monoclonal antibody and polymorphism in IgG Fc receptor FcgammaRIIIa gene, Blood (2002) 99, 754-758

[Non-patent Document 16] Nimmerjahn F, Ravetch J V., Divergent immunoglobulin g subclass activity through selective Fc receptor binding, Science (2005), 310, 1510-1512

[Non-patent Document 17] Greenwood J, Clark M, Waldmann H., Structural motifs involved in human IgG antibody effector functions, Eur. J. Immunol. 23, 1098-1104 (1993)

[Non-patent Document 18] Morgan A, Jones N D, Nesbitt A M, Chaplin L, Bodmer M W, Emtage J S., The N-terminal end of the CH2 domain of chimeric human IgG1 anti-HLA-DR is necessary for C1q, Fc gamma RI and Fc gamma RIII binding, Immunology (1995) 86, 319-324

[Non-patent Document 19] Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I., Engineered antibody Fc variants with enhanced effector function, Proc. Natl. Acad. Sci. U.S.A (2006) 103, 4005-4010

[Non-patent Document 20] Shinkawa T, Nakamura K, Yamane N, Shoji-Hosaka E, Kanda Y, Sakurada M, Uchida K, Anazawa H, Satoh M, Yamasaki M, Hanai N, Shitara K., The absence of fucose but not the presence of galactose or bisecting N-acetylglucosamine of human IgG1 complex-type oligosaccharides shows the critical role of enhancing antibody-dependent cellular cytotoxicity, J. Biol. Chem. (2003) 278, 3466-3473

[Non-patent Document 21] Tsuji T, Matsuzaki J, Kelly M P, Ramakrishna V, Vitale L, He L Z, Keler T, Odunsi K, Old L J, Ritter G, Gnjatic S., Antibody-Targeted NY-ESO-1 to Mannose Receptor or DEC-205 In Vitro Elicits Dual Human CD8+ and CD4+ T Cell Responses with Broad Antigen Specificity, J. Immunol. (2011) 186, 1218-1827

SUMMARY OF THE INVENTION

Problems to be Solved by the Invention

The present invention was achieved in view of the above circumstances. An objective of the present invention is to provide pharmaceutical compositions comprising as an active ingredient an antigen-binding molecule that induces an immune response in subjects affected with cancer or infected with foreign biological species when administered to these subjects, or therapeutic methods that use the pharmaceutical compositions. Another objective is to provide pharmaceutical compositions comprising as an active ingredient an antigen-binding molecule that induces the above-mentioned immune response and also has cytotoxicity (cytotoxic activity) or antiproliferative action (cell proliferation inhibitory activity) against cancer cells or infecting foreign biological species, or therapeutic methods that use the pharmaceutical compositions.

Means for Solving the Problems

The present inventors have discovered that in living organisms that have received an antigen-binding molecule containing an antigen-binding domain whose binding activity against an antigen changes depending on ion concentration conditions and containing an FcRn-binding domain having FcRn-binding activity under a neutral pH range, immune responses to the antigen are induced. Furthermore, the present inventors have discovered that in living organisms that have received an antigen-binding molecule containing an antigen-binding domain whose antigen-binding activity changes depending on ion concentration conditions and an FcRn-binding domain having FcRn-binding activity under a neutral pH range, immune responses to the antigen are induced, and the antigen-binding molecule can also have cytotoxicity or antiproliferative effect against cancer cells, foreign biological species, or the like that express the antigen to which the antigen-binding molecule binds. Based on these findings, the present inventors have elucidated that the antigen-binding molecules of the present invention are useful as pharmaceutical compositions for inducing an immune response in a subject infected with a foreign biological species or affected with cancer when administered to the subject. The present inventors have also elucidated that the antigen-binding molecules of the present invention are useful as pharmaceutical compositions that, when administered to a subject infected with a foreign biological species or affected with cancer, induce an immune response in the subject and also have cytotoxicity or antiproliferative effect against the cancer cells and foreign biological species. Methods for producing these pharmaceutical compositions have also been discovered.

More specifically, the present invention provides [1] to [47] below:

[1] a pharmaceutical composition that induces an immune response to an antigen, which comprises as an active ingredient an antigen-binding molecule, wherein the antigen-binding molecule comprises an antigen-binding domain whose binding activity to the antigen changes depending on an ion concentration condition and comprises an FcRn-binding domain having binding activity to FcRn in a neutral pH range;

[2] the pharmaceutical composition of [1], wherein the ion concentration is a calcium ion concentration;

[3] the pharmaceutical composition of [2], wherein the antigen-binding domain is an antigen-binding domain whose antigen-binding activity is higher under a high calcium ion concentration condition than under a low calcium ion concentration condition;

[4] the pharmaceutical composition of [1], wherein the ion concentration condition is a pH condition;

[5] the pharmaceutical composition of [4], wherein the antigen-binding domain is an antigen-binding domain whose antigen-binding activity is higher in a neutral pH range than under an acidic pH range;

[6] the pharmaceutical composition of any one of [1] to [5], wherein the antigen-binding molecule has neutralizing activity against the antigen;

[7] the pharmaceutical composition of any one of [1] to [6], wherein the antigen-binding molecule has cytotoxic activity against a cell expressing the antigen;

[8] the pharmaceutical composition of any one of [1] to [7], wherein the FcRn-binding domain comprises an antibody Fc region;

[9] the pharmaceutical composition of [8], wherein the Fc region is an Fc region in which at least one or more amino acids selected from the group consisting of amino acids at positions 257, 308, 428, and 434 according to EU numbering in the Fc region are different from amino acids at corresponding positions in a naturally-occurring Fc region;

[10] the pharmaceutical composition of [8] or [9], wherein the Fc region comprises at least one or more amino acids selected from the group consisting of:
Ala at amino acid position 257;
Pro at amino acid position 308;
Leu at amino acid position 428; and
Tyr at amino acid position 434,
according to EU numbering in the Fc region;

[11] the pharmaceutical composition of any one of [8] to [10], wherein the Fcγ receptor-binding activity of the Fc region is higher than that of a naturally-occurring human IgG Fc region in which the sugar chain attached at position 297 according to EU numbering is a fucose-containing sugar chain;

[12] the pharmaceutical composition of [11], wherein the Fcγ receptor is FcγRIa, FcγRIIa(R), FcγRIIa(H), FcγRIIb, FcγRIIIa(V), or FcγRIIIa(F);

[13] the pharmaceutical composition of [11] or [12], wherein the Fc region is an Fc region in which at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 according to EU numbering in the Fc region are different from amino acids at corresponding positions in a naturally-occurring Fc region;

[14] the pharmaceutical composition of any one of [11] to [13], wherein the Fc region comprises at least one or more amino acids selected from the group consisting of:
either Lys or Tyr at amino acid position 221;
any one of Phe, Trp, Glu, and Tyr at amino acid position 222;
any one of Phe, Trp, Glu, and Lys at amino acid position 223;
any one of Phe, Trp, Glu, and Tyr at amino acid position 224;
any one of Glu, Lys, and Trp at amino acid position 225;
any one of Glu, Gly, Lys, and Tyr at amino acid position 227;
any one of Glu, Gly, Lys, and Tyr at amino acid position 228;
any one of Ala, Glu, Gly, and Tyr at amino acid position 230;
any one of Glu, Gly, Lys, Pro, and Tyr at amino acid position 231;
any one of Glu, Gly, Lys, and Tyr at amino acid position 232;
any one of Ala, Asp, Phe, Gly, His, Ile, Lys, Leu, Met, Asn, Gln, Arg, Ser, Thr, Val, Trp, and Tyr at amino acid position 233;
any one of Ala, Asp, Glu, Phe, Gly, His, Ile, Lys, Met, Asn, Pro, Gln, Arg, Ser, Thr, Val, Trp, and Tyr at amino acid position 234;
any one of Ala, Asp, Glu, Phe, Gly, His, Ile, Lys, Met, Asn, Pro, Gln, Arg, Ser, Thr, Val, Trp, and Tyr at amino acid position 235;
any one of Ala, Asp, Glu, Phe, His, Ile, Lys, Leu, Met, Asn, Pro, Gln, Arg, Ser, Thr, Val, Trp, and Tyr at amino acid position 236;
any one of Asp, Glu, Phe, His, Ile, Lys, Leu, Met, Asn, Pro, Gln, Arg, Ser, Thr, Val, Trp, and Tyr at amino acid position 237;
any one of Asp, Glu, Phe, Gly, His, Ile, Lys, Leu, Met, Asn, Gln, Arg, Ser, Thr, Val, Trp, and Tyr at amino acid position 238;
any one of Asp, Glu, Phe, Gly, His, Ile, Lys, Leu, Met, Asn, Pro, Gln, Arg, Thr, Val, Trp, and Tyr at amino acid position 239;
any one of Ala, Ile, Met, and Thr at amino acid position 240;
any one of Asp, Glu, Leu, Arg, Trp, and Tyr at amino acid position 241;
any one of Leu, Glu, Leu, Gln, Arg, Trp, and Tyr at amino acid position 243;
His at amino acid position 244;
Ala at amino acid position 245;
any one of Asp, Glu, His, and Tyr at amino acid position 246;
any one of Ala, Phe, Gly, His, Ile, Leu, Met, Thr, Val, and Tyr at amino acid position 247;
any one of Glu, His, Gln, and Tyr at amino acid position 249;
either Glu or Gln at amino acid position 250;
Phe at amino acid position 251;
any one of Phe, Met, and Tyr at amino acid position 254;
any one of Glu, Leu, and Tyr at amino acid position 255;
any one of Ala, Met, and Pro at amino acid position 256;
any one of Asp, Glu, His, Ser, and Tyr at amino acid position 258;
any one of Asp, Glu, His, and Tyr at amino acid position 260;
any one of Ala, Glu, Phe, Ile, and Thr at amino acid position 262;
any one of Ala, Ile, Met, and Thr at amino acid position 263;
any one of Asp, Glu, Phe, Gly, His, Ile, Lys, Leu, Met, Asn, Pro, Gln, Arg, Ser, Thr, Trp, and Tyr at amino acid position 264;
any one of Ala, Leu, Phe, Gly, His, Ile, Lys, Leu, Met, Asn, Pro, Gln, Arg, Ser, Thr, Val, Val, Trp, and Tyr at amino acid position 265;
any one of Ala, Ile, Met, and Thr at amino acid position 266;
any one of Asp, Glu, Phe, His, Ile, Lys, Leu, Met, Asn, Pro, Gln, Arg, Thr, Val, Trp, and Tyr at amino acid position 267;
any one of Asp, Glu, Phe, Gly, Ile, Lys, Leu, Met, Pro, Gln, Arg, Thr, Val, and Trp at amino acid position 268;
any one of Phe, Gly, His, Ile, Lys, Leu, Met, Asn, Pro, Arg, Ser, Thr, Val, Trp, and Tyr at amino acid position 269;
any one of Glu, Phe, Gly, His, Ile, Leu, Met, Pro, Gln, Arg, Ser, Thr, Trp, and Tyr at amino acid position 270;
any one of Ala, Asp, Glu, Phe, Gly, His, Ile, Lys, Leu, Met, Asn, Gln, Arg, Ser, Thr, Val, Trp, and Tyr at amino acid position 271;
any one of Asp, Phe, Gly, His, Ile, Lys, Leu, Met, Pro, Arg, Ser, Thr, Val, Trp, and Tyr at amino acid position 272;
either Phe or Ile at amino acid position 273;

any one of Asp, Glu, Phe, Gly, His, Ile, Leu, Met, Asn, Pro, Arg, Ser, Thr, Val, Trp, and Tyr at amino acid position 274;
either Leu or Trp at amino acid position 275;
any one of Asp, Glu, Phe, Gly, His, Ile, Leu, Met, Pro, Arg, Ser, Thr, Val, Trp, and Tyr at amino acid position 276;
any one of Asp, Glu, Gly, His, Ile, Lys, Leu, Met, Asn, Pro, Gln, Arg, Ser, Thr, Val, and Trp at amino acid position 278;
Ala at amino acid position 279;
any one of Ala, Gly, His, Lys, Leu, Pro, Gln, Trp, and Tyr at amino acid position 280;
any one of Asp, Lys, Pro, and Tyr at amino acid position 281;
any one of Glu, Gly, Lys, Pro, and Tyr at amino acid position 282;
any one of Ala, Gly, His, Ile, Lys, Leu, Met, Pro, Arg, and Tyr at amino acid position 283;
any one of Asp, Glu, Leu, Asn, Thr, and Tyr at amino acid position 284;
any one of Asp, Glu, Lys, Gln, Trp, and Tyr at amino acid position 285;
any one of Glu, Gly, Pro, and Tyr at amino acid position 286;
any one of Asn, Asp, Glu, and Tyr at amino acid position 288;
any one of Asp, Gly, His, Leu, Asn, Ser, Thr, Trp, and Tyr at amino acid position 290;
any one of Asp, Glu, Gly, His, Ile, Gln, and Thr at amino acid position 291;
any one of Ala, Asp, Glu, Pro, Thr, and Tyr at amino acid position 292;
any one of Phe, Gly, His, Ile, Leu, Met, Asn, Pro, Arg, Ser, Thr, Val, Trp, and Tyr at amino acid position 293;
any one of Phe, Gly, His, Ile, Lys, Leu, Met, Asn, Pro, Arg, Ser, Thr, Val, Trp, and Tyr at amino acid position 294;
any one of Asp, Glu, Phe, Gly, His, Ile, Lys, Met, Asn, Pro, Arg, Ser, Thr, Val, Trp, and Tyr at amino acid position 295;
any one of Ala, Asp, Glu, Gly, His, Ile, Lys, Leu, Met, Asn, Gln, Arg, Ser, Thr, and Val at amino acid position 296;
any one of Asp, Glu, Phe, Gly, His, Ile, Lys, Leu, Met, Pro, Gln, Arg, Ser, Thr, Val, Trp, and Tyr at amino acid position 297;
any one of Ala, Asp, Glu, Phe, His, Ile, Lys, Met, Asn, Gln, Arg, Thr, Val, Trp, and Tyr at amino acid position 298;
any one of Ala, Asp, Glu, Phe, Gly, His, Ile, Lys, Leu, Met, Asn, Pro, Gln, Arg, Ser, Val, Trp, and Tyr at amino acid position 299;
any one of Ala, Asp, Glu, Gly, His, Ile, Lys, Leu, Met, Asn, Pro, Gln, Arg, Ser, Thr, Val, and Trp at amino acid position 300;
any one of Asp, Glu, His, and Tyr at amino acid position 301;
Ile at amino acid position 302;
any one of Asp, Gly, and Tyr at amino acid position 303;
any one of Asp, His, Leu, Asn, and Thr at amino acid position 304;
any one of Glu, Ile, Thr, and Tyr at amino acid position 305;
any one of Ala, Asp, Asn, Thr, Val, and Tyr at amino acid position 311;
Phe at amino acid position 313;
Leu at amino acid position 315;
either Glu or Gln at amino acid position 317;
any one of His, Leu, Asn, Pro, Gln, Arg, Thr, Val, and Tyr at amino acid position 318;
any one of Asp, Phe, Gly, His, Ile, Leu, Asn, Pro, Ser, Thr, Val, Trp, and Tyr at amino acid position 320;
any one of Ala, Asp, Phe, Gly, His, Ile, Pro, Ser, Thr, Val, Trp, and Tyr at amino acid position 322;
Ile at amino acid position 323;
any one of Asp, Phe, Gly, His, Ile, Leu, Met, Pro, Arg, Thr, Val, Trp, and Tyr at amino acid position 324;
any one of Ala, Asp, Glu, Phe, Gly, His, Ile, Lys, Leu, Met, Pro, Gln, Arg, Ser, Thr, Val, Trp, and Tyr at amino acid position 325;
any one of Ala, Asp, Glu, Gly, Ile, Leu, Met, Asn, Pro, Gln, Ser, Thr, Val, Trp, and Tyr at amino acid position 326;
any one of Ala, Asp, Glu, Phe, Gly, His, Ile, Lys, Leu, Met, Asn, Pro, Arg, Thr, Val, Trp, and Tyr at amino acid position 327;
any one of Ala, Asp, Glu, Phe, Gly, His, Ile, Lys, Met, Asn, Pro, Gln, Arg, Ser, Thr, Val, Trp, and Tyr at amino acid position 328;
any one of Asp, Glu, Phe, Gly, His, Ile, Lys, Leu, Met, Asn, Gln, Arg, Ser, Thr, Val, Trp, and Tyr at amino acid position 329;
any one of Cys, Glu, Phe, Gly, His, Ile, Lys, Leu, Met, Asn, Pro, Arg, Ser, Thr, Val, Trp, and Tyr at amino acid position 330;
any one of Asp, Phe, His, Ile, Leu, Met, Gln, Arg, Thr, Val, Trp, and Tyr at amino acid position 331;
any one of Ala, Asp, Glu, Phe, Gly, His, Lys, Leu, Met, Asn, Pro, Gln, Arg, Ser, Thr, Val, Trp, and Tyr at amino acid position 332;
any one of Ala, Asp, Glu, Phe, Gly, His, Ile, Leu, Met, Pro, Ser, Thr, Val, and Tyr at amino acid position 333;
any one of Ala, Glu, Phe, Ile, Leu, Pro, and Thr at amino acid position 334;
any one of Asp, Phe, Gly, His, Ile, Leu, Met, Asn, Pro, Arg, Ser, Val, Trp, and Tyr at amino acid position 335;
any one of Glu, Lys, and Tyr at amino acid position 336;
any one of Glu, His, and Asn at amino acid position 337;
any one of Asp, Phe, Gly, Ile, Lys, Met, Asn, Gln, Arg, Ser, and Thr at amino acid position 339;
either Ala or Val at amino acid position 376;
either Gly or Lys at amino acid position 377;
Asp at amino acid position 378;
Asn at amino acid position 379;
any one of Ala, Asn, and Ser at amino acid position 380;
either Ala or Ile at amino acid position 382;
Glu at amino acid position 385;
Thr at amino acid position 392;
Leu at amino acid position 396;
Lys at amino acid position 421;
Asn at amino acid position 427;
either Phe or Leu at amino acid position 428;
Met at amino acid position 429;
Trp at amino acid position 434;
Ile at amino acid position 436; and
any one of Gly, His, Ile, Leu, and Tyr at amino acid position 440;
according to EU numbering in the Fc region;
[15] the pharmaceutical composition of any one of [11] to [14], wherein the naturally-occurring Fc region is an Fc region of any one of human IgG1, human IgG2, human IgG3, and human IgG4 in which the sugar chain attached at position 297 according to EU numbering is a fucose-containing sugar chain;

[16] the pharmaceutical composition of any one of [11] to [15], wherein the Fc region is modified so that the percentage of the Fc region to which a fucose-deficient sugar chain is attached, or bisecting N-acetylglucosamine is added, at position 297 according to EU numbering in the Fc region, will become higher.

[17] a method for inducing an immune response in a living organism, which comprises the step of administering the antigen-binding molecule of any one of [1] to [16] to the living organism;

[18] a method for producing an antigen-binding molecule that induces an immune response, which comprises imparting FcRn-binding activity in a neutral pH range to an FcRn-binding domain that is contained in an antigen-binding molecule containing an antigen-binding domain whose antigen-binding activity changes depending on an ion concentration condition;

[19] the method of [18], wherein the ion concentration is a calcium ion concentration;

[20] the method of [19], wherein the antigen-binding domain is an antigen-binding domain whose antigen-binding activity is higher under a high calcium ion concentration condition than under a low calcium ion concentration condition;

[21] the method of [18], wherein the ion concentration condition is a pH condition;

[22] the method of [21], wherein the antigen-binding domain is an antigen-binding domain whose antigen-binding activity is higher in a neutral pH range than in an acidic pH range;

[23] the method of any one of [18] to [22], wherein the antigen-binding molecule has neutralizing activity against the antigen;

[24] the method of any one of [18] to [23], wherein the antigen-binding molecule has cytotoxic activity against a cell expressing the antigen;

[25] the method of any one of [18] to [24], wherein the FcRn-binding domain comprises an antibody Fc region;

[26] the method of [25], comprising the step of substituting at least one or more amino acids selected from the group consisting of amino acids at positions 239, 252, 257, 286, 307, 308, 428, and 434 according to EU numbering in the Fc region;

[27] the method of [25] or [26], comprising the step of performing at least one or more amino acid substitutions selected from the group consisting of:
amino acid substitution with Ala at position 257;
amino acid substitution with Pro at position 308;
amino acid substitution with Leu at position 428; and
amino acid substitution with Tyr at position 434,
according to EU numbering in the Fc region;

[28] the method of any one of [25] to [27], comprising the step of enhancing the Fcγ receptor-binding activity of the Fc region as compared to that of a naturally-occurring human IgG Fc region in which the sugar chain attached at position 297 according to EU numbering is a fucose-containing sugar chain;

[29] the method of [28], wherein the Fcγ receptor is FcγRIa, FcγRIIa(R), FcγRIIa(H), FcγRIIb, FcγRIIIa (V), or FcγRIIIa(F);

[30] the method of [28] or [29], comprising the step of substituting at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 according to EU numbering in the Fc region;

[31] the method of any one of [28] to [30], comprising the step of performing at least one or more amino acid substitutions selected from the group consisting of:
amino acid substitution with either Lys or Tyr at position 221;
amino acid substitution with any one of Phe, Trp, Glu, and Tyr at position 222;
amino acid substitution with any one of Phe, Trp, Glu, and Lys at position 223;
amino acid substitution with any one of Phe, Trp, Glu, and Tyr at position 224;
amino acid substitution with any one of Glu, Lys, and Trp at position 225;
amino acid substitution with any one of Glu, Gly, Lys, and Tyr at position 227;
amino acid substitution with any one of Glu, Gly, Lys, and Tyr at position 228;
amino acid substitution with any one of Ala, Glu, Gly, and Tyr at position 230;
amino acid substitution with any one of Glu, Gly, Lys, Pro, and Tyr at position 231;
amino acid substitution with any one of Glu, Gly, Lys, and Tyr at position 232;
amino acid substitution with any one of Ala, Asp, Phe, Gly, His, Ile, Lys, Leu, Met, Asn, Gln,
Arg, Ser, Thr, Val, Trp, and Tyr at position 233;
amino acid substitution with any one of Ala, Asp, Glu, Phe, Gly, His, Ile, Lys, Met, Asn, Pro, Gln, Arg, Ser, Thr, Val, Trp, and Tyr at position 234;
amino acid substitution with any one of Ala, Asp, Glu, Phe, Gly, His, Ile, Lys, Met, Asn, Pro, Gln, Arg, Ser, Thr, Val, Trp, and Tyr at position 235;
amino acid substitution with any one of Ala, Asp, Glu, Phe, His, Ile, Lys, Leu, Met, Asn, Pro, Gln, Arg, Ser, Thr, Val, Trp, and Tyr at position 236;
amino acid substitution with any one of Asp, Glu, Phe, His, Ile, Lys, Leu, Met, Asn, Pro, Gln, Arg, Ser, Thr, Val, Trp, and Tyr at position 237;
amino acid substitution with any one of Asp, Glu, Phe, Gly, His, Ile, Lys, Leu, Met, Asn, Gln, Arg, Ser, Thr, Val, Trp, and Tyr at position 238;
amino acid substitution with any one of Asp, Glu, Phe, Gly, His, Ile, Lys, Leu, Met, Asn, Pro, Gln, Arg, Thr, Val, Trp, and Tyr at position 239;
amino acid substitution with any one of Ala, Ile, Met, and Thr at position 240;
amino acid substitution with any one of Asp, Glu, Leu, Arg, Trp, and Tyr at position 241;
amino acid substitution with any one of Leu, Glu, Leu, Gln, Arg, Trp, and Tyr at position 243;
amino acid substitution with His at position 244;
amino acid substitution with Ala at position 245;
amino acid substitution with any one of Asp, Glu, His, and Tyr at position 246;
amino acid substitution with any one of Ala, Phe, Gly, His, Ile, Leu, Met, Thr, Val, and Tyr at position 247;

amino acid substitution with any one of Glu, His, Gln, and Tyr at position 249;
amino acid substitution with either Glu or Gln at position 250;
amino acid substitution with Phe at position 251;
amino acid substitution with any one of Phe, Met, and Tyr at position 254;
amino acid substitution with any one of Glu, Leu, and Tyr at position 255;
amino acid substitution with any one of Ala, Met, and Pro at position 256;
amino acid substitution with any one of Asp, Glu, His, Ser, and Tyr at position 258;
amino acid substitution with any one of Asp, Glu, His, and Tyr at position 260;
amino acid substitution with any one of Ala, Glu, Phe, Ile, and Thr at position 262;
amino acid substitution with any one of Ala, Ile, Met, and Thr at position 263;
amino acid substitution with any one of Asp, Glu, Phe, Gly, His, Ile, Lys, Leu, Met, Asn, Pro, Gln, Arg, Ser, Thr, Trp, and Tyr at position 264;
amino acid substitution with any one of Ala, Leu, Phe, Gly, His, Ile, Lys, Leu, Met, Asn, Pro, Gln, Arg, Ser, Thr, Val, Val, Trp, and Tyr at position 265;
amino acid substitution with any one of Ala, Ile, Met, and Thr at position 266;
amino acid substitution with any one of Asp, Glu, Phe, His, Ile, Lys, Leu, Met, Asn, Pro, Gln, Arg, Thr, Val, Trp, and Tyr at position 267;
amino acid substitution with any one of Asp, Glu, Phe, Gly, Ile, Lys, Leu, Met, Pro, Gln, Arg, Thr, Val, and Trp at position 268;
amino acid substitution with any one of Phe, Gly, His, Ile, Lys, Leu, Met, Asn, Pro, Arg, Ser, Thr, Val, Trp, and Tyr at position 269;
amino acid substitution with any one of Glu, Phe, Gly, His, Ile, Leu, Met, Pro, Gln, Arg, Ser, Thr, Trp, and Tyr at position 270;
amino acid substitution with any one of Ala, Asp, Glu, Phe, Gly, His, Ile, Lys, Leu, Met, Asn, Gln, Arg, Ser, Thr, Val, Trp, and Tyr at position 271;
amino acid substitution with any one of Asp, Phe, Gly, His, Ile, Lys, Leu, Met, Pro, Arg, Ser, Thr, Val, Trp, and Tyr at position 272;
amino acid substitution with either Phe or Ile at position 273;
amino acid substitution with any one of Asp, Glu, Phe, Gly, His, Ile, Leu, Met, Asn, Pro, Arg, Ser, Thr, Val, Trp, and Tyr at position 274;
amino acid substitution with either Leu or Trp at position 275;
amino acid substitution with any one of Asp, Glu, Phe, Gly, His, Ile, Leu, Met, Pro, Arg, Ser, Thr, Val, Trp, and Tyr at position 276;
amino acid substitution with any one of Asp, Glu, Gly, His, Ile, Lys, Leu, Met, Asn, Pro, Gln, Arg, Ser, Thr, Val, and Trp at position 278;
amino acid substitution with Ala at position 279;
amino acid substitution with any one of Ala, Gly, His, Lys, Leu, Pro, Gln, Trp, and Tyr at position 280;
amino acid substitution with any one of Asp, Lys, Pro, and Tyr at position 281;
amino acid substitution with any one of Glu, Gly, Lys, Pro, and Tyr at position 282;
amino acid substitution with any one of Ala, Gly, His, Ile, Lys, Leu, Met, Pro, Arg, and Tyr at position 283;
amino acid substitution with at position 284 is any one of Asp, Glu, Leu, Asn, Thr, and Tyr;
amino acid substitution with any one of Asp, Glu, Lys, Gln, Trp, and Tyr at position 285;
amino acid substitution with any one of Glu, Gly, Pro, and Tyr at position 286;
amino acid substitution with any one of Asn, Asp, Glu, and Tyr at position 288;
amino acid substitution with any one of Asp, Gly, His, Leu, Asn, Ser, Thr, Trp, and Tyr at position 290;
amino acid substitution with any one of Asp, Glu, Gly, His, Ile, Gln, and Thr at position 291;
amino acid substitution with any one of Ala, Asp, Glu, Pro, Thr, and Tyr at position 292;
amino acid substitution with any one of Phe, Gly, His, Ile, Leu, Met, Asn, Pro, Arg, Ser, Thr, Val, Trp, and Tyr at position 293;
amino acid substitution with any one of Phe, Gly, His, Ile, Lys, Leu, Met, Asn, Pro, Arg, Ser, Thr, Val, Trp, and Tyr at position 294;
amino acid substitution with any one of Asp, Glu, Phe, Gly, His, Ile, Lys, Met, Asn, Pro, Arg, Ser, Thr, Val, Trp, and Tyr at position 295;
amino acid substitution with any one of Ala, Asp, Glu, Gly, His, Ile, Lys, Leu, Met, Asn, Gln, Arg, Ser, Thr, and Val at position 296;
amino acid substitution with any one of Asp, Glu, Phe, Gly, His, Ile, Lys, Leu, Met, Pro, Gln, Arg, Ser, Thr, Val, Trp, and Tyr at position 297;
amino acid substitution with any one of Ala, Asp, Glu, Phe, His, Ile, Lys, Met, Asn, Gln, Arg, Thr, Val, Trp, and Tyr at position 298;
amino acid substitution with any one of Ala, Asp, Glu, Phe, Gly, His, Ile, Lys, Leu, Met, Asn, Pro, Gln, Arg, Ser, Val, Trp, and Tyr at position 299;
amino acid substitution with any one of Ala, Asp, Glu, Gly, His, Ile, Lys, Leu, Met, Asn, Pro, Gln, Arg, Ser, Thr, Val, and Trp at position 300;
amino acid substitution with any one of Asp, Glu, His, and Tyr at position 301;
amino acid substitution with Ile at position 302;
amino acid substitution with any one of Asp, Gly, and Tyr at position 303;
amino acid substitution with at position 304 is any one of Asp, His, Leu, Asn, and Thr;
amino acid substitution with any one of Glu, Ile, Thr, and Tyr at position 305;
amino acid substitution with any one of Ala, Asp, Asn, Thr, Val, and Tyr at position 311;
amino acid substitution with Phe at position 313;
amino acid substitution with Leu at position 315;
amino acid substitution with either Glu or Gln at position 317;
amino acid substitution with any one of His, Leu, Asn, Pro, Gln, Arg, Thr, Val, and Tyr at position 318;
amino acid substitution with any one of Asp, Phe, Gly, His, Ile, Leu, Asn, Pro, Ser, Thr, Val, Trp, and Tyr at position 320;
amino acid substitution with any one of Ala, Asp, Phe, Gly, His, Ile, Pro, Ser, Thr, Val, Trp, and Tyr at position 322;
amino acid substitution with Ile at position 323;
amino acid substitution with any one of Asp, Phe, Gly, His, Ile, Leu, Met, Pro, Arg, Thr, Val, Trp, and Tyr at position 324;

amino acid substitution with any one of Ala, Asp, Glu, Phe, Gly, His, Ile, Lys, Leu, Met, Pro, Gln, Arg, Ser, Thr, Val, Trp, and Tyr at position 325;
amino acid substitution with any one of Ala, Asp, Glu, Gly, Ile, Leu, Met, Asn, Pro, Gln, Ser, Thr, Val, Trp, and Tyr at position 326;
amino acid substitution with any one of Ala, Asp, Glu, Phe, Gly, His, Ile, Lys, Leu, Met, Asn, Pro, Arg, Thr, Val, Trp, and Tyr at position 327;
amino acid substitution with any one of Ala, Asp, Glu, Phe, Gly, His, Ile, Lys, Met, Asn, Pro, Gln, Arg, Ser, Thr, Val, Trp, and Tyr at position 328;
amino acid substitution with any one of Asp, Glu, Phe, Gly, His, Ile, Lys, Leu, Met, Asn, Gln, Arg, Ser, Thr, Val, Trp, and Tyr at position 329;
amino acid substitution with any one of Cys, Glu, Phe, Gly, His, Ile, Lys, Leu, Met, Asn, Pro, Arg, Ser, Thr, Val, Trp, and Tyr at position 330;
amino acid substitution with any one of Asp, Phe, His, Ile, Leu, Met, Gln, Arg, Thr, Val, Trp, and Tyr at position 331;
amino acid substitution with any one of Ala, Asp, Glu, Phe, Gly, His, Lys, Leu, Met, Asn, Pro, Gln, Arg, Ser, Thr, Val, Trp, and Tyr at position 332;
amino acid substitution with any one of Ala, Asp, Glu, Phe, Gly, His, Ile, Leu, Met, Pro, Ser, Thr, Val, and Tyr at position 333;
amino acid substitution with any one of Ala, Glu, Phe, Ile, Leu, Pro, and Thr at position 334;
amino acid substitution with any one of Asp, Phe, Gly, His, Ile, Leu, Met, Asn, Pro, Arg, Ser, Val, Trp, and Tyr at position 335;
amino acid substitution with any one of Glu, Lys, and Tyr at position 336;
amino acid substitution with any one of Glu, His, and Asn at position 337;
amino acid substitution with any one of Asp, Phe, Gly, Ile, Lys, Met, Asn, Gln, Arg, Ser, and Thr at position 339;
amino acid substitution with either Ala or Val at position 376;
amino acid substitution with either Gly or Lys at position 377;
amino acid substitution with Asp at position 378;
amino acid substitution with Asn at position 379;
amino acid substitution with any one of Ala, Asn, and Ser at position 380;
amino acid substitution with either Ala or Ile at position 382;
amino acid substitution with Glu at position 385;
amino acid substitution with Thr at position 392;
amino acid substitution with Leu at position 396;
amino acid substitution with Lys at position 421;
amino acid substitution with Asn at position 427;
amino acid substitution with either Phe or Leu at position 428;
amino acid substitution with Met at position 429;
amino acid substitution with Trp at position 434;
amino acid substitution with Ile at position 436; and
amino acid substitution with any one of Gly, His, Ile, Leu, and Tyr at position 440,
according to EU numbering in the Fc region;

[32] the method of any one of [28] to [31], wherein the naturally-occurring Fc region is an Fc region of any one of human IgG1, human IgG2, human IgG3, and human IgG4 in which the sugar chain attached at position 297 according to EU numbering is a fucose-containing sugar chain;

[33] the method of any one of [28] to [32], comprising the step of modifying the Fc region so that the percentage of the Fc region to which a fucose-deficient sugar chain is attached, or bisecting N-acetylglucosamine is added, at position 297 according to EU numbering in the Fc region, will become higher;

[34] a method for producing a pharmaceutical composition which induces an immune response, which comprises the steps of:
(a) determining the antigen-binding activity of an antigen-binding domain under a high calcium ion concentration condition;
(b) determining the antigen-binding activity of the antigen-binding domain under a low calcium ion concentration condition;
(c) selecting the antigen-binding domain whose antigen-binding activity determined in (a) is higher than that determined in (b);
(d) linking a polynucleotide encoding the antigen-binding domain selected in (c) to a polynucleotide encoding an FcRn-binding domain having FcRn-binding activity in a neutral pH range;
(e) culturing a cell into which a vector to which the polynucleotide obtained in (d) is operably linked has been introduced; and
(f) collecting an antigen-binding molecule from culture fluid of the cell cultured in (e);

[35] a method for producing a pharmaceutical composition which induces an immune response, which comprises the steps of:
(a) determining the antigen-binding activity of an antibody under a high calcium ion concentration condition;
(b) determining the antigen-binding activity of the antibody under a low calcium ion concentration condition;
(c) selecting the antibody whose antigen-binding activity determined in (a) is higher than that determined in (b);
(d) linking a polynucleotide encoding the antigen-binding domain of the antibody selected in (c) to a polynucleotide encoding an FcRn-binding domain having FcRn-binding activity in a neutral pH range;
(e) culturing a cell into which a vector to which the polynucleotide obtained in (d) is operably linked has been introduced; and
(f) collecting an antigen-binding molecule from culture fluid of the cell cultured in (e);

[36] a method for producing an antigen-binding molecule, which comprises the steps of:
(a) determining the antigen-binding activity of an antigen-binding domain in a neutral pH range;
(b) determining the antigen-binding activity of the antigen-binding domain in an acidic pH range;
(c) selecting the antigen-binding domain whose antigen-binding activity determined in (a) is higher than that determined in (b);
(d) linking a polynucleotide encoding the antigen-binding domain selected in (c) to a polynucleotide encoding an FcRn-binding domain having FcRn-binding activity in a neutral pH range;
(e) culturing a cell into which a vector to which the polynucleotide obtained in (d) is operably linked has been introduced; and
(f) collecting an antigen-binding molecule from culture fluid of the cell cultured in (e);

[37] a method for producing an antigen-binding molecule, which comprises the steps of:
(a) determining the antigen-binding activity of an antibody in a neutral pH range;

(b) determining the antigen-binding activity of the antibody in an acidic pH range;
(c) selecting the antibody whose antigen-binding activity determined in (a) is higher than that determined in (b);
(d) linking a polynucleotide encoding the antigen-binding domain of the antibody selected in (c) to a polynucleotide encoding an FcRn-binding domain having FcRn-binding activity in a neutral pH range;
(e) culturing a cell into which a vector to which the polynucleotide obtained in (d) is operably linked has been introduced; and
(f) collecting an antigen-binding molecule from culture fluid of the cell cultured in (e);
[38] the method of any one of [34] to [37], wherein the antigen-binding molecule has neutralizing activity against the antigen;
[39] the method of any one of [34] to [38], wherein the antigen-binding molecule has cytotoxic activity against a cell expressing the antigen;
[40] the method of any one of [34] to [39], wherein the FcRn-binding domain comprises an antibody Fc region;
[41] the method of [40], wherein the Fc region is an Fc region in which at least one or more amino acids selected from the group consisting of amino acids at positions 257, 308, 428, and 434 according to EU numbering in the Fc region are different from amino acids at corresponding positions in a naturally-occurring Fc region;
[42] the method of [40] or [41], wherein the Fc region comprises at least one or more amino acids selected from the group consisting of:
Ala at amino acid position 257;
Pro at amino acid position 308;
Leu at amino acid position 428; and
Tyr at amino acid position 434,
according to EU numbering in the Fc region;
[43] the method of any one of [40] to [42], wherein the Fcγ receptor-binding activity of the Fc region is higher than that of a naturally-occurring human IgG Fc region in which the sugar chain attached at position 297 according to EU numbering is a fucose-containing sugar chain;
[44] the method of [43], wherein the Fcγ receptor is FcγRIa, FcγRIIa(R), FcγRIIa(H), FcγRIIb, FcγRIIIa (V), or FcγRIIIa(F);
[45] the method of [43] or [44], wherein the Fc region comprises at least one or more amino acids selected from the group consisting of:
either Lys or Tyr at amino acid position 221;
any one of Phe, Trp, Glu, and Tyr at amino acid position 222;
any one of Phe, Trp, Glu, and Lys at amino acid position 223;
any one of Phe, Trp, Glu, and Tyr at amino acid position 224;
any one of Glu, Lys, and Trp at amino acid position 225;
any one of Glu, Gly, Lys, and Tyr at amino acid position 227;
any one of Glu, Gly, Lys, and Tyr at amino acid position 228;
any one of Ala, Glu, Gly, and Tyr at amino acid position 230;
any one of Glu, Gly, Lys, Pro, and Tyr at amino acid position 231;
any one of Glu, Gly, Lys, and Tyr at amino acid position 232;
any one of Ala, Asp, Phe, Gly, His, Ile, Lys, Leu, Met, Asn, Gln, Arg, Ser, Thr, Val, Trp, and Tyr at amino acid position 233;
any one of Ala, Asp, Glu, Phe, Gly, His, Ile, Lys, Met, Asn, Pro, Gln, Arg, Ser, Thr, Val, Trp, and Tyr at amino acid position 234;
any one of Ala, Asp, Glu, Phe, Gly, His, Ile, Lys, Met, Asn, Pro, Gln, Arg, Ser, Thr, Val, Trp, and Tyr at amino acid position 235;
any one of Ala, Asp, Glu, Phe, His, Ile, Lys, Leu, Met, Asn, Pro, Gln, Arg, Ser, Thr, Val, Trp, and Tyr at amino acid position 236;
any one of Asp, Glu, Phe, His, Ile, Lys, Leu, Met, Asn, Pro, Gln, Arg, Ser, Thr, Val, Trp, and Tyr at amino acid position 237;
any one of Asp, Glu, Phe, Gly, His, Ile, Lys, Leu, Met, Asn, Gln, Arg, Ser, Thr, Val, Trp, and Tyr at amino acid position 238;
any one of Asp, Glu, Phe, Gly, His, Ile, Lys, Leu, Met, Asn, Pro, Gln, Arg, Thr, Val, Trp, and Tyr at amino acid position 239;
any one of Ala, Ile, Met, and Thr at amino acid position 240;
any one of Asp, Glu, Leu, Arg, Trp, and Tyr at amino acid position 241;
any one of Leu, Glu, Leu, Gln, Arg, Trp, and Tyr at amino acid position 243;
His at amino acid position 244;
Ala at amino acid position 245;
any one of Asp, Glu, His, and Tyr at amino acid position 246;
any one of Ala, Phe, Gly, His, Ile, Leu, Met, Thr, Val, and Tyr at amino acid position 247;
any one of Glu, His, Gln, and Tyr at amino acid position 249;
either Glu or Gln at amino acid position 250;
Phe at amino acid position 251;
any one of Phe, Met, and Tyr at amino acid position 254;
any one of Glu, Leu, and Tyr at amino acid position 255;
any one of Ala, Met, and Pro at amino acid position 256;
any one of Asp, Glu, His, Ser, and Tyr at amino acid position 258;
any one of Asp, Glu, His, and Tyr at amino acid position 260;
any one of Ala, Glu, Phe, Ile, and Thr at amino acid position 262;
any one of Ala, Ile, Met, and Thr at amino acid position 263;
any one of Asp, Glu, Phe, Gly, His, Ile, Lys, Leu, Met, Asn, Pro, Gln, Arg, Ser, Thr, Trp, and Tyr at amino acid position 264;
any one of Ala, Leu, Phe, Gly, His, Ile, Lys, Leu, Met, Asn, Pro, Gln, Arg, Ser, Thr, Val, Val, Trp, and Tyr at amino acid position 265;
any one of Ala, Ile, Met, and Thr at amino acid position 266;
any one of Asp, Glu, Phe, His, Ile, Lys, Leu, Met, Asn, Pro, Gln, Arg, Thr, Val, Trp, and Tyr at amino acid position 267;
any one of Asp, Glu, Phe, Gly, Ile, Lys, Leu, Met, Pro, Gln, Arg, Thr, Val, and Trp at amino acid position 268;
any one of Phe, Gly, His, Ile, Lys, Leu, Met, Asn, Pro, Arg, Ser, Thr, Val, Trp, and Tyr at amino acid position 269;
any one of Glu, Phe, Gly, His, Ile, Leu, Met, Pro, Gln, Arg, Ser, Thr, Trp, and Tyr at amino acid position 270;

any one of Ala, Asp, Glu, Phe, Gly, His, Ile, Lys, Leu, Met, Asn, Gln, Arg, Ser, Thr, Val, Trp, and Tyr at amino acid position 271;
any one of Asp, Phe, Gly, His, Ile, Lys, Leu, Met, Pro, Arg, Ser, Thr, Val, Trp, and Tyr at amino acid position 272;
either Phe or Ile at amino acid position 273;
any one of Asp, Glu, Phe, Gly, His, Ile, Leu, Met, Asn, Pro, Arg, Ser, Thr, Val, Trp, and Tyr at amino acid position 274;
either Leu or Trp at amino acid position 275;
any one of Asp, Glu, Phe, Gly, His, Ile, Leu, Met, Pro, Arg, Ser, Thr, Val, Trp, and Tyr at amino acid position 276;
any one of Asp, Glu, Gly, His, Ile, Lys, Leu, Met, Asn, Pro, Gln, Arg, Ser, Thr, Val, and Trp at amino acid position 278;
Ala at amino acid position 279;
any one of Ala, Gly, His, Lys, Leu, Pro, Gln, Trp, and Tyr at amino acid position 280;
any one of Asp, Lys, Pro, and Tyr at amino acid position 281;
any one of Glu, Gly, Lys, Pro, and Tyr at amino acid position 282;
any one of Ala, Gly, His, Ile, Lys, Leu, Met, Pro, Arg, and Tyr at amino acid position 283;
any one of Asp, Glu, Leu, Asn, Thr, and Tyr at amino acid position 284;
any one of Asp, Glu, Lys, Gln, Trp, and Tyr at amino acid position 285;
any one of Glu, Gly, Pro, and Tyr at amino acid position 286;
any one of Asn, Asp, Glu, and Tyr at amino acid position 288;
any one of Asp, Gly, His, Leu, Asn, Ser, Thr, Trp, and Tyr at amino acid position 290;
any one of Asp, Glu, Gly, His, Ile, Gln, and Thr at amino acid position 291;
any one of Ala, Asp, Glu, Pro, Thr, and Tyr at amino acid position 292;
any one of Phe, Gly, His, Ile, Leu, Met, Asn, Pro, Arg, Ser, Thr, Val, Trp, and Tyr at amino acid position 293;
any one of Phe, Gly, His, Ile, Lys, Leu, Met, Asn, Pro, Arg, Ser, Thr, Val, Trp, and Tyr at amino acid position 294;
any one of Asp, Glu, Phe, Gly, His, Ile, Lys, Met, Asn, Pro, Arg, Ser, Thr, Val, Trp, and Tyr at amino acid position 295;
any one of Ala, Asp, Glu, Gly, His, Ile, Lys, Leu, Met, Asn, Gln, Arg, Ser, Thr, and Val at amino acid position 296;
any one of Asp, Glu, Phe, Gly, His, Ile, Lys, Leu, Met, Pro, Gln, Arg, Ser, Thr, Val, Trp, and Tyr at amino acid position 297;
any one of Ala, Asp, Glu, Phe, His, Ile, Lys, Met, Asn, Gln, Arg, Thr, Val, Trp, and Tyr at amino acid position 298;
any one of Ala, Asp, Glu, Phe, Gly, His, Ile, Lys, Leu, Met, Asn, Pro, Gln, Arg, Ser, Val, Trp, and Tyr at amino acid position 299;
any one of Ala, Asp, Glu, Gly, His, Ile, Lys, Leu, Met, Asn, Pro, Gln, Arg, Ser, Thr, Val, and Trp at amino acid position 300;
any one of Asp, Glu, His, and Tyr at amino acid position 301;

Ile at amino acid position 302;
any one of Asp, Gly, and Tyr at amino acid position 303;
any one of Asp, His, Leu, Asn, and Thr at amino acid position 304;
any one of Glu, Ile, Thr, and Tyr at amino acid position 305;
any one of Ala, Asp, Asn, Thr, Val, and Tyr at amino acid position 311;
Phe at amino acid position 313;
Leu at amino acid position 315;
either Glu or Gln at amino acid position 317;
any one of His, Leu, Asn, Pro, Gln, Arg, Thr, Val, and Tyr at amino acid position 318;
any one of Asp, Phe, Gly, His, Ile, Leu, Asn, Pro, Ser, Thr, Val, Trp, and Tyr at amino acid position 320;
any one of Ala, Asp, Phe, Gly, His, Ile, Pro, Ser, Thr, Val, Trp, and Tyr at amino acid position 322;
Ile at amino acid position 323;
any one of Asp, Phe, Gly, His, Ile, Leu, Met, Pro, Arg, Thr, Val, Trp, and Tyr at amino acid position 324;
any one of Ala, Asp, Glu, Phe, Gly, His, Ile, Lys, Leu, Met, Pro, Gln, Arg, Ser, Thr, Val, Trp, and Tyr at amino acid position 325;
any one of Ala, Asp, Glu, Gly, Ile, Leu, Met, Asn, Pro, Gln, Ser, Thr, Val, Trp, and Tyr at amino acid position 326;
any one of Ala, Asp, Glu, Phe, Gly, His, Ile, Lys, Leu, Met, Asn, Pro, Arg, Thr, Val, Trp, and Tyr at amino acid position 327;
any one of Ala, Asp, Glu, Phe, Gly, His, Ile, Lys, Met, Asn, Pro, Gln, Arg, Ser, Thr, Val, Trp, and Tyr at amino acid position 328;
any one of Asp, Glu, Phe, Gly, His, Ile, Lys, Leu, Met, Asn, Gln, Arg, Ser, Thr, Val, Trp, and Tyr at amino acid position 329;
any one of Cys, Glu, Phe, Gly, His, Ile, Lys, Leu, Met, Asn, Pro, Arg, Ser, Thr, Val, Trp, and Tyr at amino acid position 330;
any one of Asp, Phe, His, Ile, Leu, Met, Gln, Arg, Thr, Val, Trp, and Tyr at amino acid position 331;
any one of Ala, Asp, Glu, Phe, Gly, His, Lys, Leu, Met, Asn, Pro, Gln, Arg, Ser, Thr, Val, Trp, and Tyr at amino acid position 332;
any one of Ala, Asp, Glu, Phe, Gly, His, Ile, Leu, Met, Pro, Ser, Thr, Val, and Tyr at amino acid position 333;
any one of Ala, Glu, Phe, Ile, Leu, Pro, and Thr at amino acid position 334;
any one of Asp, Phe, Gly, His, Ile, Leu, Met, Asn, Pro, Arg, Ser, Val, Trp, and Tyr at amino acid position 335;
any one of Glu, Lys, and Tyr at amino acid position 336;
any one of Glu, His, and Asn at amino acid position 337;
any one of Asp, Phe, Gly, Ile, Lys, Met, Asn, Gln, Arg, Ser, and Thr at amino acid position 339;
either Ala or Val at amino acid position 376;
either Gly or Lys at amino acid position 377;
Asp at amino acid position 378;
Asn at amino acid position 379;
any one of Ala, Asn, and Ser at amino acid position 380;
either Ala or Ile at amino acid position 382;
Glu at amino acid position 385;
Thr at amino acid position 392;
Leu at amino acid position 396;
Lys at amino acid position 421;
Asn at amino acid position 427;
either Phe or Leu at amino acid position 428;
Met at amino acid position 429;
Trp at amino acid position 434;

Ile at amino acid position 436; and
any one of Gly, His, Ile, Leu, and Tyr at amino acid position 440;
according to EU numbering in the Fc region;

[46] the method of any one of [43] to [45], wherein the naturally-occurring Fc region is an Fc region of any one of human IgG1, human IgG2, human IgG3, and human IgG4 in which the sugar chain attached at position 297 according to EU numbering is a fucose-containing sugar chain;

[47] the method of any one of [43] to [46], wherein the Fc region is modified so that the percentage of the Fc region to which a fucose-deficient sugar chain is attached, or bisecting N-acetylglucosamine is added, at position 297 according to EU numbering in the Fc region, will become higher.

Effects of the Invention

The present invention provides pharmaceutical compositions comprising an antigen-binding molecule that, when administered to a living organism, can not only exhibit pharmacological actions on a target antigen but also induce an immune response to the target antigen, which was not possible with conventional antibodies, and provides methods for manufacturing them. This enables effective treatment of cancer and infectious diseases by induction of immune response to a target antigen while having binding activity to the target antigen and having cytotoxicity and antiproliferative activity against target cells, which was not possible with conventional vaccines.

MODE FOR CARRYING OUT THE INVENTION

Figure 1:
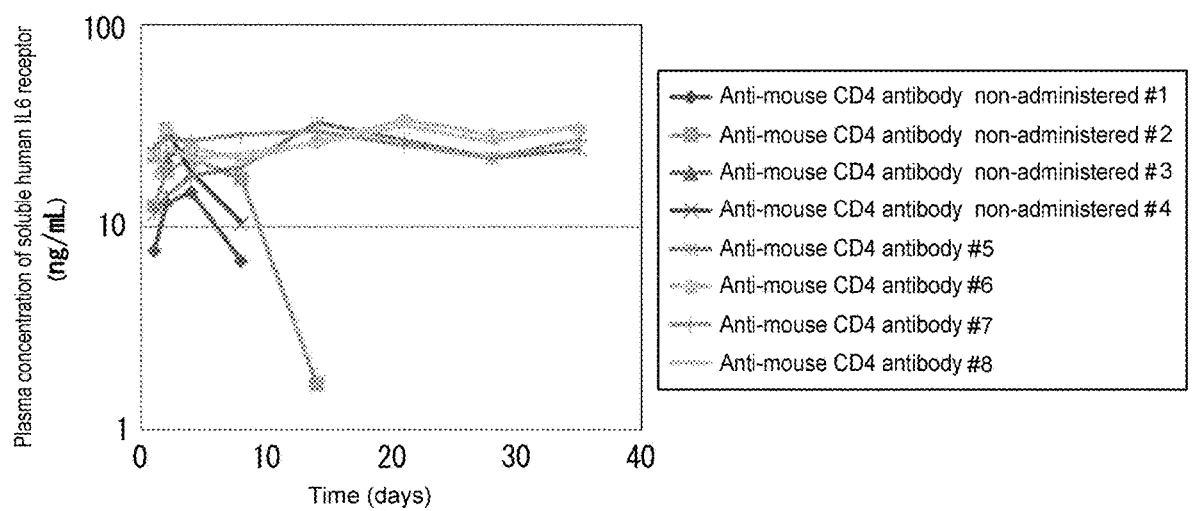
FIG. 1 shows changes in the concentration of soluble human IL-6 receptor in mice plasma for the anti-mouse CD4 antibody administration group and the non-administration group in a soluble human IL-6 receptor steady-state model. The horizontal axis shows the number of days from anti-mouse CD4 antibody administration, and the vertical axis shows the plasma concentration of soluble human IL-6 receptor.

The definitions and detailed description below are provided to help the understanding of the present invention illustrated herein.

Amino Acids

Herein, amino acids are described in one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G Trp/W, His/H, Tyr/Y, Ile/I, or Val/V.

Antigen

Herein, an antigen is not particularly limited, and may be any antigen as long as it is a molecule that may induce the immune system of an organism and thereby become a target of the immune response in that organism. Preferred examples of such antigens include molecules that are expressed specifically in tumor cells but not expressed in normal cells (neoepitopes). Molecules that are expressed in foreign biological species such as bacteria and viruses that infect an organism but not expressed in the organism are also preferred. The phrase "expressed specifically in tumor cells but not expressed in normal cells" or "expressed in foreign biological species that infect an organism but not expressed in the organism" means that there is a qualitative or quantitative difference in the molecule between "tumor cells and normal cells" or "foreign biological species that infect an organism and the organism". For example, even if a molecule is expressed in normal cells, if the amount of the molecule expressed in tumor cells is far greater than the amount expressed in the normal cells, it can be said in the present invention that there is a quantitative difference in the molecule between tumor cells and normal cells. Furthermore, even if the expression level of a polypeptide consisting of the same amino acid sequence is similar in tumor cells and normal cells, if the expressed polypeptide has undergone posttranslational modification such as phosphorylation in tumor cells but not in normal cells, it can be said in the present invention that there is a qualitative difference in the molecule between tumor cells and normal cells.

For such molecules, preferred tumor antigens may include: ALK receptor (pleiotrophin receptor), pleiotrophin; KS 1/4 pancreas carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as CEA, TAG-72, CO17-1A, GICA 19-9, CTA-1, and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation-type cell-surface antigen (TSTA); virally-induced tumor antigens including T-antigen, DNA tumor viruses and Envelope antigens of RNA tumor viruses; oncofetal antigens such as CEA of colon, 5T4 oncofetal trophoblast glycoprotein, and bladder tumor oncofetal antigen; alpha-fetoprotein; differentiation antigens such as human lung carcinoma antigens L6 and L20; antigens of fibrosarcoma; human leukemia T cell antigen-Gp37; neoglycoprotein; sphingolipids; breast cancer antigens such as EGFR (epidermal growth factor receptor); NY-BR-16; NY-BR-16 and HER2 antigen (p185HER2); polymorphic epithelial mucin (PEM) antigen; malignant human lymphocyte antigen-APO-1; differentiation antigens such as I antigen found in fetal erythrocytes; primary endoderm I antigen found in adult erythrocytes; preimplantation embryos; I(Ma) found in gastric cancer; M18, M39 found in mammary epithelium; SSEA-1 found in myeloid cells; VEP8; VEP9; Myl; VIM-D5; D156-22 found in colorectal cancer; TRA-1-85 (blood group H); SCP-1 found in testis and ovarian cancer; C14 found in colon cancer; F3 found in lung cancer; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric cancer antigen; CO-514 (blood group Lea) found in adenocarcinomas; NS-10 found in adenocarcinomas; CO-43 (blood group Leb); G49 found in EGF receptor of A431 cells; MH2 (blood group ALeb/Ley) found in colon cancer; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; subcutaneous T cell lymphoma antigen; MART-1 antigen; sialyl Tn (STn) antigen; colon cancer antigen NY-CO-45; lung cancer antigen NY-LU-12 variant A; adenocarcinoma antigen ART1; paraneoplastic associated brain-testis-cancer antigen (onconeuronal antigen MA2; paraneoplastic neuronal antigen); Neuro-oncological ventral antigen 2 (NOVA2); hemocyte carcinoma antigen gene 520; tumor-associated antigen CO-029; tumor-associated antigens MAGE-C1 (cancer/testis antigen CT7), MAGE-B 1 (MAGE-XP antigen), MAGE-B2 (DAM6), MAGE-2, MAGE-4a, MAGE-4b and MAGE-X2; Cancer-Testis Antigen (NY-EOS-1); YKL-40, and fragments of any of the aforementioned polypeptides or structures produced by modifying them (for example, modified phosphate group or sugar chain of the above-mentioned).

Antigens of foreign biological species include molecules expressed in: *Bacillus anthraces, Clostridium botulinum, Yersinia pestis, Variola major* (smallpox) and other poxviruses, *Francisella tularensis* (tularemia), and those that cause viral hemorrhagic fever, Arenaviruses such as LCM, Junin virus, Machupo virus, Guanarito virus, and those that cause Lassa fever, Bunyaviruses and Hantaviruses such as those that cause Rift-valley fever, Calicivirus, hepatitis A, hepatitis B, hepatitis C, viral encephalitis such as West Nile Virus, LaCrosse, California encephalitis, VEE, EEE, WEE, and Japanese encephalitis virus, Kyasanur forest virus, tick-borne hemorrhagic fever virus, Crimean-Congo hemorrhagic fever virus, tickborne encephalitis viruses, Yellow fever, multidrug-resistant TB, influenza, other rickettsiae and rabies, Flavirus, Dengue, Filovirus, Ebola, Marburg *Burkholderia pseudomallei, Coxiella burnetii* (Q fever), *Brucella* species (brucellosis), *Burkholderia mallei* (glanders), ricin toxin (derived from *Ricinus communis*), epsilon toxin of *Clostridium perfringens, Staphylococcus enterotoxin* B, Typhus fever (*Rickettsia prowazekii*), food and water-borne pathogens, bacteria such as diarrheagenic *E. coli*, pathogenic Vibrios, *Shigella* species, *Salmonella, Listeria monocytogenes, Campylobacter jejuni*, and *Yersinia enterocolitica*; and protozoas such as *Cryptosporidium parvum, Cyclospora cayatanensis, Giardia lamblia, Entamoeba histolytica*, Toxoplasma, and Microsporidia.

Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIAALK-2, activin RIB ALK-4, activin RIIA, activin RIIB, ADAM, ADAM10, ADAM12, ADAM15, ADAM17/TACE, ADAMS, ADAMS, ADAMTS, ADAMTS4, ADAMTS5, addressin, aFGF, ALCAM, ALK, ALK-1, ALK-7, alpha-1-antitrypsin, alpha-V/beta-1 antagonist, ANG Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV MB gp 120 V3 loop, HLA, HLA-DR, HM1.24, HMFG PEM, HRG Hrk, human cardiac myosin, human cytomegalovirus (HCMV), human growth hormone (HGH), HVEM, 1-309, TAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG; TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, SIP, Acetylcholine receptor, AdipoR1, AdipoR2, ADP ribosyl cyclase-1, alpha-4/beta-7 integrin, alpha-5/beta-1 integrin, alpha-v/beta-6 integrin, alphavbeta1 integrin, Angiopoietin ligand-2, Angptl2, Anthrax, Cadherin, Carbonic anhydrase-IX, CD105, CD155, CD158a, CD37, CD49b, CD51, CD70, CD72, Claudin 18, *Clostridium difficile* toxin, CS1, Delta-like protein ligand 4, DHICA oxidase, Dickkopf-1 ligand, Dipeptidyl peptidase IV, EPOR, F protein of RSV, Factor Ia, FasL, Folate receptor alpha, Glucagon receptor, Glucagon-like peptide 1 receptor, Glutamate carboxypeptidase II, GMCSFR, Hepatitis C virus E2 glycoprotein, Hepcidin, IL-17 receptor, IL-22 receptor, IL-23 receptor, IL-3 receptor, Kit tyrosine kinase, Leucine Rich Alpha-2-Glycoprotein 1 (LRG1), Lysosphingolipid receptor, Membrane glycoprotein OX2, Mesothelin, MET, MICA, MUC-16, Myelin associated glycoprotein, Neuropilin-1, Neuropilin-2, Nogo receptor, PLXNA1, PLXNA2, PLXNA3, PLXNA4A, PLXNA4B, PLXNB1, PLXNB2, PLXNB3, PLXNC1, PLXND1, Programmed cell death ligand 1, Proprotein convertase PC9, P-selectin glycoprotein ligand-1, RAGE, Reticulon 4, RF, RON-8, SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A, Shiga like toxin II, Sphingosine-1-phosphate receptor-1, ST2, Staphylococcal lipoteichoic acid, Tenascin, TG2, Thymic stromal lymphoprotein receptor, TNF superfamily receptor 12A, Transmembrane glycoprotein NMB, TREM-1, TREM-2, Trophoblast glycoprotein, TSH receptor, TTR, Tubulin, and ULBP2; and receptors for hormone and growth factors.

Epitope

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein.

For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Binding Activity

Examples of a method for assessing the epitope binding by a test antigen-binding molecule containing an IL-6 receptor antigen-binding domain are described below. According to the examples below, methods for assessing the epitope binding by a test antigen-binding molecule containing an antigen-binding domain for an antigen other than IL-6 receptor, can also be appropriately conducted.

For example, whether a test antigen-binding molecule containing an IL-6 receptor antigen-binding domain recognizes a linear epitope in the IL-6 receptor molecule can be confirmed for example as mentioned below. A linear peptide comprising an amino acid sequence forming the extracellular domain of IL-6 receptor is synthesized for the above purpose. The peptide can be synthesized chemically, or obtained by genetic engineering techniques using a region encoding the amino acid sequence corresponding to the extracellular domain in an IL-6 receptor cDNA. Then, a test antigen-binding molecule containing an IL-6 receptor antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6 receptor-expressing cells. These tests can demonstrate the binding activity of the antigen-binding molecule towards the linear peptide.

Whether a test antigen-binding molecule containing an IL-6 receptor antigen-binding domain recognizes a conformational epitope can be assessed as follows. IL-6 receptor-expressing cells are prepared for the above purpose. A test antigen-binding molecule containing an IL-6 receptor antigen-binding domain can be determined to recognize a conformational epitope when it strongly binds to IL-6 receptor-expressing cells upon contact, but does not substantially bind to an immobilized linear peptide comprising an amino acid sequence forming the extracellular domain of IL-6 receptor. Herein, "not substantially bind" means that the binding activity is 80% or less, generally 50% or less, preferably 30% or less, and particularly preferably 15% or less compared to the binding activity towards cells expressing human IL-6 receptor.

Methods for assaying the binding activity of a test antigen-binding molecule containing an IL-6 receptor antigen-binding domain towards IL-6 receptor-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6 receptor-expressing cells as antigen.

In the ELISA format, the binding activity of a test antigen-binding molecule containing an IL-6 receptor antigen-binding domain towards IL-6 receptor-expressing cells can be assessed quantitatively by comparing the levels of signal generated by enzymatic reaction. Specifically, a test polypeptide complex is added to an ELISA plate onto which IL-6 receptor-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6 receptor-expressing cells can be determined to compare the binding activity of the test antigen-binding molecule towards IL-6 receptor-expressing cells.

The binding of a test antigen-binding molecule towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6 receptor antigen-binding domain towards an antigen include, for example, the following method. First, IL-6 receptor-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6 receptor antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6 receptor protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6 receptor protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6 receptor protein-coated wells.

The quantity of the test antigen-binding molecule bound to the wells via the IL-6 receptor protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6 receptor antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IL-6 receptor antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6 receptor-expressing cells and cells expressing IL-6 receptor with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6 receptor" can be assessed, for example, by the following method. First, the test and control antigen-binding molecules bound to cells expressing mutant IL-6 receptor are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo-Mean) can be calculated according to the following formula to determine the ratio of increase in fluorescence intensity as a result of the binding by the antigen-binding molecule.

$$\Delta\text{Geo-Mean}=\text{Geo-Mean (in the presence of the polypeptide complex)/Geo-Mean (in the absence of the polypeptide complex)}$$

The Geometric Mean comparison value (ΔGeo-Mean value for the mutant IL-6 receptor molecule) determined by the above analysis, which reflects the quantity of a test antigen-binding molecule bound to cells expressing mutant IL-6 receptor, is compared to the ΔGeo-Mean comparison value that reflects the quantity of the test antigen-binding molecule bound to IL-6 receptor-expressing cells. In this case, the concentrations of the test antigen-binding molecule used to determine the ΔGeo-Mean comparison values for IL-6 receptor-expressing cells and cells expressing mutant IL-6 receptor are particularly preferably adjusted to be equal or substantially equal. An antigen-binding molecule that has been confirmed to recognize an epitope in IL-6 receptor is used as a control antigen-binding molecule.

If the ΔGeo-Mean comparison value of a test antigen-binding molecule for cells expressing mutant IL-6 receptor is smaller than the ΔGeo-Mean comparison value of the test antigen-binding molecule for IL-6 receptor-expressing cells by at least 80%, preferably 50%, more preferably 30%, and particularly preferably 15%, then the test antigen-binding molecule "does not substantially bind to cells expressing mutant IL-6 receptor". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Antigen-Binding Domain

An "antigen-binding domain" may be of any structure as long as it binds to an antigen of interest. Such domains preferably include, for example:

- antibody heavy-chain and light-chain variable regions;
- a module of about 35 amino acids called A domain which is contained in the in vivo cell membrane protein Avimer (WO 2004/044011, WO 2005/040229);
- Adnectin containing the 10Fn3 domain which binds to the protein moiety of fibronectin, a glycoprotein expressed on cell membrane (WO 2002/032925);
- Affibody which is composed of a 58-amino acid three-helix bundle based on the scaffold of the IgG-binding domain of Protein A (WO 1995/001937);
- Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (WO 2002/020565);
- Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (WO 2003/029462); and
- the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such epitope can be present, for example, in a protein comprising the amino acid sequence of SEQ ID NO: 1. Alternatively, each of the antigen-binding domains of antigen-binding molecules of the present invention can bind to a different epitope. Herein, the different epitope can be present in, for example, a protein comprising the amino acid sequence of SEQ ID NO: 1.

Specificity

"Specific" means that one of molecules that specifically binds to does not show any significant binding to molecules other than a single or a number of binding partner molecules. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope.

Antibodies

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is an example that describes a method for producing an antibody that binds to IL-6 receptor (anti-IL-6 receptor antibody). Antibodies that bind to an antigen other than IL-6 receptor can also be produced according to the example described below.

Anti-IL-6 receptor antibodies can be obtained as polyclonal or monoclonal antibodies using known methods. The anti-IL-6 receptor antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6 receptor protein as a sensitizing antigen. Resulting immune cells are fused with known parental cells by conventional cell fusion methods. Then, hybridomas producing an anti-IL-6 receptor antibody can be selected by screening for monoclonal antibody-producing cells using conventional screening methods.

Specifically, monoclonal antibodies are prepared as mentioned below. First, the IL-6 receptor gene whose nucleotide sequence is disclosed in SEQ ID NO: 2 can be expressed to produce an IL-6 receptor protein shown in SEQ ID NO: 1, which will be used as a sensitizing antigen for antibody preparation. That is, a gene sequence encoding IL-6 receptor is inserted into a known expression vector, and appropriate host cells are transformed with this vector. The desired human IL-6 receptor protein is purified from the host cells or their culture supernatants by known methods. In order to obtain soluble IL-6 receptor from culture supernatants, for example, a protein consisting of the amino acids at positions 1 to 357 in the IL-6 receptor polypeptide sequence of SEQ ID NO: 1, such as described in Mullberg et al. (J. Immunol. (1994) 152 (10), 4958-4968), is expressed as a soluble IL-6 receptor, instead of the IL-6 receptor protein of SEQ ID NO: 1. Purified natural IL-6 receptor protein can also be used as a sensitizing antigen.

The purified IL-6 receptor protein can be used as a sensitizing antigen for immunization of mammals. A partial IL-6 receptor peptide may also be used as a sensitizing antigen. In this case, a partial peptide can be prepared by chemical synthesis based on the amino acid sequence of human IL-6 receptor, or by inserting a partial IL-6 receptor gene into an expression vector for expression. Alternatively, a partial peptide can be produced by degrading an IL-6 receptor protein with a protease. The length and region of the partial IL-6 receptor peptide are not limited to particular embodiments. A preferred region can be arbitrarily selected from the amino acid sequence at amino acid positions 20 to 357 in the amino acid sequence of SEQ ID NO: 1. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6 receptor protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6 receptor to be used as a sensitizing antigen, and immunization methods using IL-6 receptor are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:
immunostimulation can be provided while retaining the structure of a membrane protein such as IL-6 receptor; and
there is no need to purify the antigen for immunization.

In order to prepare a monoclonal antibody of the present invention using DNA immunization, first, a DNA expressing an IL-6 receptor protein is administered to an animal to be immunized. The IL-6 receptor-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6 receptor can also be produced by the methods described in WO 2003/104453.

After immunizing a mammal as described above, an increase in the titer of an IL-6 receptor-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:
P3(P3x63Ag8.653) (J. Immunol. (1979) 123 (4), 1548-1550);
P3x63Ag8U.1 (Current Topics in Microbiology and Immunology (1978) 81, 1-7);
NS-1 (C. Eur. J. Immunol. (1976) 6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.
Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) prewarmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6 receptor-binding monoclonal antibody can bind to IL-6 receptor expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6 receptor-expressing cells are first prepared. Cells preferably used for screening are mammalian cells in which IL-6 receptor is forcedly expressed. As control, the activity of an antibody to bind to cell-surface IL-6 receptor can be selectively detected using non-transformed mammalian cells as host cells. Specifically, hybridomas producing an anti-IL-6 receptor monoclonal antibody can be isolated by selecting hybridomas that produce an antibody which binds to cells forced to express IL-6 receptor, but not to host cells.

Alternatively, the activity of an antibody to bind to immobilized IL-6 receptor-expressing cells can be assessed based on the principle of ELISA. For example, IL-6 receptor-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6 receptor antibody is prepared from hybridoma cells expressing the anti-IL-6 receptor antibody. For this purpose, total RNA is first extracted from hybridomas. Methods used for extracting mRNAs from cells include, for example:
the guanidine ultracentrifugation method (Biochemistry (1979) 18(24), 5294-5299), and
the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase.

cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IL-6 receptor-binding activity of a reshaped immunoglobulin as an indicator. For example, when the objective is to isolate an antibody against IL-6 receptor, it is more preferred that the binding of the antibody to IL-6 receptor is specific. An IL-6 receptor-binding antibody can be screened, for example, by the following steps:

(1) contacting an IL-6 receptor-expressing cell with an antibody comprising the V region encoded by a cDNA isolated from a hybridoma;
(2) detecting the binding of the antibody to the IL-6 receptor-expressing cell; and
(3) selecting an antibody that binds to the IL-6 receptor-expressing cell.

Methods for detecting the binding of an antibody to IL-6 receptor-expressing cells are known. Specifically, the binding of an antibody to IL-6 receptor-expressing cells can be detected by the above-described techniques such as FACS. Immobilized samples of IL-6 receptor-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6 receptor antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6 receptor antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-IL-6 receptor monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described later, a peptide having the amino acid sequence MGWSCIILFLVATATGVHS (SEQ ID NO: 3) are used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6 receptor antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/11523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.
(1) mammalian cells: CHO, COS, myeloma, baby hamster kidney (BHK), HeLa, Vero, human embryonic kidney (HEK) 293, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
yeasts: the *Saccharomyces* genus such as *Saccharomyces cerevisiae*, and the *Pichia* genus such as *Pichia pastoris*; and
filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat (3-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When a polypeptide complex described herein is administered to human, an antigen-binding domain derived from a genetically recombinant antibody that has been artificially modified to reduce the heterologous antigenicity against human and such, can be appropriately used as the antigen-binding domain of the complex. Such genetically recombinant antibodies include, for example, humanized antibodies. These modified antibodies are appropriately produced by known methods.

An antibody variable region used to produce the antigen-binding domain of a polypeptide complex described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering System and Kabat's Numbering System

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated according to Kabat's numbering system, while constant region amino acids are indicated according to EU numbering system based on Kabat's amino acid positions.

Conditions of Ion Concentration

Conditions of Metal Ion Concentration

In a non-limiting embodiment of the present invention, the ion concentration refers to a metal ion concentration. "Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine a receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, the conditions of calcium ion concentration include low calcium ion concentrations and high calcium ion concentrations. "The binding activity varies depending on calcium ion concentrations" means that the antigen-binding activity of an antigen-binding molecule varies due to the difference in the conditions between low and high calcium ion concentrations. For example, the antigen-binding activity of an antigen-binding molecule may be higher at a high calcium ion concentration than at a low calcium ion concentration. Alternatively, the antigen-binding activity of an antigen-binding molecule may be higher at a low calcium ion concentration than at a high calcium ion concentration.

Herein, the high calcium ion concentration is not particularly limited to a specific value; however, the concentration may preferably be selected between 100 µM and 10 mM. In another embodiment, the concentration may be selected between 200 µM and 5 mM. In an alternative embodiment, the concentration may be selected between 500 µM and 2.5 mM. In still another embodiment, the concentration may be selected between 200 µM and 2 mM. Furthermore, the concentration may be selected between 400 µM and 1.5 mM. In particular, a concentration selected between 500 µM and 2.5 mM, which is close to the plasma (blood) concentration of calcium ion in vivo, is preferred.

Herein, the low calcium ion concentration is not particularly limited to a specific value; however, the concentration may preferably be selected between 0.1 µM and 30 µM. In another embodiment, the concentration may be selected between 0.2 µM and 20 µM. In still another embodiment, the concentration may be selected between 0.5 µM and 10 µM. In an alternative embodiment, the concentration may be selected between 1 µM and 5 µM. Furthermore, the concentration may be selected between 2 µM and 4 µM. In particular, a concentration selected between 1 µM and 5 µM, which is close to the concentration of ionized calcium in early endosomes in vivo, is preferred.

Herein, "the antigen-binding activity is lower at a low calcium ion concentration than at a high calcium ion concentration" means that the antigen-binding activity of an antigen-binding molecule is weaker at a calcium ion concentration selected between 0.1 µM and 30 µM than at a calcium ion concentration selected between 100 µM and 10 mM. Preferably, it means that the antigen-binding activity of an antigen-binding molecule is weaker at a calcium ion concentration selected between 0.5 µM and 10 µM than at a calcium ion concentration selected between 200 µM and 5 mM. It particularly preferably means that the antigen-binding activity at the calcium ion concentration in the early endosome in vivo is weaker than that at the in vivo plasma calcium ion concentration; and specifically, it means that the antigen-binding activity of an antigen-binding molecule is weaker at a calcium ion concentration selected between 1 µM and 5 µM than at a calcium ion concentration selected between 500 µM and 2.5 mM.

Whether the antigen-binding activity of an antigen-binding molecule is changed depending on metal ion concentrations can be determined, for example, by the use of known measurement methods such as those described in the section "Binding Activity" above. For example, in order to confirm that the antigen-binding activity of an antigen-binding molecule becomes higher at a high calcium ion concentration than at a low calcium ion concentration, the antigen-binding activity of the antigen-binding molecule at low and high calcium ion concentrations is compared.

In the present invention, the expression "the antigen-binding activity is lower at a low calcium ion concentration than at a high calcium ion concentration" can also be expressed as "the antigen-binding activity of an antigen-binding molecule is higher at a high calcium ion concentration than at a low calcium ion concentration". In the present invention, "the antigen-binding activity is lower at a low calcium ion concentration than at a high calcium ion concentration" is sometimes written as "the antigen-binding ability is weaker at a low calcium ion concentration than at a high calcium ion concentration". Also, "the antigen-binding activity at a low calcium ion concentration is reduced to be lower than that at a high calcium ion concentration" may be written as "the antigen-binding ability at a low calcium ion concentration is made weaker than that at a high calcium ion concentration".

When determining the antigen-binding activity, the conditions other than calcium ion concentration can be appropriately selected by those skilled in the art, and are not particularly limited. For example, the activity can be determined at 37° C. in HEPES buffer. For example, Biacore (GE Healthcare) or such can be used for the determination. When the antigen is a soluble antigen, the antigen-binding activity of an antigen-binding molecule can be assessed by flowing the antigen as an analyte over a chip onto which the antigen-binding molecule is immobilized. When the antigen is a membrane antigen, the binding activity of an antigen-binding molecule to the membrane antigen can be assessed by flowing the antigen-binding molecule as an analyte over a chip onto which the antigen is immobilized.

As long as the antigen-binding activity of an antigen-binding molecule of the present invention is weaker at a low calcium ion concentration than at a high calcium ion concentration, the ratio of the antigen-binding activity between low and high calcium ion concentrations is not particularly limited. However, the ratio of the KD (dissociation constant) of the antigen-binding molecule for an antigen at a low calcium ion concentration with respect to the KD at a high calcium ion concentration, i.e. the value of KD (3 μM Ca)/KD (2 mM Ca), is preferably 2 or more, more preferably 10 or more, and still more preferably 40 or more. The upper limit of the KD (3 μM Ca)/KD (2 mM Ca) value is not particularly limited, and may be any value such as 400, 1000, or 10000 as long as the molecule can be produced by techniques known to those skilled in the art. Furthermore, it may also be specified by the KD (Ca 3 μM)/KD (Ca 1.2 mM) value. Specifically, the KD (Ca 3 μM)/KD (Ca 1.2 mM) value is 2 or greater, preferably the KD (Ca 3 μM)/KD (Ca 1.2 mM) value is 10 or greater, and more preferably the KD (Ca 3 μM)/KD (Ca 1.2 mM) value is 40 or greater. The upper limit of the KD (Ca 3 μM)/KD (Ca 1.2 mM) value is not particularly limited, and may be any value such as 400, 1000, or 10000 as long as the molecule can be produced by techniques known to those skilled in the art.

When the antigen is a soluble antigen, KD (dissociation constant) can be used to represent the antigen-binding activity. Meanwhile, when the antigen is a membrane antigen, apparent KD (apparent dissociation constant) can be used to represent the activity. KD (dissociation constant) and apparent KD (apparent dissociation constant) can be determined by methods known to those skilled in the art, for example, using Biacore (GE healthcare), Scatchard plot, or flow cytometer.

Alternatively, for example, the dissociation rate constant (kd) can also be preferably used as an index to represent the ratio of the antigen-binding activity of an antigen-binding molecule of the present invention between low and high calcium concentrations. When the dissociation rate constant (kd) is used instead of the dissociation constant (KD) as an index to represent the binding activity ratio, the ratio of the dissociation rate constant (kd) between low and high calcium concentrations, i.e. the value of kd (low calcium concentration)/kd (high calcium concentration), is preferably 2 or more, more preferably 5 or more, still more preferably 10 or more, and yet more preferably 30 or more. The upper limit of the Kd (low calcium concentration)/kd (high calcium concentration) value is not particularly limited, and can be any value such as 50, 100, or 200 as long as the molecule can be produced by techniques known to those skilled in the art.

When the antigen is a soluble antigen, kd (dissociation rate constant) can be used to represent the antigen-binding activity. Meanwhile, when the antigen is a membrane antigen, apparent kd (apparent dissociation rate constant) can be used to represent the antigen-binding activity. The kd (dissociation rate constant) and apparent kd (apparent dissociation rate constant) can be determined by methods known to those skilled in the art, for example, using Biacore (GE healthcare) or flow cytometer. In the present invention, when the antigen-binding activity of an antigen-binding molecule is determined at different calcium ion concentrations, it is preferable to use the same conditions except for the calcium concentrations.

For example, an antigen-binding domain or antibody whose antigen-binding activity is lower at a low calcium ion concentration than at a high calcium ion concentration, which is one embodiment of the present invention, can be obtained via screening of antigen-binding domains or antibodies including the steps of:

(a) determining the antigen-binding activity of an antigen-binding domain or antibody at a low calcium concentration;

(b) determining the antigen-binding activity of an antigen-binding domain or antibody at a high calcium concentration; and (c) selecting an antigen-binding domain or antibody whose antigen-binding activity is lower at a low calcium concentration than at a high calcium concentration.

Moreover, an antigen-binding domain or antibody whose antigen-binding activity is lower at a low calcium ion concentration than at a high calcium ion concentration, which is one embodiment of the present invention, can be obtained via screening of antigen-binding domains or antibodies, or a library thereof, including the steps of:

(a) contacting an antigen with an antigen-binding domain or antibody, or a library thereof at a high calcium concentration;

(b) incubating at a low calcium concentration an antigen-binding domain or antibody that has bound to the antigen in step (a); and (c) isolating an antigen-binding domain or antibody dissociated in step (b).

Furthermore, an antigen-binding domain or antibody whose antigen-binding activity is lower at a low calcium ion concentration than at a high calcium ion concentration, which is one embodiment of the present invention, can be obtained via screening of antigen-binding domains or antibodies, or a library thereof, including the steps of:
- (a) contacting an antigen with a library of antigen-binding domains or antibodies at a low calcium concentration;
- (b) selecting an antigen-binding domain or antibody which does not bind to the antigen in step (a);
- (c) allowing the antigen-binding domain or antibody selected in step (c) to bind to the antigen at a high calcium concentration; and
- (d) isolating an antigen-binding domain or antibody that has bound to the antigen in step (c).

In addition, an antigen-binding domain or antibody whose antigen-binding activity is lower at a low calcium ion concentration than at a high calcium ion concentration, which is one embodiment of the present invention, can be obtained by a screening method comprising the steps of:
- (a) contacting at a high calcium concentration a library of antigen-binding domains or antibodies with a column onto which an antigen is immobilized;
- (b) eluting an antigen-binding domain or antibody that has bound to the column in step (a) from the column at a low calcium concentration; and
- (c) isolating the antigen-binding domain or antibody eluted in step (b).

Furthermore, an antigen-binding domain or antibody whose antigen-binding activity is lower at a low calcium ion concentration than at a high calcium ion concentration, which is one embodiment of the present invention, can be obtained by a screening method comprising the steps of:
- (a) allowing at a low calcium concentration a library of antigen-binding domains or antibodies to pass through a column onto which an antigen is immobilized;
- (b) collecting an antigen-binding domain or antibody that has been eluted without binding to the column in step (a);
- (c) allowing the antigen-binding domain or antibody collected in step (b) to bind to the antigen at a high calcium concentration; and
- (d) isolating an antigen-binding domain or antibody that has bound to the antigen in step (c).

Moreover, an antigen-binding domain or antibody whose antigen-binding activity is lower at a low calcium ion concentration than at a high calcium ion concentration, which is one embodiment of the present invention, can be obtained by a screening method comprising the steps of:
- (a) contacting an antigen with a library of antigen-binding domains or antibodies at a high calcium concentration;
- (b) obtaining an antigen-binding domain or antibody that has bound to the antigen in step (a);
- (c) incubating at a low calcium concentration the antigen-binding domain or antibody obtained in step (b); and
- (d) isolating an antigen-binding domain or antibody whose antigen-binding activity in step (c) is weaker than the criterion for the selection of step (b).

The above-described steps may be repeated twice or more times. Thus, the present invention provides antigen-binding domains or antibodies whose antigen-binding activity is lower at a low calcium ion concentration than at a high calcium ion concentration, which are obtained by screening methods that further comprises the step of repeating twice or more times steps (a) to (c) or (a) to (d) in the above-described screening methods. The number of cycles of steps (a) to (c) or (a) to (d) is not particularly limited, but generally is 10 or less.

In the screening methods of the present invention, the antigen-binding activity of an antigen-binding domain or antibody at a low calcium concentration is not particularly limited as long as it is antigen-binding activity at an ionized calcium concentration of between 0.1 µM and 30 µM, but preferably is antigen-binding activity at an ionized calcium concentration of between 0.5 µM and 10 µM. More preferably, it is antigen-binding activity at the ionized calcium concentration in the early endosome in vivo, specifically, between 1 µM and 5 µM. Meanwhile, the antigen-binding activity of an antigen-binding domain or antibody at a high calcium concentration is not particularly limited, as long as it is antigen-binding activity at an ionized calcium concentration of between 100 µM and 10 mM, but preferably is antigen-binding activity at an ionized calcium concentration of between 200 µM and 5 mM. More preferably, it is antigen-binding activity at the ionized calcium concentration in plasma in vivo, specifically, between 0.5 mM and 2.5 mM.

The antigen-binding activity of an antigen-binding domain or antibody can be measured by methods known to those skilled in the art. Conditions other than the ionized calcium concentration can be determined by those skilled in the art. The antigen-binding activity of an antigen-binding domain or antibody can be evaluated as a dissociation constant (KD), apparent dissociation constant (apparent KD), dissociation rate constant (kd), apparent dissociation constant (apparent kd), and such. These can be determined by methods known to those skilled in the art, for example, using Biacore (GE healthcare), Scatchard plot, or FACS.

In the present invention, the step of selecting an antigen-binding domain or antibody whose antigen-binding activity is higher at a high calcium concentration than at a low calcium concentration is synonymous with the step of selecting an antigen-binding domain or antibody whose antigen-binding activity is lower at a low calcium concentration than at a high calcium concentration.

As long as the antigen-binding activity is higher at a high calcium concentration than at a low calcium concentration, the difference in the antigen-binding activity between high and low calcium concentrations is not particularly limited; however, the antigen-binding activity at a high calcium concentration is preferably twice or more, more preferably 10 times or more, and still more preferably 40 times or more than that at a low calcium concentration.

Antigen-binding domains or antibodies of the present invention to be screened by the screening methods described above may be any antigen-binding domains and antibodies. For example, it is possible to screen the above-described antigen-binding domains or antibodies. For example, antigen-binding domains or antibodies having natural sequences or substituted amino acid sequences may be screened.

Libraries

In an embodiment, an antigen-binding domain or antibody of the present invention can be obtained from a library that is mainly composed of a plurality of antigen-binding molecules whose sequences are different from one another and whose antigen-binding domains have at least one amino acid residue that alters the antigen-binding activity of the antigen-binding molecules depending on ion concentrations. The ion concentrations preferably include, for example, metal ion concentration and hydrogen ion concentration.

Herein, a "library" refers to a plurality of antigen-binding molecules or a plurality of fusion polypeptides containing antigen-binding molecules, or nucleic acids or polynucleotides encoding their sequences. The sequences of a plurality of antigen-binding molecules or a plurality of fusion polypeptides containing antigen-binding molecules in a library are not identical, but are different from one another.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10-10000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$ molecules, and particularly preferably $10^8$ to $10^{12}$ molecules whose sequences are different from one another.

Herein, the phrase "a plurality of" in the expression "a library mainly composed of a plurality of antigen-binding molecules" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there are a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules of the present invention.

In addition, herein, the phrase "mainly composed of" in the expression "a library mainly composed of a plurality of antigen-binding molecules" reflects the number of antigen-binding molecules whose antigen-binding activity varies depending on ion concentrations, among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least 10' antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules whose antigen-binding activity varies depending on ion concentrations with respect to the number of independent clones having different sequences in a library. Specifically, antigen-binding domains of the present invention can be obtained from a library in which antigen-binding molecules having such binding activity account for 0.1% to 80%, preferably 0.5% to 60%, more preferably 1% to 40%, still more preferably 2% to 20%, and particularly preferably 4% to 10% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions.

Amino Acids that Alter the Antigen-Binding Activity of Antigen-Binding Domains Depending on Calcium Ion Concentrations Antigen-binding domains or antibodies of the present invention to be screened by the above-described screening methods may be prepared in any manner. For example, when the metal ion is calcium ion, it is possible to use preexisting antibodies, preexisting libraries (phage library, etc.), antibodies or libraries prepared from hybridomas obtained by immunizing animals or from B cells of immunized animals, antibodies or libraries obtained by introducing amino acids capable of chelating calcium (for example, aspartic acid and glutamic acid) or unnatural amino acid mutations into the above-described antibodies or libraries (calcium-chelatable amino acids (such as aspartic acid and glutamic acid), libraries with increased content of unnatural amino acids, libraries prepared by introducing calcium-chelatable amino acids (such as aspartic acid and glutamic acid) or unnatural amino acid mutations at particular positions, or the like.

Examples of the amino acids that alter the antigen-binding activity of antigen-binding molecules depending on ion concentrations as described above may be any types of amino acids as long as the amino acids form a calcium-binding motif. Calcium-binding motifs are well known to those skilled in the art and have been described in details (for example, Springer et al. (Cell (2000) 102, 275-277); Kawasaki and Kretsinger (Protein Prof (1995) 2, 305-490); Moncrief et al. (J. Mol. Evol. (1990) 30, 522-562); Chauvaux et al. (Biochem. J. (1990) 265, 261-265); Bairoch and Cox (FEBS Lett. (1990) 269, 454-456); Davis (New Biol. (1990) 2, 410-419); Schaefer et al. (Genomics (1995) 25, 638-643); Economou et al. (EMBO J. (1990) 9, 349-354); Wurzburg et al. (Structure. (2006) 14, 6, 1049-1058)). Specifically, any known calcium-binding motifs, including type C lectins such as ASGPR, CD23, MBR, and DC-SIGN, can be included in antigen-binding molecules of the present invention. Preferred examples of such preferred calcium-binding motifs also include, in addition to those described above, for example, the calcium-binding motif in the antigen-binding domain of SEQ ID NO: 4, 9, or 10.

Furthermore, as amino acids that alter the antigen-binding activity of antigen-binding molecules depending on calcium ion concentrations, for example, amino acids having metal-chelating activity may also be preferably used. Examples of such metal-chelating amino acids include, for example, serine (Ser(S)), threonine (Thr(T)), asparagine (Asn(N)), glutamine (Gln(Q)), aspartic acid (Asp(D)), and glutamic acid (Glu(E)).

Positions in the antigen-binding domains at which the above-described amino acids are contained are not particularly limited to particular positions, and may be any positions within the heavy chain variable region or light chain variable region that forms an antigen-binding domain, as long as they alter the antigen-binding activity of antigen-binding molecules depending on calcium ion concentrations. Specifically, antigen-binding domains of the present invention can be obtained from a library mainly composed of antigen-binding molecules whose sequences are different from one another and whose heavy chain antigen-binding domains contain amino acids that alter the antigen-binding activity of the antigen-binding molecules depending on calcium ion concentrations. In another non-limiting embodiment, antigen-binding domains of the present invention can be obtained from a library mainly composed of antigen-binding molecules whose sequences are different from one another and whose heavy chain CDR3 domains contain the above-mentioned amino acids. In still another non-limiting embodiment, antigen-binding domains of the present invention can be obtained from a library mainly composed of antigen-binding molecules whose sequences are different from one another and whose heavy chain CDR3 domains contain the above-mentioned amino acids at positions 95, 96, 100a, and/or 101 as indicated according to the Kabat numbering system.

Meanwhile, in a non-limiting embodiment of the present invention, antigen-binding domains of the present invention can be obtained from a library mainly composed of antigen-binding molecules whose sequences are different from one another and whose light chain antigen-binding domains contain amino acids that alter the antigen-binding activity of antigen-binding molecules depending on calcium ion concentrations. In another embodiment, antigen-binding domains of the present invention can be obtained from a library mainly composed of antigen-binding molecules whose sequences are different from one another and whose light chain CDR1 domains contain the above-mentioned amino acids. In still another embodiment, antigen-binding domains of the present invention can be obtained from a library mainly composed of antigen-binding molecules whose sequences are different from one another and whose light chain CDR1 domains contain the above-mentioned amino acids at positions 30, 31, and/or 32 as indicated according to the Kabat numbering system.

In another non-limiting embodiment, antigen-binding domains of the present invention can be obtained from a library mainly composed of antigen-binding molecules whose sequences are different from one another and whose light chain CDR2 domains contain the above-mentioned amino acid residues. In yet another embodiment, the present invention provides libraries mainly composed of antigen-binding molecules whose sequences are different from one another and whose light chain CDR2 domains contain the above-mentioned amino acid residues at position 50 as indicated according to the Kabat numbering system.

In still another non-limiting embodiment of the present invention, antigen-binding domains of the present invention can be obtained from a library mainly composed of antigen-binding molecules whose sequences are different from one another and whose light chain CDR3 domains contain the above-mentioned amino acid residues. In an alternative embodiment, antigen-binding domains of the present invention can be obtained from a library mainly composed of antigen-binding molecules whose sequences are different from one another and whose light chain CDR3 domains contain the above-mentioned amino acid residues at position 92 as indicated according to the Kabat numbering system.

Furthermore, in a different embodiment of the present invention, antigen-binding domains of the present invention can be obtained from a library mainly composed of antigen-binding molecules whose sequences are different from one another and in which two or three CDRs selected from the above-described light chain CDR1, CDR2, and CDR3 contain the aforementioned amino acid residues. Moreover, antigen-binding domains of the present invention can be obtained from a library mainly composed of antigen-binding molecules whose sequences are different from one another and whose light chains contain the aforementioned amino acid residues at any one or more of positions 30, 31, 32, 50, and/or 92 as indicated according to the Kabat numbering system.

In a particularly preferred embodiment, the framework sequences of the light chain and/or heavy chain variable region of an antigen-binding molecule preferably contain human germ line framework sequences. Thus, in an embodiment of the present invention, when the framework sequences are completely human sequences, it is expected that when such an antigen-binding molecule of the present invention is administered to humans (for example, to treat diseases), it induces little or no immunogenic response. In the above sense, the phrase "containing a germ line sequence" in the present invention means that a part of the framework sequences of the present invention is identical to a part of any human germ line framework sequences. For example, when the heavy chain FR2 sequence of an antigen-binding molecule of the present invention is a combination of heavy chain FR2 sequences of different human germ line framework sequences, such a molecule is also an antigen-binding molecule of the present invention "containing a germ line sequence".

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:

subgroup VH1 (for example, VH1-2, VH1-3, VH1-8, VH1-18, VH1-24, VH1-45, VH1-46, VH1-58, and VH1-69);

subgroup VH2 (for example, VH2-5, VH2-26, and VH2-70);

subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);

subgroup VH4 (VH4-4, VH4-28, VH4-31, VH4-34, VH4-39, VH4-59, and VH4-61);

subgroup VH5 (VH5-51);

subgroup VH6 (VH6-1); and subgroup VH7 (VH7-4 and VH7-81).

These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human VK sequences preferably include, but are not limited to, for example:

A20, A30, L1, L4, L5, L8, L9, L11, L12, L14, L15, L18, L19, L22, L23, L24, O2, O4, O8, O12, O14, and O18 grouped into subgroup Vk1;

A1, A2, A3, A5, A7, A17, A18, A19, A23, O1, and O11, grouped into subgroup Vk2;

A11, A27, L2, L6, L10, L16, L20, and L25, grouped into subgroup Vk3;

B3, grouped into subgroup Vk4;

B2 (herein also referred to as Vk5-2), grouped into subgroup Vk5; and

A10, A14, and A26, grouped into subgroup VK6
(Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human VL sequences preferably include, but are not limited to, for example:

V1-2, V1-3, V1-4, V1-5, V1-7, V1-9, V1-11, V1-13, V1-16, V1-17, V1-18, V1-19, V1-20, and V1-22, grouped into subgroup VL1;

V2-1, V2-6, V2-7, V2-8, V2-11, V2-13, V2-14, V2-15, V2-17, and V2-19, grouped into subgroup VL1;

V3-2, V3-3, and V3-4, grouped into subgroup VL3;

V4-1, V4-2, V4-3, V4-4, and V4-6, grouped into subgroup VL4; and

V5-1, V5-2, V5-4, and V5-6, grouped into subgroup VL5
(Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding molecule depending on ion concentrations" of the present invention. Other examples of the fully human frameworks used in combination with "at least one amino acid residue that alters the antigen-binding activity of an antigen-binding molecule depending on ion concentrations" of the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce antigen-binding molecules of the present invention in which the above-described framework sequences contain amino acids that alter the antigen-binding activity of the antigen-binding molecules depending on calcium ion concentrations.

For example, a library which contains a plurality of antigen-binding molecules of the present invention whose sequences are different from one another can be constructed by combining heavy chain variable regions prepared as a randomized variable region sequence library with a light chain variable region selected as a framework sequence originally containing at least one amino acid residue that alters the antigen-binding activity of the antigen-binding molecule depending on calcium ion concentrations. Non-limiting examples of such libraries when the ion concentration is calcium ion concentration include a library in which a light chain variable region sequence belonging to the Vk5-2 family represented by the light chain variable region sequence of SEQ ID NO: 4 (Vk5-2) is combined with heavy chain variable regions produced as a randomized variable region sequence library.

Alternatively, a light chain variable region sequence selected as a framework region originally containing at least one amino acid residue that alters the antigen-binding activity of an antigen-binding molecule as mentioned above can be design to contain various amino acid residues other than the above amino acid residues. Herein, such residues are referred to as flexible residues. The number and position of flexible residues are not particularly limited as long as the antigen-binding activity of the antigen-binding molecule of the present invention varies depending on ion concentrations. Specifically, the CDR sequences and/or FR sequences of the heavy chain and/or light chain may contain one or more flexible residues. For example, when the ion concentration is calcium ion concentration, non-limiting examples of flexible residues to be introduced into the light chain variable region sequence of SEQ ID NO: 4 (Vk5-2) include the amino acid residues listed in Tables 1 or 2.

TABLE 1

| CDR | Kabat numbering | Amino acid in 70% of the total | | | |
|---|---|---|---|---|---|
| CDR1 | 28 | S: 100% | | | |
| | 29 | I: 100% | | | |
| | 30 | E: 72% | N: 14% | S: 14% | |
| | 31 | D: 100% | | | |
| | 32 | D: 100% | | | |
| | 33 | L: 100% | | | |
| | 34 | A: 70% | N: 30% | | |
| CDR2 | 50 | E: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

TABLE 2

| CDR | Kabat numbering | Amino acid in 30% of the total | | | |
|---|---|---|---|---|---|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

Herein, flexible residues refer to amino acid residue variations present at hypervariable positions at which several different amino acids are present on the light chain and heavy chain variable regions when the amino acid sequences of known and/or native antibodies or antigen-binding domains are compared. Hypervariable positions are generally located in the CDR regions. In an embodiment, the data provided by Kabat, Sequences of Proteins of Immunological Interest (National Institute of Health Bethesda Md.) (1987 and 1991) is useful to determine hypervariable positions in known and/or native antibodies. Furthermore, databases on the Internet (http://vbase.mrc-cpe.cam.ac.uk/, http://www.bioinforg.uk/abs/index.html) provide the collected sequences of many human light chains and heavy chains and their locations. The information on the sequences and locations is useful to determine hypervariable positions in the present invention. According to the present invention, when a certain amino acid position has preferably about 2 to about 20 possible amino acid residue variations, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variations, the position is hypervariable. In some embodiments, a certain amino acid position may have preferably at least about 2, preferably at least about 4, preferably at least about 6, preferably at least about 8, preferably about 10, and preferably about 12 amino acid residue variations.

Alternatively, a library containing a plurality of antigen-binding molecules of the present invention whose sequences are different from one another can be constructed by combining heavy chain variable regions produced as a randomized variable region sequence library with light chain variable regions into which at least one amino acid residue that alters the antigen-binding activity of antigen-binding molecules depending on ion concentrations as mentioned above is introduced. When the ion concentration is calcium ion concentration, non-limiting examples of such libraries preferably include, for example, libraries in which heavy chain variable regions produced as a randomized variable region sequence library are combined with light chain variable region sequences in which a particular residue(s) in a germ line sequence such as SEQ ID NO: 5 (Vk1), SEQ ID NO: 6 (Vk2), SEQ ID NO: 7 (Vk3), or SEQ ID NO: 8 (Vk4) has been substituted with at least one amino acid residue that alters the antigen-binding activity of an antigen-binding molecule depending on calcium ion concentrations. Non-limiting examples of such amino acid residues include amino acid residues in light chain CDR1. Furthermore, non-limiting examples of such amino acid residues include amino acid residues in light chain CDR2. In addition, non-limiting examples of such amino acid residues also include amino acid residues in light chain CDR3.

Non-limiting examples of such amino acid residues contained in light chain CDR1 include those at positions 30, 31, and/or 32 in the CDR1 of light chain variable region as indicated by Kabat numbering. Furthermore, non-limiting examples of such amino acid residues contained in light chain CDR2 include an amino acid residue at position 50 in the CDR2 of light chain variable region as indicated by Kabat numbering. Moreover, non-limiting examples of such amino acid residues contained in light chain CDR3 include an amino acid residue at position 92 in the CDR3 of light chain variable region as indicated by Kabat numbering. These amino acid residues can be contained alone or in combination as long as they form a calcium-binding motif and/or as long as the antigen-binding activity of an antigen-binding molecule varies depending on calcium ion concentrations. Meanwhile, as troponin C, calmodulin, parvalbumin, and myosin light chain, which have several calcium ion-binding sites and are believed to be derived from a common origin in terms of molecular evolution, are known, the light chain CDR1, CDR2, and/or CDR3 can be designed to have their binding motifs. For example, it is possible to use cadherin domains, EF hand of calmodulin, C2 domain of Protein kinase C, Gla domain of blood coagulation protein FactorIX, C type lectins of acyaroglycoprotein receptor and mannose-binding receptor, A domains of LDL receptors, annexin, thrombospondin type 3 domain, and EGF-like domains in an appropriate manner for the above purposes.

When heavy chain variable regions produced as a randomized variable region sequence library and light chain variable regions into which at least one amino acid residue that alters the antigen-binding activity of an antigen-binding molecule depending on ion concentrations has been introduced are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on ion concentrations. Specifically, the CDR sequences and/or FR sequences of heavy chain and/or light chain can contain one or more flexible residues. When the ion concentration is calcium ion concentration, non-limiting examples of flexible residues to be introduced into the sequence of light chain variable region include the amino acid residues listed in Tables 1 and 2.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

In another non-limiting embodiment of the present invention, a naive library, which is constructed from antibody genes derived from lymphocytes of healthy persons and whose repertoire consists of naive sequences, which are antibody sequences with no bias, can also be particularly preferably used as a randomized variable region library (Gejima et al. (Human Antibodies (2002) 11, 121-129); Cardoso et al. (Scand. J. Immunol. (2000) 51, 337-344)). Herein, an amino acid sequence comprising a naive sequence refers to an amino acid sequence obtained from such a naive library.

In one embodiment of the present invention, an antigen-binding domain of the present invention can be obtained from a library containing a plurality of antigen-binding molecules of the present invention whose sequences are different from one another, prepared by combining light chain variable regions constructed as a randomized variable region sequence library with a heavy chain variable region selected as a framework sequence that originally contains "at least one amino acid residue that alters the antigen-binding activity of an antigen-binding molecule depending on ion concentrations". When the ion concentration is calcium ion concentration, non-limiting examples of such libraries preferably include those constructed by combining light chain variable regions constructed as a randomized variable region sequence library with the sequence of heavy chain variable region of SEQ ID NO: 9 (6RL #9-IgG1) or SEQ ID NO: 10 (6KC4-1 #85-IgG1). Alternatively, such a library can be constructed by selecting appropriate light chain variable regions from those having germ line sequences, instead of light chain variable regions constructed as a randomized variable region sequence library. Such preferred libraries include, for example, those in which the sequence of heavy chain variable region of SEQ ID NO: 9 (6RL #9-IgG1) or SEQ ID NO: 10 (6KC4-1 #85-IgG1) is combined with light chain variable regions having germ line sequences.

Alternatively, the sequence of a heavy chain variable region selected as a framework sequence that originally contains "at least one amino acid residue that alters the antigen-binding activity of an antigen-binding molecule" as mentioned above can be designed to contain flexible residues. The number and position of the flexible residues are not particularly limited as long as the antigen-binding activity of an antigen-binding molecule of the present invention varies depending on ion concentrations. Specifically, the CDR and/or FR sequences of heavy chain and/or light chain can contain one or more flexible residues. When the ion concentration is calcium ion concentration, non-limiting examples of flexible residues to be introduced into the sequence of heavy chain variable region of SEQ ID NO: 9 (6RL #9-IgG1) include all amino acid residues of heavy chain CDR1 and CDR2 and the amino acid residues of the heavy chain CDR3 except those at positions 95, 96, and/or 100a as indicated by Kabat numbering. Alternatively, non-limiting examples of flexible residues to be introduced into the sequence of heavy chain variable region of SEQ ID NO: 10 (6KC4-1 #85-IgG1) include all amino acid residues of heavy chain CDR1 and CDR2 and the amino acid residues of the heavy chain CDR3 except those at amino acid positions 95 and/or 101 as indicated by Kabat numbering.

Alternatively, a library containing a plurality of antigen-binding molecules whose sequences are different from one another can be constructed by combining light chain variable regions constructed as a randomized variable region sequence library or light chain variable regions having germ line sequences with heavy chain variable regions into which "at least one amino acid residue responsible for the ion concentration-dependent change in the antigen-binding activity of an antigen-binding molecule" has been introduced as mentioned above. When the ion concentration is calcium ion concentration, non-limiting examples of such libraries preferably include those in which light chain variable regions constructed as a randomized variable region sequence library or light chain variable regions having germ line sequences are combined with the sequence of a heavy chain variable region in which a particular residue(s) has been substituted with at least one amino acid residue that alters the antigen-binding activity of an antigen-binding molecule depending on calcium ion concentrations. Non-limiting examples of such amino acid residues include amino acid residues of the heavy chain CDR1. Further non-limiting examples of such amino acid residues include amino acid residues of the heavy chain CDR2. In addition, non-limiting examples of such amino acid residues also include amino acid residues of the heavy chain CDR3. Non-limiting examples of such amino acid residues of heavy chain CDR3 include the amino acids of positions 95, 96, 100a, and/or 101 in the CDR3 of heavy chain variable region as indicated by the Kabat numbering. Furthermore, these amino acid residues can be contained alone or in combination as long as they form a calcium-binding motif and/or the antigen-binding activity of an antigen-binding molecule varies depending on calcium ion concentrations.

When light chain variable regions constructed as a randomized variable region sequence library or light chain variable regions having germ line sequence are combined with a heavy chain variable region into which at least one amino acid residue that alter the antigen-binding activity of an antigen-binding molecule depending on ion concentrations as mentioned above has been introduced, the sequence of the heavy chain variable region can also be designed to contain flexible residues in the same manner as described above. The number and position of flexible residues are not particularly limited as long as the antigen-binding activity of an antigen-binding molecule of the present invention varies depending on ion concentrations. Specifically, the heavy chain CDR and/or FR sequences may contain one or more flexible residues.

Furthermore, randomized variable region libraries can be preferably used as amino acid sequences of CDR1, CDR2, and/or CDR3 of the heavy chain variable region other than the amino acid residues that alter the antigen-binding activity of an antigen-binding molecule. When germ line sequences are used as light chain variable regions, non-limiting examples of such sequences include those of SEQ ID NO: 5 (Vk1), SEQ ID NO: 6 (Vk2), SEQ ID NO: 7 (Vk3), and SEQ ID NO: 8 (Vk4).

Any of the above-described amino acids that alter the antigen-binding activity of an antigen-binding molecule depending on calcium ion concentrations can be preferably used, as long as they form a calcium-binding motif. Specifically, such amino acids include electron-donating amino acids. Preferred examples of such electron-donating amino acids include, serine, threonine, asparagine, glutamic acid, aspartic acid, and glutamic acid.

Condition of Hydrogen Ion Concentrations

In an embodiment of the present invention, the condition of ion concentrations refers to the condition of hydrogen ion concentrations or pH condition. In the present invention, the concentration of proton, i.e., the nucleus of hydrogen atom, is treated as synonymous with hydrogen index (pH). When the activity of hydrogen ion in an aqueous solution is represented as aH+, pH is defined as $-\log 10 aH+$. When the ionic strength of the aqueous solution is low (for example, lower than $10^{-3}$), aH+ is nearly equal to the hydrogen ion strength. For example, the ionic product of water at 25° C. and 1 atmosphere is $Kw=aH+aOH=10^{-14}$, and therefore in pure water, $aH+=aOH=10^{-7}$. In this case, pH=7 is neutral; an aqueous solution whose pH is lower than 7 is acidic or whose pH is greater than 7 is alkaline.

In the present invention, when pH condition is used as the ion concentration condition, pH conditions include high hydrogen ion concentrations or low pHs, i.e., an acidic pH range, and low hydrogen ion concentrations or high pHs, i.e., a neutral pH range. "The binding activity varies depending on pH condition" means that the antigen-binding activity of an antigen-binding molecule varies due to the difference in conditions of a high hydrogen ion concentration or low pH (an acidic pH range) and a low hydrogen ion concentration or high pH (a neutral pH range). This includes, for example, the case where the antigen-binding activity of an antigen-binding molecule is higher in a neutral pH range than in an acidic pH range and the case where the antigen-binding activity of an antigen-binding molecule is higher in an acidic pH range than in a neutral pH range.

Herein, neutral pH range is not limited to a specific value and is preferably selected from between pH 6.7 and pH 10.0. In another embodiment, the pH can be selected from between pH 6.7 and pH 9.5. In still another embodiment, the pH can be selected from between pH 7.0 and pH 9.0. In yet another embodiment, the pH can be selected from between pH 7.0 and pH 8.0. In particular, the preferred pH includes pH 7.4, which is close to the pH of plasma (blood) in vivo.

Herein, an acidic pH range is not limited to a specific value and is preferably selected from between pH 4.0 and pH 6.5. In another embodiment, the pH can be selected from between pH 4.5 and pH 6.5. In still another embodiment, the pH can be selected from between pH 5.0 and pH 6.5. In yet another embodiment, the pH can be selected from between pH 5.5 and pH 6.5. In particular, the preferred pH includes pH 5.8, which is close to the ionized calcium concentration in the early endosome in vivo.

In the present invention, "the antigen-binding activity of an antigen-binding molecule at a high hydrogen ion concentration or low pH (an acidic pH range) is lower than that at a low hydrogen ion concentration or high pH (a neutral pH range)" means that the antigen-binding activity of an antigen-binding molecule at a pH selected from between pH 4.0 and pH 6.5 is weaker than that at a pH selected from between pH 6.7 and pH 10.0; preferably means that the antigen-binding activity of an antigen-binding molecule at a pH selected from between pH4.5 and pH 6.5 is weaker than that at a pH selected from between pH 6.7 and pH 9.5; more preferably, means that the antigen-binding activity of an antigen-binding molecule at a pH selected from between pH 5.0 and pH 6.5 is weaker than that at a pH selected from between pH 7.0 and pH 9.0; still more preferably means that the antigen-binding activity of an antigen-binding molecule at a pH selected from between pH 5.5 and pH 6.5 is weaker than that at a pH selected from between pH 7.0 and pH 8.0; particularly preferably means that the antigen-binding activity at the pH in the early endosome in vivo is weaker than the antigen-binding activity at the pH of plasma in vivo; and specifically means that the antigen-binding activity of an antigen-binding molecule at pH 5.8 is weaker than the antigen-binding activity at pH 7.4.

Whether the antigen-binding activity of an antigen-binding molecule has changed by the pH condition can be determined, for example, by the use of known measurement methods such as those described in the section "Binding Activity" above. Specifically, the binding activity is measured under different pH conditions using the measurement methods described above. For example, the antigen-binding activity of an antigen-binding molecule is compared under the conditions of acidic pH range and neutral pH range to confirm that the antigen-binding activity of the antigen-binding molecule changes to be higher under the condition of neutral pH range than that under the condition of acidic pH range.

Furthermore, in the present invention, the expression "the antigen-binding activity at a high hydrogen ion concentration or low pH, i.e., in an acidic pH range, is lower than that at a low hydrogen ion concentration or high pH, i.e., in a neutral pH range" can also be expressed as "the antigen-binding activity of an antigen-binding molecule at a low hydrogen ion concentration or high pH, i.e., in a neutral pH range, is higher than that at a high hydrogen ion concentration or low pH, i.e., in an acidic pH range". In the present invention, "the antigen-binding activity at a high hydrogen ion concentration or low pH, i.e., in an acidic pH range, is lower than that at a low hydrogen ion concentration or high pH, i.e., in a neutral pH range" may be described as "the antigen-binding activity at a high hydrogen ion concentration or low pH, i.e., in an acidic pH range, is weaker than the antigen-binding ability at a low hydrogen ion concentration or high pH, i.e., in a neutral pH range". Alternatively, "the antigen-binding activity at a high hydrogen ion concentration or low pH, i.e., in an acidic pH range, is reduced to be lower than that at a low hydrogen ion concentration or high pH, i.e., in a neutral pH range" may be described as "the antigen-binding activity at a high hydrogen ion concentration or low pH, i.e., in an acidic pH range, is reduced to be weaker than the antigen-binding ability at a low hydrogen ion concentration or high pH, i.e., in a neutral pH range".

The conditions other than hydrogen ion concentration or pH for measuring the antigen-binding activity may be suitably selected by those skilled in the art and are not particularly limited. Measurements can be carried out, for example, at 37° C. using HEPES buffer. Measurements can be carried out, for example, using Biacore (GE Healthcare). When the antigen is a soluble antigen, the antigen-binding activity of an antigen-binding molecule can be determined by assessing the binding activity to the soluble antigen by pouring the antigen as an analyte into a chip immobilized with the antigen-binding molecule. When the antigen is a membrane antigen, the binding activity to the membrane antigen can be assessed by pouring the antigen-binding molecule as an analyte into a chip immobilized with the antigen.

As long as the antigen-binding activity of an antigen-binding molecule of the present invention at a high hydrogen ion concentration or low pH, i.e., in an acidic pH range is weaker than that at a low hydrogen ion concentration or high pH, i.e., in a neutral pH range, the ratio of the antigen-binding activity between that at a high hydrogen ion concentration or low pH, i.e., an acidic pH range, and at a low hydrogen ion concentration or high pH, i.e., a neutral pH range is not particularly limited, and the value of KD (pH 5.8)/KD (pH 7.4), which is the ratio of the dissociation constant (KD) for an antigen at a high hydrogen ion concentration or low pH, i.e., in an acidic pH range to the KD at a low hydrogen ion concentration or high pH, i.e., in a neutral pH range, is preferably 2 or more; more preferably the value of KD (pH 5.8)/KD (pH 7.4) is 10 or more; and still more preferably the value of KD (pH 5.8)/KD (pH 7.4) is 40 or more. The upper limit of KD (pH 5.8)/KD (pH 7.4) value is not particularly limited, and may be any value such as 400, 1000, or 10000, as long as the molecule can be produced by the techniques of those skilled in the art.

When the antigen is a soluble antigen, the dissociation constant (KD) can be used as the value for antigen-binding activity. Meanwhile, when the antigen is a membrane antigen, the apparent dissociation constant (KD) can be used. The dissociation constant (KD) and apparent dissociation constant (KD) can be measured by methods known to those skilled in the art, and Biacore (GE healthcare), Scatchard plot, flow cytometer, and such can be used.

Alternatively, for example, the dissociation rate constant (kd) can be suitably used as an index for indicating the ratio of the antigen-binding activity of an antigen-binding molecule of the present invention between that at a high hydrogen ion concentration or low pH, i.e., an acidic pH range and a low hydrogen ion concentration or high pH, i.e., a neutral pH range. When kd (dissociation rate constant) is used as an index for indicating the binding activity ratio instead of KD (dissociation constant), the value of kd (in an acidic pH range)/kd (in a neutral pH range), which is the ratio of kd (dissociation rate constant) for the antigen at a high hydrogen ion concentration or low pH, i.e., in an acidic pH range to kd (dissociation rate constant) at a low hydrogen ion concentration or high pH, i.e., in a neutral pH range, is preferably 2 or more, more preferably 5 or more, still more preferably 10 or more, and yet more preferably 30 or more. The upper limit of kd (in an acidic pH range)/kd (in a neutral pH range) value is not particularly limited, and may be any value such as 50, 100, or 200, as long as the molecule can be produced by the techniques of those skilled in the art.

When the antigen is a soluble antigen, the dissociation rate constant (kd) can be used as the value for antigen-binding activity and when the antigen is a membrane antigen, the apparent dissociation rate constant (kd) can be used. The dissociation rate constant (kd) and apparent dissociation rate constant (kd) can be determined by methods known to those skilled in the art, and Biacore (GE healthcare), flow cytometer, and such may be used. In the present invention, when the antigen-binding activity of an antigen-binding molecule is measured at different hydrogen ion concentrations, i.e., pHs, conditions other than the hydrogen ion concentration, i.e., pH, are preferably the same.

For example, an antigen-binding domain or antibody whose antigen-binding activity at a high hydrogen ion concentration or low pH, i.e., in an acidic pH range is lower than that at a low hydrogen ion concentration or high pH, i.e., in a neutral pH range, which is one embodiment provided by the present invention, can be obtained via screening of antigen-binding domains or antibodies, comprising the following steps (a) to (c):

(a) obtaining the antigen-binding activity of an antigen-binding domain or antibody in an acidic pH range;

(b) obtaining the antigen-binding activity of an antigen-binding domain or antibody in a neutral pH range; and (c) selecting an antigen-binding domain or antibody whose antigen-binding activity in the acidic pH range is lower than that in the neutral pH range.

Alternatively, an antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is one embodiment provided by the present invention, can be obtained via screening of antigen-binding domains or antibodies, or a library thereof, comprising the following steps (a) to (c):

(a) contacting an antigen-binding domain or antibody, or a library thereof, in a neutral pH range with an antigen;

(b) placing in an acidic pH range the antigen-binding domain or antibody bound to the antigen in step (a); and (c) isolating the antigen-binding domain or antibody dissociated in step (b).

An antigen-binding domain or antibody whose antigen-binding activity at a high hydrogen ion concentration or low pH, i.e., in an acidic pH range is lower than that at a low hydrogen ion concentration or high pH, i.e., in a neutral pH range, which is another embodiment provided by the present invention, can be obtained via screening of antigen-binding domains or antibodies, or a library thereof, comprising the following steps (a) to (d):

(a) contacting in an acidic pH range an antigen with a library of antigen-binding domains or antibodies;

(b) selecting the antigen-binding domain or antibody which does not bind to the antigen in step (a);

(c) allowing the antigen-binding domain or antibody selected in step (b) to bind with the antigen in a neutral pH range; and (d) isolating the antigen-binding domain or antibody bound to the antigen in step (c).

An antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is even another embodiment provided by the present invention, can be obtained by a screening method comprising the following steps (a) to (c):

(a) contacting in a neutral pH range a library of antigen-binding domains or antibodies with a column immobilized with an antigen;
(b) eluting in an acidic pH range from the column the antigen-binding domain or antibody bound to the column in step (a); and
(c) isolating the antigen-binding domain or antibody eluted in step (b).

An antigen-binding domain or antibody whose antigen-binding activity at a high hydrogen ion concentration or low pH, i.e., in an acidic pH, range is lower than that at a low hydrogen ion concentration or high pH, i.e., in a neutral pH range, which is still another embodiment provided by the present invention, can be obtained by a screening method comprising the following steps (a) to (d):
(a) allowing, in an acidic pH range, a library of antigen-binding domains or antibodies to pass a column immobilized with an antigen;
(b) collecting the antigen-binding domain or antibody eluted without binding to the column in step (a);
(c) allowing the antigen-binding domain or antibody collected in step (b) to bind with the antigen in a neutral pH range; and
(d) isolating the antigen-binding domain or antibody bound to the antigen in step (c).

An antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is yet another embodiment provided by the present invention, can be obtained by a screening method comprising the following steps (a) to (d):
(a) contacting an antigen with a library of antigen-binding domains or antibodies in a neutral pH range;
(b) obtaining the antigen-binding domain or antibody bound to the antigen in step (a);
(c) placing in an acidic pH range the antigen-binding domain or antibody obtained in step (b); and
(d) isolating the antigen-binding domain or antibody whose antigen-binding activity in step (c) is weaker than the criterion for the selection in step (b).

The above-described steps may be repeated twice or more times. Thus, the present invention provides antigen-binding domains and antibodies whose antigen-binding activity in an acidic pH range is lower than that in a neutral pH range, which are obtained by a screening method that further comprises the steps of repeating steps (a) to (c) or (a) to (d) in the above-described screening methods. The number of times that steps (a) to (c) or (a) to (d) is repeated is not particularly limited; however, the number is 10 or less in general.

In the screening methods of the present invention, the antigen-binding activity of an antigen-binding domain or antibody at a high hydrogen ion concentration or low pH, i.e., in an acidic pH range, is not particularly limited, as long as it is the antigen-binding activity at a pH of between 4.0 and 6.5, and includes the antigen-binding activity at a pH of between 4.5 and 6.6 as the preferred pH. The antigen-binding activity also includes that at a pH of between 5.0 and 6.5, and that at a pH of between 5.5 and 6.5 as another preferred pH. The antigen-binding activity also includes that at the pH in the early endosome in vivo as the more preferred pH, and specifically, that at pH 5.8. Meanwhile, the antigen-binding activity of an antigen-binding domain or antibody at a low hydrogen ion concentration or high pH, i.e., in a neutral pH range, is not particularly limited, as long as it is the antigen-binding activity at a pH of between 6.7 and 10, and includes the antigen-binding activity at a pH of between 6.7 and 9.5 as the preferred pH. The antigen-binding activity also includes that at a pH of between 7.0 and 9.5 and that at a pH of between 7.0 and 8.0 as another preferred pH. The antigen-binding activity also includes that at the pH of plasma in vivo as the more preferred pH, and specifically, that at pH 7.4.

The antigen-binding activity of an antigen-binding domain or antibody can be measured by methods known to those skilled in the art. Those skilled in the art can suitably determine conditions other than ionized calcium concentration. The antigen-binding activity of an antigen-binding domain or antibody can be assessed based on the dissociation constant (KD), apparent dissociation constant (KD), dissociation rate constant (kd), apparent dissociation rate constant (kd), and such. These can be determined by methods known to those skilled in the art, for example, using Biacore (GE healthcare), Scatchard plot, or FACS.

Herein, the step of selecting an antigen-binding domain or antibody whose antigen-binding activity at a low hydrogen ion concentration or high pH, i.e., in a neutral pH range, is higher than that at a high hydrogen ion concentration or low pH, i.e., in an acidic pH range, is synonymous with the step of selecting an antigen-binding domain or antibody whose antigen-binding activity at a high hydrogen ion concentration or low pH, i.e., in an acidic pH range, is lower than that at a low hydrogen ion concentration or high pH, i.e., in a neutral pH range.

As long as the antigen-binding activity at a low hydrogen ion concentration or high pH, i.e., in a neutral pH range, is higher than that at a high hydrogen ion concentration or low pH, i.e., in an acidic pH range, the difference between the antigen-binding activity at a low hydrogen ion concentration or high pH, i.e., a neutral pH range, and that at a high hydrogen ion concentration or low pH, i.e., an acidic pH range, is not particularly limited; however, the antigen-binding activity at a low hydrogen ion concentration or high pH, i.e., in a neutral pH range, is preferably twice or more, more preferably 10 times or more, and still more preferably 40 times or more than that at a high hydrogen ion concentration or low pH, i.e., in an acidic pH range.

The antigen binding domain or antibody of the present invention screened by the screening methods described above may be any antigen-binding domain or antibody, and the above-mentioned antigen-binding domain or antibody may be screened. For example, antigen-binding domain or antibody having the native sequence may be screened, and antigen-binding domain or antibody in which their amino acid sequences have been substituted may be screened.

The antigen-binding domain or antibody of the present invention to be screened by the above-described screening methods may be prepared in any manner. For example, conventional antibodies, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with amino acids with a side chain pKa of 4.0-8.0 (for example, histidine and glutamic acid) or unnatural amino acid mutations at specific positions, etc.) obtained by introducing amino acids with a side chain pKa of 4.0-8.0 (for example, histidine and glutamic acid) or unnatural amino acid mutations into the above-described antibodies or libraries may be used.

Methods for obtaining an antigen-binding domain or antibody whose antigen-binding activity at a low hydrogen ion concentration or high pH, i.e., in a neutral pH range, is higher than that at a high hydrogen ion concentration or low pH, i.e., in an acidic pH range, from an antigen-binding domains or antibodies prepared from hybridomas obtained by immunizing animals or from B cells of immunized animals preferably include, for example, the antigen-binding molecule or antibody in which at least one of the amino acids of the antigen-binding domain or antibody is substituted with an amino acid with a side chain pKa of 4.0-8.0 (for example, histidine and glutamic acid) or an unnatural amino acid mutation, or the antigen-binding domain or antibody inserted with an amino acid with a side chain pKa of 4.0-8.0 (for example, histidine and glutamic acid) or unnatural amino acid, such as those described in WO 2009/125825.

The sites of introducing mutations of amino acids with a side chain pKa of 4.0-8.0 (for example, histidine and glutamic acid) or unnatural amino acids are not particularly limited, and may be any position as long as the antigen-binding activity in an acidic pH range becomes weaker than that in a neutral pH range (the value of KD (in an acidic pH range)/KD (in a neutral pH range) or kd (in an acidic pH range)/kd (in a neutral pH range) is increased) as compared to before substitution or insertion. For example, when the antigen-binding molecule is an antibody, antibody variable region and CDRs are suitable. Those skilled in the art can appropriately determine the number of amino acids to be substituted with or the number of amino acids with a side chain pKa of 4.0-8.0 (for example, histidine and glutamic acid) or unnatural amino acids to be inserted. It is possible to substitute with a single amino acid having a side chain pKa of 4.0-8.0 (for example, histidine and glutamic acid) or a single unnatural amino acid; it is possible to insert a single amino acid having a side chain pKa of 4.0-8.0 (for example, histidine and glutamic acid) or a single unnatural amino acid; it is possible to substitute with two or more amino acids having a side chain pKa of 4.0-8.0 (for example, histidine and glutamic acid) or two or more unnatural amino acids; and it is possible to insert two or more amino acids having a side chain pKa of 4.0-8.0 (for example, histidine and glutamic acid) or two or more unnatural amino acids. Alternatively, other amino acids can be deleted, added, inserted, and/or substituted concomitantly, aside from the substitution into amino acids having a side chain pKa of 4.0-8.0 (for example, histidine and glutamic acid) or unnatural amino acids, or the insertion of amino acids having a side chain pKa of 4.0-8.0 (for example, histidine and glutamic acid) or unnatural amino acids. Substitution into or insertion of amino acids with a side chain pKa of 4.0-8.0 (for example, histidine and glutamic acid) or unnatural amino acids can performed randomly by methods such as histidine scanning, in which the alanine of alanine scanning known to those skilled in the art is replaced with histidine. Antigen-binding molecules exhibiting a greater value of KD (in an acidic pH range)/KD (in a neutral pH range) or kd (in an acidic pH range)/kd (in a neutral pH range) as compared to before the mutation can be selected from antigen-binding domains or antibodies introduced with random insertions or substitution mutations of amino acids with a side chain pKa of 4.0-8.0 (for example, histidine and glutamic acid) or unnatural amino acids.

Preferred examples of antigen-binding molecules containing the mutation into amino acids with a side chain pKa of 4.0-8.0 (for example, histidine and glutamic acid) or unnatural amino acids as described above and whose antigen-binding activity in an acidic pH range is lower than that in a neutral pH range include, antigen-binding molecules whose antigen-binding activity in the neutral pH range after the mutation into amino acids with a side chain pKa of 4.0-8.0 (for example, histidine and glutamic acid) or unnatural amino acids is comparable to that before the mutation into amino acids with a side chain pKa of 4.0-8.0 (for example, histidine and glutamic acid) or unnatural amino acids. Herein, "an antigen-binding molecule after the mutation with amino acids having a side chain pKa of 4.0-8.0 (for example, histidine and glutamic acid) or unnatural amino acids has an antigen-binding activity comparable to that before the mutation with amino acids having a side chain pKa of 4.0-8.0 (for example, histidine and glutamic acid) or unnatural amino acids" means that, when taking the antigen-binding activity of an antigen-binding molecule before the mutation with amino acids having a side chain pKa of 4.0-8.0 (for example, histidine and glutamic acid) or unnatural amino acids as 100%, the antigen-binding activity of an antigen-binding molecule after the mutation with amino acids having a side chain pKa of 4.0-8.0 (for example, histidine and glutamic acid) or unnatural amino acids is at least 10% or more, preferably 50% or more, more preferably 80% or more, and still more preferably 90% or more. The antigen-binding activity after the mutation of amino acids with a side chain pKa of 4.0-8.0 (for example, histidine and glutamic acid) or unnatural amino acids at pH 7.4 may be higher than that before the mutation of amino acids with a side chain pKa of 4.0-8.0 (for example, histidine and glutamic acid) or unnatural amino acids at pH 7.4. If the antigen-binding activity of an antigen-binding molecule is decreased due to insertion of or substitution into amino acids with a side chain pKa of 4.0-8.0 (for example, histidine and glutamic acid) or unnatural amino acids, the antigen-binding activity can be made to be comparable to that before the insertion of or substitution into amino acids with a side chain pKa of 4.0-8.0 (for example, histidine and glutamic acid) or unnatural amino acids, by introducing a substitution, deletion, addition, and/or insertion of one or more amino acids of the antigen-binding molecule. The present invention also includes antigen-binding molecules whose binding activity has been adjusted to be comparable by substitution, deletion, addition, and/or insertion of one or more amino acids after substitution or insertion of amino acids with a side chain pKa of 4.0-8.0 (for example, histidine and glutamic acid) or unnatural amino acids. Meanwhile, when an antigen-binding molecule is a substance containing an antibody constant region, preferred embodiments of antigen-binding molecules whose antigen-binding activity at an acidic pH range is lower than that in a neutral pH range include methods in which the antibody constant regions contained in the antigen-binding molecules have been modified. Specific examples of modified antibody constant regions preferably include the constant regions of SEQ ID NOs: 11, 12, 13, and 14.

Amino Acids that Alter the Antigen-Binding Activity of Antigen-Binding Domain Depending on the Hydrogen Ion Concentration Conditions Antigen-binding domains or antibodies of the present invention to be screened by the above-described screening methods may be prepared in any manner. For example, when ion concentration condition is hydrogen ion concentration condition or pH condition, conventional antibodies, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with mutations of amino acids with a side chain pKa of 4.0-8.0 (for example, histidine and glutamic acid) or unnatural amino acids at specific positions, etc.) obtained by introducing mutations of amino acids with a side chain pKa of 4.0-8.0 (for example, histidine and glutamic acid) or unnatural amino acids into the above-described antibodies or libraries may be used.

In one non-limiting embodiment of the present invention, a library containing multiple antigen-binding molecules of the present invention whose sequences are different from one another can also be constructed by combining heavy chain variable regions, produced as a randomized variable region sequence library, with light chain variable regions introduced with "at least one amino acid residue that changes the antigen-binding activity of an antigen-binding molecule depending on the hydrogen ion concentration condition".

Such amino acid residues include, but are not limited to, for example, amino acid residues contained in the light chain CDR1. The amino acid residues also include, but are not limited to, for example, amino acid residues contained in the light chain CDR2. The amino acid residues also include, but are not limited to, for example, amino acid residues contained in the light chain CDR3.

The above-described amino acid residues contained in the light chain CDR1 include, but are not limited to, for example, amino acid residues of positions 24, 27, 28, 31, 32, and/or 34 according to Kabat numbering in the CDR1 of light chain variable region. Meanwhile, the amino acid residues contained in the light chain CDR2 include, but are not limited to, for example, amino acid residues of positions 50, 51, 52, 53, 54, 55, and/or 56 according to Kabat numbering in the CDR2 of light chain variable region. Furthermore, the amino acid residues in the light chain CDR3 include, but are not limited to, for example, amino acid residues of positions 89, 90, 91, 92, 93, 94, and/or 95A according to Kabat numbering in the CDR3 of light chain variable region. Moreover, the amino acid residues can be contained alone or can be contained in combination of two or more amino acids as long as they allow the change in the antigen-binding activity of an antigen-binding molecule depending on the hydrogen ion concentration.

Even when the heavy chain variable region produced as a randomized variable region sequence library is combined with the above-described light chain variable region introduced with "at least one amino acid residue that changes the antigen-binding activity of an antigen-binding molecule depending on the hydrogen ion concentration condition", it is possible to design so that the flexible residues are contained in the sequence of the light chain variable region in the same manner as described above. The number and position of the flexible residues are not particularly limited to a specific embodiment, as long as the antigen-binding activity of an antigen-binding molecule of the present invention changes depending on the hydrogen ion concentration condition. Specifically, the CDR and/or FR sequences of heavy chain and/or light chain can contain one or more flexible residues. For example, flexible residues to be introduced into the sequences of the light chain variable regions include, but are not limited to, for example, the amino acid residues listed in Tables 3 and 4. Meanwhile, amino acid sequences of light chain variable regions other than the flexible residues and amino acid residues that change the antigen-binding activity of an antigen-binding molecule depending on the hydrogen ion concentration condition suitably include, but are not limited to, germ line sequences such as Vk1 (SEQ ID NO: 5), Vk2 (SEQ ID NO: 6), Vk3 (SEQ ID NO: 7), and Vk4 (SEQ ID NO: 8).

TABLE 3

| POSITION | AMINO ACID | | | | | | | |
|---|---|---|---|---|---|---|---|---|
| CDR1 | | | | | | | | |
| 28 | S: 100% | | | | | | | |
| 29 | I: 100% | | | | | | | |
| 30 | N: 25% | S: 25% | R: 25% | H: 25% | | | | |
| 31 | S: 100% | | | | | | | |
| 32 | H: 100% | | | | | | | |
| 33 | L: 100% | | | | | | | |
| 34 | A: 50% | N: 50% | | | | | | |
| CDR2 | | | | | | | | |
| 50 | H: 100% | | | | OR A: 25% | D: 25% | G: 25% | K: 25% |
| 51 | A: 100% | | | | A: 100% | | | |
| 52 | S: 100% | | | | S: 100% | | | |
| 53 | K: 33.3% | N: 33.3% | S: 33.3% | | H: 100% | | | |
| 54 | L: 100% | | | | L: 100% | | | |
| 55 | Q: 100% | | | | Q: 100% | | | |
| 56 | S: 100% | | | | S: 100% | | | |
| CDR3 | | | | | | | | |
| 90 | Q: 100% | | | | OR Q: 100% | | | |
| 91 | H: 100% | | | | S: 33.3% | R: 33.3% | Y: 33.3% | |
| 92 | G: 25% | N: 25% | S: 25% | Y: 25% | H: 100% | | | |
| 93 | H: 33.3% | N: 33.3% | S: 33.3% | | H: 33.3% | N: 33.3% | S: 33.3% | |
| 94 | S: 50% | Y: 50% | | | S: 50% | Y: 50% | | |
| 95 | P: 100% | | | | P: 100% | | | |
| 96 | L: 50% | Y: 50% | | | L: 50% | Y: 50% | | |

(Position indicates Kabat numbering)

TABLE 4

| CDR | POSITION | AMINO ACID | | | |
|---|---|---|---|---|---|
| CDR1 | 28 | S: 100% | | | |
| | 29 | I: 100% | | | |
| | 30 | H: 30% | N: 10% | S: 50% | R: 10% |

TABLE 4-continued

| CDR | POSITION | AMINO ACID | | | | |
|---|---|---|---|---|---|---|
|  | 31 | N: 35% | S: 65% | | | |
|  | 32 | H: 40% | N: 20% | Y: 40% | | |
|  | 33 | L: 100% | | | | |
|  | 34 | A: 70% | N: 30% | | | |
| CDR2 | 50 | A: 25% | D: 15% | G: 25% | H: 30% | K: 5% |
|  | 51 | A: 100% | | | | |
|  | 52 | S: 100% | | | | |
|  | 53 | H: 30% | K: 10% | N: 15% | S: 45% | |
|  | 54 | L: 100% | | | | |
|  | 55 | Q: 100% | | | | |
|  | 56 | S: 100% | | | | |
| CDR3 | 90 | Q: 100% | | | | |
|  | 91 | H: 30% | S: 15% | R: 10% | Y: 45% | |
|  | 92 | G: 20% | H: 30% | N: 20% | S: 15% | Y: 15% |
|  | 93 | H: 30% | N: 25% | S: 45% | | |
|  | 94 | S: 50% | Y: 50% | | | |
|  | 95 | P: 100% | | | | |
|  | 96 | L: 50% | Y: 50% | | | |

(Position indicates Kabat numbering)

Any amino acid residue may be suitably used as the above-described amino acid residues that change the antigen-binding activity of an antigen-binding molecule depending on the hydrogen ion concentration condition. Specifically, such amino acid residues include amino acids with a side chain pKa of 4.0-8.0. Such electron-releasing amino acids preferably include, for example, naturally occurring amino acids such as histidine and glutamic acid, as well as unnatural amino acids such as histidine analogs (US20090035836), m-NO2-Tyr (pKa 7.45), 3,5-Br2-Tyr (pKa 7.21), and 3,5-I2-Tyr (pKa 7.38) (Bioorg. Med. Chem. (2003) 11 (17), 3761-2768). Particularly preferred amino acid residues include, for example, amino acids with a side chain pKa of 6.0-7.0. Such electron-releasing amino acid residues preferably include, for example, histidine.

Known methods such as site-directed mutagenesis (Kunkel et al. (Proc. Natl. Acad. Sci. USA (1985) 82, 488-492)) and Overlap extension PCR can be appropriately employed to modify the amino acids of antigen-binding domains. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

The preferred heavy chain variable region that is used in combination includes, for example, randomized variable region libraries. Known methods are appropriately combined as a method for producing a randomized variable region library. In a non-limiting embodiment of the present invention, an immune library constructed based on antibody genes derived from animals immunized with specific antigens, patients with infection or persons with an elevated antibody titer in blood as a result of vaccination, cancer patients, or lymphocytes of auto immune diseases may be suitably used as a randomized variable region library.

In another non-limiting embodiment of the present invention, in the same manner as described above, a synthetic library in which the CDR sequences of V genes from genomic DNA or functional reconstructed V genes are replaced with a set of synthetic oligonucleotides containing the sequences encoding codon sets of an appropriate length can also be suitably used as a randomized variable region library. In this case, the CDR3 sequence alone may be replaced because variety in the gene sequence of heavy chain CDR3 is observed. The basis for giving rise to amino acid variations in the variable region of an antigen-binding molecule is to generate variations of amino acid residues of surface-exposed positions of the antigen-binding molecule. The surface-exposed position refers to a position where an amino acid is exposed on the surface and/or contacted with an antigen based on the conformation, structural ensemble, and/or modeled structure of an antigen-binding molecule, and in general, such positions are the CDRs. The surface-exposed positions are preferably determined using the coordinates derived from a three-dimensional model of the antigen-binding molecule using computer programs such as InsightII program (Accelrys). The surface-exposed positions can be determined using algorithms known in the art (for example, Lee and Richards (J. Mol. Biol. (1971) 55, 379-400); Connolly (J. Appl. Cryst. (1983) 16, 548-558)). The surface-exposed positions can be determined based on the information on the three dimensional structure of antibodies using software suitable for protein modeling. Software which is suitably used for this purpose includes the SYBYL biopolymer module software (Tripos Associates). When the algorithm requires the input size parameter from the user, the "size" of probe for use in computation is generally or preferably set at about 1.4 angstrom or less in radius. Furthermore, a method for determining surface-exposed region and area using PC software is described by Pacios (Comput. Chem. (1994) 18 (4), 377-386; and J. Mol. Model. (1995) 1, 46-53).

In still another non-limiting embodiment of the present invention, a naive library constructed from antibody genes derived from lymphocytes of healthy persons and consisting of naive sequences, which are unbiased repertoire of antibody sequences, can also be particularly suitably used as a randomized variable region library (Gejima et al. (Human Antibodies (2002) 11, 121-129); and Cardoso et al. (Scand. J. Immunol. (2000) 51, 337-344)).

FcRn

Unlike Fcγ receptor belonging to the immunoglobulin superfamily, FcRn, human FcRn in particular, is structurally similar to polypeptides of major histocompatibility complex (MHC) class I, exhibiting 22% to 29% sequence identity to class I MHC molecules (Ghetie el al., Immunol. Today (1997) 18 (12): 592-598). FcRn is expressed as a heterodimer consisting of soluble β or light chain (β2 microglobulin) complexed with transmembrane a or heavy chain. Like MHC, FcRn α chain comprises three extracellular domains (α1, α2, and α3) and its short cytoplasmic domain anchors the protein onto the cell surface. α1 and α2 domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0.

Human FcRn whose precursor is a polypeptide having the signal sequence of SEQ ID NO: 15 (the polypeptide with the signal sequence is shown in SEQ ID NO: 16) forms a complex with human β2-microglobulin in vivo. As shown in the Reference Examples described below, soluble human FcRn complexed with β2-microglobulin is produced by using conventional recombinant expression techniques. FcRn regions of the present invention can be assessed for their binding activity to such a soluble human FcRn complexed with β2-microglobulin. Herein, unless otherwise specified, human FcRn refers to a form capable of binding to an FcRn region of the present invention. Examples include a complex between human FcRn and human β2-microglobulin.

FcRn-Binding Domains

An embodiment of the present invention provides pharmaceutical compositions that induce an immune response to the aforementioned antigen, which comprises as an active ingredient an antigen-binding molecule containing an antigen-binding domain whose antigen-binding activity changes depending on ion concentration conditions and an FcRn-binding domain having FcRn-binding activity in a neutral pH range.

Antigen-binding molecules of the present invention have an FcRn-binding domain. The FcRn-binding domain is not particularly limited as long as the antigen-binding molecule has FcRn-binding activity in a neutral pH range, and it may be a domain that has activity of directly or indirectly binding to FcRn. Preferred examples of such domains include Fc regions of IgG immunoglobulins, albumin, albumin domain 3, anti-FcRn antibodies, anti-FcRn peptides, anti-FcRn scaffold molecules, and such, which have activity of directly binding to FcRn, or molecules that bind to IgG or albumin, which have activity of indirectly binding to FcRn. For the anti-FcRn scaffold, it is possible to use a domain with any structure of the aforementioned antigen-binding domains characterized by binding to FcRn. In the present invention, a domain having binding activity to FcRn in an acidic pH range and neutral pH range are preferred. Such a domain may be preferably used as it is if it is a domain already having FcRn-binding activity in a neutral pH range. When the domain has no or weak FcRn-binding activity in a neutral pH range, amino acids in the antigen-binding molecule can be modified to impart FcRn-binding activity. Alternatively, FcRn binding activity may be enhanced by altering amino acids in the domain already having FcRn-binding activity in a neutral pH range. Desired amino acid alterations in the FcRn-binding domain can be identified by comparing the FcRn-binding activity in a neutral pH range before and after amino acid alteration.

Furthermore, in a different embodiment of the present invention, an FcRn binding domain that has FcRn-binding activity under a low calcium ion concentration condition and high calcium ion concentration condition is preferably used. Such a domain may be preferably used as it is if the domain already has FcRn-binding activity under a high calcium ion concentration condition. When the domain has no or weak FcRn-binding activity under a high calcium ion concentration condition, amino acids in the antigen-binding molecule can be modified to impart FcRn-binding activity. Alternatively, FcRn binding activity may be increased by altering amino acids in the domain already having FcRn-binding activity under a high calcium ion concentration condition. Desired amino acid alterations in the FcRn-binding domain can be identified by comparing the FcRn-binding activity under a high calcium ion concentration condition before and after amino acid alteration. FcRn-binding domains may be obtained by methods based on the methods of screening or producing antigen-binding domains having antigen-binding activity that changes depending on calcium ion concentration conditions as mentioned above in the section of "Conditions of ion concentration". Examples of such FcRn-binding domains include anti-FcRn antibodies, anti-FcRn peptides, anti-FcRn scaffold molecules, and such.

The preferred human FcRn-binding domain is a region that directly binds to FcRn. Such preferred FcRn-binding domains include, for example, antibody Fc regions. Meanwhile, regions capable of binding to a polypeptide such as albumin or IgG; which has FcRn-binding activity, can indirectly bind to FcRn via albumin, IgG; or such. Therefore, for the FcRn-binding region in the present invention, a region that binds to a polypeptide having FcRn-binding activity may be preferably used. An Fc region contains an amino acid sequence derived from the constant region of an antibody heavy chain. An Fc region is a portion of the antibody heavy chain constant region beginning from the N terminus of the hinge region at the papain cleavage site, which is on the amino acid at approximately position 216 according to EU numbering, and including the hinge, CH2 and CH3 domains.

The binding activity of an FcRn binding domain of the present invention to FcRn, human FcRn in particular, can be measured by methods known to those skilled in the art, as described in the section "Binding Activity" above. Those skilled in the art can appropriately determine the conditions other than pH. The antigen-binding activity and human FcRn-binding activity of an antigen-binding molecule can be assessed based on the dissociation constant (KD), apparent dissociation constant (KD), dissociation rate (kd), apparent dissociation rate (kd), and such. These can be measured by methods known to those skilled in the art. For example, Biacore (GE healthcare), Scatchard plot, or flow cytometer may be used.

When the human FcRn-binding activity of an FcRn-binding domain is measured, conditions other than the pH are not particularly limited, and can be appropriately selected by those skilled in the art. Measurements can be carried out, for example, at 37° C. using MES buffer, as described in WO 2009/125825. Alternatively, the FcRn-binding activity of an FcRn-binding domain can be measured by methods known to those skilled in the art, and may be measured by using, for example, Biacore (GE Healthcare) or such. The binding activity of an FcRn-binding domain to FcRn can be assessed by pouring, as an analyte, FcRn, an FcRn-binding domain, or an antigen-binding molecule of the present invention containing the FcRn-binding domain into a chip immobilized with an FcRn-binding domain, an antigen-binding molecule of the present invention containing the FcRn-binding domain, or FcRn.

The acidic pH range as a condition under which the FcRn-binding domain in the antigen-binding molecule of the present invention has FcRn-binding activity usually refers to pH4.0 to pH6.5. It preferably refers to pH5.5 to pH6.5, and particularly preferably pH5.8 to pH6.0, which is close to the pH in the early-stage endosome in vivo. Furthermore, the neutral pH range as a condition under which the FcRn-binding domain in the antigen-binding molecule of the present invention has FcRn-binding activity usually refers to pH6.7 to pH10.0. The neutral pH range is preferably a range indicated by any pH value within pH7.0 to pH8.0, and is preferably selected from pH7.0, 7.1, 7.2, 7.3, 7.4, 7.5, 7.6, 7.7, 7.8, 7.9, and 8.0, and is particularly preferably pH7.4, which is close to the plasma (blood) pH in vivo. When the binding affinity between a human FcRn-binding domain and human FcRn is difficult to evaluate because the binding affinity at pH7.4 is low, pH7.0 can be used instead of pH7.4. For the temperature to be used for the measurement conditions, the binding affinity between the FcRn binding domain and FcRn can be evaluated at any temperature from 10° C. to 50° C. Preferably, a temperature from 15° C. to 40° C. is used to determine the binding affinity between an FcRn-binding domain and human FcRn. More preferably, any temperature from 20° C. to 35° C., such as any temperature selected from 20, 21, 22, 23, 24, 25, 26, 27, 28, 29, 30, 31, 32, 33, 34, and 35° C., is used similarly to determine the binding affinity between an FcRn binding domain and FcRn. In an embodiment of the present invention, 25° C. is a non-limiting example of such temperature.

According to the Journal of Immunology (2009) 182: 7663-7671, the human FcRn-binding activity of naturally occurring human IgG1 is a KD of 1.7 µM in the acidic pH range (pH6.0), but hardly detectable in the neutral pH range. Therefore, in a preferred embodiment, antigen-binding molecules of the present invention having human FcRn-binding activity in an acidic pH range may be used, which include antigen-binding molecules whose human FcRn-binding activity in an acidic pH range is a KD of 20 µM or stronger, and whose human FcRn-binding activity in a neutral pH range is equivalent to that of naturally-occurring human IgG In a more preferred embodiment, antigen-binding molecules of the present invention including antigen-binding molecules whose human FcRn-binding activity in an acidic pH range is a KD of 2.0 µM or stronger may be used. In an even more preferred embodiment, antigen-binding molecules whose human FcRn-binding activity in an acidic pH range is a KD of 0.5 µM or stronger may be used. The above-mentioned KD values are determined by the method described in the Journal of Immunology (2009) 182: 7663-7671 (antigen-binding molecules are immobilized onto a chip and human FcRn is allowed to flow as an analyte).

In the present invention, an Fc region having FcRn-binding activity in an acidic pH range is preferred. If such a domain is an Fc region already having FcRn-binding activity in an acidic pH range, it may be used as it is. If the domain has no or weak FcRn-binding activity in an acidic pH range, an Fc region having desired FcRn-binding activity may be obtained by altering amino acids in the antigen-binding molecule. Also, an Fc region having desired or enhanced FcRn-binding activity in an acidic pH range may be suitably obtained by altering amino acids in the Fc region. Amino acid alterations of the Fc region that lead to such desired binding activity may be determined by comparing the FcRn-binding activity in an acidic pH range before and after amino acid alteration. Persons skilled in the art can appropriately perform amino acid alteration using known methods such as overlap extension PCR and site-directed mutagenesis (Kunkel et al. (Proc. Natl. Acad. Sci. USA (1985) 82, 488-492)) similarly to the aforementioned methods used to alter antigen-binding activity.

An Fc region having FcRn-binding activity in an acidic pH range that is contained in the antigen-binding molecules of the present invention may be obtained by any methods, but specifically, an FcRn-binding domain having FcRn-binding activity or enhanced FcRn-binding activity in an acidic pH range may be obtained by altering amino acids of human IgG immunoglobulin that is used as a starting Fc region. Examples of preferred IgG immunoglobulin Fc regions to be altered include the Fc region of human IgG (IgG1, IgG2, IgG3, or IgG4, and their variants). Amino acids at any positions may be altered to other amino acids as long as the Fc region has FcRn-binding activity in an acidic pH range or its human FcRn-binding activity in an acidic range can be enhanced. When an antigen-binding molecule includes the Fc region of human IgG1, it is preferred to include alterations that result in enhancement of FcRn-binding in an acidic pH range as compared to the binding activity of the starting Fc region of human IgG1. Examples of amino acids to which such alterations can be made preferably include, for example, amino acids at positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 according to EU numbering, as described in WO 2000/042072. Similarly, examples of amino acids to which such alterations can be made also preferably include amino acids at positions 251, 252, 254, 255, 256, 308, 309, 311, 312, 385, 386, 387, 389, 428, 433, 434, and/or 436 according to EU numbering, as described in WO 2002/060919. Furthermore, examples of amino acids to which such alterations can be made also include amino acids at positions 250, 314, and 428 according to EU numbering as described in WO 2004/092219. In addition, examples of amino acids to which such alterations can be made also preferably include amino acids at positions 251, 252, 307, 308, 378, 428, 430, 434, and/or 436 according to EU numbering as described in WO 2010/045193. Alteration of these amino acids enhances the binding of an IgG immunoglobulin Fc region to FcRn in an acidic pH range.

In the present invention, an Fc region having FcRn-binding activity in a neutral pH range is preferred. If the domain is an Fc region already having FcRn-binding activity in a neutral pH range, it may be used as it is. When the domain has no or weak FcRn-binding activity in a neutral pH range, an Fc region having desired FcRn-binding activity may be obtained by altering the amino acids in the antigen-binding molecule. Also, an Fc region having desired or enhanced FcRn-binding activity in a neutral pH range may be suitably obtained by altering amino acids in the Fc region. Amino acid alterations of the Fc region that lead to such desired binding activity may be determined by comparing the FcRn-binding activity in a neutral pH range before and after amino acid alteration. Persons skilled in the art can suitably perform amino acid alteration using known methods such as overlap extension PCR or site-directed mutagenesis (Kunkel et al. (Proc. Natl. Acad. Sci. USA (1985) 82, 488-492)) similarly to the aforementioned methods used to alter antigen-binding activity.

An Fc region having FcRn-binding activity in a neutral pH range that is contained in the antigen-binding molecule of the present invention may be obtained by any method, but specifically, an FcRn-binding domain having FcRn-binding activity or enhanced FcRn-binding activity in a neutral pH range may be obtained by amino acid modification of human IgG immunoglobulin used as a starting Fc region. Examples of preferred IgG immunoglobulin Fc regions to be modified include the Fc region of human IgG (IgG1, IgG2, IgG3, or IgG4, and their variants). Amino acids at any positions may be altered to other amino acids as long as the Fc region has FcRn-binding activity in a neutral pH range or its human FcRn-binding activity in the neutral range can be enhanced. When an antigen-binding molecule includes the Fc region of human IgG1, it is preferred to include alterations that result in enhancement of FcRn-binding in a neutral pH range compared to the binding activity of the starting Fc region of human IgG1. KD values for FcRn in a neutral pH range are determined as described above by the method described in the Journal of Immunology (2009) 182: 7663-7671 (antigen-binding molecules are immobilized onto a chip and human FcRn is allowed to flow as the analyte).

Examples of preferred IgG immunoglobulin Fc regions to be altered include the Fc region of human IgG (IgG1, IgG2, IgG3, or IgG4, and their variants). Amino acids at any positions may be altered to other amino acids as long as the Fc region has FcRn-binding activity in a neutral pH range or its human FcRn-binding activity in a neutral range can be enhanced. When an antigen-binding molecule includes the Fc region of human IgG1, it is preferred to include alterations that result in enhancement of FcRn-binding in a neutral pH range compared to the binding activity of the starting Fc region of human IgG1. In order to produce Fc regions to which such alterations have been made, various mutations shown in Table 5 were introduced into VH3-IgG1 (SEQ ID NO: 17) and evaluated. Variants (IgG1-F1 to IgG1-F1052) each containing a produced heavy chain and a light chain, L (WT) (SEQ ID NO: 18), were expressed and purified according to the methods described in Reference Example 1.

Binding between an antibody and human FcRn was analyzed according to the method described in Example 3-3. The binding activity of the variants to human FcRn under neutral conditions (pH7.0) measured using Biacore are shown in Table 5 (Table 5-1 to Table 5-33).

TABLE 5-1

| VARIANT | KD (M) | AMINO ACID ALTERATION POSITION |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/N434W |
| F11 | 3.10E−07 | M252Y/N434Y |
| F12 | 1.70E−07 | M252Y/N434W |
| F13 | 3.20E−07 | M252W/N434Y |
| F14 | 1.80E−07 | M252W/N434W |
| F19 | 4.60E−07 | P257L/N434Y |
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−06 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−07 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |

TABLE 5-2

| F42 | 1.00E−06 | M252Y/S254T/T256E/N434A |
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |
| F52 | 3.10E−06 | H433K/N434F/Y436H |

TABLE 5-2-continued

| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |
| F66 | 4.30E−07 | M252Y/S254T/T256E/N434H |
| F67 | 6.30E−07 | M252Y/N434F |
| F68 | 9.30E−07 | M252Y/N434H |
| F69 | 5.10E−07 | M428L/N434W |
| F70 | 1.50E−06 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |

TABLE 5-3

| F79 | 5.90E−06 | S254T/T256E/N434A |
| F80 | 2.70E−06 | M252Y/T256E/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−06 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |
| F92 | 1.10E−08 | M252Y/S254T/T256E/V308P/M428L/N434W |
| F93 | 7.40E−07 | M252W/M428L/N434W |
| F94 | 3.70E−07 | P257L/M428L/N434Y |
| F95 | 2.60E−07 | M252Y/S254T/T256E/M428L/N434F |
| F99 | 6.20E−07 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | M252Y/D265A/V308P/N434Y |
| F105 | 7.50E−08 | M252Y/T307A/V308P/N434Y |
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M428L |

TABLE 5-4

| F120 | 6.30E−08 | P257L/V308P/M428L/N434Y |
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |

TABLE 5-4-continued

| | | |
|---|---|---|
| F133 | 4.10E−07 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |

TABLE 5-5

| | | |
|---|---|---|
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332V/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−08 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |
| F205 | 2.00E−07 | M252Y/T307H/N434Y |
| F206 | 2.30E−07 | M252Y/T307I/N434Y |

TABLE 5-6

| | | |
|---|---|---|
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |

TABLE 5-6-continued

| | | |
|---|---|---|
| F218 | 2.60E−07 | M252Y/G385H/N434Y |
| F219 | 2.50E−07 | M252Y/T289H/N434Y |
| F220 | 2.50E−07 | M252Y/Q311H/N434Y |
| F221 | 3.10E−07 | M252Y/D312H/N434Y |
| F222 | 3.40E−07 | M252Y/N315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |

TABLE 5-7

| | | |
|---|---|---|
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/N434Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−07 | M252Y/V305A/M428F/N434Y |
| F270 | 6.60E−07 | M252Y/N325G/M428F/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |

TABLE 5-8

| | | |
|---|---|---|
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |
| F289 | 4.80E−07 | M252Y/T256E/M428F/N434Y |
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−07 | S239K/M252Y/E380A/E382A/M428F/N434Y |

TABLE 5-8-continued

| | | |
|---|---|---|
| F296 | 4.90E−07 | M252Y/Q311A/M428Y/N434Y |
| F297 | 5.10E−07 | M252Y/D312A/M428Y/N434Y |
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |
| F302 | 1.90E−07 | M252Y/T256E/T307P/N434Y |
| F303 | 6.70E−07 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−07 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−08 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |

TABLE 5-9

| | | |
|---|---|---|
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |

TABLE 5-9-continued

| | | |
|---|---|---|
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−07 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−08 | P257V/T307Q/N325G/M428I/N434Y |
| F363 | 4.10E−08 | P257V/T307Q/Q311A/M428I/N434Y |
| F364 | 3.50E−08 | P257V/T307Q/Q311A/N325G/M428I/N434Y |

TABLE 5-10

| | | |
|---|---|---|
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428L/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−09 | S239K/M252W/N286E/V308P/M428Y/N434Y |
| F376 | 9.60E−09 | S239K/M252Y/T256E/D270F/N286E/V308P/N434Y |
| F377 | 1.30E−07 | S239K/M252Y/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428Y/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |

TABLE 5-11

| | | |
|---|---|---|
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |

TABLE 5-11-continued

| | | |
|---|---|---|
| F416 | 9.40E−08 | P257V/T307A/P387E/M428L/N434Y |
| F418 | 6.20E−07 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |
| F433 | 6.00E−08 | P257V/T307Q/Q311A/N325G/N434Y |
| F434 | 2.00E−08 | P257V/T307Q/Q311A/N325G/M428Y/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−07 | P257A/T307Q/N434Y |
| F438 | 3.60E−08 | P257A/T307Q/M428Y/N434Y |
| F439 | 4.00E−08 | P257A/T307Q/M428F/N434Y |
| F440 | 1.50E−08 | P257V/N286E/T307Q/Q311A/N325G/M428L/N434Y |

TABLE 5-12

| | | |
|---|---|---|
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |
| F446 | 1.10E−07 | P257A/T307A/Q311H/M428L/N434Y |
| F447 | 1.40E−07 | P257A/N286E/T307Q/M428L/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/N325G/M428L/N434Y |
| F459 | 1.30E−08 | P257V/T307Q/V308P/Q311A/N325G/M428L/N434Y |
| F460 | 4.70E−08 | P257V/T307Q/V308P/N325G/M428Y/N434Y |
| F462 | 8.50E−08 | P257A/V308P/N325G/M428Y/N434Y |
| F463 | 1.30E−07 | P257A/T307A/V308P/M428L/N434Y |
| F464 | 5.50E−08 | P257A/T307Q/V308P/M428L/N434Y |
| F465 | 2.10E−08 | P257A/T307Q/N325G/M428L/N434Y |
| F466 | 3.50E−08 | T256E/P257V/N434Y |
| F467 | 5.70E−07 | T256E/P257T/N434Y |
| F468 | 5.70E−08 | S239K/P257T/V308P/M428L/N434Y |
| F469 | 5.60E−08 | P257V/V308P/N325G/M428L/N434Y |
| F470 | 5.40E−08 | T256E/P257T/V308P/N325G/M428L/N434Y |
| F471 | 6.60E−08 | P257T/V308P/N325G/E382A/M428L/N434Y |
| F472 | 5.40E−08 | P257T/V308P/N325G/P387E/M428L/N434Y |
| F473 | 4.50E−07 | P257T/V308P/L309P/N325G/M428L/N434Y |
| F474 | 3.50E−07 | P257T/V308P/L309R/N325G/M428L/N434Y |
| F475 | 4.30E−08 | T256E/P257/L309E/T307Q/M428L/N434Y |

TABLE 5-13

| | | |
|---|---|---|
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309Q/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |

TABLE 5-13-continued

| | | |
|---|---|---|
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/T307A/M428V/N434Y |
| F500 | 4.30E−08 | P257S/T307Q/M428L/N434Y |
| F506 | 1.90E−07 | P257V/N297A/T307Q/M428L/N434Y |
| F507 | 5.10E−08 | P257V/N286E/T307Q/M428L/N434Y |
| F508 | 1.10E−07 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−07 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−08 | P257T/T307Q/M428Y/N434Y |
| F527 | 9.40E−09 | P257V/T307Q/V308P/N325G/M428Y/N434Y |
| F529 | 2.50E−08 | P257T/T307Q/M428F/N434Y |
| F533 | 1.20E−08 | P257A/N286E/T307Q/M428F/N434Y |
| F534 | 1.20E−08 | P257A/N286E/T307Q/M428Y/N434Y |

TABLE 5-14

| | | |
|---|---|---|
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−08 | S239K/M252Y/S254T/V308P/N434Y |
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−07 | M252Y/N286E/T307Q/Q311A |
| F580 | 8.60E−07 | M252Y/N286E/T307Q/Q311H |
| F581 | 7.20E−08 | M252Y/T256E/N286E/N434Y |
| F582 | 7.50E−07 | S239K/M252Y/V308P |
| F583 | 7.80E−07 | S239K/M252Y/V308P/E382A |
| F584 | 6.30E−07 | S239K/M252Y/T256E/V308P |
| F585 | 2.90E−07 | S239K/M252Y/N286E/V308P |

TABLE 5-15

| | | |
|---|---|---|
| F586 | 1.40E−07 | S239K/M252Y/N286E/V308P/M428I |
| F587 | 1.90E−07 | M252Y/N286E/M428L/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−08 | S239K/M252Y/T256E/V308P/M428I/N434Y |
| F595 | 1.80E−07 | S239K/M252Y/M428I/N434Y |
| F596 | 4.00E−07 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |
| F600 | 2.80E−07 | M252Y/T256Q/E382A/N434Y |
| F601 | 9.60E−09 | M252Y/N286E/V308P/N434Y |

TABLE 5-15-continued

| | | |
|---|---|---|
| F608 | | G236A/S239D/I332E |
| F611 | 2.80E-07 | M252Y/V305T/T307P/V308I/L309A/N434Y |
| F612 | 3.60E-07 | M252Y/T307P/V308I/L309A/N434Y |
| F613 | | S239D/A330L/I332E |
| F616 | | S239D/K326D/L328Y |
| F617 | 7.40E-07 | S239K/N434W |
| F618 | 6.40E-07 | S239K/V308F/N434Y |
| F619 | 3.10E-07 | S239K/M252Y/N434Y |
| F620 | 2.10E-07 | S239K/M252Y/S254T/N434Y |
| F621 | 1.50E-07 | S239K/M252Y/T307A/Q311H/N434Y |
| F622 | 3.50E-07 | S239K/M252Y/T256Q/N434Y |
| F623 | 1.80E-07 | S239K/M252Y/N434W |
| F624 | 1.40E-08 | S239K/P257A/N286E/T307Q/M428L/N434Y |
| F625 | 7.60E-08 | S239K/P257A/T307Q/M428L/N434Y |
| F626 | 1.30E-06 | V308P |
| F629 | 3.90E-08 | M252Y/V279L/V308P/N434Y |
| F630 | 3.70E-08 | S239K/M252Y/V279L/V308P/N434Y |
| F633 | 2.40E-08 | M252Y/V282D/V308P/N434Y |
| F634 | 3.20E-08 | S239K/M252Y/V282D/V308P/N434Y |
| F635 | 4.50E-08 | M252Y/V284K/V308P/N434Y |
| F636 | 4.80E-08 | S239K/M252Y/V284K/V308P/N434Y |
| F637 | 1.50E-07 | M252Y/K288S/V308P/N434Y |

TABLE 5-16

| | | |
|---|---|---|
| F638 | 1.40E-07 | S239K/M252Y/K288S/V308P/N434Y |
| F639 | 2.70E-08 | M252Y/V308P/G385R/N434Y |
| F640 | 3.60E-08 | S239K/M252Y/V308P/G385R/N434Y |
| F641 | 3.00E-08 | M252Y/V308P/Q386K/N434Y |
| F642 | 3.00E-08 | S239K/M252Y/V308P/Q386K/N434Y |
| F643 | 3.20E-08 | L235G/G236R/S239K/M252Y/V308P/N434Y |
| F644 | 3.00E-08 | G236R/S239K/M252Y/V308P/N434Y |
| F645 | 3.30E-08 | S239K/M252Y/V308P/L328R/N434Y |
| F646 | 3.80E-08 | S239K/M252Y/N297A/V308P/N434Y |
| F647 | 2.90E-08 | P238D/M252Y/V308P/N434Y |
| F648 | | P238D |
| F649 | 1.20E-07 | S239K/M252Y/N286E/N434Y |
| F650 | 1.70E-07 | S239K/M252Y/T256E/N434Y |
| F651 | 1.80E-07 | S239K/M252Y/Q311A/N434Y |
| F652 | 2.40E-07 | P238D/M252Y/N434Y |
| F654 | 3.20E-08 | L235K/S239K/M252Y/V308P/N434Y |
| F655 | 3.40E-08 | L235R/S239K/M252Y/V308P/N434Y |
| F656 | 3.30E-08 | G237K/S239K/M252Y/V308P/N434Y |
| F657 | 3.20E-08 | G237R/S239K/M252Y/V308P/N434Y |
| F658 | 3.20E-08 | P238K/S239K/M252Y/V308P/N434Y |
| F659 | 3.00E-08 | P238R/S239K/M252Y/V308P/N434Y |
| F660 | 3.10E-08 | S239K/M252Y/V308P/P329K/N434Y |
| F661 | 3.40E-08 | S239K/M252Y/V308P/P329R/N434Y |
| F663 | 6.40E-09 | S239K/M252Y/N286E/T307Q/V308P/Q311A/N434Y |
| F664 | 3.90E-08 | M252Y/N286A/V308P/N434Y |
| F665 | 2.00E-08 | M252Y/N286D/V308P/N434Y |
| F666 | 2.10E-08 | M252Y/N286F/V308P/N434Y |
| F667 | 3.00E-08 | M252Y/N286G/V308P/N434Y |
| F668 | 4.00E-08 | M252Y/N286H/V308P/N434Y |
| F669 | 3.50E-08 | M252Y/N286I/V308P/N434Y |
| F670 | 2.10E-07 | M252Y/N286K/V308P/N434Y |
| F671 | 2.20E-08 | M252Y/N286L/V308P/N434Y |
| F672 | 2.40E-08 | M252Y/N286M/V308P/N434Y |
| F673 | 2.30E-08 | M252Y/N286P/V308P/N434Y |

TABLE 5-17

| | | |
|---|---|---|
| F674 | 3.20E-08 | M252Y/N286Q/V308P/N434Y |
| F675 | 5.10E-08 | M252Y/N286R/V308P/N434Y |
| F676 | 3.20E-08 | M252Y/N286S/V308P/N434Y |
| F677 | 4.70E-08 | M252Y/N286T/V308P/N434Y |
| F678 | 3.30E-08 | M252Y/N286V/V308P/N434Y |
| F679 | 1.70E-08 | M252Y/N286W/V308P/N434Y |
| F680 | 1.50E-08 | M252Y/N286Y/V308P/N434Y |
| F681 | 4.90E-08 | M252Y/K288A/V308P/N434Y |
| F682 | 8.20E-08 | M252Y/K288D/V308P/N434Y |
| F683 | 5.00E-08 | M252Y/K288E/V308P/N434Y |
| F684 | 5.10E-08 | M252Y/K288F/V308P/N434Y |
| F685 | 5.30E-08 | M252Y/K288G/V308P/N434Y |
| F686 | 4.60E-08 | M252Y/K288H/V308P/N434Y |

TABLE 5-17-continued

| | | |
|---|---|---|
| F687 | 4.90E-08 | M252Y/K288I/V308P/N434Y |
| F688 | 2.80E-08 | M252Y/K288L/V308P/N434Y |
| F689 | 4.10E-08 | M252Y/K288M/V308P/N434Y |
| F690 | 1.00E-07 | M252Y/K288N/V308P/N434Y |
| F691 | 3.20E-07 | M252Y/K288P/V308P/N434Y |
| F692 | 3.90E-08 | M252Y/K288Q/V308P/N434Y |
| F693 | 3.60E-08 | M252Y/K288R/V308P/N434Y |
| F694 | 4.70E-08 | M252Y/K288V/V308P/N434Y |
| F695 | 4.00E-08 | M252Y/K288W/V308P/N434Y |
| F696 | 4.40E-08 | M252Y/K288Y/V308P/N434Y |
| F697 | 3.10E-08 | S239K/M252Y/V308P/N325G/N434Y |
| F698 | 2.20E-08 | M252Y/N286E/T307Q/Q311A/N434Y |
| F699 | 2.30E-08 | S239K/M252Y/N286E/T307Q/Q311A/N434Y |
| F700 | 5.20E-08 | M252Y/V308P/L328E/N434Y |
| F705 | 7.10E-09 | M252Y/N286E/V308P/M428I/N434Y |
| F706 | 1.80E-08 | M252Y/N286E/T307Q/Q311A/M428I/N434Y |
| F707 | 5.90E-09 | M252Y/N286E/T307Q/V308P/Q311A/N434Y |
| F708 | 4.10E-09 | M252Y/N286E/T307Q/V308P/Q311A/M428I/N434Y |
| F709 | 2.00E-08 | S239K/M252Y/N286E/T307Q/Q311A/M428I/N434Y |
| F710 | 1.50E-08 | P238D/M252Y/N286E/T307Q/Q311A/M428I/N434Y |
| F711 | 6.50E-08 | S239K/M252Y/T307Q/Q311A/N434Y |

TABLE 5-18

| | | |
|---|---|---|
| F712 | 6.00E-08 | P238D/M252Y/T307Q/Q311A/N434Y |
| F713 | 2.00E-08 | P238D/M252Y/N286E/T307Q/Q311A/N434Y |
| F714 | 2.30E-07 | P238D/M252Y/N325S/N434Y |
| F715 | 2.30E-07 | P238D/M252Y/N325M/N434Y |
| F716 | 2.70E-07 | P238D/M252Y/N325L/N434Y |
| F717 | 2.60E-07 | P238D/M252Y/N325I/N434Y |
| F718 | 2.80E-07 | P238D/M252Y/Q295M/N434Y |
| F719 | 7.40E-08 | P238D/M252Y/N325G/N434Y |
| F720 | 2.40E-08 | M252Y/T307Q/V308P/Q311A/N434Y |
| F721 | 1.50E-08 | M252Y/T307Q/V308P/Q311A/M428I/N434Y |
| F722 | 2.70E-07 | P238D/M252Y/A327G/N434Y |
| F723 | 2.80E-07 | P238D/M252Y/L328D/N434Y |
| F724 | 2.50E-07 | P238D/M252Y/L328E/N434Y |
| F725 | 4.20E-08 | L235K/G237R/S239K/M252Y/V308P/N434Y |
| F726 | 3.70E-08 | L235K/P238K/S239K/M252Y/V308P/N434Y |
| F729 | 9.20E-07 | T307A/Q311A/N434Y |
| F730 | 6.00E-07 | T307Q/Q311A/N434Y |
| F731 | 8.50E-07 | T307A/Q311H/N434Y |
| F732 | 6.80E-07 | T307Q/Q311H/N434Y |
| F733 | 3.20E-07 | M252Y/L328E/N434Y |
| F734 | 3.10E-07 | G236D/M252Y/L328E/N434Y |
| F736 | 3.10E-07 | M252Y/S267M/L328E/N434Y |
| F737 | 3.10E-07 | M252Y/S267L/L328E/N434Y |
| F738 | 3.50E-07 | P238D/M252Y/T307P/N434Y |
| F739 | 2.20E-07 | M252Y/T307P/Q311A/N434Y |
| F740 | 2.90E-07 | M252Y/T307P/Q311H/N434Y |
| F741 | 3.10E-07 | P238D/T250A/M252Y/N434Y |
| F744 | 9.90E-07 | P238D/T250F/M252Y/N434Y |
| F745 | 6.60E-07 | P238D/T250G/M252Y/N434Y |
| F746 | 6.00E-07 | P238D/T250H/M252Y/N434Y |
| F747 | 2.80E-07 | P238D/T250I/M252Y/N434Y |
| F749 | 5.10E-07 | P238D/T250L/M252Y/N434Y |
| F750 | 3.00E-07 | P238D/T250M/M252Y/N434Y |
| F751 | 5.30E-07 | P238D/T250N/M252Y/N434Y |

TABLE 5-19

| | | |
|---|---|---|
| F753 | 1.80E-07 | P238D/T250Q/M252Y/N434Y |
| F755 | 3.50E-07 | P238D/T250S/M252Y/N434Y |
| F756 | 3.70E-07 | P238D/T250V/M252Y/N434Y |
| F757 | 1.20E-06 | P238D/T250W/M252Y/N434Y |
| F758 | 1.40E-06 | P238D/T250Y/M252Y/N434Y |
| F759 | | L235K/S239K |
| F760 | | L235R/S239K |
| F761 | 1.10E-06 | P238D/N434Y |
| F762 | 3.60E-08 | L235K/S239K/M252Y/N286E/T307Q/Q311A/N434Y |
| F763 | 3.50E-08 | L235R/S239K/M252Y/N286E/T307Q/Q311A/N434Y |
| F764 | 6.30E-07 | P238D/T307Q/Q311A/N434Y |
| F765 | 8.50E-08 | P238D/M252Y/T307Q/L309E/Q311A/N434Y |
| F766 | 6.00E-07 | T307A/L309E/Q311A/N434Y |
| F767 | 4.30E-07 | T307Q/L309E/Q311A/N434Y |

TABLE 5-19-continued

| | | |
|---|---|---|
| F768 | 6.40E-07 | T307A/L309E/Q311H/N434Y |
| F769 | 4.60E-07 | T307Q/L309E/Q311H/N434Y |
| F770 | 3.00E-07 | M252Y/T256A/N434Y |
| F771 | 4.00E-07 | M252Y/E272A/N434Y |
| F772 | 3.80E-07 | M252Y/K274A/N434Y |
| F773 | 3.90E-07 | M252Y/V282A/N434Y |
| F774 | 4.00E-07 | M252Y/N286A/N434Y |
| F775 | 6.20E-07 | M252Y/K338A/N434Y |
| F776 | 3.90E-07 | M252Y/K340A/N434Y |
| F777 | 3.90E-07 | M252Y/E345A/N434Y |
| F779 | 3.90E-07 | M252Y/N361A/N434Y |
| F780 | 3.90E-07 | M252Y/Q362A/N434Y |
| F781 | 3.70E-07 | M252Y/S375A/N434Y |
| F782 | 3.50E-07 | M252Y/Y391A/N434Y |
| F783 | 4.00E-07 | M252Y/D413A/N434Y |
| F784 | 5.00E-07 | M252Y/L309A/N434Y |
| F785 | 7.40E-07 | M252Y/L309H/N434Y |
| F786 | 2.80E-08 | M252Y/S254T/N286E/T307Q/Q311A/N434Y |
| F787 | 8.80E-08 | M252Y/S254T/T307Q/L309E/Q311A/N434Y |
| F788 | 4.10E-07 | M252Y/N315A/N434Y |

TABLE 5-20

| | | |
|---|---|---|
| F789 | 1.50E-07 | M252Y/N315D/N434Y |
| F790 | 2.70E-07 | M252Y/N315E/N434Y |
| F791 | 4.40E-07 | M252Y/N315F/N434Y |
| F792 | 4.40E-07 | M252Y/N315G/N434Y |
| F793 | 3.30E-07 | M252Y/N315I/N434Y |
| F794 | 4.10E-07 | M252Y/N315K/N434Y |
| F795 | 3.10E-07 | M252Y/N315L/N434Y |
| F796 | 3.40E-07 | M252Y/N315M/N434Y |
| F798 | 3.50E-07 | M252Y/N315Q/N434Y |
| F799 | 4.10E-07 | M252Y/N315R/N434Y |
| F800 | 3.80E-07 | M252Y/N315S/N434Y |
| F801 | 4.40E-07 | M252Y/N315T/N434Y |
| F802 | 3.30E-07 | M252Y/N315V/N434Y |
| F803 | 3.60E-07 | M252Y/N315W/N434Y |
| F804 | 4.00E-07 | M252Y/N315Y/N434Y |
| F805 | 3.00E-07 | M252Y/N325A/N434Y |
| F806 | 3.10E-07 | M252Y/N384A/N434Y |
| F807 | 3.20E-07 | M252Y/N389A/N434Y |
| F808 | 3.20E-07 | M252Y/N389A/N390A/N434Y |
| F809 | 2.20E-07 | M252Y/S254T/T256S/N434Y |
| F810 | 2.20E-07 | M252Y/A378V/N434Y |
| F811 | 4.90E-07 | M252Y/E380S/N434Y |
| F812 | 2.70E-07 | M252Y/E382V/N434Y |
| F813 | 2.80E-07 | M252Y/S424E/N434Y |
| F814 | 1.20E-07 | M252Y/N434Y/Y436I |
| F815 | 5.50E-07 | M252Y/N434Y/T437R |
| F816 | 3.60E-07 | P238D/T250V/M252Y/T307P/N434Y |
| F817 | 9.80E-08 | P238D/T250V/M252Y/T307Q/Q311A/N434Y |
| F819 | 1.40E-07 | P238D/M252Y/N286E/N434Y |
| F820 | 3.40E-07 | L235K/S239K/M252Y/N434Y |
| F821 | 3.10E-07 | L235R/S239K/M252Y/N434Y |
| F822 | 1.10E-06 | P238D/T250V/M252Y/W313Y/N434Y |
| F823 | 1.10E-06 | P238D/T250V/M252Y/W313F/N434Y |
| F828 | 2.50E-06 | P238D/T250V/M252Y/I253V/N434Y |

TABLE 5-21

| | | |
|---|---|---|
| F831 | 1.60E-06 | P238D/T250V/M252Y/R255A/N434Y |
| F832 | 2.60E-06 | P238D/T250V/M252Y/R255D/N434Y |
| F833 | 8.00E-07 | P238D/T250V/M252Y/R255E/N434Y |
| F834 | 8.10E-07 | P238D/T250V/M252Y/R255F/N434Y |
| F836 | 5.00E-07 | P238D/T250V/M252Y/R255H/N434Y |
| F837 | 5.60E-07 | P238D/T250V/M252Y/R255I/N434Y |
| F838 | 4.30E-07 | P238D/T250V/M252Y/R255K/N434Y |
| F839 | 3.40E-07 | P238D/T250V/M252Y/R255L/N434Y |
| F840 | 4.20E-07 | P238D/T250V/M252Y/R255M/N434Y |
| F841 | 1.10E-06 | P238D/T250V/M252Y/R255N/N434Y |
| F843 | 6.60E-07 | P238D/T250V/M252Y/R255Q/N434Y |
| F844 | 1.30E-06 | P238D/T250V/M252Y/R255S/N434Y |
| F847 | 3.40E-07 | P238D/T250V/M252Y/R255W/N434Y |
| F848 | 8.30E-07 | P238D/T250V/M252Y/R255Y/N434Y |
| F849 | 3.30E-07 | M252Y/D280A/N434Y |

TABLE 5-21-continued

| | | |
|---|---|---|
| F850 | 2.90E-07 | M252Y/D280E/N434Y |
| F852 | 3.30E-07 | M252Y/D280G/N434Y |
| F853 | 3.20E-07 | M252Y/D280H/N434Y |
| F855 | 3.20E-07 | M252Y/D280K/N434Y |
| F858 | 3.20E-07 | M252Y/D280N/N434Y |
| F860 | 3.30E-07 | M252Y/D280Q/N434Y |
| F861 | 3.20E-07 | M252Y/D280R/N434Y |
| F862 | 3.00E-07 | M252Y/D280S/N434Y |
| F863 | 2.70E-07 | M252Y/D280T/N434Y |
| F867 | 2.80E-07 | M252Y/N384A/N389A/N434Y |
| F868 | 2.00E-08 | G236A/S239D/M252Y/N286E/T307Q/Q311A/N434Y |
| F869 | | G236A/S239D |
| F870 | 7.30E-08 | L235K/S239K/M252Y/T307Q/Q311A/N434Y |
| F871 | 7.10E-08 | L235R/S239K/M252Y/T307Q/Q311A/N434Y |
| F872 | 1.30E-07 | L235K/S239K/M252Y/N286E/N434Y |
| F873 | 1.20E-07 | L235R/S239K/M252Y/N286E/N434Y |
| F875 | 4.80E-07 | M252Y/N434Y/Y436A |
| F877 | 8.30E-07 | M252Y/N434Y/Y436E |
| F878 | 1.90E-07 | M252Y/N434Y/Y436F |

TABLE 5-22

| | | |
|---|---|---|
| F879 | 9.20E-07 | M252Y/N434Y/Y436G |
| F880 | 3.90E-07 | M252Y/N434Y/Y436H |
| F881 | 3.10E-07 | M252Y/N434Y/Y436K |
| F882 | 1.30E-07 | M252Y/N434Y/Y436L |
| F883 | 2.10E-07 | M252Y/N434Y/Y436M |
| F884 | 4.00E-07 | M252Y/N434Y/Y436N |
| F888 | 4.80E-07 | M252Y/N434Y/Y436S |
| F889 | 2.20E-07 | M252Y/N434Y/Y436T |
| F890 | 1.10E-07 | M252Y/N434Y/Y436V |
| F891 | 1.70E-07 | M252Y/N434Y/Y436W |
| F892 | 7.10E-08 | M252Y/S254T/N434Y/Y436I |
| F893 | 9.80E-08 | L235K/S239K/M252Y/N434Y/Y436I |
| F894 | 9.20E-08 | L235R/S239K/M252Y/N434Y/Y436I |
| F895 | 2.10E-08 | L235K/S239K/M252Y/N286E/T307Q/Q311A/N315E/N434Y |
| F896 | 2.00E-08 | L235R/S239K/M252Y/N286E/T307Q/Q311A/N315E/N434Y |
| F897 | 9.70E-08 | M252Y/N315D/N384A/N389A/N434Y |
| F898 | 1.70E-07 | M252Y/N315E/N384A/N389A/N434Y |
| F899 | 1.10E-07 | M252Y/N315D/G316A/N434Y |
| F900 | 1.70E-07 | M252Y/N315D/G316D/N434Y |
| F901 | 1.30E-07 | M252Y/N315D/G316E/N434Y |
| F902 | 2.20E-07 | M252Y/N315D/G316F/N434Y |
| F903 | 2.30E-07 | M252Y/N315D/G316H/N434Y |
| F904 | 1.00E-07 | M252Y/N315D/G316I/N434Y |
| F905 | 1.30E-07 | M252Y/N315D/G316K/N434Y |
| F906 | 1.50E-07 | M252Y/N315D/G316L/N434Y |
| F907 | 1.30E-07 | M252Y/N315D/G316M/N434Y |
| F908 | 1.50E-07 | M252Y/N315D/G316N/N434Y |
| F909 | 1.30E-07 | M252Y/N315D/G316P/N434Y |
| F910 | 1.40E-07 | M252Y/N315D/G316Q/N434Y |
| F911 | 1.30E-07 | M252Y/N315D/G316R/N434Y |
| F912 | 1.20E-07 | M252Y/N315D/G316S/N434Y |
| F913 | 1.10E-07 | M252Y/N315D/G316T/N434Y |
| F914 | 1.50E-07 | M252Y/N315D/G316V/N434Y |
| F915 | 2.30E-07 | M252Y/N315D/G316W/N434Y |

TABLE 5-23

| | | |
|---|---|---|
| F917 | 2.50E-07 | M252Y/N286S/N434Y |
| F918 | 2.80E-07 | M252Y/D280E/N384A/N389A/N434Y |
| F919 | 3.30E-07 | M252Y/D280G/N384A/N389A/N434Y |
| F920 | 2.50E-07 | M252Y/N286S/N384A/N389A/N434Y |
| F921 | 1.20E-07 | M252Y/N286E/N384A/N389A/N434Y |
| F922 | 5.90E-08 | L235K/S239K/M252Y/N286E/N434Y/Y436I |
| F923 | 6.00E-08 | L235R/S239K/M252Y/N286E/N434Y/Y436I |
| F924 | 3.40E-08 | L235K/S239K/M252Y/T307Q/Q311A/N434Y/Y436I |
| F925 | 3.20E-08 | L235R/S239K/M252Y/T307Q/Q311A/N434Y/Y436I |
| F926 | 1.10E-07 | L235K/S239K/M252Y/S254T/N434Y/Y436I |
| F927 | 1.00E-07 | L235R/S239K/M252Y/S254T/N434Y/Y436I |
| F928 | 2.90E-08 | M252Y/T307Q/Q311A/N434Y/Y436I |
| F929 | 2.90E-08 | M252Y/S254T/T307Q/Q311A/N434Y/Y436I |
| F930 | 1.40E-07 | P238D/T250V/M252Y/N286E/N434Y |

TABLE 5-23-continued

| | | |
|---|---|---|
| F931 | 1.20E-07 | P238D/T250V/M252Y/N434Y/Y436I |
| F932 | 3.20E-07 | T250V/M252Y/N434Y |
| F933 | 3.00E-07 | L234R/P238D/T250V/M252Y/N434Y |
| F934 | 3.10E-07 | G236K/P238D/T250V/M252Y/N434Y |
| F935 | 3.20E-07 | G237K/P238D/T250V/M252Y/N434Y |
| F936 | 3.20E-07 | G237R/P238D/T250V/M252Y/N434Y |
| F937 | 3.10E-07 | P238D/S239K/T250V/M252Y/N434Y |
| F938 | 1.60E-07 | L235K/S239K/M252Y/N434Y/Y436V |
| F939 | 1.50E-07 | L235R/S239K/M252Y/N434Y/Y436V |
| F940 | 1.50E-07 | P238D/T250V/M252Y/N434Y/Y436V |
| F941 | 1.20E-08 | M252Y/N286E/T307Q/Q311A/N434Y/Y436V |
| F942 | 4.20E-08 | L235K/S239K/M252Y/T307Q/Q311A/N434Y/Y436V |
| F943 | 4.00E-08 | L235R/S239K/M252Y/T307Q/Q311A/N434Y/Y436V |
| F944 | 1.70E-07 | T250V/M252Y/N434Y/Y436V |
| F945 | 1.70E-08 | T250V/M252Y/V308P/N434Y/Y436V |
| F946 | 4.30E-08 | T250V/M252Y/T307Q/Q311A/N434Y/Y436V |
| F947 | 1.10E-08 | T250V/M252Y/T307Q/V308P/Q311A/N434Y/Y436V |
| F954 | 5.30E-07 | M252Y/N434Y/H435K/Y436V |
| F957 | 7.70E-07 | M252Y/N434Y/H435N/Y436V |
| F960 | 8.00E-07 | M252Y/N434Y/H435R/Y436V |

TABLE 5-24

| | | |
|---|---|---|
| F966 | 3.10E-07 | M252Y/S254A/N434Y |
| F970 | 2.50E-06 | M252Y/S254G/N434Y |
| F971 | 2.60E-06 | M252Y/S254H/N434Y |
| F972 | 2.60E-07 | M252Y/S254I/N434Y |
| F978 | 1.30E-06 | M252Y/S254Q/N434Y |
| F980 | 1.80E-07 | M252Y/S254V/N434Y |
| F987 | 4.00E-08 | P238D/T250V/M252Y/T307Q/Q311A/N434Y/Y436V |
| F988 | 6.90E-08 | P238D/T250V/M252Y/N286E/N434Y/Y436V |
| F989 | 1.40E-08 | L235R/S239K/M252Y/V308P/N434Y/Y436V |
| F990 | 9.40E-09 | L235R/S239K/M252Y/T307Q/V308P/Q311A/N434Y/Y436V |
| F991 | 1.30E-08 | L235R/S239K/M252Y/N286E/T307Q/Q311A/N434Y/Y436V |
| F992 | 5.10E-08 | L235R/S239K/M252Y/T307Q/Q311A/M428I/N434Y/Y436V |
| F993 | 3.80E-08 | M252Y/T307Q/Q311A/N434Y/Y436V |
| F994 | 2.80E-07 | M252Y/N325G/N434Y |
| F995 | 2.90E-07 | L235R/P238D/S239K/M252Y/N434Y |
| F996 | 1.30E-07 | L235R/P238D/S239K/M252Y/N434Y/Y436V |
| F997 | 3.80E-07 | K248I/T250V/M252Y/N434Y/Y436V |
| F998 | 8.50E-07 | K248Y/T250V/M252Y/N434Y/Y436V |
| F999 | 2.10E-07 | T250V/M252Y/E258H/N434Y/Y436V |
| F1005 | | N325G |
| F1008 | 1.70E-07 | L235R/S239K/T250V/M252Y/N434Y/Y436V |
| F1009 | 1.20E-08 | L235R/S239K/T250V/M252Y/T307Q/V308P/Q311A/N434Y/Y436V |
| F1010 | 1.90E-07 | L235R/S239K/M252Y/T307A/Q311H/N434Y |
| F1011 | 4.50E-08 | T250V/M252Y/V308P/N434Y |
| F1012 | 4.70E-08 | L235R/S239K/T250V/M252Y/V308P/N434Y |
| F1013 | 3.00E-08 | T250V/M252Y/T307Q/V308P/Q311A/N434Y |
| F1014 | 3.20E-08 | L235R/S239K/T250V/M252Y/T307Q/V308P/Q311A/N434Y |
| F1015 | 2.20E-08 | L235R/S239K/M252Y/T307Q/V308P/Q311A/N434Y |
| F1016 | 3.80E-09 | T250V/M252Y/N286E/T307Q/V308P/Q311A/N434Y/Y436V |
| F1017 | 4.20E-09 | L235R/S239K/T250V/M252Y/N286E/T307Q/V308P/Q311A/N434Y/Y436V |
| F1018 | 3.20E-09 | L235R/S239K/M252Y/N286E/T307Q/V308P/Q311A/N434Y/Y436V |
| F1019 | 3.40E-07 | P238D/T250V/M252Y/N325G/N434Y |
| F1020 | 8.50E-08 | P238D/T250V/M252Y/T307Q/Q311A/N325G/N434Y |

TABLE 5-25

| | | |
|---|---|---|
| F1021 | 3.30E-07 | P238D/T250V/M252Y/N325A/N434Y |
| F1022 | | K326D/L328Y |
| F1023 | 4.40E-08 | S239D/T250V/M252Y/T307Q/Q311A/N434Y/Y436V |
| F1024 | 4.00E-08 | T250V/M252Y/T307Q/Q311A/K326D/L328Y/N434Y/Y436V |
| F1025 | 3.60E-08 | S239D/T250V/M252Y/T307Q/Q311A/K326D/L328Y/N434Y/Y436V |
| F1026 | 8.40E-08 | M252Y/T307A/Q311H/N434Y/Y436V |
| F1027 | 8.60E-08 | L235R/S239K/M252Y/T307A/Q311H/N434Y/Y436V |
| F1028 | 4.60E-08 | G236A/S239D/T250V/M252Y/T307Q/Q311A/N434Y/Y436V |
| F1029 | 5.10E-08 | T250V/M252Y/T307Q/Q311A/I332E/N434Y/Y436V |
| F1030 | | I332E |
| F1031 | 5.30E-08 | G236A/S239D/T250V/M252Y/T307Q/Q311A/I332E/N434Y/Y436V |
| F1032 | 4.30E-08 | P238D/T250V/M252Y/T307Q/Q311A/N325G/N434Y/Y436V |
| F1033 | 1.00E-06 | P238D/N434W |
| F1034 | 1.50E-08 | L235K/S239K/M252Y/V308P/N434Y/Y436V |
| F1035 | 1.00E-08 | L235K/S239K/M252Y/T307Q/V308P/Q311A/N434Y/Y436V |
| F1036 | 1.40E-08 | L235K/S239K/M252Y/N286E/T307Q/Q311A/N434Y/Y436V |
| F1037 | 6.10E-08 | L235K/S239K/M252Y/T307Q/Q311A/M428I/N434Y/Y436V |
| F1038 | 2.80E-07 | L235K/P238D/S239K/M252Y/N434Y |
| F1039 | 1.30E-07 | L235K/P238D/S239K/M252Y/N434Y/Y436V |
| F1040 | 2.00E-07 | L235K/S239K/T250V/M252Y/N434Y/Y436V |
| F1041 | 1.40E-08 | L235K/S239K/T250V/M252Y/T307Q/V308P/Q311A/N434Y/Y436V |
| F1042 | 2.00E-07 | L235K/S239K/M252Y/T307A/Q311H/N434Y |
| F1043 | 5.20E-08 | L235K/S239K/T250V/M252Y/V308P/N434Y |
| F1044 | 3.50E-08 | L235K/S239K/T250V/M252Y/T307Q/V308P/Q311A/N434Y |

TABLE 5-25-continued

| | | |
|---|---|---|
| F1045 | 2.50E−08 | L235K/S239K/M252Y/T307Q/V308P/Q311A/N434Y |
| F1046 | 4.50E−09 | L235K/S239K/T250V/M252Y/N286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235K/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |

TABLE 5-26

| | | |
|---|---|---|
| F1053 | 4.23E−08 | L235R/S239K/T250V/M252Y/T307Q/Q311A/N434Y/Y436V |
| F1058 | 1.31E−07 | M252Y/Q386E/N434Y/Y436V |
| F1059 | 1.39E−07 | M252Y/Q386R/N434Y/Y436V |
| F1060 | 1.43E−07 | M252Y/Q386S/N434Y/Y436V |
| F1061 | 1.19E−07 | M252Y/P387E/N434Y/Y436V |
| F1062 | 1.20E−07 | M252Y/P387R/N434Y/Y436V |
| F1063 | 1.43E−07 | M252Y/P387S/N434Y/Y436V |
| F1064 | 1.32E−07 | M252Y/V422E/N434Y/Y436V |
| F1065 | 1.38E−07 | M252Y/V422R/N434Y/Y436V |
| F1066 | 1.45E−07 | M252Y/V422S/N434Y/Y436V |
| F1067 | 1.26E−07 | M252Y/S424E/N434Y/Y436V |
| F1068 | 1.69E−07 | M252Y/S424R/N434Y/Y436V |
| F1069 | 1.39E−07 | M252Y/N434Y/Y436V/Q438E |
| F1070 | 1.73E−07 | M252Y/N434Y/Y436V/Q438R |
| F1071 | 1.24E−07 | M252Y/N434Y/Y436V/Q438S |
| F1072 | 1.35E−07 | M252Y/N434Y/Y436V/S440E |
| F1073 | 1.34E−07 | M252Y/N434Y/Y436V/S440R |
| F1074 | 1.32E−07 | S239D/M252Y/N434Y/Y436V |
| F1075 | 1.40E−07 | M252Y/K326D/L328Y/N434Y/Y436V |
| F1076 | 1.27E−07 | S239D/M252Y/K326D/L328Y/N434Y/Y436V |
| F1077 | 2.03E−06 | K248N/M252Y/N434Y |
| F1078 | 4.70E−07 | M252Y/E380N/E382S/N434Y |
| F1079 | 3.44E−07 | M252Y/E382N/N384S/N434Y |
| F1080 | 3.19E−07 | M252Y/S424N/N434Y |
| F1081 | 6.20E−07 | M252Y/N434Y/Y436N/Q438T |
| F1082 | 2.76E−07 | M252Y/N434Y/Q438N |
| F1083 | 3.45E−07 | M252Y/N434Y/S440N |
| F1094 | 2.60E−07 | M252Y/N434Y/S442N |
| F1095 | 2.86E−07 | M252Y/S383N/G385S/N434Y |
| F1096 | 2.72E−07 | M252Y/Q386T/N434Y |
| F1097 | 2.82E−07 | M252Y/G385N/P387S/N434Y |
| F1098 | 2.58E−07 | S239D/M252Y/N434Y |
| F1099 | 2.57E−07 | M252Y/K326D/L328Y/N434Y |
| F1100 | 2.41E−07 | S239D/M252Y/K326D/L328Y/N434Y |
| F1101 | 6.59E−08 | S239D/M252Y/T307Q/Q311A/N434Y |
| F1102 | 6.46E−08 | M252Y/T307Q/Q311A/K326D/L328Y/N434Y |
| F1103 | 6.11E−08 | S239D/M252Y/T307Q/Q311A/K326D/L328Y/N434Y |
| F1104 | 1.77E−07 | M252Y/V422E/S424R/N434Y/Y436V |
| F1105 | 1.54E−07 | M252Y/V422S/S424R/N434Y/Y436V |
| F1106 | 1.42E−07 | M252Y/N434Y/Y436V/Q438R/S440E |
| F1107 | 1.23E−07 | M252Y/V422D/N434Y/Y436V |
| F1108 | 1.26E−07 | M252Y/V422K/N434Y/Y436V |
| F1109 | 1.27E−07 | M252Y/V422T/N434Y/Y436V |
| F1110 | 1.33E−07 | M252Y/V422Q/N434Y/Y436V |

TABLE 5-27

| | | |
|---|---|---|
| F1111 | 1.65E−07 | M252Y/S424K/N434Y/Y436V |
| F1112 | 1.23E−07 | M252Y/N434Y/Y436V/Q438K |
| F1113 | 1.18E−07 | M252Y/N434Y/Y436V/S440D |
| F1114 | 1.31E−07 | M252Y/N434Y/Y436V/S440Q |
| F1115 | 1.35E−07 | M252Y/S424N/N434Y/Y436V |
| F1116 | 7.44E−08 | M252Y/T307Q/Q311A/S424N/N434Y |
| F1117 | 4.87E−08 | T250V/M252Y/T307Q/Q311A/S424N/N434Y/Y436V |
| F1118 | 1.32E−08 | T250V/M252Y/T307Q/V308P/Q311A/S424N/N434Y/Y436V |
| F1119 | 1.03E−08 | T250V/M252Y/T307Q/V308P/Q311A/V422E/N434Y/Y436V |
| F1120 | 1.04E−08 | T250V/M252Y/T307Q/V308P/Q311A/S424R/N434Y/Y436V |
| F1121 | 1.04E−08 | T250V/M252Y/T307Q/V308P/Q311A/V422E/S424R/N434Y/Y436V |
| F1122 | 1.37E−08 | T250V/M252Y/T307Q/V308P/Q311A/N434Y/Y436V/Q438R |
| F1123 | 9.55E−09 | T250V/M252Y/T307Q/V308P/Q311A/N434Y/Y436V/S440E |

TABLE 5-27-continued

| | | |
|---|---|---|
| F1124 | 1.22E−08 | T250V/M252Y/T307Q/V308P/Q311A/N434Y/Y436V/Q438R/S440E |
| F1125 | 5.18E−08 | M252Y/T307Q/N434Y/Y436V |
| F1126 | 8.95E−08 | M252Y/T307A/N434Y/Y436V |
| F1127 | 7.94E−08 | M252Y/Q311A/N434Y/Y436V |
| F1128 | 1.17E−07 | M252Y/Q311H/N434Y/Y436V |
| F1129 | 4.48E−08 | M252Y/T307Q/Q311H/N434Y/Y436V |
| F1130 | 5.54E−08 | M252Y/T307A/Q311A/N434Y/Y436V |
| F1131 | 1.29E−07 | L235R/S239K/M252Y/V422E/N434Y/Y436V |
| F1132 | 1.40E−07 | L235R/S239K/M252Y/V422S/N434Y/Y436V |
| F1133 | 1.58E−07 | L235R/S239K/M252Y/S424R/N434Y/Y436V |
| F1134 | 1.66E−07 | L235R/S239K/M252Y/N434Y/Y436V/Q438R |
| F1135 | 1.26E−07 | L235R/S239K/M252Y/N434Y/Y436V/S440E |
| F1136 | 1.63E−07 | L235R/S239K/M252Y/V422E/S424R/N434Y/Y436V |
| F1137 | 1.58E−07 | L235R/S239K/M252Y/V422S/S424R/N434Y/Y436V |
| F1138 | 1.65E−07 | L235R/S239K/M252Y/N434Y/Y436V/Q438R/S440E |
| F1139 | 1.52E−07 | L235R/S239K/M252Y/S424N/N434Y/Y436V |
| F1140 | 1.62E−07 | M252Y/V422E/S424R/N434Y/Y436V/Q438R/S440E |
| F1141 | 1.77E−07 | M252Y/V422S/S424R/N434Y/Y436V/Q438R/S440E |
| F1142 | 1.87E−07 | L235R/S239K/M252Y/V422E/S424R/N434Y/Y436V/Q438R/S440E |
| F1143 | 1.98E−07 | L235R/S239K/M252Y/V422S/S424R/N434Y/Y436V/Q438R/S440E |
| F1144 | 1.44E−08 | L235R/S239K/T250V/M252Y/T307Q/V308P/Q311A/N434Y/Y436V/Q438R/S440E |
| F1145 | 5.23E−08 | T250V/M252Y/T307Q/Q311A/N434Y/Y436V/Q438R/S440E |
| F1146 | 6.24E−08 | L235R/S239K/T250V/M252Y/T307Q/Q311A/N434Y/Y436V/Q438R/S440E |
| F1147 | 7.19E−08 | M252Y/T307Q/Q311A/N434Y/Q438R/S440E |
| F1148 | 7.63E−08 | L235R/S239K/M252Y/T307Q/Q311A/N434Y/Q438R/S440E |
| F1151 | 2.51E−07 | L235R/S239K/M252Y/S424N/N434Y |
| F1152 | 7.38E−08 | L235R/S239K/M252Y/T307Q/Q311A/S424N/N434Y |
| F1153 | 4.85E−08 | L235R/S239K/T250V/M252Y/T307Q/Q311A/S424N/N434Y/Y436V |
| F1154 | 1.34E−08 | L235R/S239K/T250V/M252Y/T307Q/V308P/Q311A/S424N/N434Y/Y436 |

TABLE 5-28

| | | V |
|---|---|---|
| F1157 | 2.09E−07 | M252Y/N434Y/Q438R/S440E |
| F1158 | 2.44E−07 | L235R/S239K/M252Y/N434Y/Q438R/S440E |
| F1159 | 4.79E−07 | S424N/N434W |
| F1160 | 2.88E−07 | V308F/S424N/N434Y |
| F1161 | 1.07E−06 | I332V/S424N/N434Y |
| F1162 | 3.43E−07 | P238D/T250Y/M252Y/N434Y/Y436V |
| F1163 | 1.54E−07 | P238D/T250Y/M252Y/T307Q/Q311A/N434Y |
| F1164 | 6.96E−08 | P238D/T250Y/M252Y/T307Q/Q311A/N434Y/Y436V |
| F1165 | 1.63E−08 | P238D/T250Y/M252Y/T307Q/V308P/Q311A/N434Y/Y436V |
| F1174 | 4.90E−07 | P257I/N434H |
| F1176 | 1.98E−06 | V308F |
| F1178 | 8.72E−07 | V259I/V308F/M428L |
| F1183 | 1.28E−06 | E380A/M428L/N434S |
| F1184 | 1.00E−06 | T307A/M428L/N434S |
| F1185 | 9.17E−07 | T307A/E380A/M428L/N434S |
| F1188 | 1.72E−06 | T307A/E380A/N434H |
| F1189 | 1.57E−07 | M252Y/H433D/N434Y/Y436V/Q438R/S440E |
| F1190 | 2.40E−07 | M252Y/H433E/N434Y/Y436V/Q438R/S440E |
| F1191 | 2.11E−07 | M252Y/N434Y/Y436V/T437A/Q438R/S440E |
| F1192 | 1.27E−07 | M252Y/N434Y/Y436V/T437G/Q438R/S440E |
| F1194 | 1.55E−07 | M252Y/N434Y/Y436V/Q438R/K439D/S440E |
| F1195 | 1.76E−07 | M252Y/N434Y/Y436V/Q438R/S440E/L441A |
| F1196 | 1.51E−07 | M252Y/N434Y/Y436V/Q438R/S440E/L441E |
| F1197 | 9.46E−08 | M252Y/S254T/N434Y/Y436V/Q438R/S440E |
| F1198 | 7.83E−08 | M252Y/T256E/N434Y/Y436V/Q438R/S440E |
| F1199 | 6.25E−08 | M252Y/S254T/T256E/N434Y/Y436V/Q438R/S440E |
| F1200 | 1.26E−07 | T250V/M252Y/S254T/N434Y/Y436V/Q438R/S440E |
| F1201 | 1.07E−07 | T250V/M252Y/T256E/N434Y/Y436V/Q438R/S440E |
| F1202 | 8.81E−08 | T250V/M252Y/S254T/T256E/N434Y/Y436V/Q438R/S440E |
| F1203 | 1.52E−07 | M252Y/T256Q/N434Y/Y436V/Q438R/S440E |
| F1204 | 1.18E−07 | M252Y/S254T/T256Q/N434Y/Y436V/Q438R/S440E |
| F1205 | 1.98E−07 | T250V/M252Y/T256Q/N434Y/Y436V/Q438R/S440E |
| F1206 | 1.69E−07 | T250V/M252Y/S254T/T256Q/N434Y/Y436V/Q438R/S440E |
| F1207 | 1.11E−06 | I332E/M428L/N434S |
| F1208 | 5.71E−07 | L251A/M252Y/N434Y/Y436V |
| F1211 | 1.23E−06 | L251H/M252Y/N434Y/Y436V |
| F1213 | 6.33E−07 | L251N/M252Y/N434Y/Y436V |
| F1216 | 1.16E−06 | L251S/M252Y/N434Y/Y436V |
| F1217 | 1.14E−06 | L251T/M252Y/N434Y/Y436V |
| F1218 | 2.51E−07 | L251V/M252Y/N434Y/Y436V |

TABLE 5-28-continued

| | | V |
|---|---|---|
| F1229 | 2.81E−06 | M252Y/I253V/N434Y/Y436V |
| F1230 | 1.12E−07 | M252Y/N434Y/Y436V/Q438R/S440D |
| F1231 | 9.73E−08 | M252Y/N434Y/Y436V/Q438K/S440E |

TABLE 5-29

| | | |
|---|---|---|
| F1232 | 9.79E−08 | M252Y/N434Y/Y436V/Q438K/S440D |
| F1243 | 1.25E−07 | L235R/S239K/M252Y/S254T/N434Y/Y436V/Q438R/S440E |
| F1244 | 1.02E−07 | L235R/S239K/M252Y/T256E/N434Y/Y436V/Q438R/S440E |
| F1245 | 8.20E−08 | L235R/S239K/M252Y/S254T/T256E/N434Y/Y436V/Q438R/S440E |
| F1246 | 1.73E−07 | L235R/S239K/T250V/M252Y/S254T/N434Y/Y436V/Q438R/S440E |
| F1247 | 1.45E−07 | L235R/S239K/T250V/M252Y/T256E/N434Y/Y436V/Q438R/S440E |
| F1248 | 1.20E−07 | L235R/S239K/T250V/M252Y/S254T/T256E/N434Y/Y436V/Q438R/S440E |
| F1249 | 2.06E−07 | L235R/S239K/M252Y/T256Q/N434Y/Y436V/Q438R/S440E |
| F1250 | 1.66E−07 | L235R/S239K/M252Y/S254T/T256Q/N434Y/Y436V/Q438R/S440E |
| F1251 | 2.77E−07 | L235R/S239K/T250V/M252Y/T256Q/N434Y/Y436V/Q438R/S440E |
| F1252 | 2.33E−07 | L235R/S239K/T250V/M252Y/S254T/T256Q/N434Y/Y436V/Q438R/S440E |
| F1253 | 1.12E−07 | L235R/S239K/M252Y/T307A/N434Y/Y436V/Q438R/S440E |
| F1254 | 6.42E−08 | L235R/S239K/M252Y/T307Q/N434Y/Y436V/Q438R/S440E |
| F1255 | 1.11E−07 | L235R/S239K/M252Y/Q311A/N434Y/Y436V/Q438R/S440E |
| F1256 | 1.56E−07 | L235R/S239K/M252Y/Q311H/N434Y/Y436V/Q438R/S440E |
| F1257 | 7.81E−08 | L235R/S239K/M252Y/T307A/Q311A/N434Y/Y436V/Q438R/S440E |
| F1258 | 1.05E−07 | L235R/S239K/M252Y/T307A/Q311H/N434Y/Y436V/Q438R/S440E |
| F1259 | 4.46E−08 | L235R/S239K/M252Y/T307Q/Q311A/N434Y/Y436V/Q438R/S440E |
| F1260 | 6.53E−08 | L235R/S239K/M252Y/T307Q/Q311H/N434Y/Y436V/Q438R/S440E |
| F1261 | 1.35E−07 | L235R/S239K/M252Y/N434Y/Y436V/Q438R/S440D |
| F1262 | 1.26E−07 | L235R/S239K/M252Y/N434Y/Y436V/Q438K/S440E |
| F1263 | 1.24E−07 | L235R/S239K/M252Y/N434Y/Y436V/Q438K/S440D |
| F1264 | 1.27E−07 | L235R/S239K/M252Y/T256A/N434Y/Y436V/Q438R/S440E |
| F1265 | 1.57E−07 | L235R/S239K/M252Y/T256G/N434Y/Y436V/Q438R/S440E |
| F1266 | 9.99E−08 | L235R/S239K/M252Y/T256N/N434Y/Y436V/Q438R/S440E |
| F1267 | 1.50E−07 | L235R/S239K/M252Y/S254A/N434Y/Y436V/Q438R/S440E |
| F1268 | 2.00E−07 | L235R/S239K/M252Y/H433D/N434Y/Y436V/Q438R/S440E |
| F1269 | 1.69E−07 | L235R/S239K/M252Y/H433D/N434Y/Y436V/Q438K/S440D |
| F1270 | 1.18E−07 | L235R/S239K/M252Y/S254A/N434Y/Y436V/Q438K/S440D |
| F1271 | 2.05E−07 | L235R/S239K/M252Y/S254A/H433D/N434Y/Y436V/Q438R/S440E |
| F1272 | 1.71E−07 | L235R/S239K/M252Y/S254A/H433D/N434Y/Y436V/Q438K/S440D |
| F1273 | 1.53E−07 | L235R/S239K/M252Y/T256Q/N434Y/Y436V/Q438K/S440D |
| F1274 | 2.48E−07 | L235R/S239K/M252Y/T256Q/H433D/N434Y/Y436V/Q438R/S440E |
| F1275 | 2.09E−07 | L235R/S239K/M252Y/T256Q/H433D/N434Y/Y436V/Q438K/S440D |
| F1276 | 1.02E−07 | L235R/S239K/M252Y/T256A/N434Y/Y436V/Q438K/S440D |
| F1277 | 1.69E−07 | L235R/S239K/M252Y/T256A/H433D/N434Y/Y436V/Q438R/S440E |
| F1278 | 1.40E−07 | L235R/S239K/M252Y/T256A/H433D/N434Y/Y436V/Q438K/S440D |
| F1279 | 1.23E−07 | L235R/S239K/M252Y/T256G/N436Y/Y436V/Q438K/S440D |
| F1280 | 2.09E−07 | L235R/S239K/M252Y/T256G/H433D/N434Y/Y436V/Q438R/S440E |
| F1281 | 1.74E−07 | L235R/S239K/M252Y/T256G/H433D/N434Y/Y436V/Q438K/S440D |
| F1282 | 7.69E−08 | L235R/S239K/M252Y/T256N/N434V/Y436V/Q438K/S440D |
| F1283 | 1.34E−07 | L235R/S239K/M252Y/T256N/H433D/N434Y/Y436V/Q438R/S440E |
| F1284 | 1.12E−07 | L235R/S239K/M252Y/T256N/H433D/N434Y/Y436V/Q438K/S440D |
| F1285 | 9.36E−08 | L235R/S239K/M252Y/S254T/N434Y/Y436V/Q438K/S440D |

TABLE 5-30

| | | |
|---|---|---|
| F1286 | 1.57E−07 | L235R/S239K/M252Y/S254T/H433D/N434Y/Y436V/Q438R/S440E |
| F1287 | 1.50E−07 | L235R/S239K/M252Y/S254T/H433D/N434Y/Y436V/Q438K/S440D |
| F1288 | 7.95E−08 | L235R/S239K/M252Y/T256E/N434Y/Y436V/Q438K/S440D |
| F1289 | 1.33E−07 | L235R/S239K/M252Y/T256E/H433D/N434Y/Y436V/Q438R/S440E |
| F1290 | 1.11E−07 | L235R/S239K/M252Y/T256E/H433D/N434Y/Y436V/Q438K/S440D |
| F1291 | 1.51E−07 | L235R/S239K/M252Y/H433D/N434Y/Y436V |
| F1292 | 4.24E−07 | L235R/S239K/H433D/N434W/Y436V/Q438R/S440E |
| F1293 | 1.61E−07 | L235R/S239K/M252Y/T256E/N434Y/Q438R/S440E |
| F1294 | 2.00E−07 | L235R/S239K/M252Y/T256E/N434Y/Y436T/Q438R/S440E |
| F1295 | 9.84E−08 | L235R/S239K/M252Y/T256E/N434Y/Y436F/Q438R/S440E |
| F1296 | 2.27E−07 | L235R/S239K/M252Y/T256E/H433D/N434Y/Q438R/S440E |
| F1297 | 2.5E−07 | L235R/S239K/M252Y/T256E/H433D/N434Y/Y436T/Q438R/S440E |
| F1298 | 1.47E−07 | L235R/S239K/M252Y/T256E/H433D/N434Y/Y436F/Q438R/S440E |
| F1299 | 1.50E−07 | L235R/S239K/M252Y/T256E/N434Y/Q438K/S440D |
| F1300 | 1.63E−07 | L235R/S239K/M252Y/T256E/N434Y/Y436T/Q438K/S440D |
| F1301 | 8.30E−08 | L235R/S239K/M252Y/T256E/N434Y/Y436F/Q438K/S440D |

TABLE 5-30-continued

| | | |
|---|---|---|
| F1302 | 2.15E−07 | L235R/S239K/M252Y/T256E/H433D/N434Y/Q438K/S440D |
| F1303 | 2.10E−07 | L235R/S239K/M252Y/T256E/H433D/N434Y/Y436T/Q438K/S440D |
| F1304 | 1.24E−07 | L235R/S239K/M252Y/T256E/H433D/N434Y/Y436F/Q438K/S440D |
| F1305 | 2.05E−07 | L235R/S239K/M252Y/H433D/N434Y/Y436V/Q438R/S440D |
| F1306 | 1.92E−07 | L235R/S239K/M252Y/H433D/N434Y/Y436V/Q438K/S440E |
| F1307 | 1.44E−07 | L235R/S239K/M252Y/V422A/S424A/N434Y/Y436V |
| F1308 | 2.06E−07 | L235R/S239K/M252Y/V422L/S424L/N434Y/Y436V |
| F1309 | 1.26E−07 | L235R/S239K/M252Y/N434Y/Y436V/Q438A/S440A |
| F1310 | 2.28E−07 | L235R/S239K/M252Y/N434Y/Y436V/Q438L/S440L |
| F1311 | 1.69E−07 | L235R/S239K/M252Y/V422A/S424A/H433D/N434Y/Y436V |
| F1312 | 1.79E−07 | L235R/S239K/M252Y/V422L/S424L/H433D/N434Y/Y436V |
| F1313 | 1.77E−07 | K235R/S239K/M252Y/H433D/N434Y/Y436V/Q438A/S440A |
| F1314 | 2.27E−07 | L235R/S239K/M252Y/H433D/N434Y/Y436V/Q438L/S440L |
| F1315 | 1.52E−07 | G237K/S239K/M252Y/N434Y/Y436V |
| F1316 | 1.49E−07 | G237R/S239K/M252Y/N434Y/Y436V |
| F1317 | 1.38E−07 | S239K/M252Y/P329K/N434Y/Y436V |
| F1318 | 1.43E−07 | S239K/M252Y/P329R/N434Y/Y436V |
| F1319 | 2.67E−07 | M252Y/L328Y/N434Y |
| F1320 | 1.22E−07 | L235R/S239K/M252Y/S254T/N434Y/Y436V/Q438K/S440D |
| F1321 | 1.03E−07 | L235R/S239K/M252Y/S254T/N434Y/Y436V/Q438K/S440E |
| F1322 | 1.60E−07 | L235R/S239K/M252Y/S254T/H433D/N434Y/Y436V/Q438R/S440D |
| F1323 | 1.49E−07 | L235R/S239K/M252Y/S254T/H433D/N434Y/Y436V/Q438K/S440E |
| F1324 | 1.32E−07 | L234A/L235A/M252Y/N434Y/Y436V |
| F1325 | 2.13E−07 | L234A/L235A/M252Y/N297A/N434Y/Y436V |
| F1326 | 1.09E−08 | L234A/L235A/T250V/M252Y/T307Q/V308P/Q311A/N434Y/Y436V |
| F1327 | 1.41E−08 | L234A/L235A/T250V/M252Y/N297A/T307Q/V308P/Q311A/N434Y/Y436V |
| F1328 | 1.52E−07 | L235R/G236R/S239K/M252Y/N434Y/Y436V/Q438K/S440E |
| F1329 | 1.29E−07 | L235R/G236R/S239K/M252Y/S254T/N434Y/Y436V/Q438R/S440E |

TABLE 5-31

| | | |
|---|---|---|
| F1330 | 1.03E−07 | L235R/G236R/S239K/M252Y/T256E/N434Y/Y436V/Q438R/S440E |
| F1331 | 7.75E−08 | L235R/G236R/S239K/M252Y/S254T/T256E/N434Y/Y436V/Q438R/S440E |
| F1333 | 1.23E−07 | L235R/G236R/S239K/M252Y/N434Y/Y436V |
| F1334 | 1.04E−07 | L235R/G236R/S239K/M252Y/N434Y/Y436V/Q438K/S440D |
| F1335 | 8.78E−08 | L235R/G236R/S239K/M252Y/S254T/N434Y/Y436V/Q438K/S440D |
| F1336 | 7.18E−08 | L235R/G236R/S239K/M252Y/T256E/N434Y/Y436V/Q438K/S440D |
| F1337 | 7.41E−08 | L235R/S239K/M252Y/T256E/N434Y/Y436V/Q438K/S440E |
| F1338 | 1.04E−07 | L235R/S239K/M252Y/T256E/H433D/N434Y/Y436V/Q438K/S440E |
| F1339 | 2.51E−07 | L235R/S239K/M252Y/S254T/T256E/H433D/N434Y/Y436T/Q438K/S440E |
| F1340 | 5.58E−08 | L235R/S239K/M252Y/S254T/T256E/N434Y/Y436V/Q438K/S440E |
| F1341 | 3.22E−07 | L235R/S239K/M252Y/S254T/N434Y/Y436T/Q438K/S440E |
| F1342 | 2.51E−07 | L235R/S239K/M252Y/T256E/N434Y/Y436T/Q438K/S440E |
| F1343 | 2.01E−07 | L235R/S239K/M252Y/S254T/T256E/N434Y/Y436T/Q438K/S440E |
| F1344 | 3.96E−07 | L235R/S239K/M252Y/N434Y/Y436T/Q438K/S440E |
| F1345 | 1.05E−07 | L235R/G236R/S239K/M252Y/N434Y/Y436V/Q438K/S440E |
| F1346 | 8.59E−08 | L235R/G236R/S239K/M252Y/S254T/N434Y/Y436V/Q438K/S440E |
| F1347 | 7.14E−08 | L235R/G236R/S239K/M252Y/T256E/N434Y/Y436V/Q438K/S440E |
| F1348 | 5.52E−08 | L235R/G236R/S239K/M252Y/S254T/T256E/N434Y/Y436V/Q438K/S440E |
| F1349 | 3.36E−07 | L235R/S239K/M252Y/N434Y/Y436T/Q438R/S440E |
| F1350 | 1.18E−07 | L235R/S239K/M252Y/N434Y/Y436F/Q438K/S440E |
| F1351 | 1.62E−07 | L235R/S239K/M252Y/N434Y/Y436F/Q438R/S440E |
| F1352 | 3.93E−07 | L235R/S239K/M252Y/H433D/N434Y/Y436T/Q438K/S440E |
| F1353 | 1.33E−07 | L235R/S239K/M252Y/H433D/N434Y/Y436T/Q438R/S440E |
| F1354 | 2.29E−07 | L235R/S239K/M252Y/H433D/N434Y/Y436F/Q438K/S440E |
| F1355 | 2.47E−07 | L235R/S239K/M252Y/H433D/N434Y/Y436F/Q438R/S440E |
| F1356 | 1.58E−07 | G236R/M252Y/L328R/N434Y/Y436V |
| F1357 | 2.81E−07 | L235R/S239K/M252Y/S254T/N434Y/Y436T/Q438K/S440E |
| F1358 | 9.07E−08 | L235R/S239K/M252Y/S254T/N434Y/Y436F/Q438K/S440E |
| F1359 | 1.28E−07 | L235R/S239K/M252Y/S254T/N434Y/Y436F/Q438R/S440E |
| F1360 | 3.12E−07 | L235R/S239K/M252Y/S254T/H433D/N434Y/Y436T/Q438H/S440E |
| F1361 | 3.52E−07 | L235R/S239K/M252Y/S254T/H433D/N434Y/Y436T/Q438R/S440E |
| F1362 | 1.41E−07 | L235R/S239K/M252Y/S254T/H433D/N434Y/Y436F/Q438K/S440E |
| F1363 | 1.90E−07 | L235R/S239K/M252Y/S254T/H433D/N434Y/Y436F/Q438R/S440E |
| F1364 | 7.49E−08 | L235R/S239K/M252Y/T256E/M434Y/Y436F/Q438K/S440E |
| F1365 | 3.14E−07 | L235R/S239K/M252Y/T256E/H433D/N434Y/Y436T/Q438K/S440E |
| F1366 | 1.17E−07 | L235R/S239K/M252Y/T256E/H433D/N434Y/Y436F/Q438K/S440E |
| F1367 | 1.79E−07 | L235R/S239K/M252Y/S254T/T256E/N434Y/Y436T/Q438R/S440E |
| F1368 | 5.49E−08 | L235R/S239K/M252Y/S254T/T256E/N434Y/Y436F/Q438K/S440E |
| F1369 | 7.60E−08 | L235R/S239K/M252Y/S254T/T256E/N434Y/Y436F/Q438R/S440E |
| F1370 | 9.14E−08 | L235R/S239K/M252Y/S254T/T256E/H433D/N434Y/Y436V/Q438K/S440E |

TABLE 5-32

| | | |
|---|---|---|
| F1371 | 1.09E−07 | L235R/S239K/M252Y/S254T/T256E/H433D/N434Y/Y436V/Q438R/S440E |
| F1372 | 2.28E−07 | L235R/S239K/M252Y/S254T/T256E/H433D/N434Y/Y436T/Q438R/S440E |
| F1373 | 8.67E−08 | L235R/S239K/M252Y/S254T/T256E/H433D/N434Y/Y436F/Q438K/S440E |
| F1374 | 1.20E−07 | L235R/S239K/M252Y/S254T/T256E/H433D/N434Y/Y436F/Q438R/S440E |
| F1375 | 1.03E−07 | L235R/S239K/M252Y/S254T/N434Y/Y436V |
| F1376 | 9.09E−08 | L235R/S239K/M252Y/S254T/T256E/N434Y/Y436V |
| F1377 | 8.27E−08 | L235R/S239K/M252Y/T256E/N434Y/Y436V |
| F1378 | 3.61E−07 | L235R/S239K/M252Y/N434Y/Y436T |
| F1379 | 2.85E−07 | L235R/S239K/M252Y/N434Y/Y436F |
| F1410 | 1.90E−06 | V308P/I332V |
| F1411 | 1.70E−07 | V308P/I332V/M428L/N434S |
| F1413 | 3.70E−08 | L235R/S239K/M252Y/S254T/T256E/T307Q/Q311A/H433D/N434Y/Y436V/Q438K/S440E |
| F1414 | 5.60E−08 | L235R/S239K/M252Y/S254T/T256E/T307Q/H433D/N434Y/Y436V/Q438K/S440E |
| F1415 | 5.90E−08 | L235R/S239K/M252Y/S254T/T256E/Q311A/H433D/N434Y/Y436V/Q438K/S440E |
| F1416 | 1.30E−08 | L235R/S239K/M252Y/S254T/T256E/V308P/H433D/N434Y/Y436V/Q438K/S440E |
| F1417 | 5.90E−08 | L235R/S239K/M252Y/S254T/T256E/H433D/N434W/Y436V/Q438K/S440E |
| F1418 | 7.50E−08 | L235R/S239K/M252Y/S254T/T256E/H433D/N434W/Y436V/Q438R/S440E |
| F1419 | 1.50E−07 | L235R/S239K/M252Y/H433D/N434W/Y436V/Q438R/S440E |
| F1420 | 1.30E−07 | L235R/S239K/M252Y/H433D/N434W/Y436V/Q438K/S440E |
| F1421 | 3.20E−08 | V308P/M428L/N434W |
| F1422 | 1.90E−08 | L235R/S239K/M252Y/T256E/V308P/H433D/N434Y/Y436V/Q438R/S440E |
| F1423 | 1.60E−08 | L235R/S239K/M252Y/T256E/V302D/V308P/H433D/N434Y/Y436V/Q438R/S440E |
| F1424 | 1.60E−08 | L235R/S239K/M252Y/T256E/V302E/V308P/H433D/N434Y/Y436V/Q438R/S440E |
| F1425 | 1.90E−08 | L235R/S239K/M252Y/T256E/V303D/V308P/H433D/N434Y/Y436V/Q438R/S440E |
| F1426 | 1.80E−08 | L235R/S239K/M252Y/T256E/V303E/V308P/H433D/N434Y/Y436V/Q438R/S440E |
| F1428 | 1.50E−08 | L235R/S239K/M252Y/T256E/S304E/V308P/H433D/N434Y/Y436V/Q438R/S440E |
| F1430 | 3.10E−08 | L235R/S239K/M252Y/T256E/V305K/V308P/H433D/N434Y/Y436V/Q438R/S440E |

TABLE 5-33

| | | |
|---|---|---|
| F1433 | 4.50E−08 | L235R/S239K/M252Y/T256E/T307D/V308P/H433D/N434Y/Y436V/Q438R/S440E |
| F1434 | 3.60E−08 | L235R/S239K/M252Y/T256E/T307E/V308P/H433D/N434Y/Y436V/Q438R/S440E |

In a non-limiting embodiment of the present invention, Fc regions in which at least one or more amino acids selected from the group consisting of amino acids at positions 257, 308, 428, and 434 according to EU numbering are different from the amino acids at corresponding positions in the naturally-occurring Fc region are preferably used. Non-limiting examples of such Fc regions preferably include Fc regions containing at least one or more amino acids selected from the group consisting of:

Ala at amino acid position 257;
Pro at amino acid position 308;
Leu at amino acid position 428; and
Tyr at amino acid position 434,
according to EU numbering in the Fc region.

Fcγ Receptor

Fcγ receptor refers to a receptor capable of binding to the Fc region of monoclonal IgG1, IgG2, IgG3, or IgG4 antibodies, and includes all members belonging to the family of proteins substantially encoded by an Fcγ receptor gene. In human, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (FcγRIV, CD16-2), as well as all unidentified mouse FcγRs, FcγR isoforms, and allotypes thereof. Such preferred Fcγ receptors include, for example, human FcγRI (CD64), FcγRIIa (CD32), FcγRIIb (CD32), FcγRIIIa (CD16), and/or FcγRIIIb (CD16). The polynucleotide sequence and amino acid sequence of FcγRI are shown in SEQ ID NOs: 19 (NM_000566.3) and 20 (NP_000557.1), respectively; the polynucleotide sequence and amino acid sequence of FcγRIIa are shown in SEQ ID NOs: 21 (BC020823.1) and 27 (AAH20823.1), respectively; the polynucleotide sequence and amino acid sequence of FcγIIB are shown in SEQ ID NOs: 23 (BC146678.1) and 24 (AAI46679.1), respectively; the polynucleotide sequence and amino acid sequence of FcγRIIIa are shown in SEQ ID NOs: 25 (BC033678.1) and 26 (AAH33678.1), respectively; and the polynucleotide sequence and amino acid sequence of FcγRIIIb are shown in SEQ ID NOs: 27 (BC128562.1) and 28 (AAI28563.1), respectively (RefSeq accession number is shown in each parentheses). Whether an Fcγ receptor has binding activity to the Fc region of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc region, forming an Fc/Fc ligand complex. The molecule may be derived from any organisms. The binding of an Fc ligand to Fc preferably induces one or more effector functions. Such Fc ligands include, but are not limited to, Fc receptors, FcγR, FcαR, FcεR, FcRn, C1q, and C3, mannan-binding lectin, mannose receptor, *Staphylococcus* Protein A, *Staphylococcus* Protein G, and viral FcγRs. The Fc ligands also include Fc receptor homologs (FcRH) (Davis et al., (2002) Immunological Reviews 190, 123-136), which are a family of Fc receptors homologous to FcγR. The Fc ligands also include unidentified molecules that bind to Fc.

In FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2), α chain that binds to the Fc portion of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc portion of IgG results in enhancement of the phagocytic activity and inflammatory cytokine production of macrophages, mast cell degranulation, and the enhanced function of antigen-presenting cells. Fcγ receptors having the ability to transduce the activation signal as described above are also referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are also referred to as inhibitory Fcγ receptors.

Binding Activity to Fcγ Receptor

An embodiment of the present invention provides pharmaceutical compositions inducing an immune response, which comprise as an active ingredient an antigen-binding molecule containing an FcRn-binding domain that contains an Fc region whose binding activity to human Fcγ receptors is higher than the binding activity of the Fc of human IgG to human Fcγ receptors. Whether or not the binding activity of an Fc region to any of the human Fcγ receptors, FcγRI, FcγRIIa, FcγRIIb, FcγRIIIa, and/or FcγRIIIb, is higher than the binding activity of the Fc of human IgG to these human Fcγ receptors can be confirmed by FACS or ELISA format as described above, and also by ALPHA screen (amplified luminescent proximity homogeneous assay), BIACORE method which is based on the surface plasmon resonance (SPR) phenomenon, or such (Proc. Natl. Acad. Sci. USA (2006) 103 (11), 4005-4010).

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising Fc region is immobilized to the donor beads and glutathione S-transferase (GST)-tagged Fcγ receptor is immobilized to the acceptor beads. In the absence of a competitive antigen-binding molecule comprising an altered Fc region, Fcγ receptor interacts with a polypeptide complex comprising a wild-type Fc region, inducing a signal of 520 to 620 nm as a result. A non-tagged antigen-binding molecule having the altered Fc region competes with the antigen-binding molecule comprising a wild-type Fc region for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operably linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE methods. Examples of such inhibition assay are described in Proc. Natl. Acad. Sci. USA (2006) 103(11), 4005-4010.

For the pH conditions to measure the binding activity of the Fc region and the Fcγ receptor contained in the antigen-binding molecule of the present invention, conditions in an acidic pH range or in a neutral pH range may be suitably used. The neutral pH range, as a condition to measure the binding activity of the Fc region and the Fcγ receptor contained in the antigen-binding molecule of the present invention, generally indicates pH 6.7 to pH 10.0. Preferably, it is a range indicated with arbitrary pH values between pH 7.0 and pH 8.0; and preferably, it is selected from pH 7.0, pH 7.1, pH 7.2, pH 7.3, pH 7.4, pH 7.5, pH 7.6, pH 7.7, pH 7.8, pH 7.9, and pH 8.0; and particularly preferably, it is pH 7.4, which is close to the pH of plasma (blood) in vivo. Herein, the acidic pH range, as a condition for having a binding activity of the Fc region and the Fcγ receptor contained in the antigen-binding molecule of the present invention, generally indicates pH 4.0 to pH 6.5. Preferably, it indicates pH 5.5 to pH 6.5, and particularly preferably, it indicates pH 5.8 to pH 6.0, which is close to the pH in the early endosome in vivo. With regard to the temperature used as measurement condition, the binding affinity between the Fc region and the human Fcγ receptor can be evaluated at any temperature between 10° C. and 50° C. Preferably, a temperature between 15° C. and 40° C. is used to determine the binding affinity between the human Fc region and the Fcγ receptor. More preferably, any temperature between 20° C. and 35° C., such as any from 20° C., 21° C., 22° C., 23° C., 24° C., 25° C., 26° C., 27° C., 28° C., 29° C., 30° C., 31° C., 32° C., 33° C., 34° C., or 35° C., can similarly be used to determine the binding affinity between the Fc region and the Fcγ receptor. A temperature of 25° C. is a non-limiting example in an embodiment of the present invention.

Herein, "the binding activity of an Fc region to any of the human Fcγ receptors, FcγR1, FcγRIIa, FcγRIIb, FcγRIIIa, and/or FcγRIIIb, is higher than the binding activity of the Fc region of human IgG to these human Fcγ receptors" means, for example, that based on the above-mentioned analysis methods, the binding activity of an antigen-binding molecule containing a test Fc region is 105% or greater, preferably 110% or greater, 120% or greater, 130% or greater, 140% or greater, particularly preferably 150% or greater, 160% or greater, 170% or greater, 180% or greater, 190% or greater, 200% or greater, 250% or greater, 300% or greater, 350% or greater, 400% or greater, 450% or greater, 500% or greater, 750% or greater, 10 times or greater, 20 times or greater, 30 times or greater, 40 times or greater, and 50 times or greater relative to the binding activity of an antigen-binding molecule containing the Fc region of human IgG as a control.

An Fc region with higher Fcγ receptor-binding activity than the Fcγ receptor-binding activity of a naturally-occurring Fc region may be produced by altering amino acids of the naturally-occurring Fc region. The naturally-occurring Fc region mentioned herein refers to a naturally-occurring Fc region in which the sugar chain at position 297 (EU numbering) is a fucose-attached complex-type sugar chain. Whether the Fcγ receptor-binding activity of an Fc region is higher than that of the naturally-occurring Fc region may be determined appropriately by using methods described in the "Binding activity" section mentioned above.

In the present invention, "alteration of amino acids" or "amino acid alterations" of an Fc region include alteration to an amino acid sequence that is different from the amino acid sequence of the starting Fc region. Any Fc region may be used as a starting domain as long as the modified variant of the starting Fc region can bind to human Fcγ receptors in a neutral pH range. Examples of the starting Fc region preferably include the Fc region of human IgG antibody, or more specifically, a naturally-occurring Fc region in which the sugar chain at position 297 (EU numbering) is a fucose-binding complex-type sugar chain. Furthermore, an Fc region produced by further altering an already altered Fc region used as a starting Fc region may also be preferably used as the Fc region of the present invention. The "starting Fc region" can refer to the polypeptide itself, a composition comprising the starting Fc region, or an amino acid sequence encoding the starting Fc region. Starting Fc regions can comprise a known IgG antibody Fc region produced via recombination described briefly in section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; WO 2009/086320; WO 2008/092117; WO 2007/041635; and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between a modified Fc region of the present invention and its starting Fc region. Amino acid difference between a modified Fc region of the present invention and its starting Fc region can also be preferably specified based on amino acid differences at above-described particular amino acid positions according to EU numbering system.

Known methods such as site-directed mutagenesis (Kunkel et al. (Proc. Natl. Acad. Sci. USA (1985) 82, 488-492)) and Overlap extension PCR can be appropriately employed to modify the amino acids of Fc regions. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

An Fc region having Fcγ receptor-binding activity in a neutral pH range that is contained in the antigen-binding molecules of the present invention may be obtained by any method, but specifically, an Fc region having Fcγ receptor-binding activity in the neutral pH range may be obtained by altering amino acids of human IgG immunoglobulin used as a starting Fc region. Preferred IgG immunoglobulin Fc regions to be altered include, for example, the Fc regions of human IgG (IgG1, IgG2, IgG3, or IgG4, and their variants). As preferred examples of the Fc regions of human IgG (IgG1, IgG2, IgG3, or IgG4, and their variants), the Fc regions of human IgG (IgG1, IgG2, IgG3, or IgG4, and their variants) may be preferably used. The structures of these Fc regions are presented in SEQ ID NO: 11 (A is added to the N terminus of RefSeq accession number AAC82527.1), SEQ ID NO: 12 (A is added to the N terminus of RefSeq accession number AAB59393.1), SEQ ID NO: 13 (RefSeq accession number CAA27268.1), and SEQ ID NO: 14 (A is added to the N terminus of RefSeq accession number AAB59394.1). Furthermore, when using as a test substance an antigen-binding molecule having an Fc region produced by altering an antibody of a certain isotype used as a starting Fc region, an antigen-binding molecule having the Fc region of an IgG monoclonal antibody of that isotype is used as a control to verify effects on the binding activity to Fcγ receptors by the antigen-binding molecule containing the altered Fc region. Antigen-binding molecules containing an Fc region that has been verified to have high Fcγ receptor-binding activity as described above are selected appropriately.

Amino acids at any positions may be altered to other amino acids as long as the Fc region has Fcγ receptor-binding activity in a neutral pH range, or its Fcγ receptor-binding activity in a neutral range can be enhanced. When an antigen-binding molecule contains the Fc region of human IgG1, it is preferred to include alterations that result in enhancement of Fcγ receptor-binding in a neutral pH range compared to the binding activity of the starting Fc region of human IgG1. Amino acid alterations for enhancing Fcγ receptor-binding activity in a neutral pH range have been reported, for example, in WO 2007/024249, WO 2007/021841, WO 2006/031370, WO 2000/042072, WO 2004/029207, WO 2004/099249, WO 2006/105338, WO 2007/041635, WO 2008/092117, WO 2005/070963, WO 2006/020114, WO 2006/116260, and WO 2006/023403.

Examples of such amino acids that can be altered include at least one or more amino acids selected from the group consisting of those at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 according to EU numbering. Alteration of these amino acids enhances the Fcγ receptor-binding of an IgG immunoglobulin Fc region in a neutral pH range.

Particularly preferred alterations for use in the present invention include the following alterations:
the amino acid at position 221 to either Lys or Tyr;
the amino acid at position 222 to any one of Phe, Trp, Glu, and Tyr;
the amino acid at position 223 to any one of Phe, Trp, Glu, and Lys;
the amino acid at position 224 to any one of Phe, Trp, Glu, and Tyr;
the amino acid at position 225 to any one of Glu, Lys, and Trp;
the amino acid at position 227 to any one of Glu, Gly, Lys, and Tyr;
the amino acid at position 228 to any one of Glu, Gly, Lys, and Tyr;
the amino acid at position 230 to any one of Ala, Glu, Gly, and Tyr;
the amino acid at position 231 to any one of Glu, Gly, Lys, Pro, and Tyr;
the amino acid at position 232 to any one of Glu, Gly, Lys, and Tyr;
the amino acid at position 233 to any one of Ala, Asp, Phe, Gly, His, Ile, Lys, Leu, Met, Asn, Gln, Arg, Ser, Thr, Val, Trp, and Tyr;
the amino acid at position 234 to any one of Ala, Asp, Glu, Phe, Gly, His, Ile, Lys, Met, Asn, Pro, Gln, Arg, Ser, Thr, Val, Trp, and Tyr;
the amino acid at position 235 to any one of Ala, Asp, Glu, Phe, Gly, His, Ile, Lys, Met, Asn, Pro, Gln, Arg, Ser, Thr, Val, Trp, and Tyr;
the amino acid at position 236 to any one of Ala, Asp, Glu, Phe, His, Ile, Lys, Leu, Met, Asn, Pro, Gln, Arg, Ser, Thr, Val, Trp, and Tyr;
the amino acid at position 237 to any one of Asp, Glu, Phe, His, Ile, Lys, Leu, Met, Asn, Pro, Gln, Arg, Ser, Thr, Val, Trp, and Tyr;
the amino acid at position 238 to any one of Asp, Glu, Phe, Gly, His, Ile, Lys, Leu, Met, Asn, Gln, Arg, Ser, Thr, Val, Trp, and Tyr;
the amino acid at position 239 to any one of Asp, Glu, Phe, Gly, His, Ile, Lys, Leu, Met, Asn, Pro, Gln, Arg, Thr, Val, Trp, and Tyr;
the amino acid at position 240 to any one of Ala, Ile, Met, and Thr;
the amino acid at position 241 to any one of Asp, Glu, Leu, Arg, Trp, and Tyr;
the amino acid at position 243 to any one of Leu, Glu, Leu, Gln, Arg, Trp, and Tyr;
the amino acid at position 244 to His;
the amino acid at position 245 to Ala;
the amino acid at position 246 to any one of Asp, Glu, His, and Tyr;
the amino acid at position 247 to any one of Ala, Phe, Gly, His, Ile, Leu, Met, Thr, Val, and Tyr;
the amino acid at position 249 to any one of Glu, His, Gln, and Tyr;
the amino acid at position 250 to either Glu or Gln;
the amino acid at position 251 to Phe;
the amino acid at position 254 to any one of Phe, Met, and Tyr;
the amino acid at position 255 to any one of Glu, Leu, and Tyr;
the amino acid at position 256 to any one of Ala, Met, and Pro;
the amino acid at position 258 to any one of Asp, Glu, His, Ser, and Tyr;
the amino acid at position 260 to any one of Asp, Glu, His, and Tyr;
the amino acid at position 262 to any one of Ala, Glu, Phe, Ile, and Thr;
the amino acid at position 263 to any one of Ala, Ile, Met, and Thr;
the amino acid at position 264 to any one of Asp, Glu, Phe, Gly, His, Ile, Lys, Leu, Met, Asn, Pro, Gln, Arg, Ser, Thr, Trp, and Tyr;
the amino acid at position 265 to any one of Ala, Leu, Phe, Gly, His, Ile, Lys, Leu, Met, Asn, Pro, Gln, Arg, Ser, Thr, Val, Val, Trp, and Tyr;

the amino acid at position 266 to any one of Ala, Ile, Met, and Thr;
the amino acid at position 267 to any one of Asp, Glu, Phe, His, Ile, Lys, Leu, Met, Asn, Pro, Gln, Arg, Thr, Val, Trp, and Tyr;
the amino acid at position 268 to any one of Asp, Glu, Phe, Gly, Ile, Lys, Leu, Met, Pro, Gln, Arg, Thr, Val, and Trp;
the amino acid at position 269 to any one of Phe, Gly, His, Ile, Lys, Leu, Met, Asn, Pro, Arg, Ser, Thr, Val, Trp, and Tyr;
the amino acid at position 270 to any one of Glu, Phe, Gly, His, Ile, Leu, Met, Pro, Gln, Arg, Ser, Thr, Trp, and Tyr;
the amino acid at position 271 to any one of Ala, Asp, Glu, Phe, Gly, His, Ile, Lys, Leu, Met, Asn, Gln, Arg, Ser, Thr, Val, Trp, and Tyr;
the amino acid at position 272 to any one of Asp, Phe, Gly, His, Ile, Lys, Leu, Met, Pro, Arg, Ser, Thr, Val, Trp, and Tyr;
the amino acid at position 273 to either Phe or Ile;
the amino acid at position 274 to any one of Asp, Glu, Phe, Gly, His, Ile, Leu, Met, Asn, Pro, Arg, Ser, Thr, Val, Trp, and Tyr;
the amino acid at position 275 to either Leu or Trp;
the amino acid at position 276 to any one of Asp, Glu, Phe, Gly, His, Ile, Leu, Met, Pro, Arg, Ser, Thr, Val, Trp, and Tyr;
the amino acid at position 278 to any one of Asp, Glu, Gly, His, Ile, Lys, Leu, Met, Asn, Pro, Gln, Arg, Ser, Thr, Val, and Trp;
the amino acid at position 279 to Ala;
the amino acid at position 280 to any one of Ala, Gly, His, Lys, Leu, Pro, Gln, Trp, and Tyr;
the amino acid at position 281 to any one of Asp, Lys, Pro, and Tyr;
the amino acid at position 282 to any one of Glu, Gly, Lys, Pro, and Tyr;
the amino acid at position 283 to any one of Ala, Gly, His, Ile, Lys, Leu, Met, Pro, Arg, and Tyr;
the amino acid at position 284 to any one of Asp, Glu, Leu, Asn, Thr, and Tyr;
the amino acid at position 285 to any one of Asp, Glu, Lys, Gln, Trp, and Tyr;
the amino acid at position 286 to any one of Glu, Gly, Pro, and Tyr;
the amino acid at position 288 to any one of Asn, Asp, Glu, and Tyr;
the amino acid at position 290 to any one of Asp, Gly, His, Leu, Asn, Ser, Thr, Trp, and Tyr;
the amino acid at position 291 to any one of Asp, Glu, Gly, His, Ile, Gln, and Thr;
the amino acid at position 292 to any one of Ala, Asp, Glu, Pro, Thr, and Tyr;
the amino acid at position 293 to any one of Phe, Gly, His, Ile, Leu, Met, Asn, Pro, Arg, Ser, Thr, Val, Trp, and Tyr;
the amino acid at position 294 to any one of Phe, Gly, His, Ile, Lys, Leu, Met, Asn, Pro, Arg, Ser, Thr, Val, Trp, and Tyr;
the amino acid at position 295 to any one of Asp, Glu, Phe, Gly, His, Ile, Lys, Met, Asn, Pro, Arg, Ser, Thr, Val, Trp, and Tyr;
the amino acid at position 296 to any one of Ala, Asp, Glu, Gly, His, Ile, Lys, Leu, Met, Asn, Gln, Arg, Ser, Thr, and Val;
the amino acid at position 297 to any one of Asp, Glu, Phe, Gly, His, Ile, Lys, Leu, Met, Pro, Gln, Arg, Ser, Thr, Val, Trp, and Tyr;
the amino acid at position 298 to any one of Ala, Asp, Glu, Phe, His, Ile, Lys, Met, Asn, Gln, Arg, Thr, Val, Trp, and Tyr;
the amino acid at position 299 to any one of Ala, Asp, Glu, Phe, Gly, His, Ile, Lys, Leu, Met, Asn, Pro, Gln, Arg, Ser, Val, Trp, and Tyr;
the amino acid at position 300 to any one of Ala, Asp, Glu, Gly, His, Ile, Lys, Leu, Met, Asn, Pro, Gln, Arg, Ser, Thr, Val, and Trp;
the amino acid at position 301 to any one of Asp, Glu, His, and Tyr;
the amino acid at position 302 to Ile;
the amino acid at position 303 to any one of Asp, Gly, and Tyr;
the amino acid at position 304 to any one of Asp, His, Leu, Asn, and Thr;
the amino acid at position 305 to any one of Glu, Ile, Thr, and Tyr;
the amino acid at position 311 to any one of Ala, Asp, Asn, Thr, Val, and Tyr;
the amino acid at position 313 to Phe;
the amino acid at position 315 to Leu;
the amino acid at position 317 to either Glu or Gln;
the amino acid at position 318 to any one of His, Leu, Asn, Pro, Gln, Arg, Thr, Val, and Tyr;
the amino acid at position 320 to any one of Asp, Phe, Gly, His, Ile, Leu, Asn, Pro, Ser, Thr, Val, Trp, and Tyr;
the amino acid at position 322 to any one of Ala, Asp, Phe, Gly, His, Ile, Pro, Ser, Thr, Val, Trp, and Tyr;
the amino acid at position 323 to Ile;
the amino acid at position 324 to any one of Asp, Phe, Gly, His, Ile, Leu, Met, Pro, Arg, Thr, Val, Trp, and Tyr;
the amino acid at position 325 to any one of Ala, Asp, Glu, Phe, Gly, His, Ile, Lys, Leu, Met, Pro, Gln, Arg, Ser, Thr, Val, Trp, and Tyr;
the amino acid at position 326 to any one of Ala, Asp, Glu, Gly, Ile, Leu, Met, Asn, Pro, Gln, Ser, Thr, Val, Trp, and Tyr;
the amino acid at position 327 to any one of Ala, Asp, Glu, Phe, Gly, His, Ile, Lys, Leu, Met, Asn, Pro, Arg, Thr, Val, Trp, and Tyr;
the amino acid at position 328 to any one of Ala, Asp, Glu, Phe, Gly, His, Ile, Lys, Met, Asn, Pro, Gln, Arg, Ser, Thr, Val, Trp, and Tyr;
the amino acid at position 329 to any one of Asp, Glu, Phe, Gly, His, Ile, Lys, Leu, Met, Asn, Gln, Arg, Ser, Thr, Val, Trp, and Tyr;
the amino acid at position 330 to any one of Cys, Glu, Phe, Gly, His, Ile, Lys, Leu, Met, Asn, Pro, Arg, Ser, Thr, Val, Trp, and Tyr;
the amino acid at position 331 to any one of Asp, Phe, His, Ile, Leu, Met, Gln, Arg, Thr, Val, Trp, and Tyr;
the amino acid at position 332 to any one of Ala, Asp, Glu, Phe, Gly, His, Lys, Leu, Met, Asn, Pro, Gln, Arg, Ser, Thr, Val, Trp, and Tyr;
the amino acid at position 333 to any one of Ala, Asp, Glu, Phe, Gly, His, Ile, Leu, Met, Pro, Ser, Thr, Val, and Tyr;
the amino acid at position 334 to any one of Ala, Glu, Phe, Ile, Leu, Pro, and Thr;
the amino acid at position 335 to any one of Asp, Phe, Gly, His, Ile, Leu, Met, Asn, Pro, Arg, Ser, Val, Trp, and Tyr;
the amino acid at position 336 to any one of Glu, Lys, and Tyr;
the amino acid at position 337 to any one of Glu, His, and Asn;
the amino acid at position 339 to any one of Asp, Phe, Gly, Ile, Lys, Met, Asn, Gln, Arg, Ser, and Thr;

the amino acid at position 376 to either Ala or Val;
the amino acid at position 377 to either Gly or Lys;
the amino acid at position 378 to Asp;
the amino acid at position 379 to Asn;
the amino acid at position 380 to any one of Ala, Asn, and Ser;
the amino acid at position 382 to either Ala or Ile;
the amino acid at position 385 to Glu;
the amino acid at position 392 to Thr;
the amino acid at position 396 to Leu;
the amino acid at position 421 to Lys;
the amino acid at position 427 to Asn;
the amino acid at position 428 to either Phe or Leu;
the amino acid at position 429 to Met;
the amino acid at position 434 to Trp;
the amino acid at position 436 to Ile; and
the amino acid at position 440 to any one of Gly, His, Ile, Leu, and Tyr,
according to EU numbering in the Fc region.

The number of amino acids that are altered is not particularly limited. An amino acid at one position only may be altered, or amino acids at two or more positions may be altered. Examples of combinations of amino acid alterations at two or more positions include the combinations shown in Table 6 (Tables 6-1 to 6-3).

TABLE 6-1

| Combination of amino acids | Combination of amino acids |
| --- | --- |
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |

TABLE 6-2

| | |
| --- | --- |
| F243L/V264I | S239D/N297D/I332E |
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |
| L234E/I332E | S239N/A330L/I332E |
| L234G/I332E | S239N/A330Y/I332E |
| L234I/I332E | S239N/S298A/I332E |

TABLE 6-2-continued

| | |
| --- | --- |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |

TABLE 6-3

| | |
| --- | --- |
| L328Y/I332E | S239D/A330Y/I332E/V240I |
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

Fc Region with Modified Sugar Chains

Fc regions provided by the present invention may include Fc regions that are modified so that the percentage of Fc regions to which a fucose-deficient sugar-chain is attached will become higher, or that the percentage of Fc regions to which bisecting N-acetylglucosamine is added will become higher. It is known that the affinity of an antibody Fc region for FcγRIIIa is enhanced when the fucose residue is removed from N-acetylglucosamine at the reducing end of an N-glycoside-linked complex-type sugar chain bound to the antibody Fc region (Non-Patent Document 20). IgG1 antibodies containing such Fc regions are known to have enhanced ADCC activity, which will be described later; therefore, antigen-binding molecules containing such Fc regions are also useful as antigen-binding molecules to be included in the pharmaceutical compositions of the present invention. Known examples of antibodies in which the fucose residue has been removed from N-acetylglucosamine at the reducing end of an N-glycoside-linked complex-type sugar chain bound to the antibody Fc region are the following: glycosylation-modified antibodies (for example, WO 1999/054342);

antibodies lacking fucose attached to sugar chains (for example, WO 2000/061739, WO 2002/031140, and WO 2006/067913);

antibodies having a sugar chain with bisecting GlcNAc (for example, WO 2002/079255), and such. Methods for producing these antibodies may also be applied to methods for producing antigen-binding molecules containing an altered Fc region which has been modified so that the percentage of the Fc region to which a fucose-deficient sugar-chain is attached will become higher, or that the percentage of the Fc region to which bisecting N-acetylglucosamine is added will become higher.

Antigen-Binding Molecules

In the present invention, this term is used in the broadest sense to refer to molecules containing an antigen-binding domain whose antigen-binding activity changes depending on ion concentration conditions, and an FcRn-binding domain having FcRn-binding activity in a neutral pH range. Specifically, various molecular types may be included as long as they show antigen-binding activity. Molecules in which an antigen-binding domain is linked to an Fc region include, for example, antibodies. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable α/β barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to FcRn and Fcγ receptor. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise the amino acid sequence of at least a portion of an Fc region (for example, a portion of an Fc region responsible for the binding to FcRn or a portion of an Fc region responsible for the binding to Fcγ receptor) and a non-immunoglobulin polypeptide containing, for example, the amino acid sequence of the ligand-binding domain of a receptor or a receptor-binding domain of a ligand. The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Respective domains of the present invention can be linked together via linkers or directly via polypeptide binding. The linkers comprise arbitrary peptide linkers that can be introduced by genetic engineering, synthetic linkers, and linkers disclosed in, for example, Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:
Ser
Gly•Ser
Gly•Gly•Ser
Ser•Gly•Gly
Gly•Gly•Gly•Ser (SEQ ID NO: 29)
Ser•Gly•Gly•Gly (SEQ ID NO: 30)
Gly•Gly•Gly•Gly•Ser (SEQ ID NO: 31)
Ser•Gly•Gly•Gly•Gly (SEQ ID NO: 32)
Gly•Gly•Gly•Gly•Gly•Ser (SEQ ID NO: 33)
Ser•Gly•Gly•Gly•Gly•Gly (SEQ ID NO: 34)
Gly•Gly•Gly•Gly•Gly•Gly•Ser (SEQ ID NO: 35)
Ser•Gly•Gly•Gly•Gly•Gly•Gly (SEQ ID NO: 36)
(Gly•Gly•Gly•Gly•Ser (SEQ ID NO: 31))n
(Ser•Gly•Gly•Gly•Gly (SEQ ID NO: 32))n
where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate ($BS^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSO-COES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types.

In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link respective domains via peptide linkage, polynucleotides encoding the domains are linked together in frame. Known methods for linking polynucleotides in frame include techniques such as ligation of restriction fragments, fusion PCR, and overlapping PCR. Such methods can be appropriately used alone or in combination to construct antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and genetic recombination techniques. Fusing in frame means, when two or more elements or components are polypeptides, linking two or more units of reading frames to form a continuous longer reading frame while maintaining the correct reading frames of the polypeptides. When two molecules of Fab are used as an antigen-binding domain, an antibody, which is an antigen-binding molecule of the present invention where the antigen-binding domain is linked in frame to an Fc region via peptide bond without linker, can be used as a preferred antigen-binding molecule of the present invention.

Neutralizing Activity

An embodiment of the present invention provides pharmaceutical compositions that induce an immune response, which comprise as an active ingredient an antigen-binding molecule having neutralizing activity against an antigen, and containing an antigen-binding domain whose antigen-binding activity changes depending on ion concentration conditions and an FcRn-binding domain having FcRn-binding activity in a neutral pH range. Generally, neutralizing activity refers to activity of inhibiting the biological activity of a ligand, such as viruses and toxins, having biological activity on cells. Thus, substances having neutralizing activity refer to substances that bind to the ligand or the receptor to which the ligand binds, and inhibits the binding between the ligand and the receptor. Receptors blocked from binding with the ligand by the neutralizing activity will not be able to exhibit biological activity through this receptor. When the antigen-binding molecule is an antibody, such an antibody having neutralizing activity is generally called a neutralizing antibody. Neutralizing activity of a test substance may be measured by comparing the biological activity in the presence of a ligand between when the test substance is present and absent.

For example, major possible ligands for the IL-6 receptor preferably include IL-6 as shown in SEQ ID NO: 37. The IL-6 receptor, which is an I-type membrane protein with its amino terminus forming the extracellular domain, forms a hetero-tetramer with a gp130 receptor which has been induced to dimerize by IL-6 (Heinrich et al. (Biochem. J. (1998) 334, 297-314)). Formation of the heterotetramer activates Jak which is associated with the gp130 receptor. Jak undergoes autophosphorylation and phosphorylates the receptor. The phosphorylation site of the receptor and Jak serves as a binding site for SH2-carrying molecules belonging to the Stat family such as Stat3; MAP kinase; PI3/Akt; and other SH2-carrying proteins and adapters. Next, Stat bound to the gp130 receptor is phosphorylated by Jak. The phosphorylated Stat dimerizes and moves into the nucleus, and regulates the transcription of target genes. Jak or Stat can also be involved in signal cascades via receptors of other classes. Deregulated IL-6 signal cascades are observed in inflammation and pathological conditions of autoimmune diseases, and cancers such as prostate cancer and multiple myeloma. Stat3 which may act as an oncogene is constitutively activated in many cancers. In prostate cancer and multiple myeloma, there is a crosstalk between the signaling cascade via the IL-6 receptor and the signaling cascade via the epithelial growth factor receptor (EGFR) family members (Ishikawa et al. (J. Clin. Exp. Hematopathol. (2006) 46 (2), 55-66)).

Such intracellular signaling cascades are different for each cell type; therefore, appropriate target molecules can be determined for each target cell of interest, and are not limited to the above-mentioned factors. Neutralization activity can be evaluated by measuring the activation of in vivo signaling. Furthermore, the activation of in vivo signaling can be detected by using as an index the action of inducing the transcription of a target gene that exists downstream of the in vivo signaling cascade. Change in the transcription activity of the target gene can be detected by the principle of reporter assays. Specifically, a reporter gene such as green fluorescence protein (GFP) or luciferase is placed downstream of a promoter region or a transcription factor of the target gene, its reporter activity is measured, and thereby change in the transcription activity can be measured as the reporter activity. Commercially available kits for measuring the activation of in vivo signaling can be used appropriately (for example, Mercury Pathway Profiling Luciferase System (Clontech)).

Furthermore, for methods of measuring the activity of neutralizing receptors/ligands of the EGF receptor family and such, which normally act on signaling cascades that work toward promoting cell proliferation, the neutralization activity of neutralizing antibodies can be evaluated by measuring the proliferation activity of target cells. For example, when cells are promoted to proliferate by growth factors of the EGF family such as HB-EGF, the inhibitory effect on the proliferation of such cells based on the neutralizing activity of an anti-HB-EGF antibody can be suitably evaluated or measured by the following methods: For evaluating or measuring the cell proliferation inhibitory activity in vitro, a method of measuring the incorporation of [$^3$H]-labeled thymidine added to the medium by viable cells as an index of DNA replication ability is used. As more convenient methods, a dye exclusion method, in which the ability of a cell to exclude a dye such as trypan blue from the cell is measured under the microscope, and the MTT method, are used. The latter method makes use of the ability of viable cells to convert MTT (3-(4,5-dimethylthiazol-2-yl)-2,5-diphenyl tetrazolium bromide), which is a tetrazolium salt, to a blue formazan product. More specifically, a test antibody is added as well as a ligand to the culture solution of a test cell, and after a certain period of time, the MTT solution is added to the culture solution, and this is left to stand for a while for incorporation of MTT into the cell. As a result, MTT, which is a yellow compound, is converted to a blue compound by the action of succinate dehydrogenase in the mitochondria of the cell. After dissolving this blue product for coloration, its absorbance is measured and used as an index for the number of viable cells. In addition to MTT, reagents such as MTS, XTT, WST-1, and WST-8 are also commercially available (Nacalai Tesque, and such) and can be suitably used. For measuring the activity, a binding antibody which is of the same isotype as the anti-HB-EGF antibody but does not have the cell proliferation inhibitory activity can be used as a control antibody in the same manner as the anti-HB-EGF antibody, and the activity can be determined when the anti-HB-EGF antibody shows stronger cell proliferation inhibitory activity than the control antibody.

Cells that can be preferably used for evaluating the activity include, for example, cells promoted to proliferate by HB-EGF such as ovarian cancer cell line RMG-1, and mouse Ba/F3 cells which have been transformed by a vector for expressing a gene encoding hEGFR/mG-CSFR, which is a fusion protein in which the extracellular domain of human EGFR is fused in frame with the intracellular domain of the mouse GCSF receptor. In this way, those skilled in the art can appropriately select cells to be used for evaluating the activity and use them to measure the cell proliferation activity as mentioned above.

Cytotoxic Activity

An embodiment of the present invention provides pharmaceutical compositions that induce an immune response, which comprise as an active ingredient an antigen-binding molecule that has cytotoxic activity against cells expressing an antigen, and contains an antigen-binding domain whose antigen-binding activity changes depending on ion concentration conditions and an FcRn-binding domain having FcRn-binding activity in a neutral pH range. In the present invention, the cytotoxic activity includes, for example, antibody-dependent cell-mediated cytotoxicity (ADCC) activity and complement-dependent cytotoxicity (CDC) activity. In the present invention, CDC activity refers to cytotoxic activity mediated by the complement system. ADCC activity refers to the activity of damaging a target cell when a specific antigen-binding molecule attaches to the surface antigen of an antigen-expressing cell and then a Fcγ receptor-expressing cell (immune cell, or such) binds to the Fc portion of the antigen-binding molecule via the Fcγ receptor. Whether an antigen-binding molecule of interest has ADCC activity or CDC activity can be determined using known methods (for example, Current Protocols in Immunology, Chapter 7. Immunologic studies in humans, Coligan et al. Ed. (1993)).

First, specifically, effector cells, complement solution, and target cells are prepared.

(1) Preparation of Effector Cells

Spleen is removed from a CBA/N mouse or the like, and spleen cells are isolated in RPMI1640 medium (Invitrogen). After washing the cells with the same medium containing 10% fetal bovine serum (FBS, HyClone), the concentration of the washed spleen cells may be adjusted to $5 \times 10^6$/mL to prepare effector cells.

(2) Preparation of Complement Solution

Baby Rabbit Complement (CEDARLANE) is diluted 10-fold in a culture medium (Invitrogen) containing 10% FBS to prepare a complement solution.

(3) Preparation of Target Cells

Target cells can be radioactively labeled by culturing cells expressing an antigen with 0.2 mCi sodium chromate-$^{51}$Cr (GE Healthcare Bio-Sciences) in a DMEM medium containing 10% FBS for one hour at 37° C. After radioactive labeling, the cells are washed three times with RPMI1640 medium containing 10% FBS, and the target cells can be prepared by adjusting the cell concentration to $2 \times 10^5$/mL.

ADCC activity or CDC activity can be measured by the method described below. In the case of measuring ADCC activity, 50 µL each of the target cell and antigen-binding molecule are added to a 96-well U-bottom plate (Becton Dickinson), and allowed to react for 15 minutes on ice. Thereafter, 100 µL of effector cells are added to the plate and left to stand in a carbon dioxide incubator for four hours. The final concentration of the antibody may be adjusted to, for example, 0 or 10 µg/mL. After being left to stand, 100 µL of the supernatant is collected from each well, and the radioactivity is measured with a gamma counter (COBRAII AUTO-GAMMA, MODEL D5005, Packard Instrument Company). The measured value is used to calculate cytotoxic activity (%) according to the formula: $(A-C)/(B-C) \times 100$. A represents the radioactivity (cpm) in each sample, B represents the radioactivity (cpm) in a sample to which 1% NP-40 (Nacalai Tesque) has been added, and C represents the radioactivity (cpm) of a sample containing the target cells only.

Meanwhile, in the case of measuring CDC activity, 50 µL each of the target cell and antigen-binding molecule are added to a 96-well flat-bottomed plate (Becton Dickinson), and allowed to react for 15 minutes on ice. Thereafter, 100 µL of the complement solution is added to the plate, and left to stand in a carbon dioxide incubator for four hours. The final concentration of the antibody may be adjusted to, for example, 0 or 3 µg/mL. After being left to stand, 100 µL of supernatant is collected from each well, and the radioactivity is measured with a gamma counter. The cytotoxic activity can be calculated in the same way as in the measurement of ADCC activity.

Immune Response

Anon-limiting embodiment of the present invention provides pharmaceutical compositions that induce an immune response to an antigen, which comprise as an active ingredient an antigen-binding molecule containing an antigen-binding domain whose antigen-binding activity changes depending on ion concentration conditions and an FcRn-binding domain having FcRn-binding activity in a neutral pH range.

Whether an immune response has been induced may be evaluated by measuring the response in a living organism that has received a pharmaceutical composition that induces an immune response against the aforementioned antigen and contains an antigen-binding molecule as an active ingredient. Examples of the response in the living organism mainly include two immune responses: cellular immunity (induction of cytotoxic T cells that recognize a peptide fragment of the antigen bound to MHC class I) and humoral immunity (induction of the production of antigen-binding antibodies). Methods for evaluating induction of humoral immunity (immune response) include methods for evaluating production of antibodies against an antigen in vivo.

Whether humoral immunity has been induced by a pharmaceutical composition of the present invention that induces an immune response may be evaluated by administering the pharmaceutical composition to a living organism and, in the peripheral blood isolated from the organism, detecting antibodies raised by the organism against the antigen targeted by the antigen-binding molecule contained in the pharmaceutical composition. The titer of an antibody against an antigen can be measured by applying the methods for measuring molecules that specifically bind to an administered molecule using ELISA, ECL, SPR, which are known to those skilled in the art (J. Pharm. Biomed. Anal. 2011 Jul. 15; 55(5):878-88).

Whether cellular immunity has been acquired due to a pharmaceutical composition of the present invention that induces an immune response may be evaluated by administering the pharmaceutical composition to a living organism and, in the peripheral blood isolated from the organism, detecting a subset of CD8-expressing T cells which have a memory-type phenotype and are specific to the antigen targeted by the antigen-binding molecule contained in the pharmaceutical composition. A population of CD8-expressing cells having a memory-type phenotype is a heterogeneous cell population. Specifically, it includes central memory cells, which rapidly divide in response to the antigen, and effector memory cells, which show the memory of effector functions such as cytotoxicity. These subsets are not mutually exclusive. That is, the cells may divide rapidly but may also damage target cells presenting the antigen. There is a commercially available kit (Cytokine Secretion Assay—Cell Enrichment and Detection Kit (Miltenyi Biotec)) for detecting cytokines produced as a result of performing expansion culture of such a subset of antigen-specific, CD8-expressing T cells having a memory-type phenotype. Protocols for isolating such an antigen-specific population are also provided. By using such a kit, both antigen-specific central memory cells and effector memory T cells can be grown efficiently in vitro. Antigen-presenting cells that can stimulate the proliferation of a subset of such T cells may be isolated from the peripheral blood obtained from the organism to which the aforementioned immune-response-inducing pharmaceutical composition has been administered. Dendritic cells pulsed with the antigen or dendritic cells transfected by the antigen (Overes et al. (J. Immunother. (2009) 32, 539-551) may be used as antigen-presenting cells.

Pharmaceutical Compositions

In another aspect, the present invention provides pharmaceutical compositions that induce an immune response to an antigen, which comprise as an active ingredient an antigen-binding molecule containing an antigen-binding domain whose antigen-binding activity changes depending on ion concentration conditions and an FcRn-binding domain having FcRn-binding activity in a neutral pH range. A different embodiment of the present invention relates to cell growth inhibitors or anti-cancer agents that induce an immune response to the aforementioned antigen, which comprise the antigen-binding molecule as an active ingredient. A pharmaceutical composition, a cell growth inhibitor, or an anticancer agent of the present invention is preferably administered to a subject affected with infection by foreign biological species or with cancer, or a subject that may experience recurrence.

In an embodiment of the present invention, a pharmaceutical composition, cell growth inhibitor, or an anticancer agent that induces an immune response to the aforementioned antigen, which comprises as an active ingredient an antigen-binding molecule containing an antigen-binding domain whose antigen-binding activity changes depending on ion concentration conditions and an FcRn-binding domain having FcRn-binding activity in a neutral pH range, may be expressed as use of said antigen-binding molecule in producing said pharmaceutical composition, cell growth inhibitor, or anticancer agent.

In another embodiment of the present invention, it may also be expressed as a method for inducing an immune response to an antigen, which comprises the step of administering a pharmaceutical composition, a cell growth inhibitor, or an anticancer agent which comprises as an active ingredient an antigen-binding molecule containing an antigen-binding domain whose antigen-binding activity changes depending on ion concentration conditions and an FcRn-binding domain having FcRn-binding activity in a neutral pH range.

In another embodiment of the present invention, it may be expressed as an antigen-binding molecule which contains an antigen-binding domain whose antigen-binding activity changes depending on ion concentration conditions and an FcRn-binding domain having FcRn-binding activity in a neutral pH range, for use in inducing an immune response to an antigen.

In another embodiment of the present invention, it may be expressed as a process for producing a pharmaceutical composition, a cell growth inhibitor, or an anticancer agent that induces an immune response to an antigen, which comprises the step of using an antigen-binding molecule containing an antigen-binding domain whose antigen-binding activity changes depending on ion concentration conditions and an FcRn-binding domain having FcRn-binding activity in a neutral pH range.

In the present invention, the phrase "comprises as an active ingredient an antigen-binding molecule containing an antigen-binding domain whose antigen-binding activity changes depending on ion concentration conditions and an FcRn-binding domain having FcRn-binding activity in a neutral pH range" means comprising said antigen-binding molecule as a major active component, and does not limit the content ratio of the antigen-binding molecule.

Furthermore, the present invention may provide pharmaceutical compositions, cell growth inhibitors, and anticancer agents that induce immune response to an antigen, which comprise as an active ingredient, in addition to an antigen-binding molecule that is not bound to the antigen, an antigen-binding molecule that has already bound to the antigen. Moreover, the present invention provides methods for inducing an immune response to an antigen, which comprise administering, in addition to an antigen-binding molecule that is not bound to the antigen, an antigen-binding molecule that has already bound to the antigen.

Furthermore, pharmaceutical compositions, cell growth inhibitors, and anticancer agents of the present invention may include different antigen-binding molecules when necessary. For example, a cocktail of different antigen-binding molecules of the present invention that bind to the same antigen may enhance the action of inducing an immune response, cytotoxic activity, or neutralization activity against cells expressing the antigen, resulting in increased therapeutic effects against diseases caused by the cells expressing the antigen. Alternatively, a pharmaceutical composition, cell growth inhibitor, or anticancer agent of the present invention which comprises an antigen-binding molecule of the present invention containing an antigen-binding domain that binds to an antigen expressed by cells causing a disease to be treated, and also comprises an antigen-binding molecule of the present invention containing an antigen binding domain that binds to another antigen expressed by the cells causing the same disease, is administered to increase therapeutic effects on the disease.

If necessary, a pharmaceutical composition, a cell growth inhibitor, or an anticancer agent of the present invention can be encapsulated into microcapsules (microcapsules made of hydroxymethylcellulose, gelatin, poly[methyl methacrylate], or such), and prepared as colloidal drug delivery systems (such as liposomes, albumin microspheres, microemulsion, nanoparticles, and nanocapsules) (see, for example, "Remington's Pharmaceutical Science 16th edition", Oslo Ed. (1980)). Methods for preparing a drug as a controlled-release drug are also known, and such methods may be applied to the pharmaceutical compositions, cell growth inhibitors, and anticancer agents of the present invention (J. Biomed. Mater. Res. (1981) 15, 267-277; Chemtech. (1982) 12: 98-105; U.S. Pat. No. 3,773,919; European Patent Publications EP 58481 and EP 133988; Biopolymers (1983) 22, 547-556).

The pharmaceutical compositions, cell growth inhibitors, and anticancer agents of the present invention can be administered to patients either orally or parenterally. Parenteral administration is preferred. Such administration methods specifically include administration by injection, transnasal administration, pulmonary administration, and transdermal administration. For administration by injection, a pharmaceutical composition, a cell growth inhibitor, or an anticancer agent of the present invention can be systemically or locally administered by, for example, intravenous injection, intramuscular injection, intraperitoneal injection, and subcutaneous injection. The method of administration can be selected appropriately according to the age and symptoms of the patient. The dose can be selected, for example, within the range from 0.0001 mg to 1000 mg per kilogram body weight per administration. Alternatively, the dose may be selected, for example, within the range from 0.001 mg/body to 100000 mg/body per patient. However, the pharmaceutical compositions, cell growth inhibitors, or anticancer agents of the present invention are not limited to these doses.

The pharmaceutical compositions, cell growth inhibitors, and anticancer agents of the present invention can be formulated according to conventional methods (for example, Remington's Pharmaceutical Science, latest edition, Mark Publishing Company, Easton, U.S.A), and may also contain pharmaceutically acceptable carriers and additives. Examples include surfactants, excipients, coloring agents, flavoring agents, preservatives, stabilizers, buffers, suspending agents, isotonization agents, binders, disintegrants, lubricants, fluidity-promoting agents, and corrigents. Without limitation to these, other commonly used carriers can be suitably used. Specific examples of carriers include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium-chain fatty acid triglycerides, polyoxyethylene hardened castor oil 60, saccharose, carboxymethyl cellulose, corn starch, inorganic salts, and such.

Amino acids contained in the amino acid sequences in the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

Methods for Producing Pharmaceutical Compositions

Anon-limiting embodiment of the present invention provides methods for producing an antigen-binding molecule that induces an immune response, which comprise imparting FcRn-binding activity in a neutral pH range to an FcRn-binding domain that is contained in an antigen-binding molecule containing an antigen-binding domain whose antigen-binding activity changes depending on ion concentration conditions.

In the production methods of the present invention, when the FcRn-binding activity of the FcRn-binding domain that is contained in an antigen-binding molecule containing an antigen-binding domain whose antigen-binding activity changes depending on ion concentration conditions is weak or not detected in a neutral pH range, FcRn-binding activity in the neutral pH range can be imparted to the FcRn-binding domain to produce an antigen-binding molecule of the present invention.

For example, when an antigen-binding domain containing the heavy and light chain variable regions of an anti-FcRn antibody is used as an FcRn binding domain, it is possible to obtain an FcRn-binding domain having FcRn-binding activity in a neutral pH range according to the aforementioned method for obtaining an antigen-binding domain whose antigen-binding activity changes depending on ion concentration conditions. When an Fc region whose FcRn-binding activity in a neutral pH range is weak or undetectable is used as an FcRn-binding domain, an antigen-binding molecule containing an Fc region with desired FcRn-binding activity may be obtained by altering amino acids of the Fc region contained in the antigen-binding molecule. Amino acid alterations of the Fc region that result in such desired binding activity may be identified by comparing the FcRn-binding activity in a neutral pH range before and after amino acid alteration. Those skilled in the art can carry out appropriate amino acid alterations using known methods such as overlap extension PCR or site-directed mutagenesis (Kunkel et al. (Proc. Natl. Acad. Sci. USA (1985) 82, 488-492)) similarly to the aforementioned methods used to alter antigen-binding activity.

An Fc region having FcRn-binding activity in a neutral pH range that is contained in an antigen-binding molecule of the present invention may be obtained by any methods, but specifically, an FcRn-binding domain having FcRn-binding activity or enhanced FcRn-binding activity in a neutral pH range may be obtained by altering amino acids of human IgG immunoglobulin used as a starting Fc region. Examples of preferred IgG immunoglobulin Fc regions to be altered include the Fc region of human IgG (IgG1, IgG2, IgG3, or IgG4, and their variants). Amino acids at any positions may be altered to other amino acids as long as the Fc region has FcRn-binding activity in a neutral pH range or its human FcRn-binding activity in a neutral range can be enhanced. When an antigen-binding molecule contains the Fc region of human IgG1, it is preferred to include alterations that result in enhancement of FcRn-binding in a neutral pH range compared to the binding activity of the starting Fc region of human IgG1. KD values for FcRn in a neutral pH range are determined as mentioned above by the method described in The Journal of Immunology (2009) 182: 7663-7671 (anti-gen-binding molecules are immobilized onto a chip and human FcRn is allowed to flow as an analyte).

Examples of preferred IgG immunoglobulin Fc regions to be altered include the Fc region of human IgG (IgG1, IgG2, IgG3, or IgG4, and their variants). Amino acids at any positions may be altered to other amino acids as long as the Fc region has FcRn-binding activity in a neutral pH range or its human FcRn-binding activity in the neutral range can be enhanced. When an antigen-binding molecule contains the Fc region of human IgG1, it is preferred to include alterations that result in enhancement of FcRn-binding in a neutral pH range compared to the binding activity of the starting Fc region of human IgG1. Examples of such a modified Fc region include altered Fc regions in which amino acids such as those listed in Table 5 above have been altered and which have binding activity in a neutral pH range.

A non-limiting embodiment of the present invention provides methods for producing a pharmaceutical composition that induces an immune response, which comprise the steps of:

(a) determining the antigen-binding activity of an antigen-binding domain under a high calcium ion concentration condition;

(b) determining the antigen-binding activity of the antigen-binding domain under a low calcium ion concentration condition;

(c) selecting the antigen-binding domain whose antigen-binding activity determined in (a) is higher than that determined in (b);

(d) linking a polynucleotide encoding the antigen-binding domain selected in (c) to a polynucleotide encoding an FcRn-binding domain having FcRn-binding activity in a neutral pH range;

(e) culturing cells into which a vector to which the polynucleotide obtained in (d) is operably linked has been introduced; and (f) collecting an antigen-binding molecule from the culture fluid of the cells cultured in (e).

Another non-limiting embodiment of the present invention also provides methods for producing a pharmaceutical composition that induces an immune response, which comprise the steps of:
- (a) determining the antigen-binding activity of an antibody under a high calcium ion concentration condition;
- (b) determining the antigen-binding activity of the antibody under a low calcium ion concentration condition;
- (c) selecting the antibody whose antigen-binding activity determined in (a) is higher than that determined in (b);
- (d) linking a polynucleotide encoding the antigen-binding domain of the antibody selected in (c) to a polynucleotide encoding an FcRn-binding domain having FcRn-binding activity in a neutral pH range;
- (e) culturing cells into which a vector to which the polynucleotide obtained in (d) is operably linked has been introduced; and
- (f) collecting an antigen-binding molecule from the culture fluid of the cells cultured in (e).

Furthermore, a non-limiting embodiment of the present invention provides methods for producing an antigen-binding molecule, which comprise the steps of:
- (a) determining the antigen-binding activity of an antigen-binding domain in a neutral pH range;
- (b) determining the antigen-binding activity of the antigen-binding domain in an acidic pH range;
- (c) selecting the antigen-binding domain whose antigen-binding activity determined in (a) is higher than that determined in (b);
- (d) linking a polynucleotide encoding the antigen-binding domain selected in (c) to a polynucleotide encoding an FcRn-binding domain having FcRn-binding activity in a neutral pH range;
- (e) culturing cells into which a vector to which the polynucleotide obtained in (d) is operably linked has been introduced; and
- (f) collecting an antigen-binding molecule from the culture fluid of the cells cultured in (e).

Furthermore, another non-limiting embodiment of the present invention provides methods for producing an antigen-binding molecule, which comprise the steps of:
- (a) determining the antigen-binding activity of an antibody in a neutral pH range;
- (b) determining the antigen-binding activity of the antibody in an acidic pH range;
- (c) selecting the antibody whose antigen-binding activity determined in (a) is higher than that determined in (b);
- (d) linking a polynucleotide encoding the antigen-binding domain of the antibody selected in (c) to a polynucleotide encoding an FcRn-binding domain having FcRn-binding activity in a neutral pH range;
- (e) culturing cells into which a vector to which the polynucleotide obtained in (d) is operably linked has been introduced; and
- (f) collecting an antigen-binding molecule from the culture fluid of the cells cultured in (e).

In a non-limiting embodiment of the present invention, the antigen-binding domain preferably includes a plurality of antigen-binding domains constituting an antibody fragment library. Furthermore, in a non-limiting embodiment of the present invention, the antibody preferably includes a panel of a group of antibodies that have been monocloned in advance. Methods for producing these libraries and antibodies are described in the "Antibodies" section mentioned above.

For example, the step of obtaining an antigen-binding domain whose antigen-binding activity is lower under a high hydrogen ion concentration condition or low pH, i.e. in an acidic pH range, than under a low hydrogen ion concentration condition or high pH, i.e. in a neutral pH range, which is a non-limiting embodiment of the present invention, preferably includes the step of obtaining an antigen-binding domain including the following steps:
- (a) contacting an antigen with a library of antigen-binding domains in a neutral pH range;
- (b) placing a library of the antigen-binding domains bound to the antigen in step (a) in an acidic pH range; and
- (c) isolating an antigen-binding domain that is dissociated in step (b).

For example, the step of obtaining an antigen-binding domain whose antigen-binding activity is lower under a low calcium ion concentration condition than under a high calcium ion concentration condition, which is a non-limiting embodiment of the present invention, preferably includes the step of obtaining an antigen-binding domain including the following steps:
- (a) contacting an antigen with a library of antigen-binding domains under a high calcium ion concentration condition;
- (b) placing a library of the antigen-binding domains bound to the antigen in step (a) under a low calcium ion concentration condition; and
- (c) isolating an antigen-binding domain that is dissociated in step (b).

Furthermore, the step of obtaining an antigen-binding domain whose antigen-binding activity is lower under a high hydrogen ion concentration condition or low pH, i.e. in an acidic pH range, than under a low hydrogen ion concentration condition or high pH, i.e. in a neutral pH range, which is a non-limiting embodiment of the present invention, preferably includes the step of obtaining an antigen-binding domain including the following steps:
- (a) contacting, in a neutral pH range, a library of antigen-binding domains with a column onto which an antigen has been immobilized;
- (b) eluting an antigen-binding domain bound to the column in step (a) from the column in an acidic pH range; and
- (c) isolating the antigen-binding domain eluted in step (b).

Furthermore, the step of obtaining an antigen-binding domain whose antigen-binding activity is lower under a low calcium ion concentration condition than under a high calcium ion concentration condition, which is a non-limiting embodiment of the present invention, preferably includes the step of obtaining an antigen-binding domain including the following steps:
- (a) contacting, under a high calcium ion concentration condition, a library of antigen-binding domains with a column onto which an antigen has been immobilized;
- (b) eluting an antigen-binding domain bound to the column in step (a) from the column under a low calcium ion concentration condition; and
- (c) isolating the antigen-binding domain eluted in step (b).

Furthermore, the step of obtaining an antigen-binding domain whose antigen-binding activity is lower under a high hydrogen ion concentration condition or low pH, i.e. in an acidic pH range, than under a low hydrogen ion concentration condition or high pH, i.e. in a neutral pH range, which is a non-limiting embodiment of the present invention, preferably includes the step of obtaining an antigen-binding domain including the following steps:

(a) passing, in an acidic pH range, a library of antigen-binding domains through a column onto which an antigen has been immobilized;
(b) collecting antigen-binding domains eluted without binding to the column in step (a);
(c) allowing the antigen-binding domains collected in step (b) to bind to the antigen in a neutral pH range; and
(d) isolating an antigen-binding domain bound to the antigen in step (c).

Furthermore, the step of obtaining an antigen-binding domain whose antigen-binding activity is lower under a low calcium ion concentration condition than under a high calcium ion concentration condition, which is a non-limiting embodiment of the present invention, preferably includes the step of obtaining an antigen-binding domain including the following steps:
(a) passing, under a low calcium ion concentration condition, a library of antigen-binding domains through a column onto which an antigen has been immobilized;
(b) collecting antigen-binding domains eluted without binding to the column in step (a);
(c) allowing the antigen-binding domains collected in step (b) to the antigen under a high calcium ion concentration condition; and
(d) isolating an antigen-binding domain bound to the antigen in step (c).

For example, the step of obtaining an antibody whose antigen-binding activity is lower under a high hydrogen ion concentration condition or low pH, i.e. in an acidic pH range, than under a low hydrogen ion concentration condition or high pH, i.e. in a neutral pH range, which is a non-limiting embodiment of the present invention, preferably includes the step of obtaining an antibody including the following steps:
(a) determining the antigen-binding activity of an antibody in an acidic pH range;
(b) determining the antigen-binding activity of the antibody in a neutral pH range; and
(c) selecting the antibody whose antigen-binding activity determined in the acidic pH range is lower than that determined in the neutral pH range.

For example, the step of obtaining an antibody whose antigen-binding activity is lower under a low calcium ion concentration condition than under a high calcium ion concentration condition, which is a non-limiting embodiment of the present invention, preferably includes the step of obtaining an antibody including the following steps:
(a) determining the antigen-binding activity of an antibody under a low calcium ion concentration condition;
(b) determining the antigen-binding activity of the antibody under a high calcium ion concentration condition; and
(c) selecting the antibody whose antigen-binding activity under the low calcium ion concentration condition is lower than that under the high calcium ion concentration condition.

Furthermore, the step of obtaining an antibody whose antigen-binding activity is lower under a high hydrogen ion concentration condition or low pH, i.e. in an acidic pH range, than under a low hydrogen ion concentration condition or high pH, i.e. in a neutral pH range, which is a non-limiting embodiment of the present invention, preferably includes the step of obtaining an antibody including the following steps:
(a) contacting an antibody with an antigen in a neutral pH range;
(b) obtaining the antibody bound to the antigen in step (a);
(c) placing the antibody obtained in step (b) in an acidic pH range; and
(d) selecting the antibody whose antigen-binding activity in step (c) is weaker than the criterion for the selection in step (b).

Furthermore, the step of obtaining an antibody whose antigen-binding activity is lower under a low calcium ion concentration condition than under a high calcium ion concentration condition, which is a non-limiting embodiment of the present invention, preferably includes the step of obtaining an antibody including the following steps:
(a) contacting an antibody with an antigen under a high calcium ion concentration condition;
(b) obtaining the antibody bound to the antigen in step (a);
(c) placing the antibody obtained in step (b) in a low calcium ion condition; and
(d) selecting the antibody whose antigen-binding activity in step (c) is weaker than the criterion for the selection in step (b).

The above-mentioned steps may be repeated twice or more times. Therefore, the present invention provides antigen-binding domains or antibodies whose antigen-binding activity is lower in an acidic pH range than in a neutral pH range, which are obtained by the above-mentioned screening methods which further comprise the step of repeating steps (a) to (c) or steps (a) to (d) twice or more times. The number of cycles of steps (a) to (c) or (a) to (d) is not particularly limited, but is usually ten or less.

In the aforementioned steps, the antigen-binding activity of an antigen-binding domain or antibody under a high hydrogen ion concentration condition or low pH, i.e. in an acidic pH range, is not particularly limited as long as it is antigen-binding activity at pH 4.0 to 6.5, but antigen-binding activity at pH 4.5 to 6.5 may be preferred. Alternatively, antigen-binding activity at pH 5.0 to 6.5, or antigen-binding activity at pH 5.5 to 6.0 may also be preferred.

More preferred pH includes the pH in early endosomes in vivo, and a specific example is antigen-binding activity at pH5.8. The antigen-binding activity of an antigen-binding domain or antibody under a low hydrogen ion concentration condition or high pH, i.e. in a neutral pH range, is not particularly limited as long as it is antigen-binding activity at pH 6.7 to 10, but antigen-binding activity at pH 6.7 to 9.5 may be preferred. Alternatively, antigen-binding activity at pH 7.0 to 9.5, or antigen-binding activity at pH 7.0 to 8.0 may also be preferred. More preferred pH includes the pH in blood plasma in vivo, and a specific example is antigen-binding activity at pH7.4.

In the aforementioned steps, the antigen-binding activity of an antigen-binding domain or antibody under a low calcium concentration condition is not particularly limited as long as it is antigen-binding activity at an ionized calcium concentration of 0.1 μM to 30 μM, but antigen-binding activity at an ionized calcium concentration of 0.2 μM to 20 μM may be preferred. In another embodiment, antigen-binding activity at 0.5 μM to 10 μM may be preferred. More preferred ionized calcium concentrations include the ionized calcium concentration in early endosomes in vivo, and specific examples include antigen-binding activity at 1 μM to 5 μM and antigen-binding activity at 2 μM to 4 μM. The antigen-binding activity of an antigen-binding domain or antibody under a high calcium concentration condition is not particularly limited as long as it is antigen-binding activity at an ionized calcium concentration of 100 μM to 10 mM, but antigen-binding activity at an ionized calcium concentration of 200 μM to 5 mM may be preferred. In a different embodiment, antigen-binding activity at 500 μM to 2.5 mM may be preferred, and in another embodiment, antigen-binding activity at 200 μM to 2 mM may be preferred. In a different embodiment, antigen-binding activity at 400 μM to 1.5 mM may also be preferred. More preferred ionized calcium concentrations include the ionized calcium concentration in plasma in vivo, and specific examples includes antigen-binding activity at 0.5 mM to 2.5 mM.

FcRn-binding domains having FcRn-binding activity in a neutral pH range, modified Fc regions with Fcγ-receptor-binding activity that is higher than the Fcγ-receptor-binding activity of a naturally-occurring Fc region in which fucose is attached to the sugar chain at position 297 according to EU numbering, and Fc regions including such FcRn-binding domains and modified Fc regions are obtained by methods described in the section "FcRn-binding domains" and "FcRn-binding domains" mentioned above. Polynucleotides encoding each of the domains may be obtained by known genetic recombination methods described later in this section.

Respective domains of the present invention can be linked together via linkers or directly via polypeptide binding. The linkers comprise arbitrary peptide linkers that can be introduced by genetic engineering, synthetic linkers, and linkers disclosed in, for example, Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:
Ser
Gly•Ser
Gly•Gly•Ser
Ser•Gly•Gly
Gly•Gly•Gly•Ser (SEQ ID NO: 29)
Ser•Gly•Gly•Gly (SEQ ID NO: 30)
Gly•Gly•Gly•Gly•Ser (SEQ ID NO: 31)
Ser•Gly•Gly•Gly•Gly (SEQ ID NO: 32)
Gly•Gly•Gly•Gly•Gly•Ser (SEQ ID NO: 33)
Ser•Gly•Gly•Gly•Gly•Gly (SEQ ID NO: 34)
Gly•Gly•Gly•Gly•Gly•Gly•Ser (SEQ ID NO: 35)
Ser•Gly•Gly•Gly•Gly•Gly•Gly (SEQ ID NO: 36)
(Gly•Gly•Gly•Gly•Ser (SEQ ID NO: 31))n
(Ser•Gly•Gly•Gly•Gly (SEQ ID NO: 32))n
where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS³),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types.

In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link respective domains via peptide linkage, polynucleotides encoding the domains are linked together in frame. Known methods for linking polynucleotides in frame include techniques such as ligation of restriction fragments, fusion PCR, and overlapping PCR. Such methods can be appropriately used alone or in combination to construct antigen-binding molecules of the present invention.

Known methods may be appropriately employed for isolating polynucleotides encoding each domain. For example, a polynucleotide sequence encoding an antigen-binding domain is isolated from a phage displaying an antigen-binding domain of interest from a library containing a plurality of antigen-binding domains, by PCR using primers used for constructing the library or primers having the sequence of the phage vector used for constructing the library. In order to obtain genes encoding the antibody variable regions, it is convenient to use the 5'-RACE method using primers for amplifying the variable region genes. First, RNAs extracted from hybridoma cells are used as templates to synthesize cDNAs and thereby obtain a 5'-RACE cDNA library. Commercially available kits such as SMART RACE cDNA amplification kit are appropriately used for synthesis of a 5'-RACE cDNA library.

The obtained 5'-RACE cDNA library is used as a template to amplify antibody genes by PCR. Primers for amplifying mouse antibody genes may be designed based on known antibody gene sequences. The nucleotide sequences of these primers vary depending on the subclass of immunoglobulin. Therefore, it is preferred to determine the subclass in advance using a commercially available kit such as Iso Strip mouse monoclonal antibody isotyping kit (Roche Diagnostics).

More specifically, when acquisition of genes encoding mouse IgG is intended, primers capable of amplifying genes encoding γ1, γ 2a, γ 2b, and γ 3 for the heavy chain, and genes encoding the κ chain and λ chain for the light chain, may be used. To amplify the genes of variable regions of IgG, generally, a primer that anneals to a portion corresponding to the constant region close to the variable region is used as the 3' primer. On the other hand, a primer supplied in the 5'-RACE cDNA library production kit can be used as the 5' primer.

After the polynucleotide sequence of the antigen-binding domain or antibody of the present invention isolated as described above is determined, a polynucleotide containing a fused gene in which this polynucleotide is linked in frame with a polynucleotide encoding an FcRn-binding domain having FcRn-binding activity in a neutral pH range is produced. The produced polynucleotide containing the fused gene is operably linked to a suitable expression vector so that it will be expressed in desired cells.

The terms "cell", "cell line", and "cell culture" are used synonymously herein, and such designations may include all progeny of a cell or cell line. Thus, for example, the terms "transformants" and "transformed cells" include the primary subject cell and cultures derived therefrom without regard for the number of transfers. It is also understood that all progeny may not be precisely identical in DNA content due to deliberate or inadvertent mutations. Mutant progeny that have substantially the same function or biological activity as screened for in the originally transformed cell may also be included. Where distinct designations are intended, such intention will be clear from the context of the description.

When referring to the expression of a coding sequence, the term "control sequences" refers to DNA nucleotide sequences necessary for the expression of an operably linked coding sequence in a particular host organism. The control sequences that are suitable for prokaryotes include, for example, a promoter, optionally an operator sequence, a ribosome binding site, and possibly, other as yet poorly understood sequences. Eukaryotic cells are known to utilize promoters, polyadenylation signals, and enhancers for the expression of a coding sequence.

For a nucleic acid, the term "operably linked" means that the nucleic acid is placed into a functional relationship with another nucleic acid sequence. For example, DNA for a presequence or secretory leader is operably linked to DNA for a polypeptide if it is expressed as a precursor protein that participates in the secretion of the polypeptide. A promoter or enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous and, in the case of a secretory leader, contiguous and in reading frame. However, enhancers do not have to be contiguous. Linking is accomplished by ligation at suitable restriction sites. If such sites do not exist, the synthetic oligonucleotide adaptors or linkers are used in accordance with conventional practice. Furthermore, linked nucleic acids may be produced by the above-mentioned overlap extension PCR technique.

"Ligation" refers to the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation, or by silica purification. The DNA fragments that are to be ligated together are put in solution in equimolar amounts. The solution will contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation of the fragment during the ligation step.

Production of an expression vector containing a polynucleotide encoding an antigen-binding molecule of the present invention, introduction of the expression vector into cells, expression of the polynucleotide in the cells, and acquisition of the expressed antigen-binding molecule from the culture fluid of the cells are carried out according to the methods described in the "Antibodies" section mentioned above.

All prior art references cited in the present specification are herein incorporated by reference.

EXAMPLES

Herein below, the present invention will be specifically described with reference to the Examples, but it is not to be construed as being limited thereto.

[Example 1] Production of a Mouse Model that is Immune Tolerant to Human IL-6 Receptor Since the IL-6 receptor is highly expressed in myeloma, for which the growth factor is the ligand IL-6, anti-human IL-6 receptor antibodies are known to exhibit antitumor effects in an immunodeficient mouse xenograft model of human myeloma (Eur. J. Immunol. 22, 1989-93 (1992)). If mouse anti-IL-6 receptor antibody production can be induced by administering anti-IL-6 receptor antibodies to mice, those anti-IL-6 receptor antibodies may induce acquired immunity and may be shown to be useful as cancer vaccines.

However, since the mouse immune functions do not work in immunodeficient mice that are used as the antitumor models, inducing acquired immunity is impossible. Even if soluble human IL-6 receptors are administered to normal mice, mouse-anti-human IL-6 receptor antibodies will be quickly produced against the human IL-6 receptors which are foreign substances for the mice. Therefore, normal mice cannot be used as they are as systems for evaluating effects of anti-human IL-6 receptor antibodies on the production of mouse anti-human IL-6 receptor antibodies (acquired immunity to the human IL-6 receptor).

On the other hand, in clinical situations in humans, since the antigen targeted by the antibody molecules is a human antigen, humans are immunotolerant toward that targeted self-antigen. In clinical situations in humans, when production of autoantibodies against a target antigen is induced following administration of antibodies against the target antigen, immunotolerance is presumably lost.

Therefore, for an evaluation envisioning the clinical situation in humans regarding whether the antibodies administered to mice can induce acquired immunity against the target human antigen in the mice, it is necessary that the mice is in a state close to immunotolerance against the target human antigen (simply administering a target human antigen to mice would not lead to production of antibodies against the target human antigen by the mice), and it is necessary to establish an assay system for evaluating that, upon administration of antibodies against the target antigen, the near-immunotolerant state is lost and production of autoantibodies against the target antigen is induced.

Therefore, to avoid production of autoantibodies against the target human antigen in the mice by administration of the target human antigen to the mice, an assay system was constructed, in which CD4-positive T cells necessary for inducing antibody production from antigen presentation were sufficiently removed using anti-mouse CD4 antibodies.

The following test model was constructed as a model for maintaining the plasma concentration of the soluble human IL-6 receptor, the target human antigen, at a constant state (approximately 20 ng/mL). An infusion pump (MINI-OSMOTIC PUMP MODEL 2004; alzet) filled with soluble human IL-6 receptor was implanted under the skin on the back of normal mice (C57BL/6J mouse, Charles River Japan) to prepare model animals in which the plasma concentration of soluble human IL-6 receptor was kept in a steady state.

The study was conducted in two groups (n=4 per group). To the group of mice that mimic immune tolerance, a single dose (20 mg/kg) of monoclonal anti-mouse CD4 antibody (R&D) was administered into the caudal vein to inhibit the production of mouse antibodies against soluble human IL-6 receptor. Subsequently, the antibody was similarly administered once in 10 days (hereinafter referred to as anti-mouse CD4 antibody administration group). The other group was used as a control group, i.e., anti-mouse CD4 antibody non-administration group that received no monoclonal anti-mouse CD4 antibody. Subsequently, an infusion pump filled with 92.8 µg/mL soluble human IL-6 receptor was subcutaneously implanted into the back of a mouse. After the implantation of an infusion pump, blood samples were collected over time, immediately followed by centrifugation for 15 minutes at 4° C. and 15,000 rpm to obtain plasma. The separated plasma was stored in a freezer set to −20° C. or lower until the time of measurement. The plasma concentration of soluble human IL-6 receptor (hsIL-6R) was determined by the method described below.

hsIL-6R concentration in mouse plasma was determined using electrochemiluminescence method. An hsIL-6R calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6R antibody (R&D), and tocilizumab, followed by overnight reaction at 37° C. Tocilizumab was prepared at a final concentration of 333 µg/mL. Subsequently, the reaction liquid was dispensed into an MA400 PR Streptavidin Plate (Meso Scale Discovery). In addition, after washing the reaction liquid that was allowed to react at room temperature for 1 hour, Read Buffer T (×4) (Meso Scale Discovery) was dispensed. Subsequently, the reaction liquid was immediately subjected to measurement using a SECTOR PR 400 Reader (Meso Scale Discovery). The concentration of hsIL-6R was calculated from the response of the calibration curve using the SOFTmax PRO analysis software (Molecular Devices). The change in plasma hsIL-6R concentration of each of the normal mice, which was determined by this method, is shown in FIG. 1.

As a result, in all mice of the anti-mouse CD4 antibody non-administered group, a decrease in the plasma hsIL-6R concentration was observed 14 days after implantation of the infusion pump under the skin on the back of the mice. That is, if mouse anti-human IL-6 receptor antibodies are produced, the plasma hsIL-6R concentration will decrease, and this showed that mouse anti-human IL-6 receptor antibodies are produced in these groups. On the other hand, a decrease in the plasma hsIL-6R concentration was not observed in all mice belonging to the anti-mouse CD4 antibody-administered group. Thus, this showed that mouse anti-human IL-6 receptor antibodies were not produced since, throughout the 28 days during which the infusion pump was effective, a nearly constant plasma hsIL-6R concentration (approximately 20 ng/mL) has been maintained.

The above results confirmed that prior administration of anti-mouse CD4 antibody does not lead to induction of acquired immunity in normal mice when the human IL-6 receptor, which is the target antigen, is administered alone. In the Examples that follow, the anti-mouse CD4 antibody-administered model was used as the system for evaluating the induction of acquired immunity toward human IL-6 receptor following anti-human IL-6 receptor antibody administration.

[Example 2] Comparison of the Acquired Immunity-Inducing Effects by Normal Anti-IL-6 Receptor Antibodies and pH-Dependent Anti-Human IL-6 Receptor Antibodies in Normal Mouse Model with Immune Tolerance for the Human IL-6 Receptor For induction of acquired immunity to a target antigen, the target antigen taken up into antigen-presenting cells must be appropriately degraded by lysosomes in the cells, and fragmented peptides of the target antigen must undergo antigen presentation by binding to MHC class I or MHC class II. It is considered that the larger the number of peptides presented as antigens, the stronger the induction of immunity; thus, as a method for enhancing induction of acquired immunity to the target antigen, a method for sending a larger number of the target antigen into the antigen-presenting cells was considered.

Ordinarily, when an antigen is incorporated non-specifically into an antigen-presenting cell, it is transferred as is from the endosome to the lysosome, and therefore, fragmented peptides may be presented as antigens. However, when an ordinary IgG antibody is bound to an antigen, since the IgG antibody is recycled to the cell surface (in plasma) from the inside of the endosome by binding to FcRn, the antigen bound to the antibody may not be transferred to the lysosome and may be recycled to the cell surface (in plasma). Therefore, administration of normal IgG antibodies will suppress degradation of the target antigen. As a result, fragmented peptides of the target antigen which were appropriately degraded in the lysosome in the antigen-presenting cells are not presented as antigens, and rather, induction of acquired immunity against the target antigen is thought to decrease. Accordingly, since IgG antibodies having a pH-dependent binding activity, such that they bind to the target antigen at pH7.4 in the plasma and release the antigen under acidic conditions of pH5.0 to pH6.5 in the endosome (WO 2009/125825), can dissociate the target antigen in the acidic endosomes of the antigen-presenting cells, it was considered that by using this IgG antibody, only the target antigen may translocate into the lysosomes of the antigen-presenting cells, the fragmented peptides of the target antigen may be presented as antigens, and the IgG antibodies that released the antigen may be recycled to the cell surface (in plasma) from inside the endosomes by binding to FcRn without being subjected to antigen presentation.

Therefore, the acquired immunity-inducing effects of normal anti-human IL-6 receptor IgG antibodies and of pH-dependent anti-human IL-6 receptor IgG antibodies were assessed using the normal mouse model that is immune tolerant to human IL-6 receptors, established in Example 1. H54/L28-IgG1 composed of H54-IgG1 (SEQ ID NO: 38) and L28-CK (SEQ ID NO: 39), which is described in WO 2009/125825, was used as the ordinary anti-human IL-6 receptor IgG antibody. Fv4-IgG1 composed of VH3-IgG1 (SEQ ID NO: 17) and VL3-CK (SEQ ID NO: 40), was used as the pH-dependent anti-human IL-6 receptor IgG antibody.

Antibody preparation was carried out using the method indicated in Reference Example 1.

The acquired immunity-inducing effects of H54/L28-IgG1 and Fv4-IgG1 were assessed using the human IL-6 receptor-immunotolerant mouse model established from human FcRn transgenic mice (B6.mFcRn−/−.hFcRn Tg line 32+/+ mouse, Jackson Laboratories (Methods Mol. Biol. (2010) 602: 93-104)). H54/L28-IgG1 and Fv4-IgG1 were administered to the human IL-6 receptor-immunotolerant mouse models. Specifically, in a similar manner to Example 1, three days after infusion pump implantation, anti-human IL-6 receptor antibody was administered once at 1 mg/kg into the tail vein. Blood was collected over time after administration of the anti-human IL-6 receptor antibody. The collected blood was immediately centrifuged at 15,000 rpm and 4° C. for 15 minutes to obtain the plasma. The separated plasma was stored in a freezer set at −20° C. or lower until performing the measurements. The plasma hsIL-6R concentration was measured by the same method as that described in Example 1.

Figure 2:
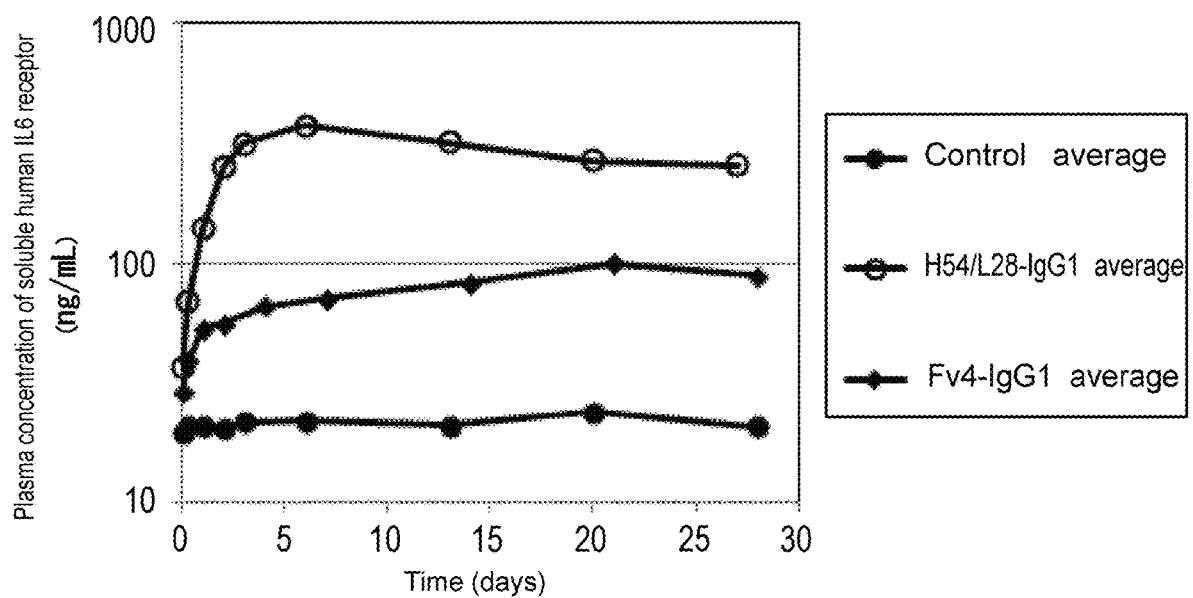
FIG. 2 shows changes in the concentration of soluble human IL-6 receptor in mice plasma for the normal anti-IL-6 receptor antibody and pH-dependent IL-6 receptor antibody administration groups in a human IL-6 receptor immunotolerance normal mouse model. The horizontal axis shows the number of days from anti-IL-6 receptor antibody administration, and the vertical axis shows the plasma concentration of soluble human IL-6 receptor. The filled circles indicate the plasma concentration of soluble human IL-6 receptor in control mice. The open circles indicate the plasma concentration of soluble human IL-6 receptor in H54/L28-IgG1-administered mice, and the diamonds indicate the plasma concentration of soluble human IL-6 receptor in Fv4-IgG1-administered mice.

The changes in the mean plasma hsIL-6R concentration for each of the control (anti-human IL-6 receptor antibody non-administered group), H54/L28-IgG1-administered, and Fv4-IgG1-administered groups are shown in FIG. 2. In all animals of the control group, the plasma hsIL-6R concentration was maintained at a nearly constant level as in Example 1, indicating that mouse anti-human IL-6 receptor antibodies are not produced. A significant elevation in the plasma hsIL-6R concentration was observed in all animals of the H54/L28-IgG1-administered group as compared with the control, and this elevated state continued for 28 days. This was thought to be because, when hsIL-6R is taken up nonspecifically into cells, it is directly degraded in the lysosomes, whereas hsIL-6R bound to an IgG antibody is recycled to the plasma as an antibody-antigen complex by FcRn, so that hsIL-6R clearance is reduced and consequently the plasma hsIL-6R concentration increases. Since this elevated state continued for 28 days, this indicated that in a similar manner to the control, mouse anti-human IL-6 receptor antibody production is not induced in the H54/L28-IgG1-administered group. In all animals of the Fv4-IgG1-administered group, the plasma hsIL-6R concentration increased as compared to that of the control, but the degree of elevation of the plasma hsIL-6R concentration was clearly reduced as compared to that of the H54/L28-IgG1-administered group. This is because the antibody with pH-dependent binding releases the antigen in the endosome, leading to suppression of reduction of hsIL-6R clearance, which then leads to suppression of elevation of plasma hsIL-6R concentration. It was considered from these results that the pH-dependently binding antibody releases more target antigens in the endosomes of antigen-presenting cells as compared with normal antibodies, and promotes translocation of the target antigen to the lysosomes. However, since the state of elevated hsIL-6R concentration was maintained for 28 days, in a similar manner to H54/L28-IgG1, it was shown that Fv4-IgG1 does not induce the production of mouse anti-human IL-6 receptor antibodies.

These results revealed that the acquired immunity cannot be induced against the target antigen using ordinary IgG antibodies and using pH-dependent binding IgG antibodies which release the antigen inside the endosomes of antigen-presenting cells for transfer to the lysosomes.

[Example 3] Effects of pH-Dependent IL-6 Receptor Binding and Enhancement of FcRn Binding at pH7.4 on Acquired Immunity-Inducing Effects in Human FcRn Transgenic Mouse Model with Immune Tolerance for the Human IL-6 Receptor (3-1) Summary In Example 2, it was confirmed that an ordinary IgG1 antibody and an IgG1 antibody with pH-dependent binding cannot induce acquired immunity against a target antigen. On the other hand, as a method for enhancing the immunogenicity of a T-cell epitope peptide, a method of fusing the T-cell epitope peptide with Fc and then enhancing the binding of the Fc portion to FcRn at pH 7.4 so that more T-cell epitope peptides are transferred to lysosomes, has been reported recently (J. Immunol. 181, 7550-61 (2008)). Since FcRn is expressed on antigen-presenting cells, enhancing binding of the Fc portion to FcRn at pH7.4 may promote antigen presentation of the T-cell epitope peptide. However, since the molecule disclosed in this method, which has an antigenic peptide directly fused to Fc, cannot bind to cancer antigens as an antigen-binding molecule, this molecule cannot exhibit any direct action on cancer cells. Furthermore, the method for enhancing FcRn-binding of the Fc portion at pH7.4 enhances immunogenicity of the T-cell epitope peptide in vitro, but on the contrary, decreases immunogenicity in vivo, and this was not effective in vivo. This way, since the molecule produced by directly fusing a target antigen with the Fc having enhanced FcRn binding at pH7.4 cannot show a binding activity toward a target antigen, it cannot act directly on a target antigen, and moreover, enhancing FcRn-binding in vivo resulted in decreasing the immunogenicity Taking into account reports made so far and Example 2, an antibody (H54/L28-F157) produced by introducing to a normal IgG1 antibody (H54/L28-IgG1) alterations that enhance FcRn binding at pH7.4, and an antibody (Fv4-F157) produced by introducing to the IgG1 antibody with pH-dependent binding (Fv4-IgG1) alterations that enhance FcRn binding at pH7.4 were administered to assess whether acquired immunity can be induced toward the target antigen.

(3-2) Antibody Production

H54/L28-F157 composed of H54-F157 (SEQ ID NO: 41) and L28-CK (SEQ ID NO: 39) was used as the normal anti-human IL-6 receptor IgG antibody with enhanced FcRn binding. Fv4-F157 composed of VH3-F157 (SEQ ID NO: 42) and VL3-CK (SEQ ID NO: 40) was used as the pH-dependent anti-human IL-6 receptor IgG antibody with enhanced FcRn binding. Antibody preparation was carried out using the method of Reference Example 1.

(3-3) Measurement of Affinity to Human FcRn

To determine the affinities of the Fc regions of Fv4-IgG1 and Fv4-F157 (referred to as IgG1 and F157, respectively) produced in Example 2 to human FcRn at pH7.0, the affinities of VH3/L(WT)-IgG1 composed of VH3-IgG1 (SEQ ID NO: 17) and L(WT)-CK (SEQ ID NO: 18) and VH3/L(WT)-F157 composed of VH3-F157 (SEQ ID NO: 42) and L(WT)-CK (SEQ ID NO: 18) to human FcRn were determined by the method shown below.

Kinetic analyses between human FcRn and the antibody were carried out using Biacore T100 (GE Healthcare). A suitable amount of protein L (ACTIGEN) was immobilized onto a Sensor chip CM4 (GE healthcare) by the amine coupling method, and antibodies of interest were captured onto it. Next, diluted solutions of FcRn and the running buffer which is the blank were injected, and human FcRn was made to interact with the antibodies captured on the sensor chip. The running buffer used was 50 mmol/L sodium phosphate, 150 mmol/L NaCl, 0.05% (w/v) Tween 20, pH7.0, and the buffer was used for the FcRn dilutions. The sensor chip was regenerated using 10 mmol/L Glycine-HCl, pH1.5. All measurements were carried out at 25° C. Based on the association rate constant ka (1/Ms) and dissociation rate constant kd (1/s), which are kinetic parameters, calculated from the sensorgram obtained by the measurement, the KD (M) (affinity) of each antibody toward human FcRn was calculated. Each parameter was calculated using the Biacore T100 Evaluation Software (GE Healthcare).

The affinities of IgG1 and F157 to human FcRn are shown in Table 7. The affinity of F157 to human FcRn was confirmed to be approximately 600-fold higher as compared with IgG1.

TABLE 7

|  | Affinity to human FcRn |
|---|---|
| IgG1 | 8.8E−05 |
| F157 | 1.5E−07 |

(3-4) Change in the Plasma Concentration of the Antigen (Soluble Human IL-6 Receptor) in the Antibody Administration Test Next, in Test 1, the mouse model with immune tolerance for the human IL-6 receptor which was established from human FcRn transgenic mice (B6.mFcRn−/−.hFcRn Tg line 32+/+ mouse, Jackson Laboratories, Methods Mol. Biol. (2010) 602, 93-104) was used. H54/L28-F157 and Fv4-F157 were administered to the human IL-6 receptor-immunotolerant mouse models. Specifically, in a similar manner to Example 1, three days after implantation of the infusion pump, an anti-human IL-6 receptor antibody was administered once at a dose of 1 mg/kg into the tail vein (three individuals in each group). Blood was collected over time after administration of the anti-human IL-6 receptor antibody to the mice. Furthermore, in Test 2, blood was collected over time after administration of Fv4-F157 alone in a similar manner. The collected blood was immediately centrifuged at 15,000 rpm and 4° C. for 15 minutes to obtain the plasma. The separated plasma was stored in a freezer at −20° C. or lower until performing the measurements. The plasma hsIL-6R concentration was measured by the same method as that described in Example 1.

Figure 3:
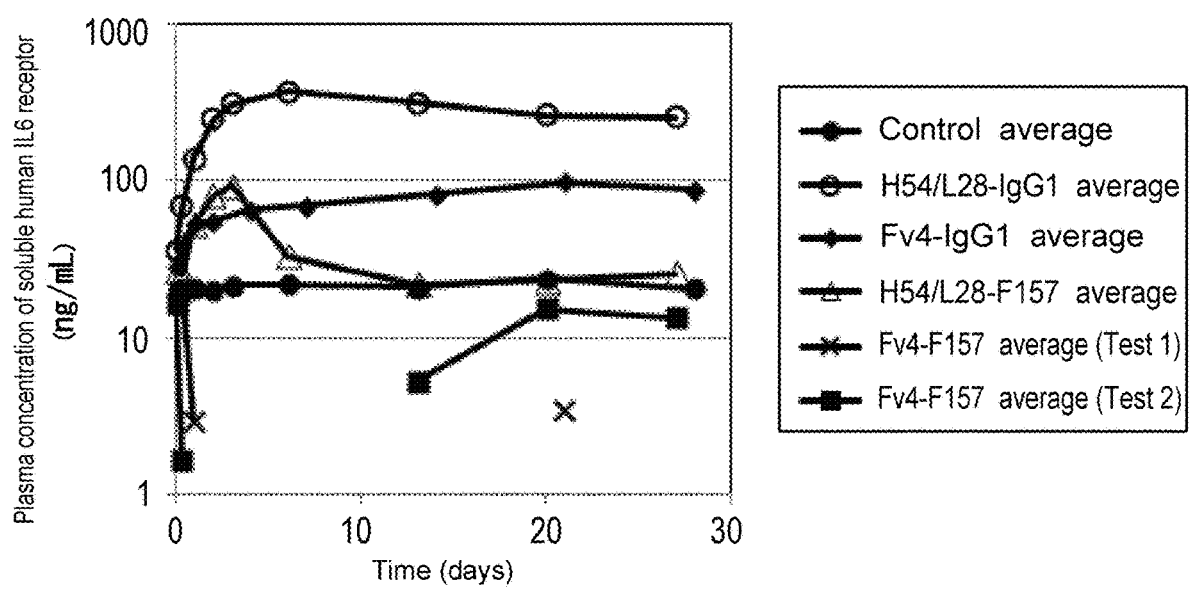
FIG. 3 shows changes in the concentration of soluble human IL-6 receptor in mice for the group to which normal anti-IL-6 receptor antibody with enhanced FcRn binding at pH7.4 was administered and the group to which pH-dependent IL-6 receptor antibody with enhanced FcRn binding at pH7.4 was administered, in a human IL-6 receptor immunotolerance normal mouse model. The horizontal axis shows the number of days from anti-IL-6 receptor antibody administration, and the vertical axis shows the plasma concentration of soluble human IL-6 receptor. The filled circles indicate the plasma concentration of soluble human IL-6 receptor in control mice. The plasma concentration of soluble human IL-6 receptor in mice to which H54/L28-IgG1, Fv4-IgG1, H54/L28-F157, or Fv4-F157 was administered is shown by the open circles, diamonds, open triangles, or X and the filled squares, respectively.

The changes in the mean plasma hsIL-6R concentration for each of the H54/L28-F157-administered and Fv4-F157-administered groups of Test 1 and the Fv4-F157-administered group of Test 2 are shown in FIG. 3, together with the change in the mean plasma hsIL-6R concentration for each of the control (antibody non-administration group), the H54/L28-IgG1-administered and Fv4-IgG1-administered groups obtained in Example 2. The H54/L28-F157-administered group showed an increase in plasma hsIL-6R concentration in a similar manner to the H54/L28-IgG1-administered group, but the increase was transient, and 13 days later, the plasma hsIL-6R concentration decreased to a level equivalent to that of the control. Thereafter, a level equivalent to that of the control was maintained for 28 days; therefore, in the same manner as H54/L28-IgG1, mouse anti-human IL-6 receptor antibodies were shown not to be produced, and it was revealed that enhancement of FcRn-binding at pH7.4 alone cannot induce acquired immunity toward the target antigen. This does not conflict with the finding that a molecule produced by fusing a T-cell epitope peptide to the Fc region with enhanced FcRn-binding at pH7.4 cannot enhance induction of acquired immunity against the T-cell epitope peptide, as reported in J. Immunol. (2008), 181, 7550-7561. In contrast, in the Fv4-F157-administered group, a rapid reduction of the plasma hsIL-6R concentration was observed after antibody administration, and one day after administration, the hsIL-6R concentration decreased to below detection limit (1.56 ng/mL or lower).

Figure 4:
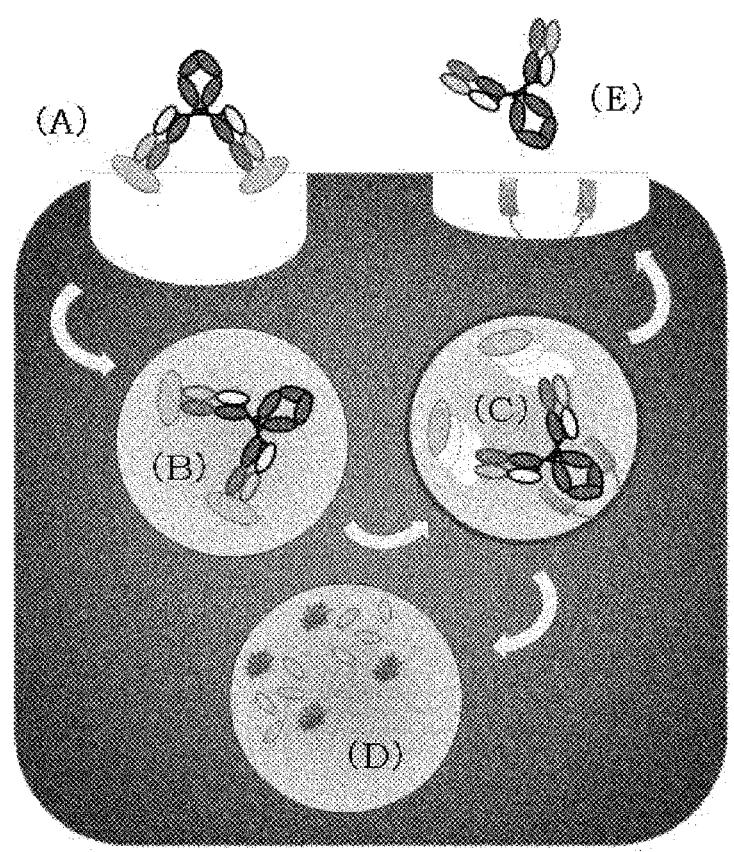
FIG. 4 shows a non-limiting action model of an ion-concentration-dependent antigen-binding molecule with regard to the lysosome transport of a soluble antigen. Under the plasma ion concentration conditions (in the neutral pH range or under high calcium ion concentration), the antigen-binding molecule that has bound to a soluble antigen in plasma (A) is taken up into a cell by non-specific endocytosis and such (B), and then is transferred to an acidic endosome where it binds to FcRn expressed in the endosome via the FcRn binding domain under the acidic pH condition, and releases the antigen under endosomal ion concentration conditions (in the acidic pH range or under low calcium ion concentration) (C). The released antigen is transferred to the lysosome and then degraded (D). On the other hand, the antigen-binding molecule that has released the antigen moves to the cell surface while being bound to FcRn, dissociates from FcRn under the neutral pH condition in the plasma, and then returns to the plasma (E).
Figure 5:
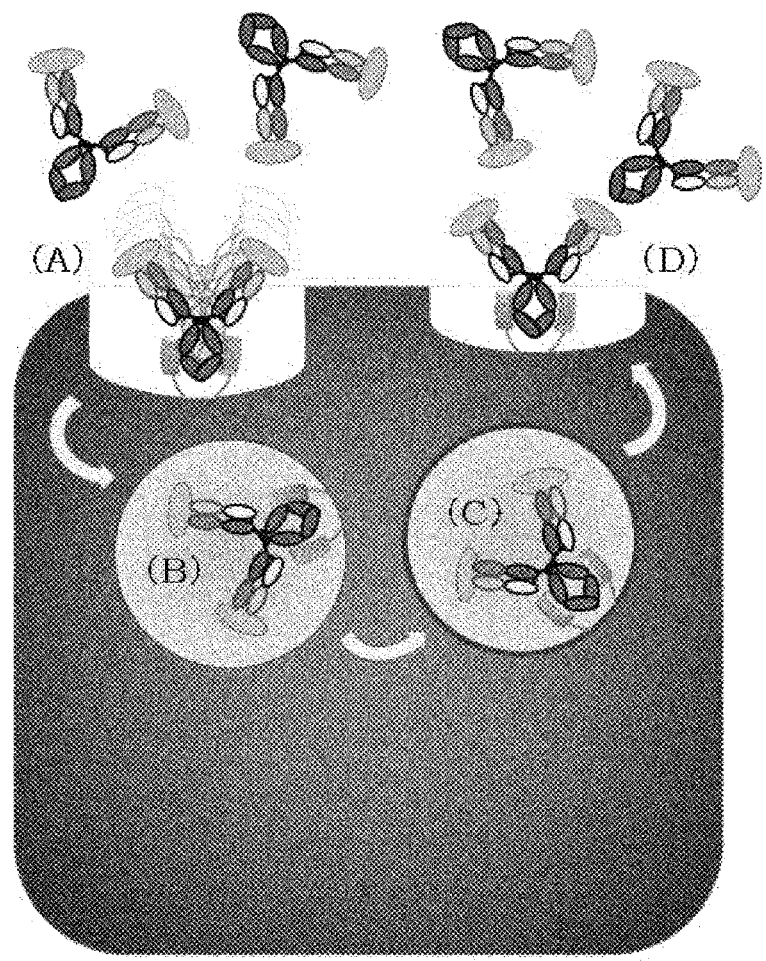
FIG. 5 shows a non-limiting action model of an antigen-binding molecule having FcRn-binding activity at pH7.4 with regard to the lysosome transport of a soluble antigen. Under the plasma ion concentration conditions (in the neutral pH range or under high calcium ion concentration), the antigen-binding molecule which has bound to a soluble antigen in plasma binds to FcRn under the neutral pH condition via the FcRn-binding domain (A), and this is then taken up into the cell by endocytosis (B). The antigen-binding molecule that has transferred to an acidic endosome does not release the antigen under endosomal ion concentration conditions (in the acidic pH range or under low calcium ion concentration) (C), and the antigen-bound antigen-binding molecule is recycled onto the cell surface while being bound to FcRn (D).
Figure 6:
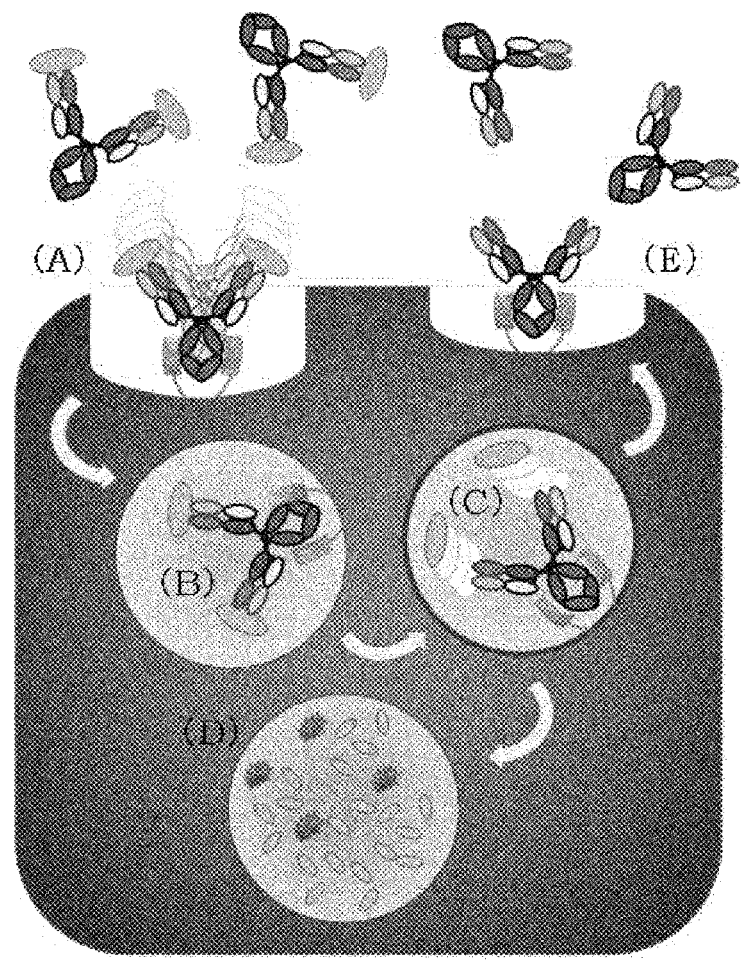
FIG. 6 shows a non-limiting action model of an ion-concentration-dependent antigen-binding molecule with enhanced FcRn binding at pH7.4 with respect to lysosome transport of a soluble antigen. Under the plasma ion concentration conditions (in the neutral pH range or under high calcium ion concentration), the antigen-binding molecule which has bound to a soluble antigen in plasma binds to FcRn under neutral pH conditions via the FcRn-binding domain (A), and this is then taken up into the cell by endocytosis (B). The antigen-binding molecule that has transferred to an acidic endosome releases the antigen under endosomal ion concentration conditions (in the acidic pH range or under low calcium ion concentration) (C). The dissociated antigen is transferred to the lysosome and then degraded (D). On the other hand, the antigen-binding molecule that has released the antigen is recycled onto the cell surface while being bound to FcRn (E).

Without being limited to a particular theory, the above-mentioned phenomena may be described as follows. Enhancement of acquired immunity to a target antigen may depend on the amount of the target antigen taken up into antigen-presenting cells by the administered antibody. The amount of the incorporated target antigen can be evaluated by determining how much the concentration of the target antigen in the plasma decreased. Although the antibody with pH-dependent binding (Fv4-IgG1) releases the target antigen in the acidic endosome after being taken up into cells, the process of incorporation into cells of the pH-dependent binding antibody that is bound to the target antigen is dependent on non-specific pinocytosis, and since the speed of incorporation is slow, the concentration of the target antigen in the plasma does not decrease to a level lower than that of the control (FIG. 4). Furthermore, the antibody (H54/L28-F157) in which only the FcRn binding at pH7.4 is enhanced is aggressively taken up into cells using the FcRn-binding at pH7.4; however, since most of it is recycled directly to the cell surface by the intrinsic function of FcRn in a state where the target antigen is still bound to the antibody, that is, as a complex of the antibody and the target antigen, the concentration of the target antigen in the plasma does not decrease to a level below that of the control (FIG. 5). In contrast, since the antibody with pH-dependent binding with enhanced FcRn-binding at pH7.4 (Fv4-F157) which was aggressively taken up into cells through FcRn-binding at pH7.4 releases the target antigen in the endosome, the antigen is sent to the lysosome, whereas the antibody that released the target antigen is recycled to the cell surface by the intrinsic function of FcRn, binds again to a target antigen, and can similarly send the target antigen again to the lysosome (FIG. 6). It was considered that only the antibodies with pH-dependent binding that have enhanced FcRn-binding at pH7.4 are able to reduce the concentration of the target antigen in the plasma to a level that is significantly lower than that of the control by repeating this cycle.

Figure 7:
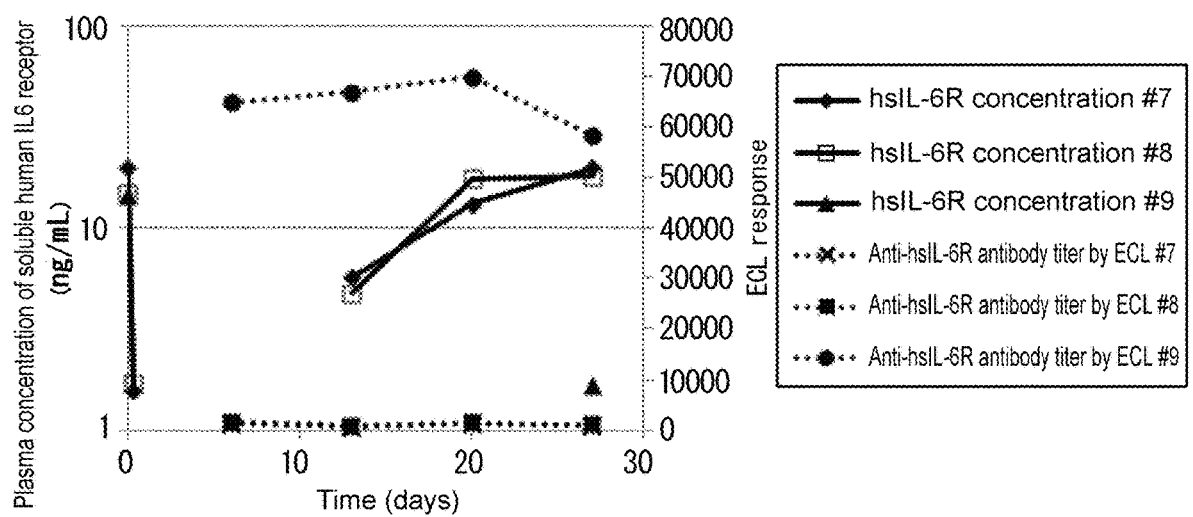
FIG. 7 shows changes in the plasma concentration of soluble human IL-6 receptor and changes in the titer of mouse anti-human IL-6 receptor antibody in each of the three Fv4-F157-administered mice (#7, 8, and 9) in Test 1. The horizontal axis shows the number of days from anti-IL-6 receptor antibody administration, the left vertical axis shows the concentration of soluble human IL-6 receptor in plasma, and the right vertical axis shows the ECL value, which serves as the indicator for the mouse anti-hsIL-6R antibody titer. The solid lines show the soluble human IL-6 receptor concentration in plasma and the dashed lines show the ECL values. The diamonds, open squares, and triangles show changes in the plasma concentration of soluble human IL-6 receptor of individuals #7, 8, and 9, respectively; and X, filled squares, and filled circles show changes in the ECL value in individuals #7, 8, and 9, respectively.
Figure 8:
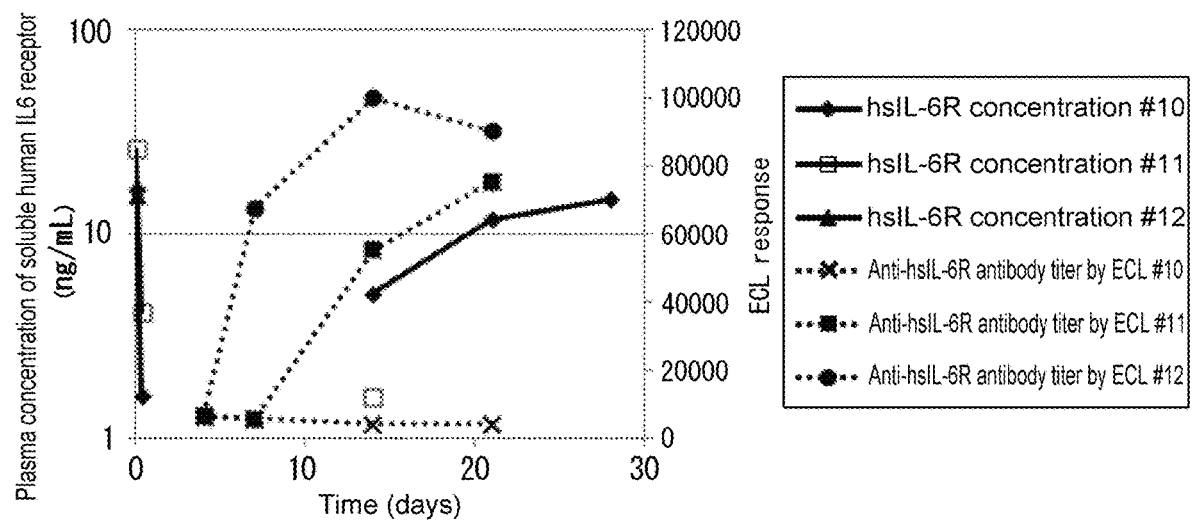
FIG. 8 shows changes in the plasma concentration of soluble human IL-6 receptor and changes in the titer of mouse anti-human IL-6 receptor antibody in each of the three Fv4-F157-administered mice (#10, 11, and 12) of Test 2. The horizontal axis shows the number of days from anti-IL-6 receptor antibody administration, the left vertical axis shows the concentration of soluble human IL-6 receptor in plasma, and the right vertical axis shows the ECL value, which serves as the indicator for the mouse anti-human IL-6 receptor antibody titer. The solid lines show the soluble human IL-6 receptor concentration in plasma and the dashed lines show the ECL values. The diamonds, open squares, and triangles show the concentration of soluble human IL-6 receptor in the plasma of individuals #10, 11, and 12, respectively; and X, filled squares, and filled circles show changes in the ECL value in individuals #10, 11, and 12, respectively.

The plasma hsIL-6R concentration for each of the six Fv4-F157-administered mice of 1 and 2 are shown in FIGS. 7 and 8. Among the six Fv4-F157-administered mice, the hsIL-6R concentration increased after day 13 in three mice, namely #7, #8, and #10, then returned to the level equivalent to that of the control, and thereafter, the level equivalent to that of the control was maintained for 28 days. On the other hand, in the remaining three mice, namely #9, #11, and #12, since the hsIL-6R concentration did not recover and maintained thereafter that low value for up to 28 days, it was considered that in these three mice, mouse anti-human IL-6 receptor antibodies were produced and were removing the human IL-6 receptors from within the plasma. Therefore, the mouse anti-human IL-6 receptor antibody titer was determined in the six Fv4-F157-administered mice by the method indicated below.

(3-4) Change in Antibody Titer of the Mouse Antibody (Mouse Anti-Human IL-6 Receptor Antibody) Against an Antigen (Soluble Human IL-6 Receptor) in Mice in an Antibody Administration Test The titer of the mouse anti-human IL-6 receptor antibody in the mouse plasma was measured by electrochemiluminescence. First, human IL-6 receptor was dispensed into MA100 PR Uncoated plate (Meso Scale Discovery), and by letting it stand overnight at 4° C., a human IL-6 receptor-immobilized plate was produced. Mouse plasma measurement samples diluted 50-fold were dispensed into the human IL-6 receptor-immobilized plate, and this was left to stand overnight at 4° C. Then, the plate on which anti-mouse IgG (whole molecule) (Sigma-Aldrich) that was ruthenium-labeled using SULFO-TAG NHS Ester (Meso Scale Discovery) was allowed to react at room temperature for one hour and then washed. After dispensing Read Buffer T (×4) (Meso Scale Discovery) into the plate, measurements were taken immediately on a SECTOR PR 400 reader (Meso Scale Discovery).

The changes in mouse anti-human IL-6 receptor antibody (anti-hsIL-6R antibody) titer in the Fv4-F157-administered group are shown in FIGS. 7 and 8. As a result, in the three mice, #7, #8, and #10, whose hsIL-6R concentration returned to the same level as that of the control, elevation of mouse anti-human IL-6 receptor antibody titer was not observed; however, in the three mice, #9, #11, and #12, which maintained low levels of hsIL-6R concentration until Day 28, elevation of mouse anti-human IL-6 receptor antibody (anti-hsIL-6R antibody) titer was observed. From the above-mentioned results, administration of Fv4-F157, which is a pH-dependent anti-human IL-6 receptor IgG antibody with enhanced FcRn-binding, to a normal mouse model with immune tolerance for the human IL-6 receptor was found to be able to induce acquired immunity to the human IL-6 receptor, which is the target antigen in three out of six cases. Accordingly, even if the normal IgG antibody (H54/L28-IgG1), or the IgG antibody (Fv4-IgG1) showing pH-dependent binding to the target antigen, or the IgG antibody (H54/L28-IgG1) with enhancement of only the FcRn-binding at pH7.4 is administered in vivo, acquired immunity to the target antigen cannot be induced, and only the IgG antibody (Fv4-F157) showing pH-dependent target-antigen-binding and enhanced FcRn-binding at pH7.4 was found to be able to induce acquired immunity to the target antigen.

(3-5) Change in Antibody Titer of the Mouse Antibody (Mouse Anti-Fv4-F157 Antibody) Against the Antibody (Fv4-F157) Administered to Mice in an Antibody Administration Test Even if production of antibodies against the target antigen becomes possible by the above-mentioned method (J. Immunol. (2008) 181, 7550-7561) that uses as a pharmaceutical agent a molecule produced by directly fusing the target antigen to Fc with enhanced FcRn-binding at pH7.4, sin

| | Affinity to human FcRn |
|---|---|
| IgG1 | 8.8E−05 |
| F157 | 1.5E−07 | ce antibodies against the target antigen will bind to the pharmaceutical agent itself, they will act as anti-pharmaceutical-agent antibodies, and will lead to reduction of the action of the pharmaceutical agent. Therefore, using a molecule having the target antigen directly fused to the pharmaceutical agent (for example, the compounds described in J. Immunol. (2008) 181, 7550-7561 and J. Immunol. (2011), 186, 1218-1227) means inducing production of antibodies against the target antigen, or more specifically, inducing anti-pharmaceutical-agent antibodies against the pharmaceutical agent itself which will lead to reduction of the action of the pharmaceutical agent, and therefore this use may not be favorable.

The pH-dependent anti-human IL-6 receptor IgG antibody (Fv4-F157) with enhanced binding to FcRn is a pharmaceutical agent having pH-dependent binding activity to the human IL-6 receptor, which is the target antigen, and is not a molecule with a directly fused target antigen. Therefore, as shown in FIGS. 7 and 8, while Fv4-F157 induced antibody production against a human IL-6 receptor, which is the target antigen, it may not have produced anti-pharmaceutical-agent antibodies against the pharmaceutical agent itself (Fv4-F157). Therefore, the mouse anti-Fv4-F157 antibody titers in the six Fv4-F157-administered mice were determined by the method indicated below.

The anti-Fv4-F157 antibody titer in mouse plasma was measured by electrochemiluminescence. First, anti-human IL-6 receptor antibody was dispensed into MA100 PR Uncoated Plate (Meso Scale Discovery), and by letting it stand overnight at 4° C., an anti-human IL-6 receptor-immobilized plate was produced. Mouse plasma measurement samples diluted 50-fold were dispensed into the anti-human IL-6 receptor antibody-immobilized plate, and this was left to stand overnight at 4° C. Then, the plate on which anti-mouse IgG (whole molecule) (Sigma-Aldrich) that was ruthenium-labeled using SULFO-TAG NHS Ester (Meso Scale Discovery) was allowed to react at room temperature for one hour, and then washed. After dispensing Read Buffer T (×4) (Meso Scale Discovery) into the plate, measurements were taken immediately on a SECTOR PR 400 reader (Meso Scale Discovery).

Figure 9:
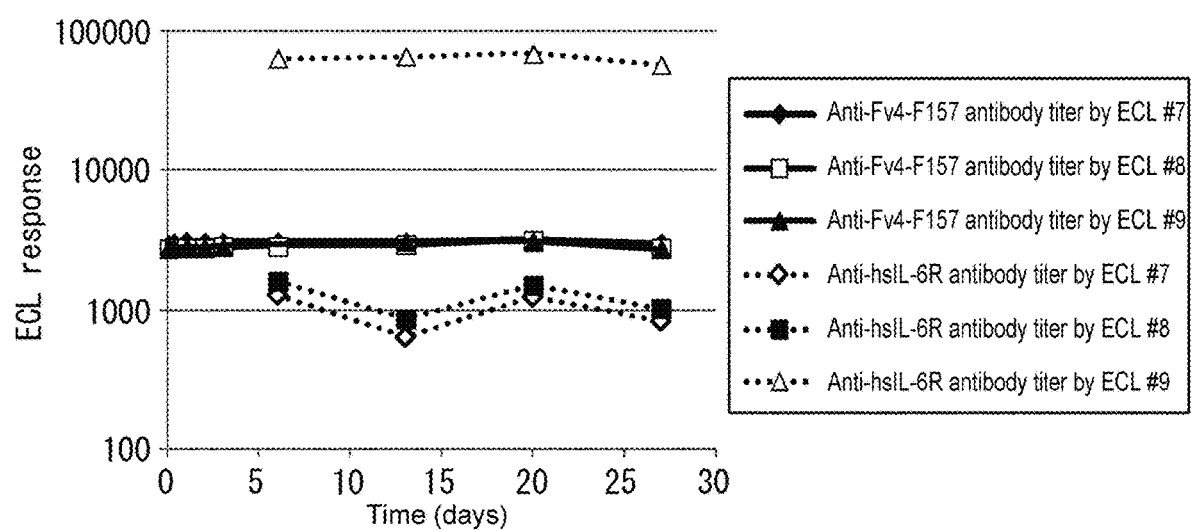
FIG. 9 shows changes in the titer of mouse anti-hsIL-6R antibody and mouse anti-Fv4-F157 antibody in each of the three Fv4-F157-administered mice (#7, 8, and 9) of Test 1. The horizontal axis shows the number of days from the administration of anti-IL-6 receptor antibody, and the vertical axis shows the ECL values, which serve as the indicators for the mouse anti-human IL-6 receptor antibody titer and mouse anti-Fv4-F157 antibody titer. The solid lines show changes in the ECL value serving as the indicator for mouse anti-Fv4-F157 antibody titer, and the dashed lines show changes in the ECL value serving as the indicator for mouse anti-human IL-6 receptor antibody titer. The diamonds, open squares, and filled triangles show changes in the ECL value serving as the indicator for mouse anti-Fv4-F157 antibody titer in individuals #7, 8, and 9, respectively; and the open squares, filled squares, and open triangles show changes in the ECL value serving as the indicator for the mouse anti-human IL-6 receptor antibody titer in individuals #7, 8, and 9, respectively.
Figure 10:
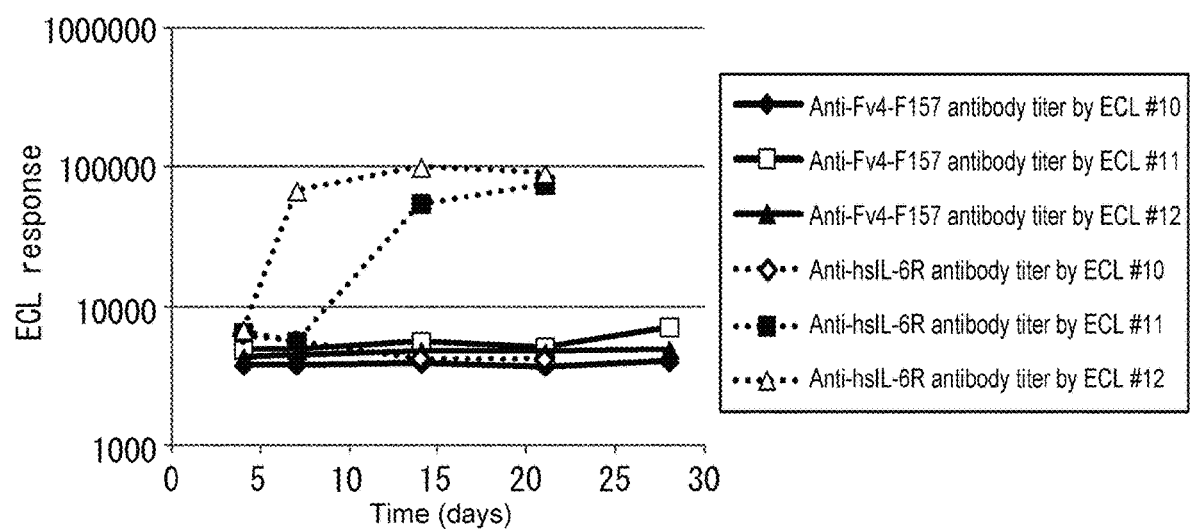
FIG. 10 shows changes in the titer of mouse anti-human IL-6 receptor antibody and changes in the titer of mouse anti-Fv4-F157 antibody in each of the three Fv4-F157-administered mice (#10, 11, and 12) of Test 2. The horizontal axis shows the number of days from the administration of anti-IL-6 receptor antibody, and the vertical axis shows the ECL values serving as the indicator for the mouse anti-human IL-6 receptor antibody titer and the indicator for the mouse anti-Fv4-F157 antibody titer. The solid lines show changes in the ECL value serving as the indicator for mouse anti-Fv4-F157 antibody titer, and the dashed lines show changes in the ECL value serving as the indicator for mouse anti-hsIL-6R antibody titer. The diamonds, open squares, and filled triangles show changes in the ECL value serving as the indicator for mouse anti-Fv4-F157 antibody titer in individuals #10, 11, and 12, respectively; and the open squares, filled squares, and open triangles show changes in the ECL value serving as the indicator for the mouse anti-human IL-6 receptor antibody titer in individuals #10, 11, and 12, respectively.

The changes in mouse anti-Fv4-F157 antibody titer and mouse anti-human IL-6 receptor antibody (anti-hsIL-6R antibody) titer in the Fv4-F157-administered group are shown in FIGS. 9 and 10. In the Fv4-F157 administration group, regardless of the production of mouse anti-human IL-6 receptor antibody (anti-hsIL-6R antibody), production of mouse anti-Fv4-F157 antibody was not observed in any mouse. Accordingly, since the pH-dependent anti-human IL-6 receptor IgG antibody with enhanced FcRn-binding at pH7.4 (Fv4-F157) induced production of antibodies against the target antigen (human IL-6 receptor) but did not induce production of antibodies against the pharmaceutical agent itself (Fv4-F157), the pH-dependent (anti-human IL-6 receptor) IgG antibody with enhanced FcRn-binding at pH7.4 was considered to be very useful as a pharmaceutical agent for inducing acquired immunity toward the target antigen.

Figure 11:
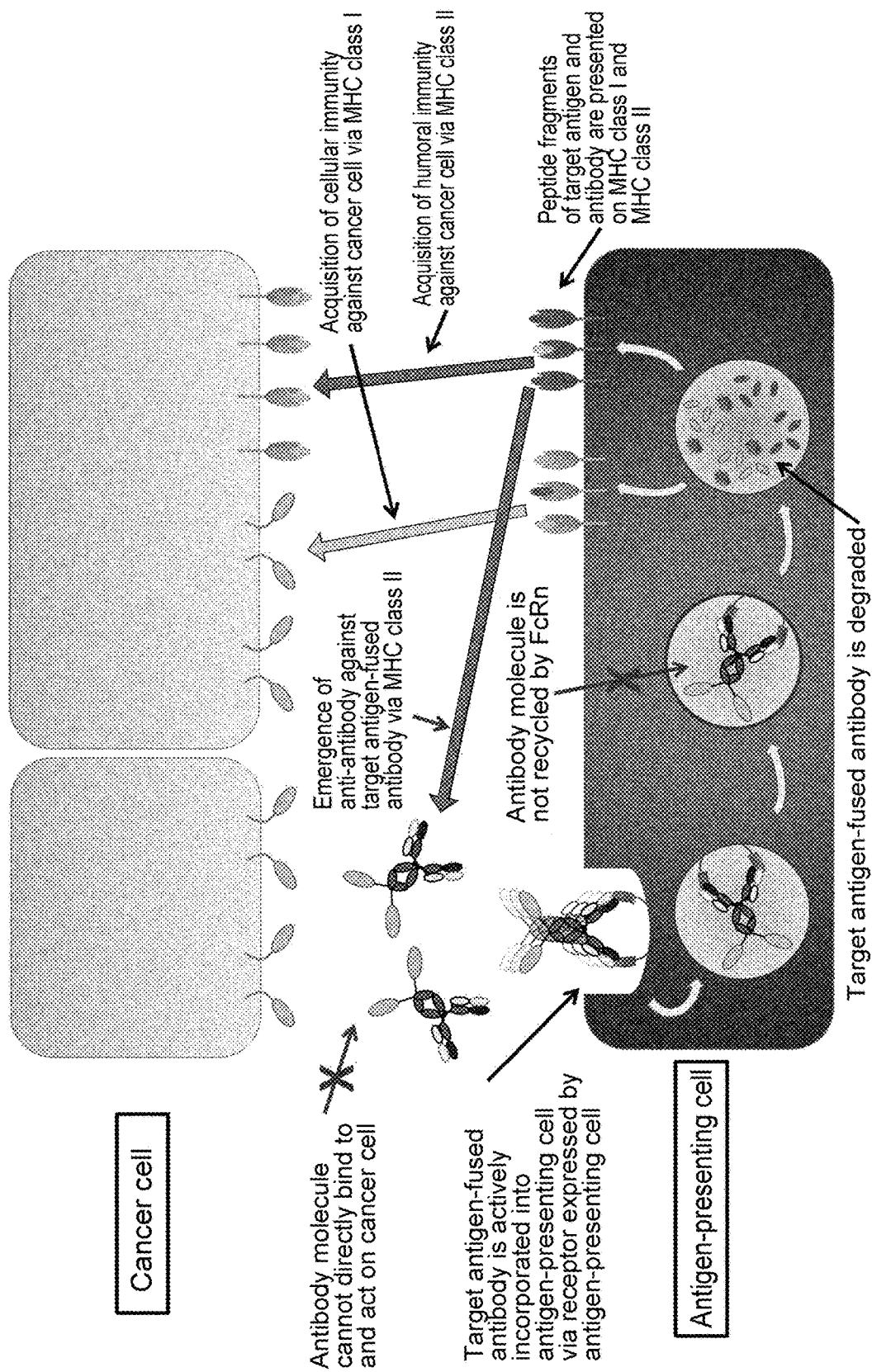
FIG. 11 depicts a non-limiting model of the mechanism of action of an antibody fused with a target antigen on cancer cells and antigen-presenting cells.

So far, as a method for inducing acquired immunity to a cancer antigen, the method of using a pharmaceutical agent molecule in which a cancer antigen against which one wants to induce acquired immunity is fused with an antibody that binds to a receptor expressed on antigen-presenting cells has been reported (J. Immunol. (2011) 186, 1218-1227). Such a pharmaceutical agent molecule cannot directly bind to cancer antigens and exhibit actions (FIG. 11). Therefore, such a pharmaceutical agent molecule cannot show direct cytotoxic activity toward cancer cells or effects of inhibiting the functions of cancer antigens similarly to conventional antibody pharmaceuticals. Furthermore, since such a pharmaceutical agent molecule is incorporated into antigen-presenting cells as a whole and then degraded, fragmented peptides of the pharmaceutical agent molecule are presented on MHC class II and MHC class I. Therefore, not only cellular immunity and humoral immunity against cancer antigens, but also humoral immunity against the pharmaceutical agent itself may also be induced, and may readily lead to reduction of effects by production of anti-pharmaceutical-agent antibodies. Therefore, such a molecule is considered unfavorable (FIG. 11).

Figure 12:
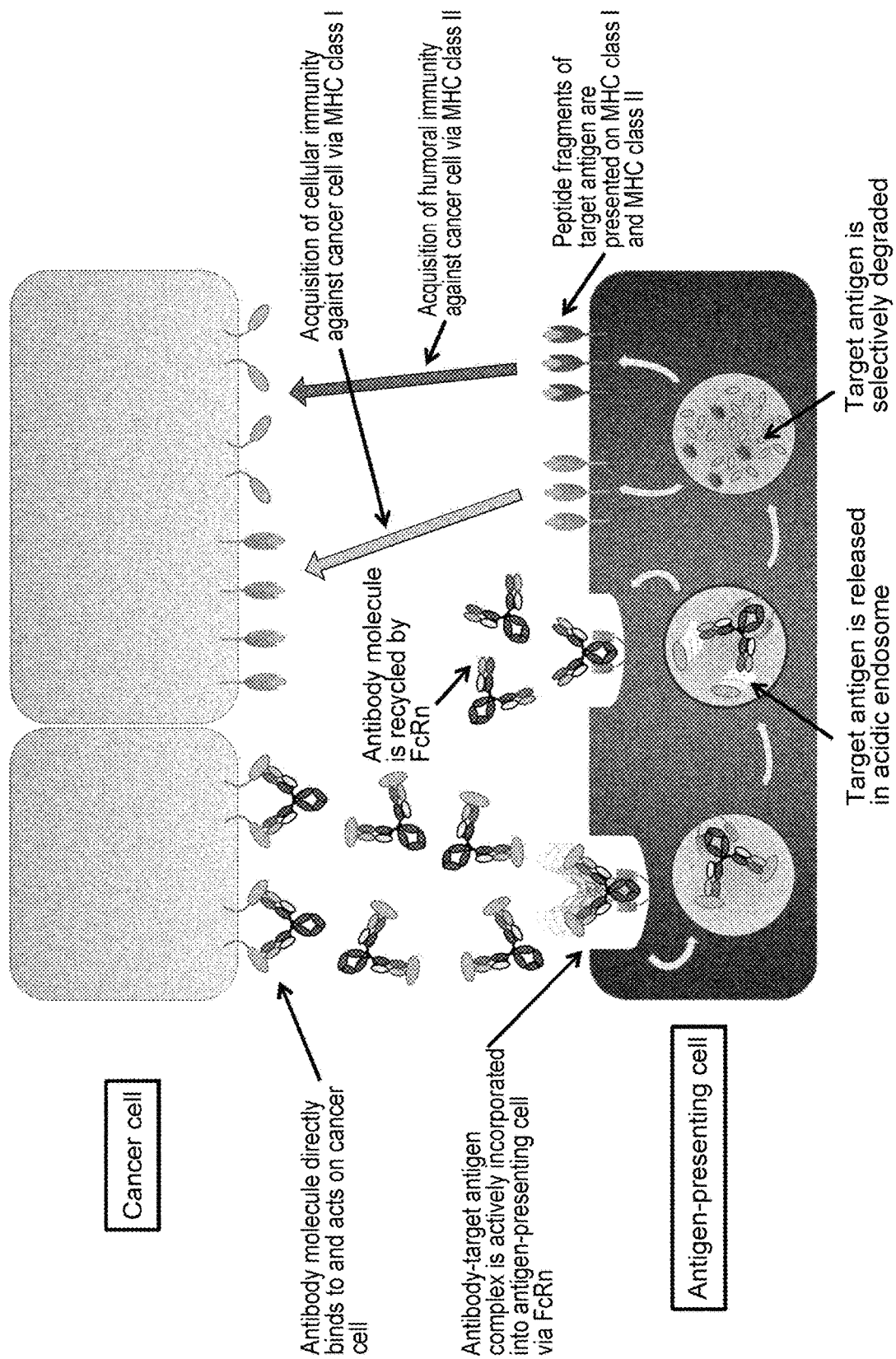
FIG. 12 depicts a non-limiting model of the mechanism of action of an antigen-binding molecule on cancer cells and antigen-presenting cells, where the antigen-binding molecule has FcRn-binding activity in the neutral pH range and has ion concentration-dependent binding activity to a target antigen.

In contrast, the antibody discovered in the present Examples, which shows pH-dependent binding to the target cancer antigen and enhanced FcRn-binding at pH7.4 can exhibit actions of binding directly to cancer antigens (FIG. 12). Therefore, it can show direct cytotoxic activity toward cancer cells and effects of inhibiting the functions of cancer antigens similarly to conventional antibody pharmaceuticals. Furthermore, such an antibody releases the target cancer antigen in the acidic endosome and the antibody itself is recycled to the cell surface so that the target cancer antigen is selectively degraded, and since peptide fragments of the target antigen are presented on MHC class II and MHC class I, production of anti-pharmaceutical-agent antibodies toward the antibody itself is not induced, and cellular immunity and humoral immunity can be induced selectively against cancer antigens (FIG. 12).

[Example 4] Effects of pH-Dependent IL-6 Receptor Binding and Enhancement of FcRn Binding at pH7.4 on Effects of Inducing Acquired Immunity Against the Endogenous Human IL-6 Receptor in Human IL-6 Receptor-Knock-In Mice (4-1) Summary As shown in Example 3, the antibody (H54/L28-F157) produced by introducing to a normal IgG1 antibody (H54/L28-IgG1) alterations that enhance FcRn binding at pH 7.4 did not induce acquired immunity to the target antigen in mice when it was administered to human FcRn transgenic mouse model with immune tolerance for the human IL-6 receptor; however, the antibody (Fv4-F157) produced by introducing, to the IgG1 antibody with pH-dependent binding (Fv4-IgG1), alterations that enhance FcRn-binding at pH 7.4 induced acquired immunity against the target antigen in mice following administration to the mice.

However, while the aforementioned model is a model that induces acquired immunity against a human antigen administered from the outside, when examining the clinical applications of the above-described induction of acquired immunity, it is preferable that the immunotolerance of the completely immunotolerant endogenous antigen is breached and whether acquired immunity is induced is confirmed.

By using the property that human IL-6 receptor-expressing human IL-6 receptor knock-in mice have immune tolerance to the endogenous human IL-6 receptor, the aforementioned antibody was administered to the mice to assess whether acquired immunity can be induced against the endogenous human IL-6 receptor.

(4-2) Antibody Production

H54/L28-mF3 containing H54-mF3 (SEQ ID NO: 124) and L28-mCK (SEQ ID NO: 125) was produced as a normal anti-human IL-6 receptor antibody with enhanced binding to mouse FcRn. Fv4-mIgG1 containing VH3-mIgG1 (SEQ ID NO: 126) and VL3-mCK (SEQ ID NO: 127), and Fv4-mIgG2a containing VH3-mIgG2a (SEQ ID NO: 128) and VL3-mCK (SEQ ID NO: 127) were produced as pH-dependent anti-human IL-6 receptor IgG antibodies. Fv4-mF3 containing VH3-mF3 (SEQ ID NO: 129) and VL3-mCK (SEQ ID NO: 127) was produced as a pH-dependent anti-human IL-6 receptor IgG antibody with enhanced binding to mouse FcRn. Furthermore, Fv4-mFa30 containing VH3-mFa30 (SEQ ID NO: 130) and VL3-mCK (SEQ ID NO: 127) was produced as a pH-dependent anti-human IL-6 receptor IgG antibody with enhanced binding to mouse FcRn as well as enhanced binding to mouse FcγR. These antibodies were prepared using the method described in Reference Example 1.

(4-3) Measurement of Affinity to Mouse FcRn and Mouse FcγR

Using the values determined according to the method shown in (3-3), affinities to mouse FcRn at pH7.0 were determined for the Fc portions mIgG1, mIgG2a, mF3, and mFa30 of the produced Fv4-mIgG1, Fv4-mIgG2a, Fv4-mF3, and Fv4-mFa30.

The extracellular domain of FcγR was prepared by the following method. First, based on the sequence information registered at NCBI, the gene of the extracellular domain of FcγR was synthesized by a method known to those skilled in the art. Specifically, genes encoding the extracellular domains of FcγR with a His-tag added to the C-terminal end of each of the polypeptides of NCBI Accession Number NP_034316 (Version number NP_034316.1) for mFcγRI, NCBI Accession Number NP_034317 (Version number NP_034317.1) for mFcγRII, NCBI Accession Number NP_034318 (Version number NP_034318.2) for FcγRIII, and NCBI Accession Number NP_653142 (Version number NP_653142.2) for FcγRIV were produced.

The obtained gene fragments were inserted into an animal cell expression vector to produce expression vectors. The expression vectors were introduced transiently into human embryonic kidney cancer cell-derived FreeStyle 293 cells (Invitrogen), and the culture supernatant of the transduced cells expressing the proteins of interest was passed through a 0.22-μm filter to obtain the culture supernatant. As a general rule, the extracellular domains of each of the FcγRs were purified from the obtained culture supernatant by the following four purification steps: ion exchange column chromatography in step 1 (step 1), affinity column chromatography for the His tag (HisTrap HP) (step 2), gel filtration column chromatography (Superdex200) (step 3), and aseptic filtration (step 4). The column for ion exchange column chromatography of step 1 was Q sepharose HP for purification of mFcγRI, SP Sepharose FF for purification of mFcγRII and mFcγRIV, and SP Sepharose HP for purification of mFcγRIII. In step 3 and subsequent purification steps, D-PBS(−) was used as the solvent, but for mFcγRIII purification, D-PBS(−) containing 0.1 M arginine was used. The absorbance at 280 nm of the purified solution containing the extracellular domain of FcγR was measured using a spectrophotometer. From the obtained absorbance values, the concentrations of the purified extracellular domain of FcγR were calculated using the absorption coefficient calculated by methods such as PACE (Protein Science (1995) 4, 2411-2423).

Analysis of interaction between each of the altered antibodies and the extracellular domain of the Fcγ receptor prepared as mentioned above was carried out using Biacore T100 (GE Healthcare), Biacore T200 (GE Healthcare), Biacore A100, and Biacore 4000. HBS-EP+(GE Healthcare) was used for the running buffer, and the interactions were measured with a measurement temperature at 25° C. Chips produced by immobilizing Protein L (ACTIGEN or BioVision) by the amine coupling method to a Series S sensor Chip CM5 (GE Healthcare) or Series S sensor Chip CM4 (GE Healthcare) were used.

After capturing of each of the altered antibodies onto these sensor chips, the extracellular domain of the Fcγ receptor diluted with the running buffer was allowed to act on the chips to measure the binding level of each of the domains to each of the antibodies, and the binding levels were compared. However, since the amount of the bound extracellular domain of the Fcγ receptor depends on the amount of the antibodies captured on the sensorchip, the amount of the bound extracellular domain of the Fcγ receptor was divided by the respective amount of captured antibody to obtain corrected values, and these values were compared. Furthermore, by reaction with 10 mM glycine-HCl having pH of 1.5, antibodies captured onto the sensor chips were washed, and the regenerated sensor chips were used repeatedly.

The KD values of each of the altered antibodies for the extracellular domain of the Fcγ receptor were calculated according to the following kinetic analysis method. Antibodies of interest were captured onto the above mentioned sensor chips, the extracellular domain of the Fcγ receptor diluted with the running buffer was allowed to interact, and by using the Biacore Evaluation Software to the obtained sensorgram to globally fit the measured results using the 1:1 Langmuir binding model, the association rate constant ka (L/mol/s) and the dissociation rate constant kd (1/s) were calculated, and from those values the dissociation constants KD (mol/L) were determined.

The affinities of mIgG1, mIgG2a, mF3, and mFa30 for mouse FcRn are shown in Table 8, and their affinity for mouse FcγR are shown in Table 9.

TABLE 8

| Variant name | KD (M) |
| --- | --- |
| IgG1 | Not detected |
| mIgG2a | Not detected |
| mF3 | 1.5E−09 |
| mFa30 | 3.5E−09 |

TABLE 9

| Variant name | mFc γ RI | mFc γ RII | mFc γ RIII | mFc γ RIV |
| --- | --- | --- | --- | --- |
| IgG1 | Not detected | 5.7E−07 | 8.5E−08 | Not detected |
| mIgG2a | 3.9E−09 | 4.8E−07 | 4.5E−08 | 3.2E−09 |
| mF3 | Not detected | 8.7E−07 | 1.4E−07 | Not detected |
| mFa30 | 9.9E−10 | 8.1E−09 | 5.3E−09 | 1.9E−08 |

(4-4) Change in Plasma Concentration of the Antigen (Soluble Human IL-6 Receptor) in the Antibody Administration Test Next, Fv4-mIgG1, Fv4-mIgG2a, Fv4-mF3, Fv4-mFa30, and H54/L28-mF3 were administered to human IL-6 receptor knock-in mice (Reference Example 25), and blood was collected from these mice over time. The collected blood was immediately centrifuged at 15,000 rpm and 4° C. for 15 minutes to obtain the plasma. The separated plasma was stored in a freezer set at −20° C. or lower until performing the measurements. The plasma hsIL-6R concentration was measured by the same method as that described in Example 1.

Figure 26:
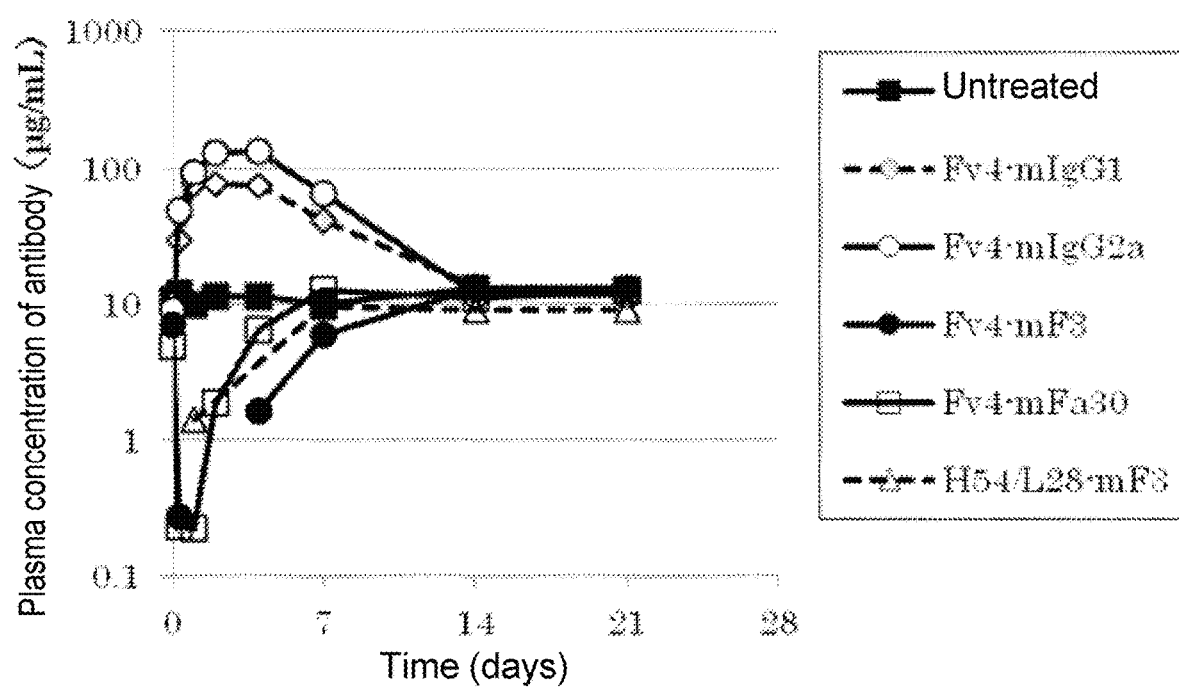
FIG. 26 shows changes in the average plasma concentration of hsIL-6R in the non-antibody administration group, and the Fv4-mIgG1, Fv4-mIgG2a, Fv4-mF3, Fv4-mFa30, and H54/L28-mF3 administration groups.
Figure 27:
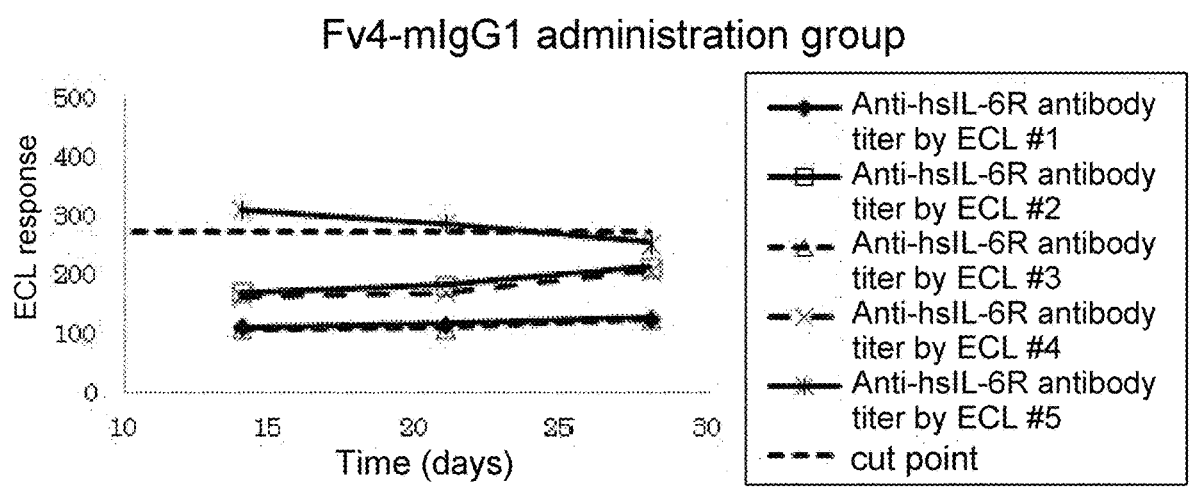
FIG. 27 shows changes in the antibody titer of mouse anti-human IL-6 receptor antibody (anti-hsIL-6R antibody) for each individual in the Fv4-mIgG1 administration group.
Figure 28:
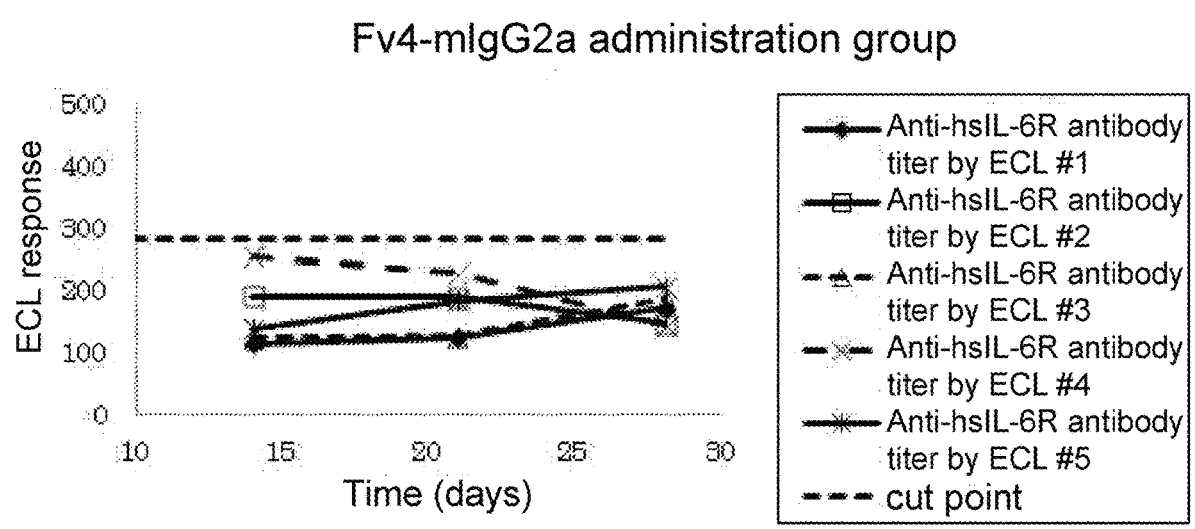
FIG. 28 shows changes in the antibody titer of mouse anti-human IL-6 receptor antibody (anti-hsIL-6R antibody) for each individual in the Fv4-mIgG2a administration group.
Figure 29:
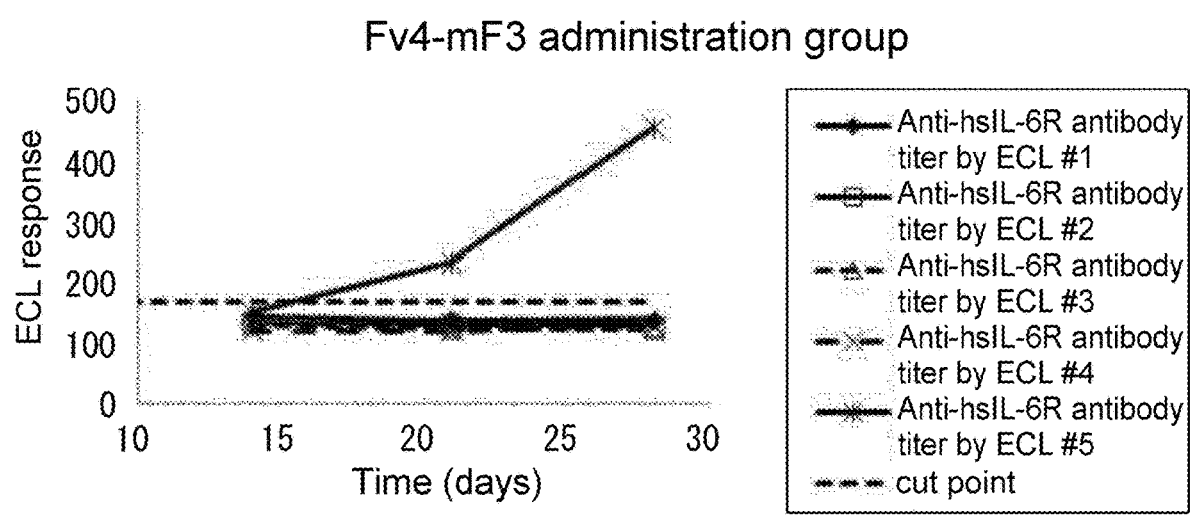
FIG. 29 shows changes in the antibody titer of mouse anti-human IL-6 receptor antibody (anti-hsIL-6R antibody) for each individual in the Fv4-mF3 administration group.
Figure 30:
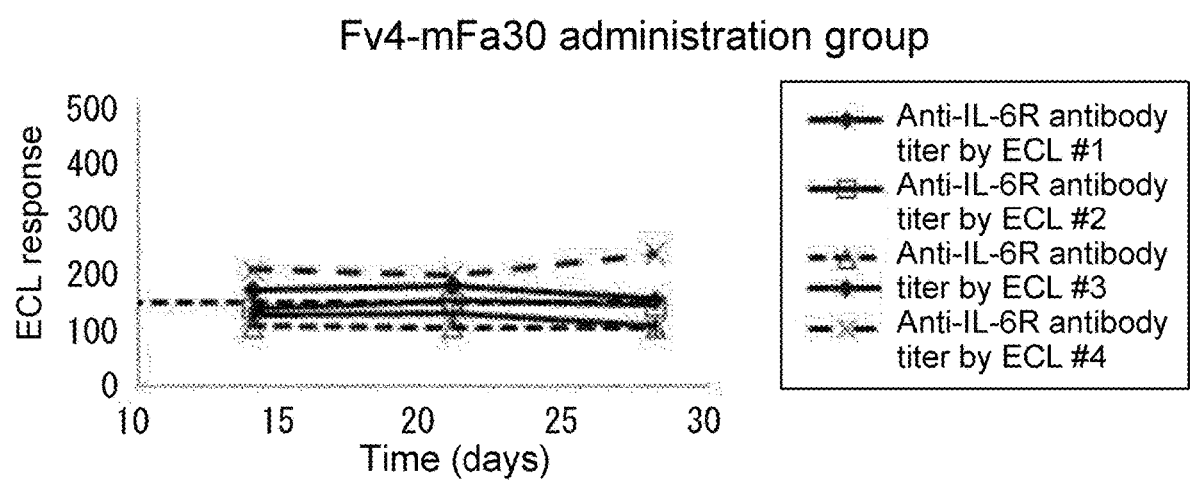
FIG. 30 shows changes in the antibody titer of mouse anti-human IL-6 receptor antibody (anti-hsIL-6R antibody) for each individual in the Fv4-mFa30 administration group.
Figure 31:
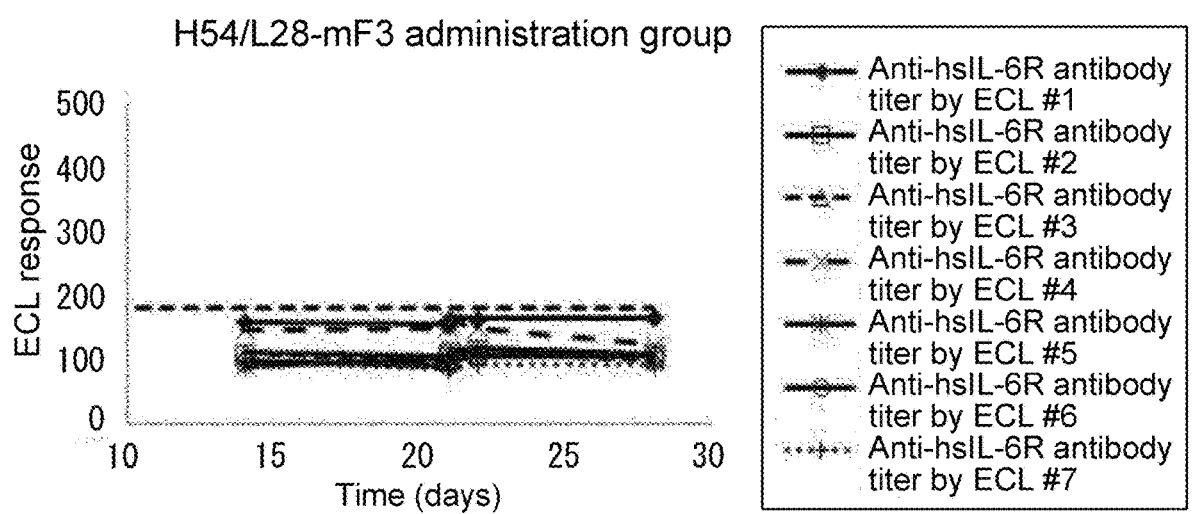
FIG. 31 shows changes in the antibody titer of mouse anti-human IL-6 receptor antibody (anti-hsIL-6R antibody) for each individual in the H54/L28-mF3 administration group.

The changes in mean plasma hsIL-6R concentration for the antibody non-administered group, and the Fv4-mIgG1, Fv4-mIgG2a, Fv4-mF3, Fv4-mFa30, and H54/L28-mF3 administration groups are shown in FIG. 26. An increase in hsIL-6R concentration was observed in the plasma of the Fv4-mIgG1 and Fv4-mIgG2a administration groups. On the other hand, a significant decrease in hsIL-6R concentration as compared to that of the antibody non-administered group was observed in the plasma of the Fv4-mF3, H54/L28-mF3, and Fv4-mFa30 administration groups, where Fv4-mF3 and H54/L28-mF3 have enhanced binding to mouse FcRn and Fv4-mFa30 has enhanced binding to mouse FcRn and mouse FcgR.

(4-5) Change in Antibody Titer of the Mouse Antibody (Mouse Anti-Human IL-6 Receptor Antibody) Against an Antigen (Soluble Human IL-6 Receptor) in Mice in an Antibody Administration Test The anti-hsIL-6R antibody titer in mouse plasma was measured by electrochemiluminescence. Mouse plasma samples diluted 50-fold and anti-Fv4 idiotype antibody adjusted to 30 µg/mL were mixed and reacted at room temperature for one hour. The idiotype antibody was obtained by purifying serum from an Fv4-M73 (WO 2009/125825) immunized rabbit on an ion exchange resin, and then performing affinity purification on a column to which Fv4-M73 has been immobilized, and subsequently adsorbing onto a human immobilized column. To the aforementioned mixed solution, 50 µg/mL of a solution containing 1 µg/mL of hsIL-6R that has been biotinylated using an EZ-Link Sulfo-NHS-Biotin and Biotinylation Kit (Pierce) and 2 µg/mL of SULFO-anti mouse IgG (H+L) antibody (BECKMAN COULTER) that has been ruthenium-labeled using SULFO-TAG NHS Ester (Meso Scale Discovery) was added, and this was mixed and allowed to react overnight at 4° C. Under these circumstances, to prevent binding of the administration sample included in the measurement sample with hsIL-6R and detection of ADA directed to the administered sample, an excess amount of anti-Fv4 idiotype antibody was added to the sample in advance. Thereafter, the aforementioned reaction solution was dispensed into an MA400 PR Streptavidin Plate (Meso Scale Discovery). To each of the wells that were further reacted at 25° C. for one hour and then washed, Read buffer T (×4) (Meso Scale Discovery) was dispensed, and absorbance of the reaction solution in each well was measured immediately using a SECTOR PR 400 reader (Meso Scale Discovery).

The changes in mouse anti-human IL-6 receptor antibody (anti-hsIL-6R antibody) titer for each individual of the antibody non-administration group, and the Fv4-mIgG1, Fv4-mIgG2a, Fv4-mF3, Fv4-mFa30, and H54/L28-mF3 administration groups are shown in FIGS. 27 to 31. An increase in mouse anti-human IL-6 receptor antibody (anti-hsIL-6R antibody) titer was not observed in the individuals of the Fv4-mIgG1-administered, Fv4-mIgG2a-administered, and H54/L28-mF3-administered groups, where Fv4-mIgG1 and Fv4-mIgG2a do not have enhanced binding to mouse FcRn and H54/L28-mF3 has enhanced binding to mouse FcRn but does not have pH-dependent binding to the human IL-6 receptor. On the other hand, individuals showing an increase in mouse anti-human IL-6 receptor antibody (anti-hsIL-6R antibody) titer were confirmed in the Fv4-mF3-administered and Fv4-mFa30-administered groups, where Fv4-mF3 is a pH dependent binding antibody with enhanced binding to mouse FcRn and Fv4-mFa30 is a pH-dependent binding antibody with enhanced binding to mouse FcRn and also enhanced binding to mouse FcgR.

From the above, it was shown that an antigen-binding molecule having a pH-dependent target-antigen-binding activity and enhanced FcRn-binding at pH7.4 is able to induce acquired immunity against an immunologically tolerated endogenous target antigen. Accordingly, since such a molecule may be able to induce acquired immunity to self cancer antigens, it is very promising as a therapeutic agent for cancer.

Reference Example 1

The antibodies were expressed by the method described below. Human embryonic kidney cancer cell-derived HEK293H cell line (Invitrogen) was suspended in DMEM medium (Invitrogen) supplemented with 10% Fetal Bovine Serum (Invitrogen) and plated at 10 ml per dish in dishes for adherent cells (10 cm in diameter; CORNING) at a cell density of $5\times10^5$ to $6\times10^5$ cells/ml. The cells were cultured in a $CO_2$ incubator (37° C., 5% $CO_2$) for a whole day and night, then the medium was removed by aspiration, and 6.9 ml of CHO-S-SFM-II medium (Invitrogen) was added to the dishes. Prepared plasmids were introduced into the cells by the lipofection method. The culture supernatants were collected, and centrifuged (approximately 2000 g, 5 min, room temperature) to remove cells. The culture supernatants were further sterilized by filtering through a 0.22-μm filter MILLEX(R)-GV (Millipore) to obtain culture supernatants. The expressed antibodies were purified from the obtained culture supernatants by a method known to those skilled in the art using rProtein A Sepharose™ Fast Flow (Amersham Biosciences). To determine the concentration of the purified antibody, absorbance was measured at 280 nm using a spectrophotometer, and antibody concentrations were calculated from the measured values using an absorbance coefficient calculated by the method described in Protein Science (1995) 4, 2411-2423).

Figure 13:
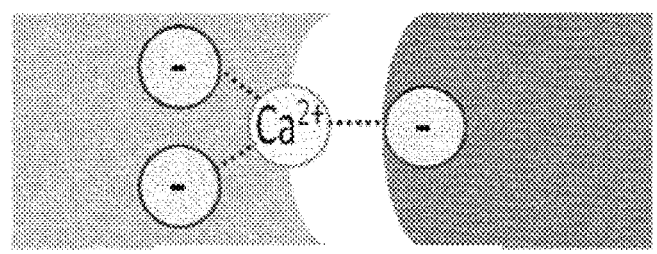
FIG. 13 depicts the manner of interaction between an antigen and a calcium-dependent binding antibody in plasma (2 mM CO and in endosome (3 μM Ca') (i), and the manner of interaction between an antigen and a pH- and calcium-dependent binding antibody in plasma (pH7.4, 2 mM CO and in endosome (pH6.0, 3 μM (ii).
Figure 13:
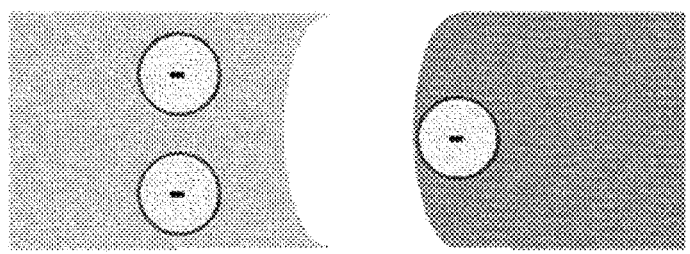
Figure 13:
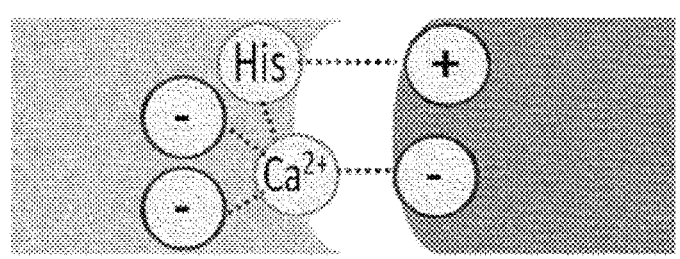
Figure 13:
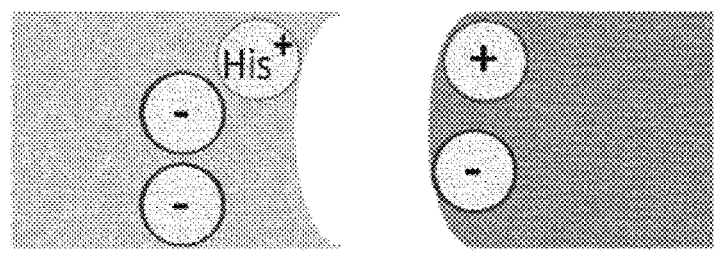

[Reference Example 2] Exploration of Human Germline Sequences that Bind to Calcium Ion (2-1) Antibody that Binds to Antigen in a Calcium-Dependent Manner Antibodies that bind to an antigen in a Ca-dependent manner (Ca-dependent antigen-binding antibodies) are those whose interactions with antigen change with calcium concentration. A Ca-dependent antigen-binding antibody is thought to bind to an antigen through calcium ion. Thus, amino acids that form an epitope on the antigen side are negatively charged amino acids that can chelate calcium ions or amino acids that can be a hydrogen-bond acceptor. These properties of amino acids that form an epitope allows targeting of an epitope other than binding molecules, which are generated by introducing histidines and bind to an antigen in a pH-dependent manner. Furthermore, as shown in FIG. 13, the use of antigen-binding molecules having calcium- and pH-dependent antigen-binding properties is thought to allow the formation of antigen-binding molecules that can individually target various epitopes having broad properties. Thus, if a population of molecules containing a calcium-binding motif (Ca library) is constructed, from which antigen-binding molecules are obtained, Ca-dependent antigen-binding antibodies are thought to be effectively obtained.

(2-2) Acquisition of Human Germline Sequences

An example of the population of molecules containing a calcium-binding motif is an example in which said molecules are antibodies. In other words, an antibody library containing a calcium-binding motif may be a Ca library.

Calcium ion-binding antibodies containing human germline sequences have not been reported. Thus, the germline sequences of antibodies having human germline sequences were cloned using as a template cDNA prepared from Human Fetal Spleen Poly RNA (Clontech) to assess whether antibodies having human germline sequences bind to calcium ion. Cloned DNA fragments were inserted into animal cell expression vectors. The nucleotide sequences of the constructed expression vectors were determined by a method known to those skilled in the art. The SEQ IDs are shown in Table 10. By PCR, polynucleotides encoding SEQ ID NO: 5 (Vk1), SEQ ID NO: 6 (Vk2), SEQ ID NO: 7 (Vk3), SEQ ID NO: 8 (Vk4), and SEQ ID NO: 43 (Vk5) were linked to a polynucleotide encoding the natural Kappa chain constant region (SEQ ID NO: 44). The linked DNA fragments were inserted into animal cell expression vectors. Furthermore, polynucleotides encoding SEQ ID NO: 46 (Vk1), SEQ ID NO: 47 (Vk2), SEQ ID NO: 48 (Vk3), SEQ ID NO: 49 (Vk4), and SEQ ID NO: 45 (Vk5) were linked by PCR to a polynucleotide encoding a polypeptide (SEQ ID NO: 11) having a deletion of two amino acids at the C terminus of IgG1. The resulting DNA fragments were inserted into animal cell expression vectors. The sequences of the constructed variants were confirmed by a method known to those skilled in the art.

TABLE 10

| Light chain germline sequence | SEQ ID NO of heavy chain variable region | SEQ ID NO of light chain variable region |
| --- | --- | --- |
| Vk1 | 46 | 5 |
| Vk2 | 47 | 6 |
| Vk3 | 48 | 7 |
| Vk4 | 49 | 8 |
| Vk5 | 45 | 43 |

(2-3) Expression and Purification of Antibodies

The constructed animal cell expression vectors inserted with the DNA fragments having the five types of human germ-line sequences were introduced into animal cells. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33\times10^6$ cells/ml (3 ml) into each well of a 6-well plate. The prepared plasmids are introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(2-4) Assessment of Antibodies Having Human Germ-Line Sequences for their Calcium Ion-Binding Activity The purified antibodies were assessed for their calcium ion-binding activity. The intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. It becomes higher when a protein is stabilized through calcium ion binding, as compared with the case where no calcium ion is bound (J. Biol. Chem. (2008) 283, 37, 25140-25149). The binding activity of calcium ion to antibody was evaluated by examining changes in the Tm value of the antibody depending on the changes in the calcium ion concentration in the antibody solution. The purified antibody was subjected to dialysis (EasySEP, TOMY) using an external solution of 20 mM Tris-HCl, 150 mM NaCl, and 2 mM $CaCl_2$ (pH 7.4) or 20 mM Tris-HCl, 150 mM NaCl, and 3 μM $CaCl_2$ (pH 7.4). DSC measurement was conducted at a heating rate of 240° C./hr from 20 to 115° C. using as a test substance an antibody solution prepared at about 0.1 mg/mL with the dialysate. The intermediate temperatures of thermal denaturation (Tm values) of the Fab domains of each antibody, calculated from the denaturation curve obtained by DSC, are shown in Table 11.

TABLE 11

| Light chain germline sequence | Calcium ion concentration | | ΔTm (° C.) |
|---|---|---|---|
| | 3 μM | 2 mM | 2 mM − 3 μM |
| hVk1 | 80.32 | 80.78 | 0.46 |
| hVk2 | 80.67 | 80.61 | −0.06 |
| hVk3 | 81.64 | 81.36 | −0.28 |
| hVk4 | 70.74 | 70.74 | 0 |
| hVk5 | 71.52 | 74.17 | 2.65 |

The result showed that the Tm values of the Fab domains of antibodies having the hVk1, hVk2, hVk3, or hVk4 sequence did not vary depending on the calcium ion concentration in the Fab domain-containing solutions. Meanwhile, the Tm value for the antibody Fab domain having the hVk5 sequence varied depending on the calcium ion concentration in the Fab domain-containing solution. This demonstrates that the hVk5 sequence binds to calcium ion.

(2-5) Assessment of the hVk5-2 Sequence for Calcium Binding

In addition to Vk5-2 (SEQ ID NO: 50 produced by fusing the kappa chain constant region SEQ ID NO: 44 to SEQ ID NO: 43), Vk5-2 variant 1 (SEQ ID NO: 51) and Vk5-2 variant 2 (SEQ ID NO: 52) classified as Vk5-2 were obtained in Reference Example 2, (2-2). These variants were assessed for their calcium binding activities. The DNA fragments of VK5-2, Vk5-2 variant 1, and Vk5-2 variant 2 were each incorporated into expression vectors for animal cells. The nucleotide sequences of the obtained expression vectors were determined by a method known to those skilled in the art. By the method described in Reference Example 2, (2-3), the animal cell expression vectors inserted with DNA fragments for each of Vk5-2, Vk5-2 variant 1, and Vk5-2 variant 2 were introduced into animal cells together with an animal expression vector carrying an insert to express CIM_H (SEQ ID NO: 45) as a heavy chain, and antibodies were purified. The purified antibodies were assessed for their calcium ion-binding activity. The purified antibodies were dialyzed (EasySEP, TOMY) against an external solution of 20 mM Tris-HCl, 150 mM NaCl, 2 mM CaCl$_2$ (pH 7.5), or an external solution of 20 mM Tris-HCl, 150 mM NaCl (pH 7.5) (indicated as a calcium ion concentration of 0 mM in Table 12). DSC measurement was carried out at a rate of temperature increase of 240° C./hr from 20° C. to 115° C., using as the test substance, antibody solutions prepared at a concentration of 0.1 mg/mL using the same solution as that for dialysis. Based on the obtained DSC denaturation curves, the intermediate temperature of thermal denaturation (Tm value) was calculated for the Fab domain of each antibody, and is shown in Table 12.

TABLE 12

| Light chain | Calcium ion concentration | | ΔTm (° C.) |
|---|---|---|---|
| | 0 mM | 2 mM | 2 mM − 0 mM |
| Vk5-2 | 71.65 | 74.38 | 2.73 |
| Vk5-2 variant 1 | 65.75 | 72.24 | 6.49 |
| Vk5-2 variant 2 | 66.46 | 72.24 | 5.78 |

The result showed that the Tm value for the Fab domains of antibodies having the sequence of Vk5-2, Vk5-2 variant 1, or Vk5-2 variant 2 varied depending on the calcium ion concentration in solutions containing antibodies having the Fab domains. This demonstrates that antibodies having a sequence classified as Vk5-2 bind to calcium ion.

[Reference Example 3] Assessment of the Human Vk5 (hVk5) Sequence (3-1) hVk5 Sequence The only hVk5 sequence registered in Kabat's database is hVk5-2 sequence. Hereinafter, hVk5 and hVk5-2 are used synonymously. WO2010/136598 discloses that the abundance ratio of the hVk5-2 sequence in the germline sequence is 0.4%. Other reports have been also made in which the abundance ratio of the hVk5-2 sequence in the germline sequence is 0-0.06% (J. Mol. Biol. (2000) 296, 57-86; Proc. Natl. Acad. Sci. USA (2009) 106, 48, 20216-20221). As described above, since the hVk5-2 sequence is a sequence of low appearance frequency in the germline sequence, it was thought to be inefficient to obtain a calcium-binding antibody from an antibody library consisting of human germline sequences or B cells obtained by immunizing a mouse expressing human antibodies. Thus, it is possible to design Ca libraries containing the sequence of human hVk5-2. Meanwhile, reported synthetic antibody libraries (WO2010/105256 and WO2010/136598) did not contain the sequence of hVk5. In addition, realization of the possibility is unknown because no report has been published on the physicochemical properties of the hVk5-2 sequence.

(3-2) Construction, Expression, and Purification of a Non-Glycosylated Form of the hVk5-2 Sequence The hVk5-2 sequence has a sequence for potential N glycosylation at position 20 amino acid (Kabat's numbering). Sugar chains attached to proteins exhibit heterogeneity. Thus, it is desirable to avoid the glycosylation from the viewpoint of substance homogeneity. In this context, variant hVk5-2_L65 (SEQ ID NO: 53) in which the Asn (N) residue at position 20 (Kabat's numbering) is substituted with Thr (T) was constructed. Amino acid substitution was carried out by a method known to those skilled in the art using the QuikChange Site-Directed Mutagenesis Kit (Stratagene). A DNA encoding the variant hVk5-2_L65 was inserted into an animal expression vector. The animal expression vector inserted with the constructed DNA encoding variant hVk5-2_L65, in combination with an animal expression vector having an insert to express CIM_H (SEQ ID NO: 45) as a heavy chain, was introduced into animal cells by the method described in Reference Example 2. The antibody comprising hVk5-2_L65 and CIM_H, which was expressed in animal cells introduced with the vectors, was purified by the method described in Reference Example 2.

Figure 14:
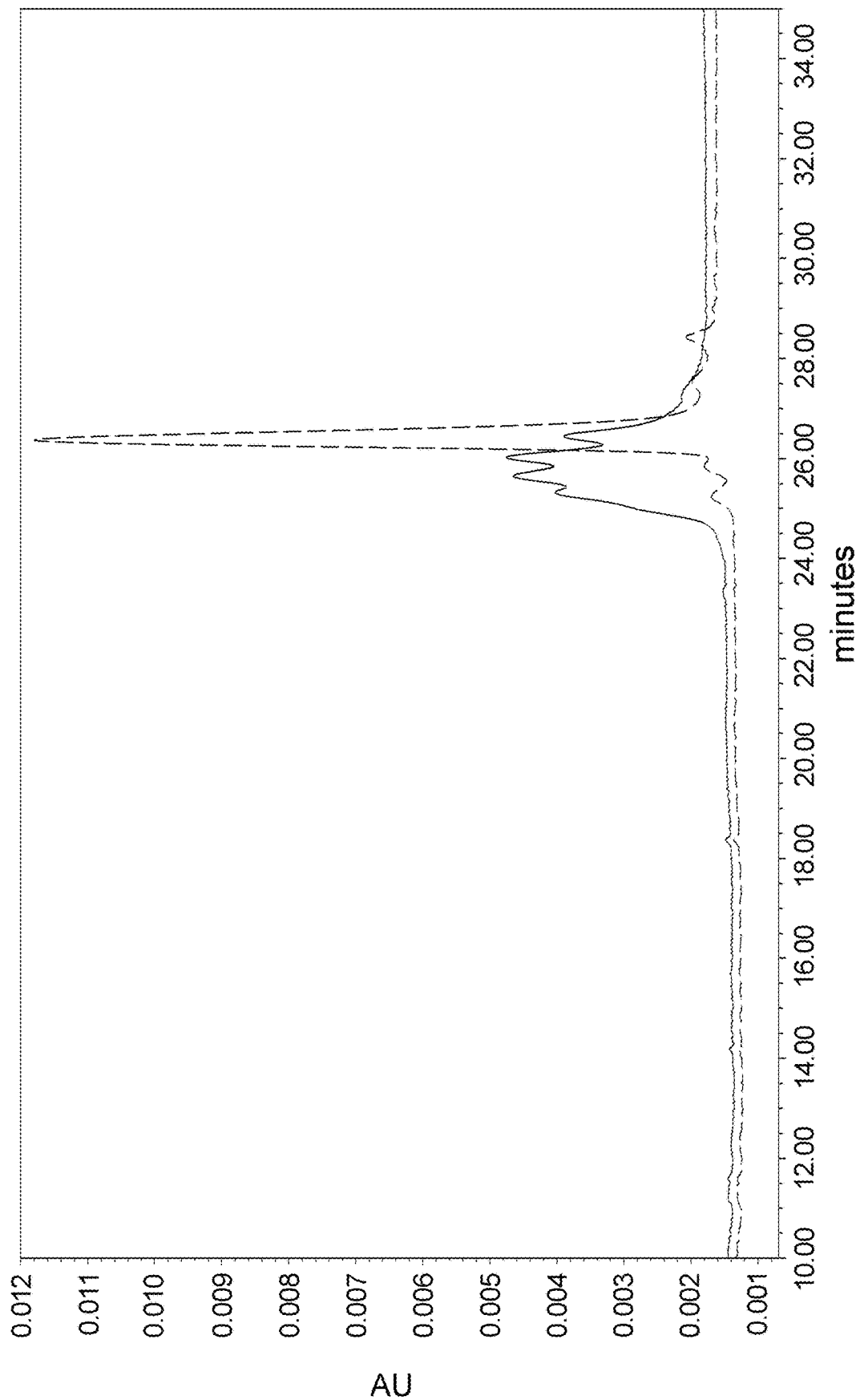
FIG. 14 shows an ion-exchange chromatogram for an antibody comprising a human Vk5-2 sequence and an antibody comprising an hVk5-2_L65 sequence which has a modified glycosylation sequence of the human Vk5-2 sequence. The solid line represents a chromatogram for the antibody comprising the human Vk5-2 sequence (heavy chain: CIM_H, SEQ ID NO: 45; and light chain: hVk5-2, SEQ ID NO: 50). The broken line represents a chromatogram for the antibody comprising the hVk5-2_L65 sequence (heavy chain: CIM_H (SEQ ID NO: 45); and light chain: hVk5-2_L65 (SEQ ID NO: 53)).

(3-3) Assessment of the Antibody Having the Non-Glycosylated hVk5-2 Sequence for Physicochemical Properties The isolated antibody having the modified sequence hVk5-2_L65 was analyzed by ion-exchange chromatography to test whether it is less heterogeneous than the antibody having the original sequence hVk5-2 before modification. The procedure of ion-exchange chromatography is shown in Table 13. The analysis result showed that hVk5-2_L65 modified at the glycosylation site was less heterogeneous than the original sequence hVk5-2, as shown in FIG. 14.

TABLE 13

| | CONDITION |
|---|---|
| COLUMN | TOSOH TSKgel DEAE-NPR |
| MOBILE PHASE | A; 10 mM Tris-HCl, 3 μM $CaCl_2$ (pH 8.0)<br>B; 10 mM Tris-HCl, 500 mM NaCl, 3 μM $CaCl_2$ (pH 8.0) |
| GRADIENT SCHEDULE | % B = 0-(5 min)-0-2%/1 min |
| COLUMN TEMPERATURE | 40° C. |
| DETECTION | 280 nm |
| INJECTION VOLUME | 100 μL (5 μg) |

Next, whether the less-heterogeneous hVk5-2_L65 sequence-comprising antibody binds to calcium ion was assessed by the method described in Reference Example 2. The result showed that the Tm value for the Fab domain of the antibody having hVk5-2_L65 with altered glycosylation site also varied depending on the calcium ion concentration in the antibody solutions, as shown in Table 14. Specifically, it was demonstrated that the Fab domain of the antibody having hVk5-2_L65 with altered glycosylation site binds to calcium ion.

TABLE 14

| LIGHT CHAIN | GLYCOSYLATED SEQUENCE | CALCIUM ION CONCENTRATION | | Δ Tm (° C.) |
|---|---|---|---|---|
| | | 3 μM | 2 mM | 2 mM − 3 μM |
| hVk5-2 | YES | 71.52 | 74.17 | 2.65 |
| hVk5-2_L65 | NO | 71.51 | 73.66 | 2.15 |

[Reference Example 4] Assessment of the Calcium Ion-Binding Activity of Antibody Molecules Having CDR Sequence of the hVk5-2 Sequence (4-1) Construction, Expression, and Purification of Modified Antibodies Having a CDR Sequence from the hVk5-2 Sequence The hVk5-2_L65 sequence is a sequence with altered amino acids at a glycosylation site in the framework of human Vk5-2 sequence. As described in Reference Example 3, it was demonstrated that calcium ion bound even after alteration of the glycosylation site. Meanwhile, from the viewpoint of immunogenicity, it is generally desirable that the framework sequence is a germ-line sequence. Thus, the present inventors assessed whether an antibody framework sequence could be substituted with the framework sequence of a non-glycosylated germline sequence while maintaining the calcium ion-binding activity of the antibody.

Polynucleotides encoding chemically synthesized sequences which comprise an altered framework sequence of the hVk5-2 sequence, hVk1, hVk2, hVk3, or hVk4 (CaVk1 (SEQ ID NO: 54), CaVk2 (SEQ ID NO: 55), CaVk3 (SEQ ID NO: 56), or CaVk4 (SEQ ID NO: 57), respectively) were linked by PCR to a polynucleotide encoding the constant region (SEQ ID NO: 44) of the natural Kappa chain. The linked DNA fragments were inserted into animal cell expression vectors. Sequences of the constructed variants were confirmed by a method known to those skilled in the art. Each plasmid constructed as described above was introduced into animal cells in combination with a plasmid inserted with a polynucleotide encoding CIM_H (SEQ ID NO: 45) by the method described in Reference Example 2. The expressed antibody molecules of interest were purified from culture fluid of the animal cells introduced with the plasmids.

(4-2) Assessment of Altered Antibodies Having the CDR Sequence of the hVk5-2 Sequence for their Calcium Ion-Binding Activity Whether calcium ion binds to altered antibodies having the CDR sequence of the hVk5-2 sequence and the framework sequences of germline sequences other than hVk5-2 (hVk1, hVk2, hVk3, and hVk4) was assessed by the method described in Reference Example 2. The assessment result is shown in Table 15. The Tm value of the Fab domain of each altered antibody was revealed to vary depending on the calcium ion concentration in the antibody solutions. This demonstrates that antibodies having a framework sequence other than the framework sequences of the hVk5-2 sequence also bind to calcium ion.

TABLE 15

| GERMLINE (LIGHT CHAIN FRAMEWORK SEQUENCE) | CALCIUM ION CONCENTRATION | | Δ Tm (° C.) |
|---|---|---|---|
| | 3 μM | 2 mM | 2 mM − 3 μM |
| hVk1 | 77.51 | 79.79 | 2.28 |
| hVk2 | 78.46 | 80.37 | 1.91 |
| hVk3 | 77.27 | 79.54 | 2.27 |
| hVk4 | 80.35 | 81.38 | 1.03 |
| hVk5-2 | 71.52 | 74.17 | 2.65 |

The thermal denaturation temperature (Tm value), as an indicator of thermal stability, of the Fab domain of each antibody altered to have the CDR sequence of the hVk5-2 sequence and the framework sequence of a germ-line sequence other than the hVk5-2 sequence (hVk1, hVk2, hVk3, or hVk4) was demonstrated to be greater than that of the Fab domain of the original antibody having the hVk5-2 sequence. This result shows that antibodies having the CDR sequence of the hVk5-2 sequence and the framework sequence of hVk1, hVk2, hVk3, or hVk4 not only have calcium ion-binding activity but also are excellent molecules from the viewpoint of thermal stability.

[Reference Example 5] Identification of the Calcium Ion-Binding Site in Human Germline hVk5-2 Sequence (5-1) Design of Mutation Site in the CDR Sequence of the hVk5-2 Sequence As described in Reference Example 4, antibodies having the light chain resulting from introduction of the CDR domain of the hVk5-2 sequence into the framework sequence of a different germline sequence were also demonstrated to bind to calcium ion. This result suggests that in hVk5-2 a calcium ion-binding site is localized within its CDR. Amino acids that bind to calcium ion, i.e., chelate calcium ion, include negatively charged amino acids and amino acids that can be a hydrogen bond acceptor. Thus, it was tested whether antibodies having a mutant hVk5-2 sequence with a substitution of an Ala (A) residue for an Asp (D) or Glu (E) residue in the CDR sequence of the hVk5-2 sequence bind to calcium ion.

(5-2) Construction of Variant hVk5-2 Sequences with Ala Substitution, and Expression and Purification of Antibodies Antibody molecules were prepared to comprise a light chain with substitution of an Ala residue for Asp and/or Glu residue in the CDR sequence of the hVk5-2 sequence. As described in Reference Example 3, non-glycosylated variant hVk5-2_L65 exhibited calcium ion binding and was assumed to be equivalent to the hVk5-2 sequence in terms of calcium ion binding. In this Reference Example, amino acid substitutions were introduced into hVk5-2_L65 as a template sequence. Constructed variants are shown in Table 16. Amino acid substitutions were carried out by methods known to those skilled in the art such as using the QuikChange Site-Directed Mutagenesis Kit (Stratagene), PCR, or the In fusion Advantage PCR Cloning Kit (TAKARA) to construct expression vectors for altered light chains having an amino acid substitution.

TABLE 16

| Light chain variant name | Altered position (Kabat numbering) | SEQ ID NO: |
|---|---|---|
| hVk5-2_L65 | Wild type | 53 |
| hVk5-2_L66 | 30 | 58 |
| hVk5-2_L67 | 31 | 59 |
| hVk5-2_L68 | 32 | 60 |
| hVk5-2_L69 | 50 | 61 |
| hVk5-2_L70 | 30, 32 | 62 |
| hVk5-2_L71 | 30, 50 | 63 |
| hVk5-2_L72 | 30, 32, 50 | 64 |
| hVk5-2_L73 | 92 | 65 |

Nucleotide sequences of the constructed expression vectors were confirmed by a method known to those skilled in the art. The expression vectors constructed for the altered light chains were transiently introduced, in combination with an expression vector for the heavy chain CIM_H (SEQ ID NO: 45), into cells of the human fetal kidney cell-derived HEK293H line (Invitrogen) or FreeStyle293 (Invitrogen) to express antibodies. From the obtained culture supernatants, antibodies were purified using the rProtein A Sepharose™ Fast Flow (GE Healthcare) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(5-3) Assessment of the Calcium Ion-Binding Activity of Antibodies Having an Ala Substitution in the hVk5-2 Sequence Whether the obtained purified antibodies bind to calcium ion was tested by the method described in Reference Example 2. The result is shown in Table 17. Some antibodies having substitution of an Asp or Glu residue in the CDR sequence of the hVk5-2 sequence with an Ala residue which cannot be involved in calcium ion binding or chelation were revealed to have an Fab domain whose Tm did not vary by the calcium ion concentration in the antibody solutions. The substitution sites at which Ala substitution did not alter the Tm (positions 32 and 92 (Kabat's numbering)) were demonstrated to be greatly important for the calcium ion-antibody binding.

TABLE 17

| LIGHT CHAIN VARIANT NAME | ALTERED POSITION (Kabat's NUMBERING) | CALCIUM ION CONCENTRATION | | Δ Tm (° C.) |
|---|---|---|---|---|
| | | 0 μM | 2 mM | 2 mM − 0 μM |
| hVk5-2_L65 | WILDTYPE | 71.71 | 73.69 | 1.98 |
| hVk5-2_L66 | 30 | 71.65 | 72.83 | 1.18 |
| hVk5-2_L67 | 31 | 71.52 | 73.30 | 1.78 |
| hVk5-2_L68 | 32 | 73.25 | 74.03 | 0.78 |
| hVk5-2_L69 | 50 | 72.00 | 73.97 | 1.97 |
| hVk5-2_L70 | 30, 32 | 73.42 | 73.60 | 0.18 |
| hVk5-2_L71 | 30, 50 | 71.84 | 72.57 | 0.73 |
| hVk5-2_L72 | 30, 32, 50 | 75.04 | 75.17 | 0.13 |
| hVk5-2_L73 | 92 | 75.23 | 75.04 | −0.19 |

[Reference Example 6] Assessment of the Calcium Ion-Binding Activity of Antibodies Having hVk1 Sequence with Calcium Ion-Binding Motif (6-1) Construction of an hVk1 Sequence with Calcium Ion-Binding Motif, and Expression and Purification of Antibodies The result described in Reference Example 4 on the calcium-binding activity of the Ala substitute demonstrates that Asp or Glu residues in the CDR sequence of the hVk5-2 sequence were important for calcium binding. Thus, the present inventors assessed whether an antibody can bind to calcium ion when the residues at positions 30, 31, 32, 50, and 92 (Kabat's numbering) alone were introduced into a different germline variable region sequence. Specifically, variant LfVk1_Ca (SEQ ID NO: 66) was constructed by substituting the residues at positions 30, 31, 32, 50, and 92 (Kabat's numbering) in the hVk5-2 sequence for the residues at positions 30, 31, 32, 50, and 92 (Kabat's numbering) in the hVk1 sequence (a human germline sequence). Specifically, it was tested whether antibodies having an hVk1 sequence introduced with only 5 residues from the hVk5-2 sequence can bind to calcium. The variants were produced by the same method as described in Reference Example 5. The resulting light chain variant LfVk1_Ca and LfVk1 having the light-chain hVk1 sequence (SEQ ID NO: 67) were co-expressed with the heavy chain CIM_H (SEQ ID NO: 45). Antibodies were expressed and purified by the same method as described in Reference Example 4.

(6-2) Assessment of the Calcium Ion-Binding Activity of Antibodies Having a Human hVk1 Sequence with Calcium Ion-Binding Motif Whether the purified antibody prepared as described above binds to calcium ion was assessed by the method described in Reference Example 2. The result is shown in Table 18. The Tm value of the Fab domain of the antibody having LfVk1 with an hVk1 sequence did not vary depending on the calcium concentration in the antibody solutions. Meanwhile, Tm of the antibody having the LfVk1_Ca sequence was shifted by 1° C. or more upon change in the calcium concentration in the antibody solutions. Thus, it was shown that the antibody having LfVk1 Ca binds to calcium. The result described above demonstrates that the entire CDR sequence of hVk5-2 is not required, while the residues introduced for construction of the LfVk1_Ca sequence alone are sufficient for calcium ion binding.

TABLE 18

| LIGHT CHAIN VARIANT | CALCIUM ION CONCENTRATION | | Δ Tm (° C.) |
|---|---|---|---|
| | 3 μM | 2 mM | 2 mM − 3 μM |
| LfVk1 | 83.18 | 83.81 | 0.63 |
| LfVk1_Ca | 79.83 | 82.24 | 2.41 |

[Reference Example 7] Design of a Population of Antibody Molecules (Ca Library) with a Calcium Ion-Binding Motif Introduced into the Variable Region to Effectively Obtain Binding Antibodies that Bind to Antigen in a Ca Concentration-Dependent Manner Preferred calcium-binding motifs include, for example, the hVk5-2 sequence and the CDR sequence, as well as residues at positions 30, 31, 32, 50, and 92 (Kabat numbering). Other calcium-binding motifs include the EF-hand motif possessed by calcium-binding proteins (e.g., calmodulin) and C-type lectin (e.g., ASGPR).

The Ca library is composed of heavy chain variable regions and light chain variable regions. Human antibody sequences were used for the heavy chain variable regions and a calcium-binding motif was introduced to the light chain variable regions. The hVk1 sequence was selected as a template sequence of the light chain variable region to which a calcium-binding motif is inserted. The antibody containing the LfVk1_Ca sequence, which has the CDR sequence of hVk5-2, one of the calcium-binding motifs, introduced into the hVk1 sequence, was shown to bind to a calcium ion as shown in Reference Example 5. Multiple amino acids were allowed to appear in the template sequence to diversify antigen-binding molecules that constitute the library. Positions exposed on the surface of a variable region which is likely to interact with the antigen were selected as those where multiple amino acids are allowed to appear. Specifically, positions 30, 31, 32, 34, 50, 53, 91, 92, 93, 94, and 96 (Kabat numbering) were selected as flexible residues.

The type and appearance frequency of amino acid residues that were subsequently allowed to appear were determined. The appearance frequency of amino acids in the flexible residues of the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the Ca library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

A Ca library containing a calcium-binding motif with emphasis on the sequence diversity as to contain multiple amino acids at each residue other than the motif were designed as a Ca library in consideration of the amino acids and appearance frequency set as described above. The detailed designs of the Ca library are shown in Tables 1 and 2 (with the positions in each table representing the Kabat numbering). When position 92 based on the Kabat numbering is Asn (N), the frequency of appearance of amino acids shown in Tables 1 and 2 may be Leu (L) rather than Ser (S) at position 94.

(Reference Example 8) Ca Library Production

A library of antibody heavy chain variable region genes was amplified by the PCR method using poly A RNA prepared from human PBMC or commercially available human poly A RNA as template. Regarding the antibody light chain variable region portions, as shown in Reference Example 7, antibody variable region light chain portions which increase the frequency of appearance of antibodies maintaining a calcium-binding motif and allows binding to antigens in a calcium-concentration-dependent manner were designed. In addition, for amino acid residues among the flexible residues other than those with a calcium-binding motif introduced, a library of antibody light chain variable regions with evenly distributed amino acids of high appearance frequency in natural human antibody sequences was designed with reference to the information of amino acid appearance frequency in natural human antibodies (KABAT, E. A. ET AL.: 'Sequences of proteins of immunological interest', vol. 91, 1991, NIH PUBLICATION). A combination of the gene libraries of antibody heavy-chain and light-chain variable regions generated as described above, was inserted into a phagemid vector to construct a human antibody phage display library that presents Fab domains consisting of human antibody sequences (Methods Mol Biol. (2002) 178, 87-100).

Figure 15:
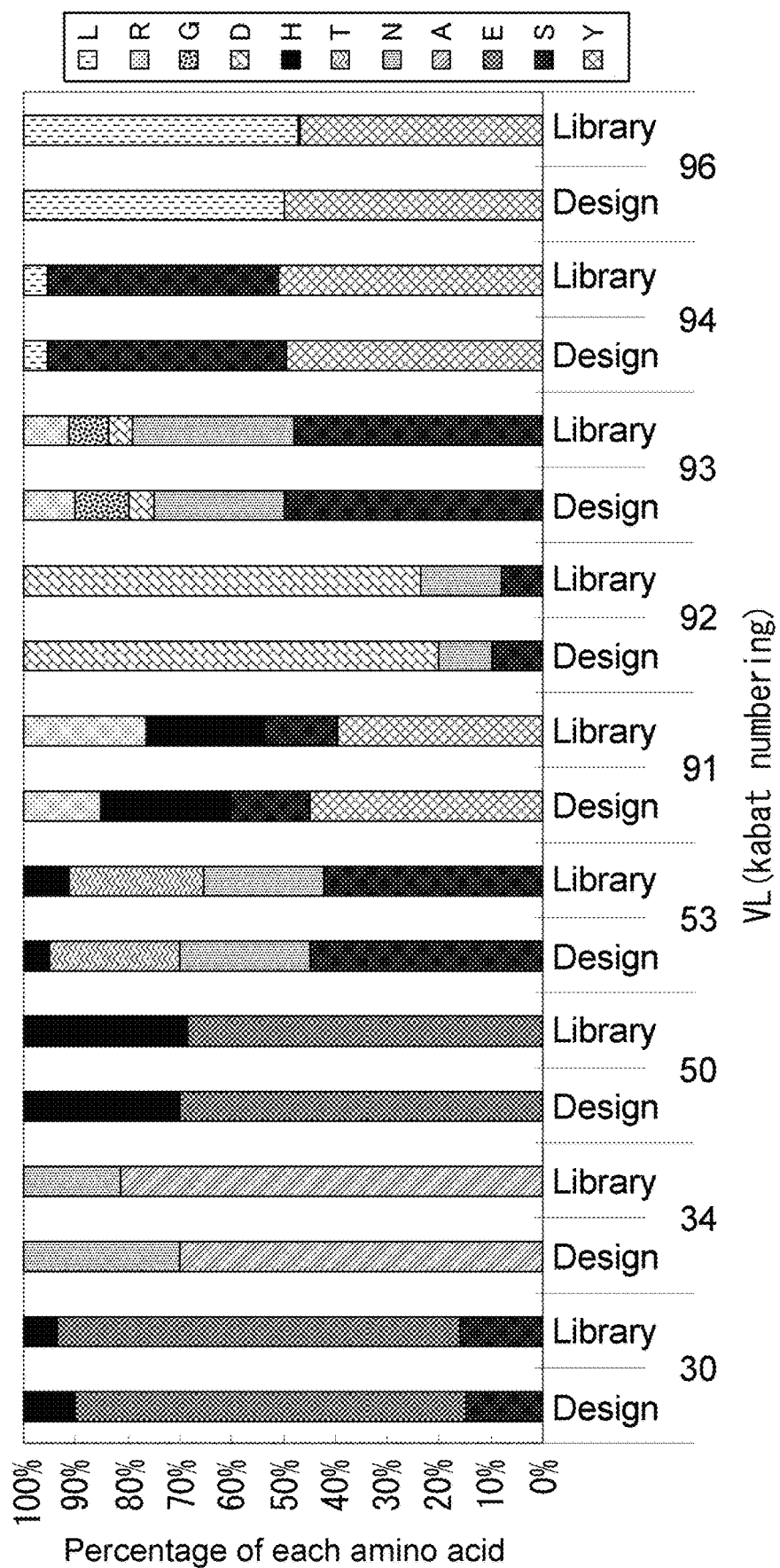
FIG. 15 shows the relationship of a designed amino acid distribution (indicated as Design) to the amino acid distribution (indicated as Library) for the sequence information on 290 clones isolated from E. coli introduced with a gene library of antibodies that bind to antigens in a Ca-dependent manner. The horizontal axis indicates amino acid positions in the Kabat numbering system. The vertical axis indicates % amino acid distribution.

Sequences of the antibody gene portions isolated from *E. coli* carrying the antibody gene library were confirmed. The amino acid distribution of the sequences of the obtained 290 clones and the designed amino acid distribution are shown in FIG. 15.

(Reference Example 9) Assessment of Calcium Ion-Binding Activity of Molecules Included in the Ca Library (9-1) Calcium Ion-Binding Activity of Molecules Included in the Ca Library As shown in Reference Example 3, the hVk5-2 sequence shown to bind to calcium ions has low frequency of appearance in the germ line sequences; therefore, trying to obtain calcium-binding antibodies from antibody libraries composed of human germline sequences or from B cells obtained by immunization of human antibody-expressing mice was considered inefficient. Accordingly, a Ca library was constructed in Reference Example 8. The constructed Ca library was assessed for the presence of clones showing calcium binding.

(9-2) Expression and Purification of Antibodies

Clones of the Ca library were introduced into animal cell expression plasmids. Antibodies were expressed using the method described below. Cells of human fetal kidney cell-derived FreeStyle 293-F line (Invitrogen) were suspended in FreeStyle 293 Expression Medium (Invitrogen), and plated at a cell density of $1.33 \times 10^6$ cells/ml (3 ml) to each well of a 6-well plate. The prepared plasmids were introduced into the cells by a lipofection method. The cells were cultured in a $CO_2$ incubator (37° C., 8% $CO_2$, 90 rpm) for four days. By a method known to those skilled in the art, antibodies were purified using rProtein A Sepharose™ Fast Flow (Amersham Biosciences) from culture supernatants obtained as described above. The absorbance of solutions of purified antibodies was measured at 280 nm using a spectrophotometer. Antibody concentrations were calculated from the measured values by using the absorption coefficient determined by PACE method (Protein Science (1995) 4, 2411-2423).

(9-3) Assessment of Calcium Ion-Binding Property of the Obtained Antibodies

Whether the purified antibodies obtained as described above bind to calcium ions was assessed by the method described in Example 6. The results are shown in Table 19. The Tm of the Fab domains of multiple antibodies included in the Ca library changed depending on the calcium ion concentration, and this showed that the library includes calcium-ion-binding molecules.

TABLE 19

| Antibody | SEQ ID NO: Heavy chain | SEQ ID NO: Light chain | Calcium ion concentration 3 μM | Calcium ion concentration 2 mM | ΔTm (° C.) 2 mM – 3 μM |
|---|---|---|---|---|---|
| Ca_B01 | 68 | 79 | 70.88 | 71.45 | 0.57 |
| Ca_E01 | 69 | 80 | 84.31 | 84.95 | 0.64 |
| Ca_H01 | 70 | 81 | 77.87 | 79.49 | 1.62 |
| Ca_D02 | 71 | 82 | 78.94 | 81.1 | 2.16 |
| Ca_E02 | 72 | 83 | 81.41 | 83.18 | 1.77 |
| Ca_H02 | 73 | 84 | 72.84 | 75.13 | 2.29 |
| Ca_D03 | 74 | 85 | 87.39 | 86.78 | −0.61 |
| Ca_C01 | 75 | 86 | 74.74 | 74.92 | 0.18 |
| Ca_G01 | 76 | 87 | 65.21 | 65.87 | 0.66 |
| Ca_A03 | 77 | 88 | 80.64 | 81.89 | 1.25 |
| Ca_B03 | 78 | 89 | 93.02 | 93.75 | 0.73 |

[Reference Example 10] Preparation of Antibodies that Bind to IL-6 Receptor in a Ca-Dependent Manner (10-1) Preparation of Antibody Fragments that Bind to the Antigen in a Ca-Dependent Manner from Library by Bead Panning Primary selection from the constructed library of antibodies that bind to IL-6 receptor in a Ca-dependent manner was carried out by enriching antibody fragments that have antigen (IL-6 receptor)-binding activity.

Phages were produced from *E. coli* carrying the constructed phagemid for phage display. To precipitate the phages produced by *E. coli*, 2.5 M NaCl/10% PEG was added to the *E. coli* culture fluid. The phage fraction was diluted with TBS to prepare a phage library solution. Then, BSA and CaCl₂ were added the phage library solution at final concentrations of 4% and 1.2 mM calcium ion, respectively. The panning method used was a conventional panning method using antigen-immobilized magnetic beads (J. Immunol. Methods. (2008) 332(1-2): 2-9; J. Immunol. Methods. (2001) 247(1-2): 191-203; Biotechnol. Prog. (2002) 18(2): 212-20; Mol. Cell Proteomics (2003) 2(2): 61-9). The magnetic beads used were NeutrAvidin-coated beads (Sera-Mag SpeedBeads NeutrAvidin-coated) and Streptavidin-coated beads (Dynabeads M-280 Streptavidin).

Specifically, 250 pmol of the biotin-labeled antigen was added to the prepared phage library solution. Thus, the solution was contacted with the antigen at room temperature for 60 minutes. Magnetic beads blocked with BSA were added, and the antigen-phage complex was allowed to bind to the magnetic beads at room temperature for 15 minutes. The beads were washed three times with 1 mL of 1.2 mM CaCl₂/TBST (TBST containing 1.2 mM CaCl₂), and then twice with 1 ml of 1.2 mM CaCl₂/TBS (TBS containing 1.2 mM CaCl₂). Thereafter, 0.5 ml of 1 mg/ml trypsin was added to the beads. After 15 minutes of dispersion at room temperature, the beads were immediately separated using a magnetic stand to collect a phage suspension. The prepared phage suspension was added to 10 ml of *E. coli* of stain ER2738 at the logarithmic growth phase (OD600=0.4 to 0.7). The *E. coli* was incubated with gentle stirring at 37° C. for one hour to infect the phages. The infected *E. coli* was seeded in a plate (225 mm×225 mm). Then, phages were collected from the culture fluid of the seeded *E. coli* to prepare a phage library solution.

In the second round panning, phages were enriched using the antigen-binding activity or the Ca-dependent binding activity as an indicator.

Specifically, when the enrichment was carried out using the antigen-binding ability as an indicator, 40 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed three times with 1 ml of 1.2 mM CaCl₂/TBST and then twice with 1.2 mM CaCl₂/TBS. Then, the beads added with 0.5 ml of 1 mg/ml trypsin were suspended at room temperature for 15 minutes. Then immediately, the beads were separated using a magnetic stand to collect a phage solution. To eliminate the ability from phages displaying on Fab to infect *E. coli*, the pIII protein (helper phage-derived pIII protein) of phages displaying no Fab was cleaved by adding 5 μl of 100 mg/ml trypsin to the collected phage solution. The collected phage solution was added to 10 mL of the *E. coli* strain ER2738 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were collected from the culture fluid of the *E. coli* after inoculation to collect a phage library solution.

When the enrichment was carried out using the Ca-dependent binding ability as an indicator, 40 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed with 1 ml of 1.2 mM CaCl₂/TBST and with 1.2 mM CaCl₂/TBS. Then, the beads added with 0.1 ml of 2 mM EDTA/TBS (TBS containing 2 mM EDTA) were suspended at room temperature. Then immediately, the beads were separated using a magnetic stand to collect a phage solution. To eliminate the ability from phages displaying on Fab to infect *E. coli*, the pIII protein (helper phage-derived pIII protein) of phages displaying no Fab was cleaved by adding 5 μl of 100 mg/ml trypsin to the collected phage solution. The collected phage solution was added to 10 mL of the *E. coli* strain ER2738 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were collected from the culture fluid of the *E. coli* after inoculation to collect a phage library solution.

(10-2) Assessment by Phage ELISA

Culture supernatants containing phages were collected from single colonies of *E. coli* obtained by the method described above according to a conventional method (Methods Mol. Biol. (2002) 178, 133-145).

BSA and CaCl₂ were added to the phage-containing culture supernatants. The supernatants were subjected to ELISA by the following procedure. A StreptaWell 96-well microtiter plate (Roche) was coated overnight with 100 μl of PBS containing the biotin-labeled antigen. The antigen was removed by washing each well of the plate with PBST. Then, the wells were blocked with 250 μl of 4% BSA-TBS for one hour or more. After removal of 4% BSA-TBS, the prepared culture supernatants were added to the each well. The plate was incubated at 37° C. for one hour so that the antibody-displaying phages were allowed to bind to the antigen on each well. After each well was washed with 1.2 mM CaCl₂/TBST, 1.2 mM CaCl₂/TBS or 1 mM EDTA/TBS was added. The plate was left for incubation at 37° C. for 30 minutes. After washing with 1.2 mM $CaCl_2$/TBST, an HRP-conjugated anti-M13 antibody (Amersham Pharmacia Biotech) diluted with TBS at an ionized calcium concentration of 1.2 mM was added to each well, and the plate was incubated for one hour. After washing with 1.2 mM $CaCl_2$/TBST, the TMB single solution (ZYMED) was added to each well. The chromogenic reaction in the solution of each well was stopped by adding sulfuric acid. Then, the developed color was assessed by measuring absorbance at 450 nm.

To clones subjected to the above phage ELISA, the base sequence of a gene amplified with specific primers was analyzed. The result of sequence analysis was shown in Table 20 below.

TABLE 20

| Library Enrichment index | Ca library Antigen-binding ability | Ca library Dependent antigen-binding ability |
|---|---|---|
| Number of panning | 2 | 2 |
| Number of examined clones | 85 | 86 |
| ELISA-positive | 77 | 75 |
| Types of ELISA-positive clone sequences | 74 | 72 |
| Types of Ca-dependent binding clone sequences | 13 | 47 |

(10-3) Expression and Purification of Antibodies

Clones that were judged to have a Ca-dependent antigen-binding activity based on the result of phage ELISA were inserted into animal cell expression plasmids. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the obtained culture supernatants, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(10-4) Assessment of Ca-Dependent Binding Ability to the Human IL-6 Receptor for the Obtained Antibodies To determine whether the antibodies obtained in Reference Example 9, i.e. 6RC1IgG_010 (heavy chain SEQ ID NO: 90, light chain SEQ ID NO: 91), 6RC1IgG_012 (heavy chain SEQ ID NO: 92, light chain SEQ ID NO: 93), and 6RC1IgG_019 (heavy chain SEQ ID NO: 94, light chain SEQ ID NO: 95), have Ca-dependent binding activity to the human IL-6 receptor, analyses of interaction between these antibodies and the human IL-6 receptor were carried out using Biacore T100 (GE Healthcare). Tocilizumab (heavy chain SEQ ID NO: 96, light chain SEQ ID NO: 97) was used as the control antibody which does not have Ca-dependent binding activity to the human IL-6 receptor. Interaction analyses were performed in a solution with a calcium ion concentration of 1.2 mM for the high calcium ion concentration condition or 3 µM for the low calcium ion concentration condition. A suitable amount of protein A/G (Invitrogen) was immobilized onto a Sensor chip CM5 (GE Healthcare) by the amine coupling method, and then antibodies of interest were captured onto the chips. Two types of buffers, 20 mM ACES, 150 mM NaCl, 0.05% (w/v) Tween 20, 1.2 mM $CaCl_2$ (pH 7.4) or 20 mM ACES, 150 mM NaCl, 0.05% (w/v) Tween 20, 3 µM $CaCl_2$ (pH 7.4), were used as the running buffer. The respective buffers were also used for dilution of the human IL-6 receptor. All measurements were taken at 37° C.

When performing interaction analyses on antigen-antibody reactions using the tocilizumab antibody, which is the control antibody, the 6RC1IgG_010 antibody, the 6RC1IgG_012 antibody, and the 6RC1IgG_019 antibody, the diluted IL-6 receptor solution and the running buffer, which is the blank, were injected at a flow rate of 5 µL/min for three minutes to allow the IL-6 receptor to interact with the tocilizumab antibody, the 6RC1IgG_010 antibody, the 6RC1IgG_012 antibody, and the 6RC1IgG_019 antibody captured onto the sensor chip. Then, 10 mM glycine-HCl (pH 1.5) was injected at a flow rate of 30 µL/min for 30 seconds to regenerate the sensor chip.

Figure 16:
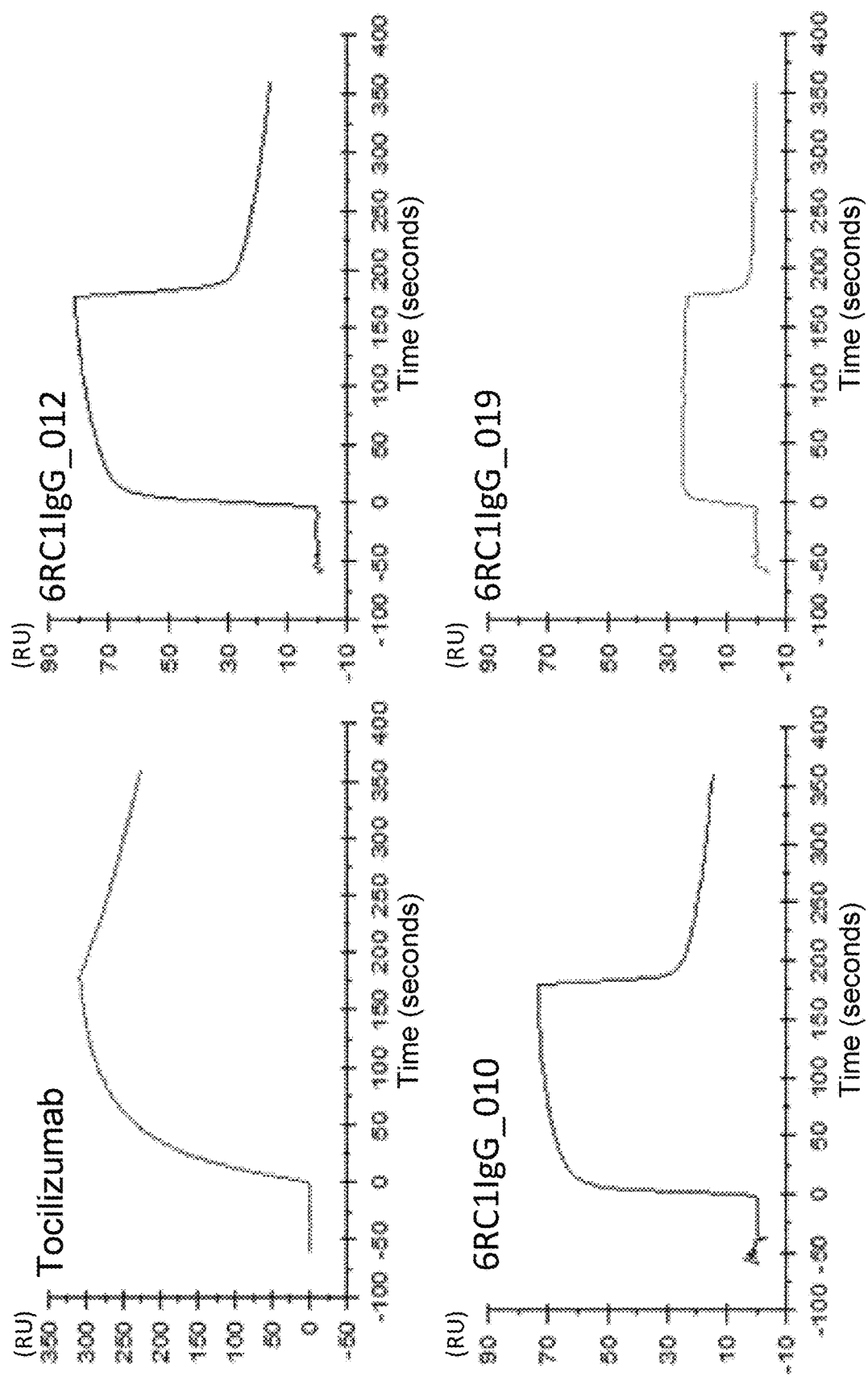
FIG. 16 shows sensorgrams for anti-IL-6R antibody (tocilizumab), antibody 6RC1IgG_010, antibody 6RC1IgG_012, and antibody 6RC1IgG_019 under a high calcium ion concentration (1.2 mM) condition.

Sensorgrams at high calcium ion concentration obtained by this method are shown in FIG. 16.

Figure 17:
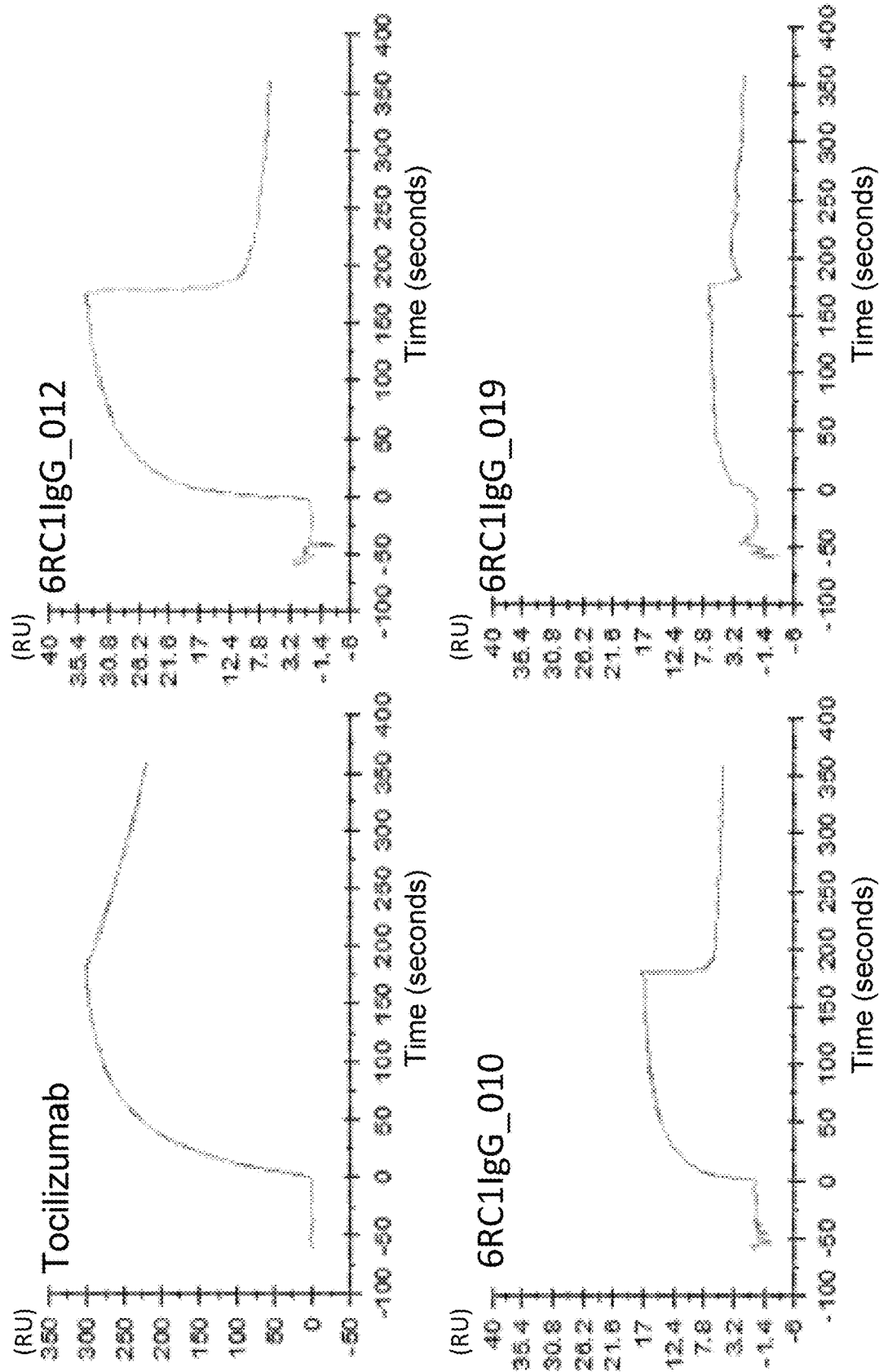
FIG. 17 shows sensorgrams for anti-IL-6R antibody (tocilizumab), antibody 6RC1IgG_010, antibody 6RC1IgG_012, and antibody 6RC1IgG_019 under a low calcium ion concentration (3 μM) condition.

Sensorgrams for the tocilizumab antibody, the 6RC1IgG_010 antibody, the 6RC1IgG_012 antibody, and the 6RC1IgG_019 antibody under low calcium ion concentration conditions were also obtained by a similar method. The sensorgrams obtained at low calcium ion concentration are shown in FIG. 17.

From the above-mentioned results, ability of the 6RC1IgG_010 antibody, the 6RC1IgG_012 antibody, and the 6RC1IgG_019 antibody to bind to the IL6 receptor was observed to be greatly reduced by setting the calcium ion concentration in the buffer to 3 µM from 1.2 mM.

[Reference Example 11] Acquisition of Antibodies that Bind to IL-6 Receptor in Ca-Dependent Manner from a Human Antibody Library Using Phage Display Technology (11-1) Preparation of a Phage Display Library for Naive Human Antibodies A phage display library for human antibodies, consisting of multiple phages presenting the Fab domains of mutually different human antibody sequences, was constructed according to a method known to those skilled in the art using a poly A RNA prepared from human PBMC, and commercial human poly A RNA as a template.

(11-2) Acquisition of Antibody Fragments that Bind to Antigen in Ca-Dependent Manner from the Library by Bead Panning The constructed phage display library for naive human antibodies was subjected to initial selection through concentration of only antibody fragments having an antigen (IL-6 receptor)-binding ability or concentration of antibody fragments using a Ca concentration-dependent antigen (IL-6 receptor)-binding ability as an indicator. Concentration of antibody fragments using a Ca concentration-dependent antigen (IL-6 receptor)-binding ability as an indicator were conducted through elution of the phage library phages bound to IL-6 receptor in the presence of Ca ions with EDTA that chelates the Ca ions Biotinylated IL-6 receptor was used as an antigen.

Phages were produced from *Escherichia coli* carrying the constructed phage display phagemid. A phage library solution was obtained by diluting with TBS a phage population precipitated by adding 2.5 M NaCl/10% PEG to the *E. coli* culture solution in which the phages were produced. Subsequently, BSA and $CaCl_2$ were added to the phage library solution at a final concentration of 4% BSA and 1.2 mM of calcium ion concentration. A common panning method using an antigen immobilized on magnetic beads was referred to as a panning method (J. Immunol. Methods. (2008) 332 (1-2), 2-9; J. Immunol. Methods. (2001) 247 (1-2), 191-203; Biotechnol. Prog. (2002) 18(2) 212-20; Mol. Cell Proteomics (2003) 2 (2), 61-9). NeutrAvidin coated beads (Sera-Mag SpeedBeads NeutrAvidin-coated) or Streptavidin coated beads (Dynabeads M-280 Streptavidin) were used as magnetic beads.

Specifically, 250 pmol of the biotin-labeled antigen was added to the prepared phage library solution to allow the contact of said phage library solution with the antigen for 60 minutes at room temperature. Magnetic beads, blocked with BSA, were added to be bound to antigen-phage complexes for 15 minutes at room temperature. The beads were washed once with 1 mL of 1.2 mM $CaCl_2$/TBS (TBS containing 1.2 mM $CaCl_2$). Subsequently, a phage solution was collected by a general elution method to concentrate an antibody fragment having an IL-6 receptor-binding ability, or by elution from beads suspended in 2 mM EDTA/TBS (TBS containing 2 mM EDTA) to concentrate an antibody fragment using an IL-6 receptor-binding ability in a Ca concentration-dependent manner as an indicator. The collected phage solution was added to 10 mL of the E. coli strain TG1 in a logarithmic growth phase (OD600 of 0.4-0.7). The E. coli was cultured with gentle stirring at 37° C. for 1 hour to allow the phages to infect the E. coli. The infected E. coli was inoculated into a 225 mm×225 mm plate. Subsequently, the phages were collected from the culture fluid of the E. coli after inoculation to prepare a phage library solution.

In the second and subsequent panning, the phages were concentrated using the Ca-dependent binding ability as an indicator. Specifically, 40 pmol of the biotin-labeled antigen was added to the prepared phage library solution to allow the contact of the phage library with the antigen for 60 minutes at room temperature. Magnetic beads, blocked with BSA, were added to be bound to antigen-phage complexes for 15 minutes at room temperature. The beads were washed with 1 mL of 1.2 mM $CaCl_2$/TBST and 1.2 mM $CaCl_2$/TBS. Subsequently, the beads, to which 0.1 mL of 2 mM EDTA/TBS was added, were suspended at room temperature. Immediately after that, the beads were separated using a magnetic stand to collect a phage solution. The collected phage solution was added to 10 mL of the E. coli strain TG1 in a logarithmic growth phase (OD600 of 0.4-0.7). The E. coli was cultured with gentle stirring at 37° C. for 1 hour to allow the phages to infect the E. coli. The infected E. coli was inoculated into a 225 mm×225 mm plate. Subsequently, the phages were collected from the culture fluid of the E. coli after inoculation to collect a phage library solution. The panning using the Ca-dependent binding ability as an indicator was repeated several times.

(11-3) Examination by Phage ELISA

A phage-containing culture supernatant was collected according to a routine method (Methods Mol. Biol. (2002) 178, 133-145) from a single colony of E. coli, obtained as described above.

A culture supernatant containing phages, to which BSA and $CaCl_2$ were added at a final concentration of 4% BSA and 1.2 mM of calcium ion concentration was subjected to ELISA as described below. A StreptaWell 96 microtiter plate (Roche) was coated overnight with 100 µL of PBS containing the biotin-labeled antigen. Each well of said plate was washed with PBST to remove the antigen, and then the wells were blocked with 250 µL of 4% BSA-TBS for 1 hour or longer. Said plate with the prepared culture supernatant added to each well, from which the 4% BSA-TBS was removed, was allowed to stand undisturbed at 37° C. for 1 hour, allowing the binding of phage-presenting antibody to the antigen present in each well. To each well washed with 1.2 mM $CaCl_2$/TBST, 1.2 mM $CaCl_2$/TBS or 1 mM EDTA/TBS was added. The plate was allowed to stand undisturbed for 30 minutes at 37° C. for incubation. After washing with 1.2 mM $CaCl_2$/TBST, an HRP-conjugated anti-M13 antibody (Amersham Pharmacia Biotech) diluted with TBS at a final concentration of 4% BSA and 1.2 mM of ionized calcium concentration was added to each well, and the plate was incubated for 1 hour. After washing with 1.2 mM $CaCl_2$/TBST, the chromogenic reaction of the solution in each well with a TMB single solution (ZYMED) added was stopped by adding sulfuric acid. Subsequently, said color was measured by measuring absorbance at 450 nm.

As a result of the above phage ELISA, the base sequence of a gene amplified with specific primers and an antibody fragment identified as having a Ca-dependent antigen-binding ability as a template was analyzed.

(11-4) Antibody Expression and Purification

As a result of the above phage ELISA, a clone identified as having a Ca-dependent antigen-binding ability was introduced into an expression plasmid for animal cells. Antibodies were expressed as described below. FreeStyle 293-F strain (Invitrogen) derived from human fetal kidney cells was suspended in FreeStyle 293 Expression Medium (Invitrogen), followed by inoculation of 3 mL into each well of a 6-well plate at a cell density of $1.33×10^6$ cell/mL. The prepared plasmid was introduced into the cells by lipofection. The cells were cultured for 4 days in a $CO_2$ incubator (37° C., 8% $CO_2$, 90 rpm). Antibodies were purified from the culture supernatant obtained above by a method known in the art using rProtein A Sepharose (trade mark) Fast Flow (Amersham Biosciences). Absorbance of the purified antibody solution was measured at 280 nm using a spectrophotometer. Antibody concentration was calculated from the measurements obtained using an extinction coefficient calculated by the PACE method (Protein Science (1995) 4, 2411-2423).

[Reference Example 12] Examination of Ca-Dependent Binding Ability of the Obtained Antibodies to Human IL-6 Receptor To examine whether or not the binding activities of antibodies 6RL #9-IgG1 [heavy chain (a sequence in which a constant region derived from IgG1 is linked to SEQ ID NO: 98) and light chain (SEQ ID NO: 99)] and FH4-IgG1 [heavy chain (SEQ ID NO: 100) and light chain (SEQ ID NO: 101)], obtained in Reference Example 11, to human IL-6 receptor are Ca-dependent, the kinetic analysis of the antigen-antibody reactions of these antibodies with human IL-6 receptor was conducted using Biacore T100 (GE Healthcare). H54/L28-IgG1 [heavy chain: SEQ ID NO: 102; and light chain: SEQ ID NO: 103], described in WO2009/125825, was used as a control antibody that has no Ca-dependent binding activity to human IL-6 receptor. The kinetic analysis of the antigen-antibody reactions was conducted in solutions with 2 mM and 3 µM calcium ion concentrations, set as high and low calcium ion concentration conditions, respectively. The antibody of interest was captured on Sensor chip CM4 (GE Healthcare) on which an appropriate amount of protein A (Invitrogen) was immobilized by an amine coupling method. Two buffers [10 mM ACES, 150 mM NaCl, 0.05% (w/v) Tween 20, and 2 mM $CaCl_2$ (pH 7.4) or 10 mM ACES, 150 mM NaCl, 0.05%

(w/v) Tween 20, and 3 μmol/L $CaCl_2$ (pH 7.4)] were used as running buffers. These buffers were used for diluting human IL-6 receptor. All the measurements were conducted at 37° C.

In the kinetic analysis of antigen-antibody reaction using H54L28-IgG1 antibody, the H54L28-IgG1 antibody captured on the sensor chip was allowed to interact with IL-6 receptor by injecting a diluent of IL-6 receptor and running buffer (blank) at a flow rate of 20 μL/min for 3 minutes. Subsequently, after the dissociation of IL-6 receptor was observed using running buffer at a flow rate of 20 μL/min for 10 minutes, the sensor chip was regenerated by injecting 10 mM glycine-HCl (pH 1.5) at a flow rate 30 μL/min for 30 seconds. Kinetics parameters, binding constant (ka) (1/Ms) and dissociation rate constant (kd) (1/s), were calculated from the sensorgrams obtained in the measurement. These values were used to calculate the dissociation constant (KD) (M) of the H54L28-IgG1 antibody for human IL-6 receptor. Each parameter was calculated using the Biacore T100 Evaluation Software (GE Healthcare).

In the kinetic analysis of antigen-antibody reaction using FH4-IgG1 and 6RL #9-IgG1 antibodies, the FH4-IgG1 or 6RL #9-IgG1 antibody captured on the sensor chip was allowed to interact with IL-6 receptor by injecting a diluent of IL-6 receptor and running buffer (blank) at a flow rate of 5 μL/min for 15 minutes. Subsequently, the sensor chip was regenerated by injecting 10 mM glycine-HCl (pH 1.5) at a flow rate 30 μL/min for 30 seconds. Dissociation constants (KD) (M) were calculated from the sensorgrams obtained in the measurement, using a steady-state affinity model. Each parameter was calculated using the Biacore T100 Evaluation Software (GE Healthcare).

The dissociation constants (KD) between each antibody and IL-6 receptor in the presence of 2 mM $CaCl_2$, determined by the above method, are shown in Table 21.

TABLE 21

| ANTIBODY | H54/L28-IgG1 | FH4-IgG1 | 6RL#9-IgG1 |
|---|---|---|---|
| kD (M) | 1.9E−9 | 5.9E−7 | 2.6E−7 |

The KD value of the H54/L28-IgG1 antibody under the condition of 3 μM Ca concentration can be calculated in the same manner as in the presence of 2 mM Ca concentration. Under the condition of 3 μM Ca concentration, FH4-IgG1 and 6RL #9-IgG1 antibodies were barely observed to be bound to IL-6 receptor, thus the calculation of KD values by the method described above is difficult. However, the KD values of these antibodies under the condition of 3 μM Ca concentration can be estimated using Equation 1 (Biacore T100 Software Handbook, BR-1006-48, AE 01/2007) below.

$$Req = C \times Rmax/(KD+C)+RI \quad \text{[Equation 1]}$$

The meaning of each parameter in the aforementioned [Equation 1] is as follows:
Req (RU): Steady state binding levels
Rmax (RU): Analyte binding capacity of the surface
RI (RU): Bulk refractive index contribution in the sample
C (M) Analyte concentration
KD (M): Equilibrium dissociation constant The approximate results of dissociation constant KD values for the antibodies and IL-6 receptor at a Ca concentration of 3 μmol/L, estimated using the above-described [Equation 1], are shown in Table 22. In Table 22, the Req, Rmax, RI, and C values are estimated based on the assay result.

TABLE 22

| ANTIBODY | H54/L28-IgG1 | FH4-IgG1 | 6RL#9-IgG1 |
|---|---|---|---|
| Req (RU) | | 5 | 10 |
| Rmax (RU) | | 39 | 72 |
| RI (RU) | | 0 | 0 |
| C (M) | | 5E−06 | 5E−06 |
| KD (M) | 2.2E−9 | 3.4E−05 | 3.1E−05 |

Based on the findings described above, it was predicted that the KD between IL-6 receptor and FH4-IgG1 antibody or 6RL #9-IgG1 antibody was increased by about 60 or 120 times (the affinity was reduced by 60 or 120 times or more) when the concentration of $CaCl_2$ in the buffer was decreased from 2 mM to 3 μM.

Table 23 summarizes the KD values at $CaCl_2$ concentrations of 2 mM and 3 μM and the Ca dependency for the three types of antibodies H54/L28-IgG1, FH4-IgG1, and 6RL #9-IgG1.

TABLE 23

| ANTIBODY | H54/L28-IgG1 | FH4-IgG1 | 6RL#9-IgG1 |
|---|---|---|---|
| KD (M) (2 mM $CaCl_2$) | 1.9E−9 | 5.9E−7 | 2.6E−7 |
| KD (M) (3 μM $CaCl_2$) | 2.2E−9 | 3.4E−5 OR MORE | 3.1E−5 OR MORE |
| Ca DEPENDENCY | ABOUT THE SAME | ABOUT 60 TIMES OR MORE | ABOUT 120 TIMES OR MORE |

No difference in the binding of the H54/L28-IgG1 antibody to IL-6 receptor due to the difference in Ca concentration was observed. On the other hand, the binding of FH4-IgG1 and 6RL #9-IgG1 antibodies to IL-6 receptor was observed to be significantly attenuated under the condition of the low Ca concentration (Table 23).

[Reference Example 13] Examination of Calcium Ion Binding to the Antibody Obtained Subsequently, the intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. The intermediate temperature of thermal denaturation (Tm value) becomes higher when a protein is stabilized through calcium ion binding, as compared with no calcium ion binding (J. Biol. Chem. (2008) 283, 37, 25140-25149). The binding activity of calcium ion to antibody was examined by examining changes in the Tm value of the antibody depending on the changes in the calcium ion concentration of the antibody solution. The purified antibody was subjected to dialysis (EasySEP, TOMY) using an external solution of 20 mM Tris-HCl, 150 mM NaCl, and 2 mM $CaCl_2$ (pH 7.4), or 20 mM Tris-HCl, 150 mM NaCl, and 3 μM $CaCl_2$ (pH 7.4). DSC measurement was conducted at a heating rate of 240° C./hr from 20 to 115° C. using an antibody solution prepared at about 0.1 mg/mL with the dialysate as a test substance. The intermediate temperatures of thermal denaturation (Tm values) of the Fab domains of each antibody, calculated based on the denaturation curve obtained by DSC, are shown in Table 24.

TABLE 24

| ANTIBODY | CALCIUM ION CONCENTRATION | | ΔTm (° C.) |
|---|---|---|---|
| | 3 μM | 2 mM | 2 mM − 3 μM |
| H54/L28-IgG1 | 92.87 | 92.87 | 0.00 |
| FH4-IgG1 | 74.71 | 78.97 | 4.26 |
| 6RL#9-IgG1 | 77.77 | 78.98 | 1.21 |

From the results shown in Table 24, it is indicated that the Tm values of the Fab of the FH4-IgG1 and 6RL #9-IgG1 antibodies, which show a calcium-dependent binding ability, varied with changes in the calcium ion concentration, while the Tm values of the Fab of the H54/L28-IgG1 antibody which shows no calcium-dependent binding ability do not vary with changes in the calcium ion concentration. The variation in the Tm values of the Fab of the FH4-IgG1 and 6RL #9-IgG1 antibodies demonstrates that calcium ions bound to these antibodies to stabilize the Fab portions. The above results show that calcium ions bound to the FH4-IgG1 and 6RL #9-IgG1 antibodies, while no calcium ion bound to the H54/L28-IgG1 antibody.

[Reference Example 14] Identification of Calcium Ion-Binding Site in Antibody 6RL #9 by X-Ray Crystallography (14-1) X-Ray Crystallography As described in Reference Example 13, the measurements of thermal denaturation temperature Tm suggested that antibody 6RL #9 binds to calcium ion. However, it was unpredictable which portion of antibody 6RL #9 binds to calcium ion. Then, by using the technique of X-ray crystallography, residues of antibody 6RL #9 that interact with calcium ion were identified.

(14-2) Expression and Purification of Antibody 6RL #9

Antibody 6RL #9 was expressed and purified for X-ray crystallography. Specifically, animal expression plasmids constructed to be capable of expressing the heavy chain (a sequence in which a constant region derived from IgG1 is linked to SEQ ID NO: 98) and light chain (SEQ ID NO: 99) of antibody 6RL #9 were introduced transiently into animal cells. The constructed plasmids were introduced by the lipofection method into cells of human fetal kidney cell-derived FreeStyle 293-F (Invitrogen) suspended in 800 ml of the FreeStyle 293 Expression Medium (Invitrogen) (final cell density: $1 \times 10^6$ cells/mL). The plasmid-introduced cells were cultured in a $CO_2$ incubator (37° C., 8% $CO_2$, 90 rpm) for five days. From the culture supernatant obtained as described above, antibodies were purified by a method known to those skilled in the art using the rProtein A Sepharose® Fast Flow (Amersham Biosciences). Absorbance at 280 nm of purified antibody solutions was measured using a spectrophotometer. Antibody concentrations were calculated from the measured values using an extinction coefficient calculated by the PACE method (Protein Science (1995) 4, 2411-2423).

(14-3) Purification of Antibody 6RL #9 Fab Fragment

Antibody 6RL #9 was concentrated to 21 mg/ml using an ultrafilter with a molecular weight cutoff of 10,000 MWCO. A 5 mg/mL antibody sample (2.5 mL) was prepared by diluting the antibody solution using 4 mM L-cysteine/5 mM EDTA/20 mM sodium phosphate buffer (pH 6.5). 0.125 mg of papain (Roche Applied Science) was added to the sample. After stirring, the sample was incubated at 35° C. for two hours. After incubation, a tablet of Protease Inhibitor Cocktail Mini, EDTA-free (Roche Applied Science) was dissolved in 10 ml of 25 mM MES buffer (pH 6) and added to the sample. The sample was incubated on ice to stop the papain proteolytic reaction. Then, the sample was loaded onto a 1-ml cation-exchange column HiTrap SP HP (GE Healthcare) equilibrated with 25 mM MES buffer (pH 6), downstream of which a 1-ml HiTrap MabSelect Sure Protein A column (GE Healthcare) was connected in tandem. A purified fraction of the Fab fragment of antibody 6RL #9 was obtained by performing elution with a linear NaCl concentration gradient up to 300 mM in the above-described buffer. Then, the resulting purified fraction was concentrated to about 0.8 ml using a 5000 MWCO ultrafilter. The concentrate was loaded onto a gel filtration column Superdex 200 10/300 GL (GE Healthcare) equilibrated with 100 mM HEPES buffer (pH 8) containing 50 mM NaCl. The purified Fab fragment of antibody 6RL #9 for crystallization was eluted from the column using the same buffer. All the column treatments described above were carried out at a low temperature of 6 to 7.5° C.

(14-4) Crystallization of the Antibody 6RL #9 Fab Fragment in the Presence of Ca Seed crystals of the 6RL #9 Fab fragment were prepared in advance under general conditions. Then, the purified Fab fragment of antibody 6RL #9 in 5 mM $CaCl_2$ was concentrated to 12 mg/ml with a 5000 MWCO ultrafilter. Next, the sample concentrated as described above was crystallized by the hanging drop vapor diffusion method using 100 mM HEPES buffer (pH 7.5) containing 20% to 29% PEG4000 as a reservoir solution. The above-described seed crystals were crushed in 100 mM HEPES buffer (pH 7.5) containing 29% PEG4000 and 5 mM $CaCl_2$, and serially diluted to 100 to 10,000 folds. Then, 0.2 μL of diluted solutions were combined with a mixture of 0.8 μl of the reservoir solution and 0.8 μl of the concentrated sample to prepare crystallization drops on a glass cover slide. The crystal drops were allowed to stand at 20° C. for two to three days to prepare thin plate-like crystals. X-ray diffraction data were collected using the crystals.

(14-5) Crystallization of the Antibody 6RL #9 Fab Fragment in the Absence of Ca

The purified Fab fragment of antibody 6RL #9 was concentrated to 15 mg/ml using a 5000 MWCO ultrafilter. Then, the sample concentrated as described above was crystallized by the hanging drop vapor diffusion method using 100 mM HEPES buffer (pH 7.5) containing 18% to 25% PEG4000 as a reservoir solution. Crystals of the antibody 6RL #9 Fab fragment obtained in the presence of Ca were crushed in 100 mM HEPES buffer (pH 7.5) containing 25% PEG4000, and serially diluted to 100 to 10,000 folds. Then, 0.2 μL of diluted solutions were combined with a mixture of 0.8 μl of the reservoir solution and 0.8 μl of the concentrated sample to prepare crystallization drops on a glass cover slide. The crystal drops were allowed to stand at 20° C. for two to three days to prepare thin plate-like crystals. X-ray diffraction data were collected using the crystals.

(14-6) X-Ray Crystallographic Measurement of Fab Fragment Crystal from Antibody 6RL #9 in the Presence of Ca Crystals of the Fab fragment of antibody 6RL #9 prepared in the presence of Ca were soaked in 100 mM HEPES buffer (pH 7.5) solution containing 35% PEG4000 and 5 mM $CaCl_2$. By removing the exterior solution from the surface of a single crystal with a micro-nylon-loop pin, the single crystal was frozen in liquid nitrogen. X-ray diffraction data of the frozen crystal was collected from beam line BL-17A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum315r (ADSC) attached to the beam line while rotating the crystal in 1° intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.2 angstrom resolution was obtained. The crystal belongs to space group P212121 with lattice constant a=45.47 angstrom, b=79.86 angstrom, c=116.25 angstrom, α=90°, β=90°, and γ=90°.

(14-7) X-Ray Crystallographic Measurement of the Fab Fragment Crystal from Antibody 6RL #9 in the Absence of Ca Crystals of the Fab fragment of antibody 6RL #9 prepared in the absence of Ca were soaked in 100 mM HEPES buffer (pH 7.5) solution containing 35% PEG4000. By removing the exterior solution from the surface of a single crystal with a micro-nylon-loop pin, the single crystal was frozen in liquid nitrogen. X-ray diffraction data of the frozen crystal was collected from beam line BL-5A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum210r (ADSC) attached to the beam line while rotating the crystal in 1° intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.3 angstrom resolution was obtained. The crystal belongs to space group P212121 with lattice constant a=45.40 angstrom, b=79.63 angstrom, c=116.07 angstrom, α=90°, β=90°, γ=90°, and thus is structurally identical to the crystal prepared in the presence of Ca.

(14-8) X-Ray Crystallographic Measurement of the Fab Fragment Crystal from Antibody 6RL #9 in the Presence of Ca The crystal structure of the antibody 6RL #9 Fab fragment in the presence of Ca was determined by a molecular replacement method using the Phaser program (CCP4 Software Suite). The number of molecules in an asymmetrical unit was estimated to be one from the size of crystal lattice and molecular weight of the antibody 6RL #9 Fab fragment. Based on the primary sequence homology, a portion of amino acid positions 112 to 220 from A chain and a portion of amino acid positions 116 to 218 from B chain in the conformational coordinate of PDB code 1ZA6 were used as model molecules for analyzing the CL and CH1 regions. Then, a portion of amino acid positions 1 to 115 from B chain in the conformational coordinate of PDB code 1ZA6 was used as a model molecule for analyzing the VH region. Finally, a portion of amino acid positions 3 to 147 of the light chain in the conformational coordinate of PDB code 2A9M was used as a model molecule for analyzing the VL region. Based on this order, an initial structure model for the antibody 6RL #9 Fab fragment was obtained by determining from translation and rotation functions the positions and orientations of the model molecules for analysis in the crystal lattice. The crystallographic reliability factor R for the reflection data at 25 to 3.0 angstrom resolution was 46.9% and Free R was 48.6% after rigid body refinement where the VH, VL, CH1, and CL domains were each allowed to deviate from the initial structure model. Then, model refinement was achieved by repeating structural refinement using program Refmac5 (CCP4 Software Suite) followed by model revision performed using program Coot (Paul Emsley) with reference to the Fo-Fc and 2Fo-F electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 21,020 reflection data at 25 to 2.2 angstrom resolution, eventually the crystallographic reliability factor R became 20.0% and free R became 27.9% for the model consisting of 3440 atoms.

(14-9) Measurement of X-Ray Diffraction Data of the Fab Fragment Crystal from Antibody 6RL #9 in the Absence of Ca The crystal structure of the antibody 6RL #9 Fab fragment in the absence of Ca was determined based on the structure of the crystal prepared in the presence of Ca. Water and Ca ion molecules were omitted from the conformational coordinate of the crystal of the antibody 6RL #9 Fab fragment prepared in the presence of Ca. The crystallographic reliability factor R for the data of reflection at 25 to 3.0 angstrom resolution was 30.3% and Free R was 31.7% after the rigid body refinement where the VH, VL, CH1, and CL domains were each allowed to deviate. Then, model refinement was achieved by repeating structural refinement using program Refmac5 (CCP4 Software Suite) followed by model revision performed using program Coot (Paul Emsley) with reference to the Fo-Fc and 2Fo-Fc electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 18,357 reflection data at 25 to 2.3 angstrom resolution, eventually the crystallographic reliability factor R became 20.9% and free R became 27.7% for the model consisting of 3351 atoms.

Figure 18:
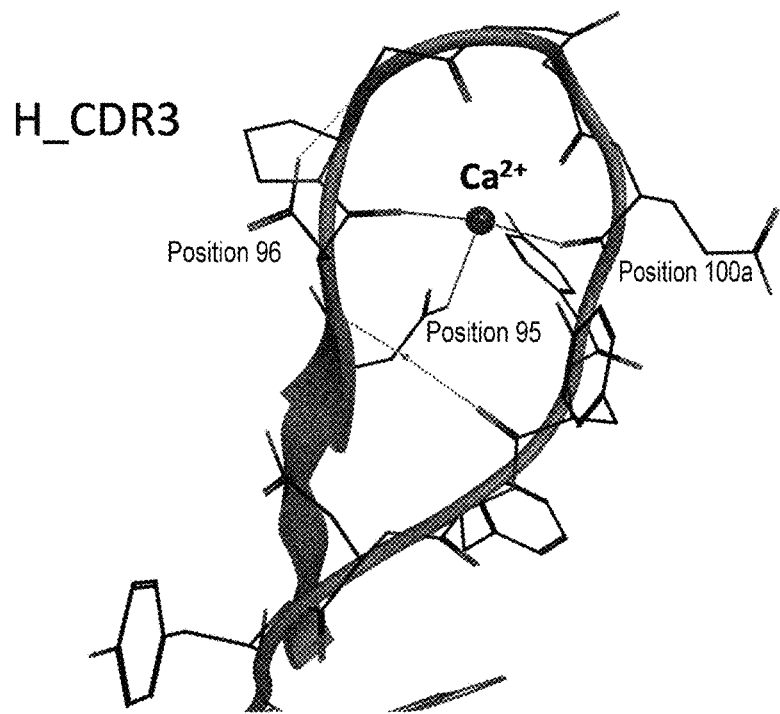
FIG. 18 depicts the structure of heavy-chain CDR3 of an Fab fragment of antibody 6RL #9 determined by X-ray crystallography. The heavy-chain CDR3 portion in the crystal structure obtained by crystallization in the presence of calcium ions is shown in (i), and the heavy-chain CDR3 portion in the crystal structure obtained by crystallization in the absence of calcium ions is shown in (ii).
Figure 18:
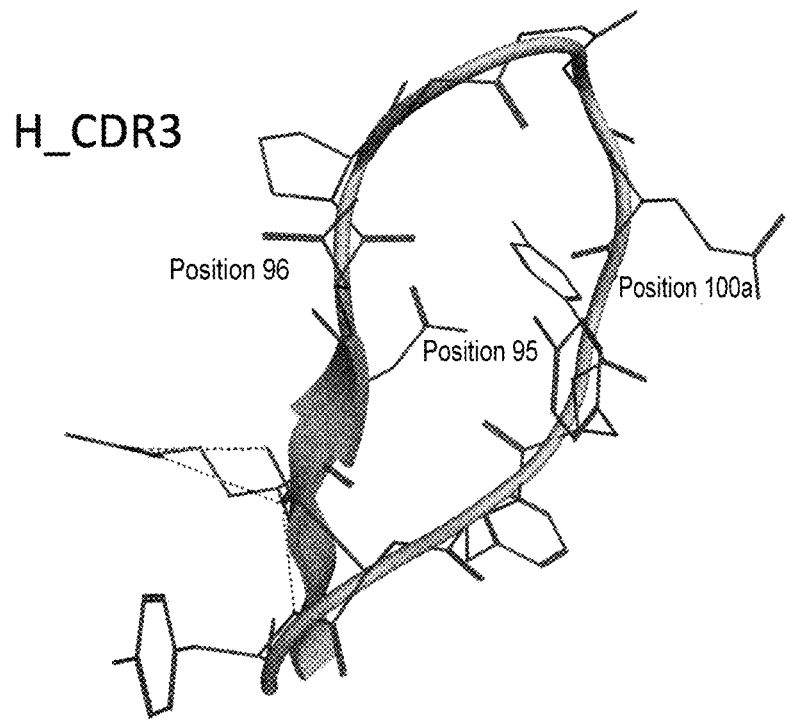
Figure 19:
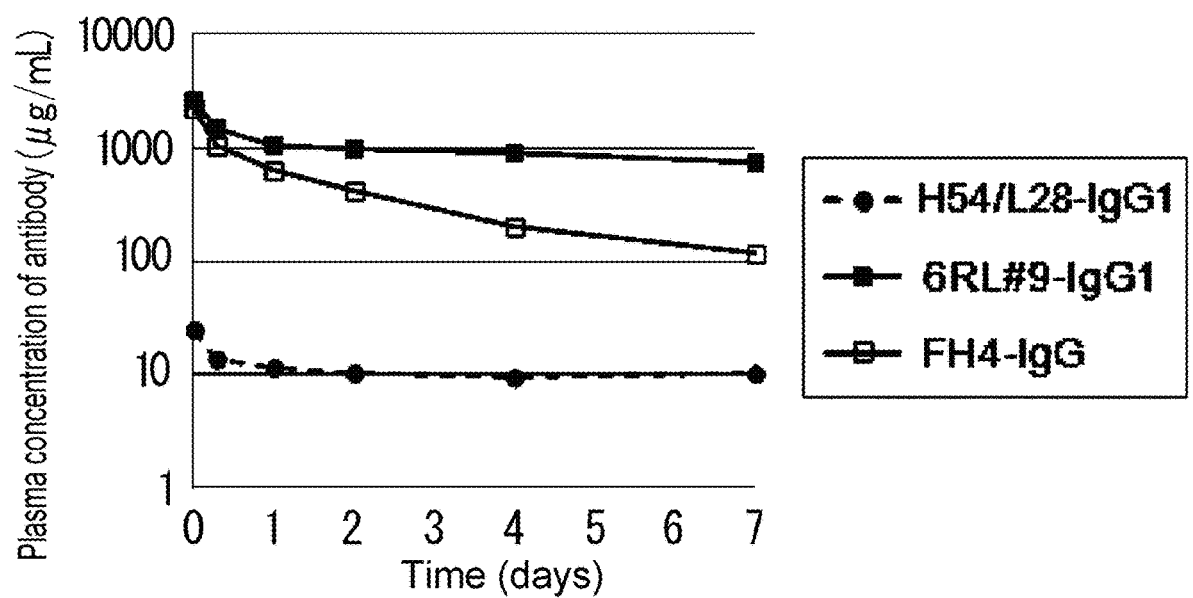
FIG. 19 shows changes in plasma antibody concentrations in normal mice for the H54/L28-IgG1 antibody, the FH4-IgG1 antibody, and the 6RL #9-IgG1 antibody.

(14-10) Comparison of X-Ray Crystallographic Diffraction Data of the Fab Fragments of Antibody 6RL #9 Between in the Presence and Absence of Ca When the crystallographic structures of the Fab fragments of antibody 6RL #9 are compared between in the presence and absence of Ca, significant changes are seen in the heavy chain CDR3. The structure of the heavy chain CDR3 of the antibody 6RL #9 Fab fragment determined by X-ray crystallography is shown in FIG. 18. Specifically, a calcium ion resided at the center of the heavy chain CDR3 loop region of the antibody 6RL #9 Fab fragment prepared in the presence of Ca. The calcium ion was assumed to interact with positions 95, 96, and 100a (Kabat's numbering) of the heavy chain CDR3. It was believed that the heavy chain CDR3 loop which is important for the antigen binding was stabilized by calcium binding in the presence of Ca, and became an optimum structure for antigen binding. There is no report demonstrating that calcium binds to the antibody heavy chain CDR3. Thus, the calcium-bound structure of the antibody heavy chain CDR3 is a novel structure.

The calcium-binding motif that was found to exist in the heavy chain CDR3 from the structure of the Fab fragment of the 6RL #9 antibody may also be a new component in the design of a Ca library such as those described in Reference Example 7. That is, while the calcium-binding motif was introduced into the light chain variable region in Reference Example 7, one may consider, for example, a library containing the 6RL #9 antibody heavy chain CDR3 and flexible residues in other CDRs including the light chain.

[Reference Example 15] Preparation of Antibodies that Bind to IL-6 in a Ca-Dependent Manner from a Human Antibody Library Using Phage Display Techniques (15-1) Construction of a Phage Display Library of Naïve Human Antibodies A human antibody phage display library containing multiple phages that display various human antibody Fab domain sequences was constructed by a method known to those skilled in the art using, as a template, polyA RNA prepared from human PBMC, commercially available human polyA RNA, and such.

(15-2) Preparation of Antibody Fragments that Bind to the Antigen in a Ca-Dependent Manner from Library by Bead Panning Primary selection from the constructed phage display library of naïve human antibodies was carried out by enriching antibody fragments that have antigen (IL-6)-binding activity. The antigen used was biotin-labeled IL-6.

Phages were produced from *E. coli* carrying the constructed phagemid for phage display. To precipitate the phages produced by *E. coli*, 2.5 M NaCl/10% PEG was added to the *E. coli* culture fluid. The phage fraction was diluted with TBS to prepare a phage library solution. Then, BSA and $CaCl_2$ were added the phage library solution at final concentrations of 4% and 1.2 mM calcium ion concentration, respectively. The panning method used was a conventional panning method using antigen-immobilized magnetic beads (J. Immunol. Methods. (2008) 332(1-2): 2-9; J. Immunol. Methods. (2001) 247(1-2): 191-203; Biotechnol. Prog. (2002) 18(2): 212-20; Mol. Cell Proteomics (2003) 2(2): 61-9). The magnetic beads used were NeutrAvidin-coated beads (Sera-Mag SpeedBeads NeutrAvidin-coated) and Streptavidin-coated beads (Dynabeads M-280 Streptavidin).

Specifically, 250 pmol of the biotin-labeled antigen was added to the prepared phage library solution. Thus, the solution was contacted with the antigen at room temperature for 60 minutes. Magnetic beads blocked with BSA were added, and the antigen-phage complex was allowed to bind to the magnetic beads at room temperature for 15 minutes. The beads were washed three times with 1.2 mM $CaCl_2$/TBST (TBST containing 1.2 mM $CaCl_2$), and then twice with 1 ml of 1.2 mM $CaCl_2$/TBS (TBS containing 1.2 mM $CaCl_2$). Thereafter, 0.5 ml of 1 mg/ml trypsin was added to the beads. After 15 minutes of dispersion at room temperature, the beads were immediately separated using a magnetic stand to collect a phage suspension. The prepared phage suspension was added to 10 ml of *E. coli* of stain TG1 at the logarithmic growth phase (OD600=0.4 to 0.7). The *E. coli* was incubated with gentle stirring at 37° C. for one hour to infect the phages. The infected *E. coli* was seeded in a plate (225 mm×225 mm). Then, phages were collected from the culture fluid of the seeded *E. coli* to prepare a phage library solution.

In the second round and subsequent panning, phages were enriched using the Ca-dependent binding activity as an indicator. Specifically, 40 pmol of the biotin-labeled antigen was added to the prepared phage library solution. Thus, the phage library was contacted with the antigen at room temperature for 60 minutes. Magnetic beads blocked with BSA were added, and the antigen-phage complex was allowed to bind to the magnetic beads at room temperature for 15 minutes. The beads were washed with 1 ml of 1.2 mM $CaCl_2$/TBST and 1.2 mM $CaCl_2$/TBS. Next, 0.1 ml of 2 mM EDTA/TBS was added to the beads. After dispersion at room temperature, the beads were immediately separated using a magnetic stand to collect a phage suspension. The pIII protein (helper phage-derived protein pIII) was cleaved from phages that did not display Fab by adding 5 μl of 100 mg/ml trypsin to the collected phage suspension to eliminate the ability of phages displaying no Fab to infect *E. coli*. Phages collected from the trypsinized liquid phage stock was added to 10 ml of *E. coli* cells of the TG1 strain at the logarithmic growth phase (OD600=0.4 to 0.7). The *E. coli* was incubated while gently stirring at 37° C. for one hour to infect phage. The infected *E. coli* was seeded in a plate (225 mm×225 mm). Then, phages were collected from the culture fluid of the seeded *E. coli* to prepare a liquid stock of phage library. Panning was performed three times using the Ca-dependent binding activity as an indicator.

(15-3) Assessment by Phage ELISA

Culture supernatants containing phages were collected from single colonies of *E. coli* obtained by the method described above according to a conventional method (Methods Mol. Biol. (2002) 178, 133-145). BSA and $CaCl_2$ were added at final concentrations of 4% and 1.2 mM calcium ion concentration, respectively, to the phage-containing culture supernatants.

The supernatants were subjected to ELISA by the following procedure. A StreptaWell 96-well microtiter plate (Roche) was coated overnight with 100 μl of PBS containing the biotin-labeled antigen. The antigen was removed by washing each well of the plate with PBST. Then, the wells were blocked with 250 μl of 4% BSA-TBS for one hour or more. After removal of 4% BSA-TBS, the prepared culture supernatants were added to the each well. The plate was incubated at 37° C. for one hour so that the antibody-displaying phages were allowed to bind to the antigen on each well. After each well was washed with 1.2 mM $CaCl_2$/TBST, 1.2 mM $CaCl_2$/TBS or 1 mM EDTA/TBS was added. The plate was left for incubation at 37° C. for 30 minutes. After washing with 1.2 mM $CaCl_2$/TBST, an HRP-conjugated anti-M13 antibody (Amersham Pharmacia Biotech) diluted with TBS containing BSA and calcium ion at final concentrations of 4% and 1.2 mM calcium ion concentration was added to each well, and the plate was incubated for one hour. After washing with 1.2 mM $CaCl_2$/TBST, the TMB single solution (ZYMED) was added to each well. The chromogenic reaction in the solution of each well was stopped by adding sulfuric acid. Then, the developed color was assessed by measuring absorbance at 450 nm.

From the 96 clones isolated, antibody 6KC4-1 #85 having Ca-dependent IL-6-binding activity was obtained by phage ELISA. Using antibody fragments that were predicted to have a Ca-dependent antigen-binding activity based on the result of the phage ELISA described above as a template, genes were amplified with specific primers and their sequences were analyzed. The heavy-chain and light-chain variable region sequences of antibody 6KC4-1 #85 are shown in SEQ ID NOs: 10 and 104, respectively. The polynucleotide encoding the heavy-chain variable region of antibody 6KC4-1 #85 (SEQ ID NO: 10) was linked to a polynucleotide encoding an IgG1-derived sequence by PCR method. The resulting DNA fragment was inserted into an animal cell expression vector to construct an expression vector for the heavy chain of SEQ ID NO: 105. A polynucleotide encoding the light-chain variable region of antibody 6KC4-1 #85 (SEQ ID NO: 104) was linked to a polynucleotide encoding the constant region of the natural Kappa chain (SEQ ID NO: 44) by PCR. The linked DNA fragment was inserted into an animal cell expression vector. Sequences of the constructed variants were confirmed by a method known to those skilled in the art. Sequences of the constructed variants were confirmed by a method known to those skilled in the art.

(15-4) Expression and Purification of Antibodies

Clone 6KC4-1 #85 that was predicted to have a Ca-dependent antigen-binding activity based on the result of phage ELISA was inserted into animal cell expression plasmids. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells are cultured for four days in a $CO_2$ incubator (37° C., 8% $CO_2$, 90 rpm). From the culture supernatants, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

[Reference Example 16] Assessment of Antibody 6KC4-1 #85 for Calcium Ion Binding Calcium-dependent antigen-binding antibody 6KC4-1 #85 which was isolated from a human antibody library was assessed for its calcium binding. Whether the measured Tm value varies depending on the ionized calcium concentration condition was assessed by the method described in Reference Example 2.

Tm values for the Fab domain of antibody 6KC4-1 #85 are shown in Table 25. As shown in Table 25, the Tm value of the 6KC4-1 #85 antibody Fab domain varied depending on the calcium ion concentration. This demonstrates that antibody 6KC4-1 #85 binds to calcium.

TABLE 25

| ANTIBODY | CALCIUM ION CONCENTRATION | | ΔTm (° C.) |
| --- | --- | --- | --- |
| | 3 μM | 2 mM | 2 mM − 3 μM |
| 6KC4-1#85 | 71.49 | 75.39 | 3.9 |

[Reference Example 17] Identification of Calcium Ion-Binding Site in Antibody 6KC4-1 #85

As demonstrated in Reference Example 16, antibody 6KC4-1 #85 binds to calcium ion. However, 6KC4-1 #85 does not have a calcium-binding motif such as the hVk5-2 sequence which was revealed from assessment to have a calcium-binding motif. Then, whether calcium ion binds to either or both of the heavy chain and the light chain of antibody 6KC4-1 #85 was confirmed by assessing the calcium ion binding of altered antibodies resulting from exchanging the heavy chain and light chain of 6KC4-1 #85 respectively with those of an anti-glypican 3 antibody (heavy chain sequence GC_H (SEQ ID NO: 106), light chain sequence GC_L (SEQ ID NO: 107)) which does not bind calcium ion. The Tm values of altered antibodies measured according to the method described in Reference Example 2 are shown in Table 26. The result suggests that the heavy chain of antibody 6KC4-1 #85 binds to calcium, because the Tm values of the altered antibody having the heavy chain of antibody 6KC4-1 #85 changed depending on calcium ion concentration.

TABLE 26

| HEAVY CHAIN | LIGHT CHAIN | CALCIUM ION CONCENTRATION | | ΔTm (° C.) |
| --- | --- | --- | --- | --- |
| | | 3 μM | 2 mM | 2 mM − 3 μM |
| 6KC4-1#85 | 6KC4-1#85 | 71.46 | 75.18 | 3.72 |
| 6KC4-1#85 | GC_L | 78.87 | 80.01 | 1.14 |
| GC_H | 6KC4-1#85 | 75.69 | 75.94 | 0.25 |
| GC_H | GC_L | 79.94 | 80.01 | 0.07 |

Thus, to further identify residues responsible for the calcium ion binding of antibody 6KC4-1 #85, altered heavy chains (6_H1-11 (SEQ ID NO: 108), 6_H1-12 (SEQ ID NO: 109), 6_H1-13 (SEQ ID NO: 110), 6_H1-14 (SEQ ID NO: 111), 6_H1-15 (SEQ ID NO: 112)) or altered light chains (6_L1-5 (SEQ ID NO: 113) and 6_L1-6 (SEQ ID NO: 114)) were constructed by substituting an Asp (D) residue in the CDR of antibody 6KC4-1 #85 with an Ala (A) residue which does not participate in the binding or chelation of calcium ion. By the method described in Reference Example 15, altered antibodies were purified from the culture supernatants of animal cells introduced with expression vectors carrying the altered antibody genes. The purified altered antibodies were assessed for their calcium binding according to the method described in Reference Example 2. The measurement result is shown in Table 27. As shown in Table 27, substitution of an Ala residue for the residue at position 95 or 101 (Kabat numbering) in the heavy chain CDR3 of antibody 6KC4-1 #85 resulted in loss of the calcium-binding activity of antibody 6KC4-1 #85. This suggests that these residues are responsible for calcium binding. The calcium-binding motif located at the base of the CDR3 loop in the heavy chain of antibody 6KC4-1 #85, which was found based on the calcium binding capacity of the antibody altered from antibody 6KC4-1 #85, can be a new factor for designing Ca libraries as described in Reference Example 7. In Reference Example 7, calcium-binding motifs were introduced into the light chain variable region. Meanwhile, such libraries include, for example, those containing the heavy chain CDR3 from antibody 6KC4-1 #85 and flexible residues in the CDRs other than the heavy chain CDR3 but including the light chain CDRs.

TABLE 27

| HEAVY CHAIN | LIGHT CHAIN | ALTERED RESIDUE | CALCIUM ION CONCENTRATION | | Δ Tm (° C.) |
|---|---|---|---|---|---|
| | | | 3 μM | 2 mM | 2 mM − 3 μM |
| 6KC4-1#85 | 6KC4-1#85 | WILD-TYPE | 71.49 | 75.39 | 3.9 |
| 6H1-11 | 6KC4-1#85 | H CHAIN POSITION 61 (Kabat NUMBERING) | 71.73 | 75.56 | 3.83 |
| 6H1-12 | 6KC4-1#85 | H CHAIN POSITION 95 (Kabat NUMBERING) | 72.9 | 73.43 | 0.53 |
| 6H1-13 | 6KC4-1#85 | H CHAIN POSITION 100a (Kabat NUMBERING) | 70.94 | 76.25 | 5.31 |
| 6H1-14 | 6KC4-1#85 | H CHAIN POSITION 100g (Kabat NUMBERING) | 73.95 | 75.14 | 1.19 |
| 6H1-15 | 6KC4-1#85 | H CHAIN POSITION 101 (Kabat NUMBERING) | 65.37 | 66.25 | 0.87 |
| 6KC4-1#85 | 6L1-5 | L CHAIN POSITION 50 (Kabat NUMBERING) | 71.92 | 76.08 | 4.16 |
| 6KC4-1#85 | 6L1-6 | L CHAIN POSITION 92 (Kabat NUMBERING) | 72.13 | 78.74 | 6.61 |

[Reference Example 18] Examination of Effects of Ca-Dependent Binding Antibody on Plasma Retention of Antigen Using Normal Mice (18-1) In Vivo Test Using Normal Mice To a normal mouse (C57BL/6J mouse, Charles River Japan), hsIL-6R (soluble human IL-6 receptor prepared in Reference Example 21) alone was administered, or hsIL-6R and anti-human IL-6 receptor antibody were administered simultaneously to examine the kinetics of the hsIL-6R and anti-human IL-6 receptor antibody in vivo. A single dose (10 mL/kg) of the hsIL-6R solution (5 μg/mL) or a mixture of hsIL-6R and anti-human IL-6 receptor antibody was administered into the caudal vein. The above H54/L28-IgG1, 6RL #9-IgG1, and FH4-IgG1 were used as anti-human IL-6 receptor antibodies.

The hsIL-6R concentration in all the mixtures is 5 μg/mL. The concentrations of anti-human IL-6 receptor antibody vary with the antibodies: 0.1 mg/mL for H54/L28-IgG1 and 10 mg/mL for 6RL #9-IgG1 and FH4-IgG1. At this time, it is thought that most of the hsIL-6Rs bind to the antibody because the anti-human IL-6 receptor antibody against hsIL-6R exists in a sufficient or excessive amount. Blood samples were collected at 15 minutes, 7 hours and 1, 2, 4, 7, 14, 21, and 28 days after the administration. The blood samples obtained were immediately centrifuged for 15 minutes at 4° C. and 12,000 rpm to separate plasma. The separated plasma was stored in a freezer set to −20° C. or lower until the time of measurement.

(18-2) Determination of Plasma Anti-Human IL-6 Receptor Antibody Concentration in Normal Mice by ELISA The plasma concentration of anti-human IL-6 receptor antibody in a mouse was determined by ELISA. First, Anti-Human IgG (γ-chain specific) F(ab')2 Fragment of Antibody (SIGMA) was dispensed into a Nunc-Immuno Plate, MaxiSoup (Nalge Nunc International), and was allowed to stand undisturbed overnight at 4° C. to prepare an anti-human IgG-solid phase plate. Calibration curve samples at a plasma concentration of 0.64, 0.32, 0.16, 0.08, 0.04, 0.02, or 0.01 μg/mL, and mouse plasma measurement samples diluted by 100-fold or above were each dispensed into the anti-human IgG-solid phase plate, followed by incubation for 1 hour at 25° C. Subsequently, the plate was allowed to react with a biotinylated anti-human IL-6 R antibody (R&D) for 1 hour at 25° C., followed by reaction with Streptavidin-PolyHRP80 (Stereospecific Detection Technologies) for 0.5 hours at 25° C. The chromogenic reaction was conducted using TMB One Component HRP Microwell Substrate (BioFX Laboratories) as a substrate. After the chromogenic reaction was stopped by adding 1N-sulfuric acid (Showa Chemical), absorbance at 450 nm of the color solution was measured using a microplate reader. The plasma concentration in the mouse was calculated from the absorbance of the calibration curve using the SOFTmax PRO analysis software (Molecular Devices). Changes in the plasma concentrations of antibodies, H54/L28-IgG1, 6RL #9-IgG1, and FH4-IgG1, in the normal mice after intravenous administration, measured as described above, are shown in FIG. 42.

Figure 20:
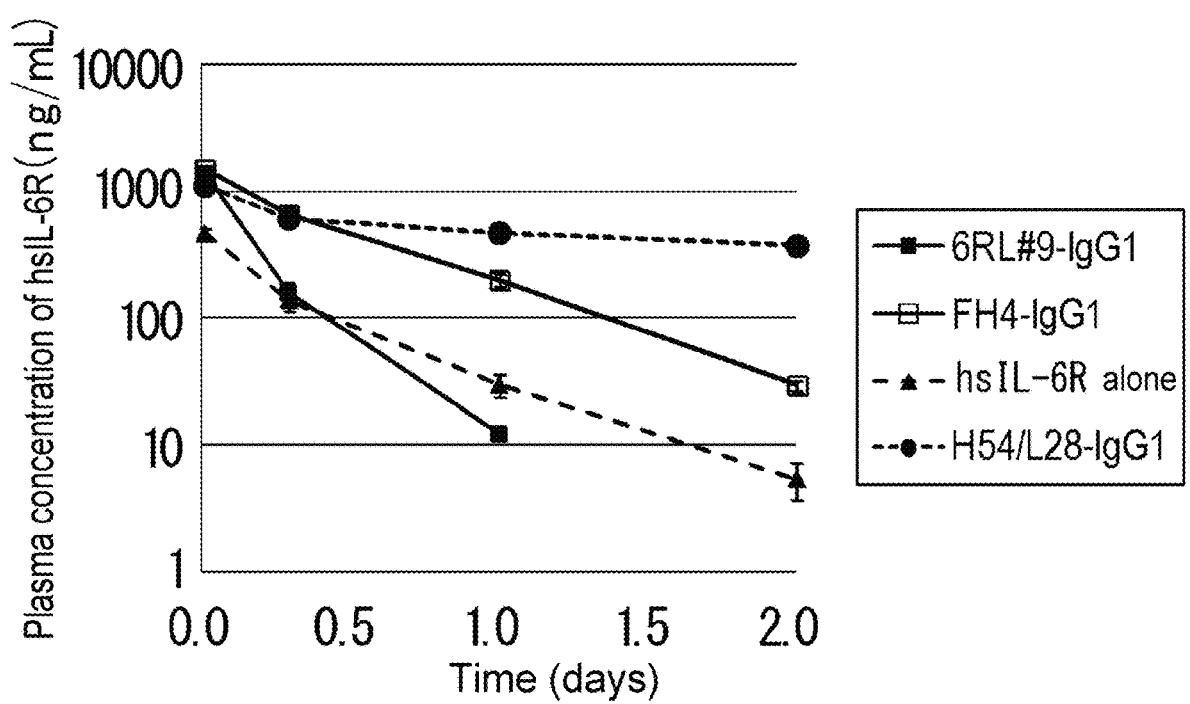
FIG. 20 shows changes in the plasma concentration of soluble human IL-6 receptor (hsIL-6R) in normal mice for the H54/L28-IgG1 antibody, the FH4-IgG1 antibody, and the 6RL #9-IgG1 antibody.

(18-3) Determination of Plasma hsIL-6R Concentration by an Electrochemiluminescence Method The plasma concentration of hsIL-6R in a mouse was determined by an electrochemiluminescence method. An hsIL-6R calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6 R antibody (R&D), and tocilizumab (heavy chain SEQ ID NO: 96, light chain SEQ ID NO: 97), followed by overnight reaction at 4° C. At that time, the assay buffer contained 10 mM EDTA to reduce the free Ca concentration in the sample and dissociate almost all the hsIL-6Rs in the sample from 6RL #9-IgG1 or FH4-IgG1 to be bound to the added tocilizumab. Subsequently, said reaction liquid was dispensed into an MA400 PR Streptavidin Plate (Meso Scale Discovery). In addition, after washing each well of the plate that was allowed to react for 1 hour at 25° C., Read Buffer T (×4) (Meso Scale Discovery) was dispensed into each well. Immediately, the reaction liquid was subjected to measurement using a SECTOR PR 400 reader (Meso Scale Discovery). The concentration of hsIL-6R was calculated from the response of the calibration curve using the SOFTmax PRO analysis software (Molecular Devices). Changes in the plasma concentration of hsIL-6R in the normal mouse after intravenous administration, determined as described above, are shown in FIG. 20.

As a result, the disappearance of hsIL-6R was very rapid when hsIL-6R was administered alone, while the disappearance of hsIL-6R was significantly delayed when hsIL-6R was administered simultaneously with H54/L28-IgG1, a conventional antibody having no Ca-dependent binding ability to hsIL-6R. In contrast, the disappearance of hsIL-6R was significantly accelerated when hsIL-6R was administered simultaneously with 6RL #9-IgG1 or FH4-IgG1 having 100-fold or higher Ca-dependent binding ability to hsIL-6R. The plasma concentrations of hsIL-6R one day after hsIL-6R was administered simultaneously with 6RL #9-IgG1 and FH4-IgG1 were reduced 39-fold and 2-fold, respectively, as compared with simultaneous administration with H54/L28-IgG1. Thus, the calcium-dependent binding antibodies were confirmed to be able to accelerate antigen disappearance from the plasma.

[Reference Example 19] Trials to Improve the Antigen Elimination-Accelerating Effect of Antibody with Ca-Dependent Antigen-Binding (Preparation of Antibodies)

(19-1) Regarding the Binding of IgG Antibody to FcRn

IgG antibodies have longer plasma retention time as a result of FcRn binding. The binding between IgG and FcRn is observed only under an acidic condition (pH 6.0). By contrast, the binding is almost undetectable under a neutral condition (pH 7.4). An IgG antibody is taken up into cells in a nonspecific manner. The antibody returns to the cell surface by binding to endosomal FcRn under the endosomal acidic condition, and then dissociates from FcRn under the plasma neutral condition. When the FcRn binding under the acidic condition is lost by introducing mutations into the IgG Fc region, the antibody retention time in plasma is markedly impaired because the antibody no longer recycles to the plasma from the endosome.

A reported method for improving the plasma retention of an IgG antibody is to enhance the FcRn binding under acidic conditions. Amino acid mutations are introduced into its Fc region of an IgG antibody to improve its FcRn binding under acidic conditions. This increases the efficiency of recycling of IgG antibody to the plasma from the endosome, resulting in improvement of the plasma retention of IgG antibody. When introducing amino acid substitution, it is considered important not to increase the binding to FcRn under neutral conditions. IgG antibodies that bind to FcRn under neutral conditions can return onto the cell surface through binding to FcRn under the acidic condition of the endosome, but IgG antibodies do not dissociate from the FcRn in plasma under neutral conditions and are not recycled to the plasma, and thus plasma retention of IgG antibodies was thought to be inversely impaired.

For example, as described by Dall'Acqua et al. (J. Immunol. (2002) 169 (9), 5171-5180), the plasma retention of IgG1 antibody that was allowed to bind to mouse FcRn under a neutral condition (pH 7.4) was exacerbated as a result of introducing an amino acid substitution into a mouse. In addition, as described by Yeung et al. (J. Immunol. (2009) 182 (12), 7663-7671), Datta-Mannan et al. (J. Biol. Chem. (2007) 282 (3), 1709-1717), and Dall'Acqua et al. (J. Immunol. (2002) 169 (9), 5171-5180), IgG1 antibody variants whose binding to human FcRn under an acidic condition (pH 6.0) is improved by introducing an amino acid substitution is also observed to bind to human FcRn under a neutral condition (pH 7.4). Reportedly, the plasma retention of said antibody administered to a cynomolgus monkey was not improved, showing no change in the plasma retention. Thus, in antibody engineering technology for improving antibody functions, efforts have been made to improve the plasma retention of antibody by increasing its binding to human FcRn under acidic conditions without increasing its binding to human FcRn under a neutral condition (pH 7.4). In other words, no report has been published on the advantages of IgG1 antibodies whose binding to human FcRn under a neutral condition (pH 7.4) is increased by introducing amino acid substitutions into the Fc region.

Antibodies that bind to an antigen in a Ca-dependent manner are extremely useful, because they have an effect of accelerating the disappearance of soluble antigen and the repeated binding of a single antibody molecule to soluble antigen. A method of enhancing binding to FcRn under a neutral condition (pH 7.4) was examined as a method to further improve the accelerating effect on antigen disappearance.

(19-2) Preparation of Ca-Dependent Human IL-6 Receptor-Binding Antibodies Having FcRn-Binding Ability Under Neutral Conditions An amino acid mutation was introduced into the Fc regions of FH4-IgG1 and 6RL #9-IgG1 having a calcium-dependent antigen-binding ability and H54/L28-IgG1 having no calcium-dependent antigen-binding ability (used as a control) to prepare variants having an FcRn-binding ability under a neutral condition (pH 7.4). The amino acid mutation was introduced by a method known in the art using PCR. Specifically, FH4-N434W (heavy chain SEQ ID NO: 115, light chain SEQ ID NO: 101), 6RL #9-N434W (heavy chain SEQ ID NO: 116, light chain SEQ ID NO: 99), and H54/L28-N434W (heavy chain SEQ ID NO: 117, light chain SEQ ID NO: 39) with Asn (an amino acid at position 434 represented by the EU numbering) substituted by Trp in the heavy chain constant region of IgG1 were prepared. An animal cell expression vector into which a polynucleotide encoding a variant with the amino acid substitution was inserted was prepared using the QuikChange Site-Directed Mutagenesis Kit (Stratagene) by the method described in the accompanying instructions. Antibody expression and purification, and concentration measurement were conducted according to the method described in Reference Example 11.

[Reference Example 20] Examination of the Effect of Accelerating Disappearance of Ca-Dependent Binding Antibodies Using Normal Mice (20-1) In Vivo Test Using Normal Mice To a normal mouse (C57BL/6J mouse, Charles River Japan), hsIL-6R (soluble human IL-6 receptor prepared in Reference Example 20) alone was administered, or hsIL-6R and anti-human IL-6 receptor antibody were administered simultaneously to examine the kinetics of the hsIL-6R and anti-human IL-6 receptor antibody in vivo. A single dose (10 mL/kg) of hsIL-6R solution (5 µg/mL) or a mixture of hsIL-6R and anti-human IL-6 receptor antibody was administered into the caudal vein. The above H54/L28-N434W, 6RL #9-N434W, and FH4-N434W were used as anti-human IL-6 receptor antibodies.

The concentration of hsIL-6R in all the mixtures is 5 µg/mL. The concentrations of anti-human IL-6 receptor antibody vary with the antibodies: prepared at 0.042 mg/mL for H54/L28-N434W, 0.55 mg/mL for 6RL #9-N434W, and 1 mg/mL for FH4-N434W. At this time, it was thought that most of the hsIL-6Rs bind to the antibody because the anti-human IL-6 receptor antibody against hsIL-6R exists in a sufficient or excessive amount. Blood samples were collected at 15 minutes, 7 hours and 1, 2, 4, 7, 14, 21, and 28 days after the administration. The blood samples were immediately centrifuged for 15 minutes at 4° C. and 12,000 rpm to separate plasma. The separated plasma was stored in a freezer set to −20° C. or lower until the time of measurement.

Figure 21:
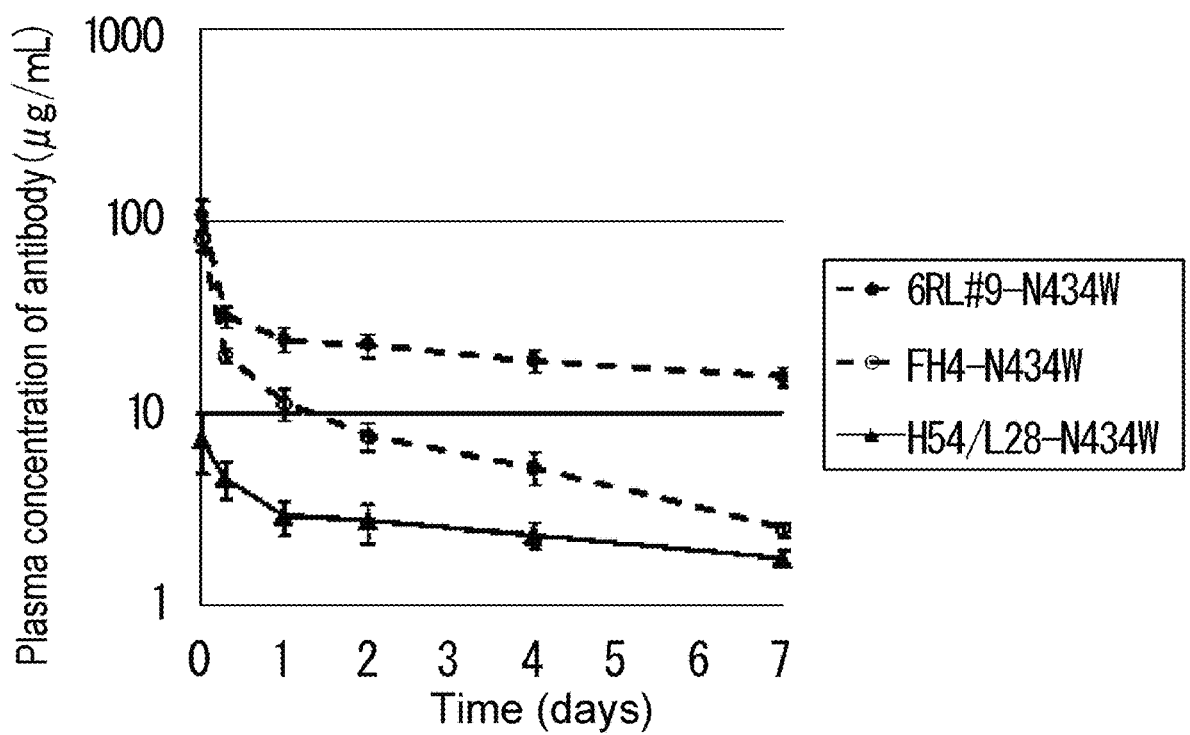
FIG. 21 shows changes in the plasma antibody concentrations in normal mice for the H54/L28-N434W antibody, the FH4-N434W antibody, and the 6RL #9-N434W antibody.

(20-2) Determination of Plasma Anti-Human IL-6 Receptor Antibody Concentration in Normal Mice by ELISA The plasma concentration of anti-human IL-6 receptor antibody in a mouse was determined by ELISA as described in Reference Example 18. Changes in the plasma concentrations of antibodies, H54/L28-N434W, 6RL #9-N434W, and FH4-N434W, in the normal mice after intravenous administration measured as described above are shown in FIG. 21.

Figure 22:
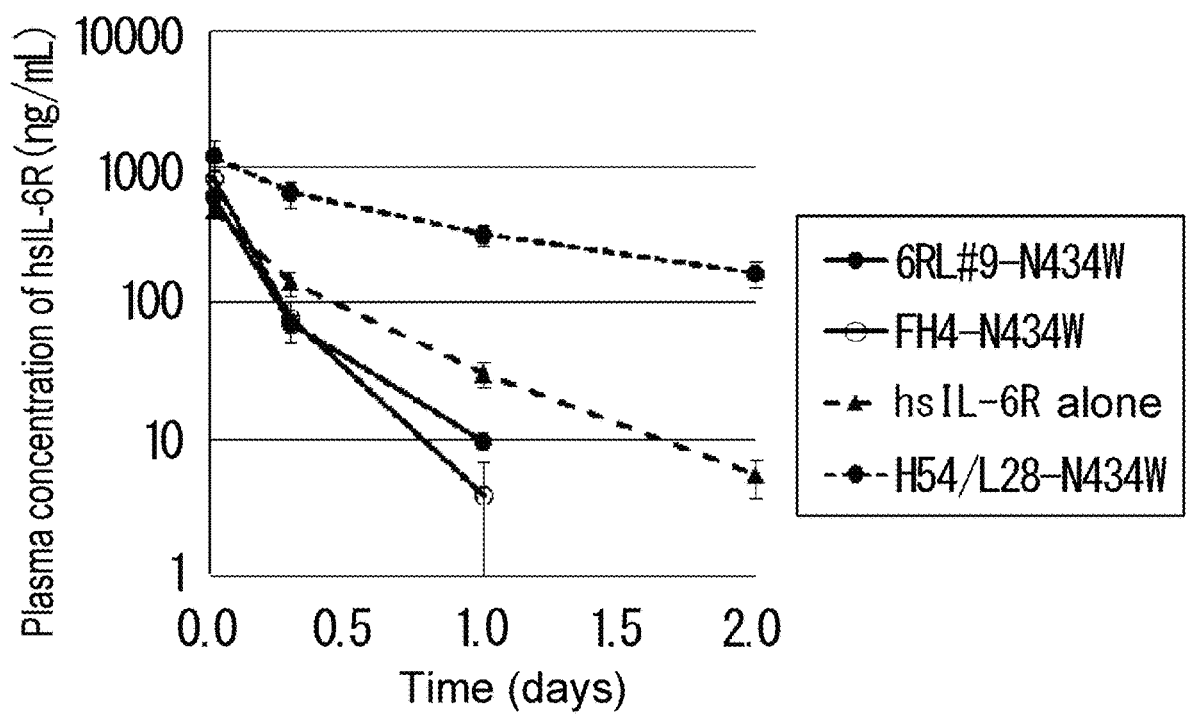
FIG. 22 shows changes in the plasma concentration of soluble human IL-6 receptor (hsIL-6R) in normal mice for the H54/L28-N434W antibody, the FH4-N434W antibody, and the 6RL #9-N434W antibody.

(20-3) Determination of Plasma hsIL-6R Concentration by an Electrochemiluminescence Method The plasma concentration of hsIL-6R in a mouse was determined by an electrochemiluminescence method. An hsIL-6R calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery) and a biotinylated anti-human IL-6 R antibody (R&D), followed by overnight reaction at 4° C. At that time, the assay buffer contained 10 mM EDTA to reduce the free Ca concentration in the sample and dissociate almost all hsIL-6Rs in the sample from 6RL #9-N434W or FH4-N434W to exist in a free state. Subsequently, said reaction liquid was dispensed into an MA400 PR Streptavidin Plate (Meso Scale Discovery). In addition, after washing each well of the plate that was allowed to react for 1 hour at 25° C., Read Buffer T (×4) (Meso Scale Discovery) was dispensed into each well. Immediately, the reaction liquid was subjected to measurement using a SECTOR PR 400 reader (Meso Scale Discovery). The concentration of hsIL-6R was calculated from the response of the calibration curve using the SOFTmax PRO analysis software (Molecular Devices). Changes in the plasma concentration of hsIL-6R in the normal mouse after intravenous administration determined as described above are shown in FIG. 22.

As a result, in comparison with the administration of hsIL-6R alone, simultaneous administration of hsIL-6R with the H54/L28-N434W antibody which has FcRn-binding activity at pH 7.4 and does not have Ca-dependent binding activity to hsIL-6R had a significantly delayed disappearance of hsIL-6R. In contrast, the disappearance of hsIL-6R was accelerated when hsIL-6R was administered simultaneously with the 6RL #9-N434W or FH4-N434W antibody which has 100-fold or higher Ca-dependent binding ability to hsIL-6R and FcRn-binding activity at pH 7.4, as compared with the administration of hsIL-6R alone. The plasma concentrations of hsIL-6R one day after hsIL-6R was administered simultaneously with the 6RL #9-N434W or FH4-N434W antibody were reduced 3-fold and 8-fold, respectively, as compared with the administration of hsIL-6R alone. As a result, it was confirmed that the disappearance of antigen from plasma could be further accelerated by imparting FcRn-binding activity at pH 7.4 to an antibody that binds to antigen in a calcium-dependent manner.

The 6RL #9-IgG1 or FH4-IgG1 antibody having 100-fold or higher Ca-dependent binding activity to hsIL-6R was confirmed to increase the disappearance of hsIL-6R, as compared with the H54/L28-IgG1 antibody having no Ca-dependent binding activity to hsIL-6R. The 6RL #9-N434W or FH4-N434W antibody which has 100-fold or higher Ca-dependent binding activity to hsIL-6R and FcRn-binding activity at pH 7.4 was confirmed to more strongly accelerate the disappearance of hsIL-6R, as compared with the administration of hsIL-6R alone.

These data suggest that an antibody that binds to an antigen in a Ca-dependent manner dissociates from antigen in the endosome, similarly to an antibody that binds to antigen in a pH-dependent manner.

(Reference Example 21) Preparation of Soluble Human IL-6 Receptor (hsIL-6R)

Recombinant human IL-6 receptor of the human IL-6 receptor, which is the antigen, was prepared as follows. A CHO cell line constitutively expressing soluble human IL-6 receptor (hereinafter referred to as hsIL-6R) having the amino acid sequence of positions 1 to 357 from the N terminus as reported by Mullberg et al. (J. Immunol. (1994) 152, 4958-4968) was established by a method known to those skilled in the art. This expression line was cultured to express hsIL-6R. hsIL-6R was purified from the obtained culture supernatant by Blue Sepharose 6 FF column chromatography and gel filtration column chromatography. A fraction eluted as the main peak in the final step was used as the final purification product.

[Reference Example 22] Design of pH-Dependent Binding Antibody Library (22-1) Method for Acquiring pH-Dependent Binding Antibodies WO2009/125825 discloses a pH-dependent antigen-binding antibody whose properties are changed in neutral and acidic pH regions by introducing a histidine into an antigen-binding molecule. The disclosed pH-dependent binding antibody is obtained by modification to substitute a part of the amino acid sequence of the antigen-binding molecule of interest with a histidine. To obtain a pH-dependent binding antibody more efficiently without preliminarily obtaining the antigen-binding molecule of interest to be modified, one method may be obtaining an antigen-binding molecule that binds to a desired antigen from a population of antigen-binding molecules (referred to as His library) with a histidine introduced into the variable region (more preferably, a region potentially involved in antigen binding). It may be possible to efficiently obtain an antigen-binding molecule having desired properties from a His library, because histidine appears more frequently in antigen-binding molecules from His library than those from conventional antibody libraries.

(22-2) Design of a Population of Antibody Molecules (his Library) with Histidine Residue Introduced into their Variable Region to Effectively Acquire Binding Antibodies that Bind to Antigen in a pH-Dependent Manner First, positions for introducing a histidine were selected in a His library. WO2009/125825 discloses generation of pH-dependent antigen-binding antibodies by substituting amino acid residues in the sequences of IL-6 receptor, IL-6, and IL-31 receptor antibodies with a histidine. In addition, anti-egg white lysozyme (FEBS Letter 11483, 309, 1, 85-88) and anti-hepcidin (WO 2009/139822) antibodies having a pH-dependent antigen-binding ability were generated by substituting the amino acid sequence of the antigen-binding molecule with histidines. Positions where histidines were introduced in the IL-6 receptor antibody, IL-6 antibody, IL-31 receptor antibody, egg white lysozyme antibody, and hepcidin antibody are shown in Table 28. Positions shown in Table 28 may be listed as candidate positions that can control the antigen-antibody binding. In addition, besides the position shown in Table 28, positions that are likely to have contact with antigen were also considered to be suitable for introduction of histidines.

TABLE 28

| ANTIBODY | CHAIN | POSITION (Kabat) | | | | | | | | |
|---|---|---|---|---|---|---|---|---|---|---|
| IL-6 RECEPTOR ANTIBODY | H | 27 | 31 | 32 | 35 | 50 | 58 | 62 | 100B | 102 |
| | L | 28 | 31 | 32 | 53 | 56 | 92 | | | |
| IL-6 ANTIBODY | H | 32 | 59 | 61 | 99 | | | | | |
| | L | 53 | 54 | 90 | 94 | | | | | |
| IL-31 RECEPTOR ANTIBODY | H | 33 | | | | | | | | |
| | L | | | | | | | | | |
| EGG-WHILE LYSOZYME ANTIBODY | H | 33 | 98 | | | | | | | |
| | L | 54 | | | | | | | | |
| HEPCIDIN ANTIBODY | H | 52 | 57 | 99 | 107 | | | | | |
| | L | 27 | 89 | | | | | | | |

In the His library consisting of heavy-chain and light-chain variable regions, a human antibody sequence was used for the heavy chain variable region, and histidines were introduced into the light chain variable region. The positions listed above and positions that may be involved in antigen binding, i.e., positions 30, 32, 50, 53, 91, 92, and 93 (Kabat numbering, Kabat E A et al. 1991. Sequence of Proteins of Immunological Interest. NIH) in the light chain were selected as positions for introducing histidines in the His library. In addition, the Vk1 sequence was selected as a template sequence of the light chain variable region for introducing histidines. Multiple amino acids were allowed to appear in the template sequence to diversify antigen-binding molecules that constitute the library. Positions exposed on the surface of a variable region that is likely to interact with the antigen were selected as those where multiple amino acids are allowed to appear. Specifically, positions 30, 31, 32, 34, 50, 53, 91, 92, 93, 94, and 96 of the light chain (Kabat numbering, Kabat E A et al. 1991. Sequence of Proteins of Immunological Interest. NIH) were selected as flexible residues.

The type and appearance frequency of amino acid residues that were subsequently allowed to appear were determined. The appearance frequency of amino acids in the flexible residues in the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the His library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

As His libraries, His library 1 which is fixed to necessarily incorporate a single histidine into each CDR, and His library 2 which is more emphasized on sequence diversity than the His library 1 were designed by taking the amino acids and appearance frequency set as described above into consideration. The detailed designs of His libraries 1 and 2 are shown in Tables 3 and 4 (with the positions in each table representing the Kabat numbering). Ser (S) at position 94 can be excluded if position 92 represented by the Kabat numbering is Asn (N) for the appearance frequency of amino acids as described in Tables 3 and 4.

Figure 23:
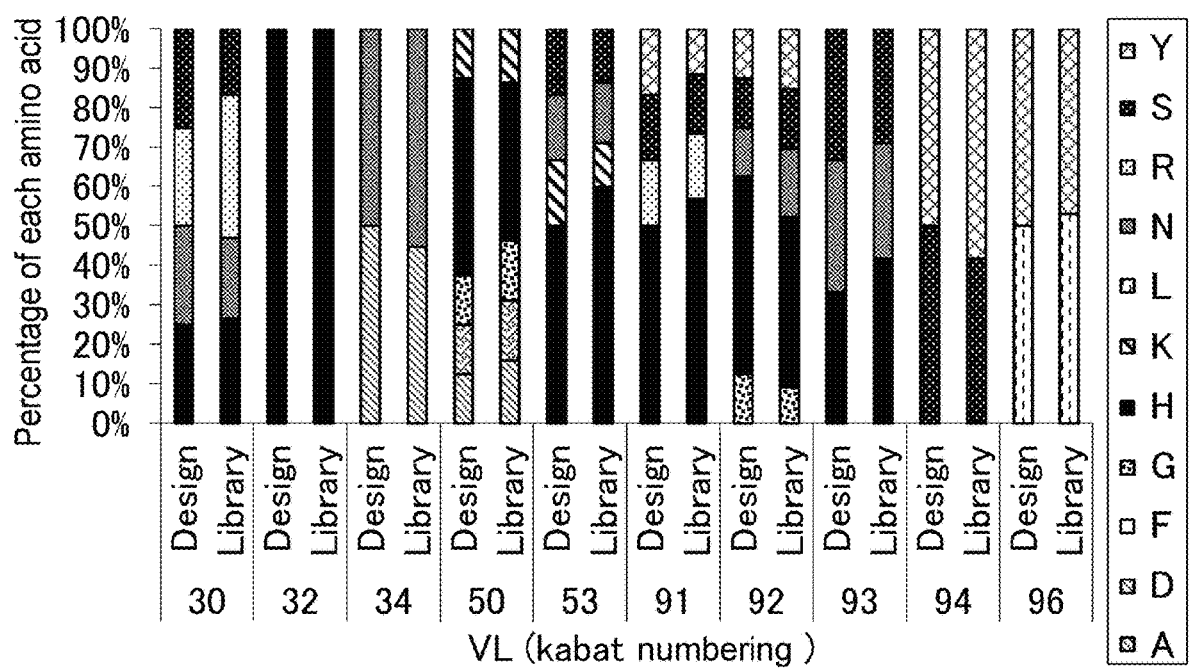
FIG. 23 shows the relationship of a designed amino acid distribution (indicated as Design) to the amino acid distribution (indicated as Library) for the sequence information on 132 clones isolated from E. coli introduced with a gene library of antibodies that bind to antigens in a pH-dependent manner. The horizontal axis indicates amino acid positions in the Kabat numbering system. The vertical axis indicates % amino acid distribution.

[Reference Example 23] Preparation of a Phage Display Library for Human Antibodies (his Library 1) to Obtain an Antibody that Binds to Antigen in a pH-Dependent Manner A gene library of antibody heavy-chain variable regions was amplified by PCR using a poly A RNA prepared from human PBMC, and commercial human poly A RNA as a template. A gene library of antibody light-chain variable regions designed as His library 1 as described in Reference Example 2 was amplified using PCR. A combination of the gene libraries of antibody heavy-chain and light-chain variable regions generated as described above was inserted into a phagemid vector to construct a human antibody phage display library which presents Fab domains consisting of human antibody sequences. For the construction method, Methods Mol Biol. (2002) 178, 87-100 was used as a reference. For the construction of the library, a linker region connecting the phagemid Fab to the phage pIII protein, and the sequences of a phage display library with a trypsin cleavage sequence inserted between the N2 and CT domains of the helper phage pIII protein gene were used. Sequences of the antibody gene portions isolated from $E.$ $coli$ into which the antibody gene library was introduced were identified, and sequence information was obtained for 132 clones. The designed amino acid distribution and the amino acid distribution of the identified sequences are shown in FIG. 23. A library containing various sequences corresponding to the designed amino acid distribution was constructed.

[Reference Example 24] Isolation of Antibodies that Bind to IL-6R in a pH-Dependent Manner
(24-1) Isolation of Antibody Fragments, which Bind to Antigens in a pH-Dependent Manner, from the Library by Bead Panning The first selection from the constructed His library 1 was performed by enriching only antibody fragments with antigen (IL-6R) binding ability.

Phages were produced by $E.$ $coli$ containing the constructed phagemids for phage display. To precipitate the phages, 2.5 M NaCl/10% PEG was added to the *E. coli* culture fluid of phage production. The precipitated phage population was diluted with TBS to prepare a phage library solution. BSA and CaCl$_2$ were added to the phage library solution to adjust the final BSA concentration to 4% and the final calcium ion concentration to 1.2 mM. Regarding the panning method, the present inventors referred to general panning methods using antigens immobilized onto magnetic beads (J. Immunol. Methods. (2008) 332 (1-2), 2-9; J. Immunol. Methods. (2001) 247 (1-2), 191-203; Biotechnol. Prog. (2002) 18(2) 212-20, Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed three times with 1 ml of 1.2 mM CaCl$_2$/TBST (TBS containing 1.2 mM CaCl$_2$ and 0.1% Tween20) and then twice with 1 ml of 1.2 mM CaCl$_2$/TBS (pH 7.6). Then, the beads added with 0.5 ml of 1 mg/ml trypsin were suspended at room temperature for 15 minutes, and then immediately separated using a magnetic stand to collect a phage solution. The collected phage solution was added to 10 ml of *E. coli* strain ER2738 in a logarithmic growth phase (OD600 of 0.4-0.7). The *E. coli* was infected with the phages by culturing them while gently stirring at 37° C. for one hour. The infected *E. coli* was plated in a 225 mm×225 mm plate. Then, the phages were collected from the culture fluid of the plated *E. coli* to prepare a phage library solution.

To enrich the phages, the second and subsequent rounds of panning were performed using the antigen-binding ability or the pH-dependent binding ability as an indicator. Specifically, 40 pmol of the biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed multiple times with 1 ml of 1.2 mM CaCl$_2$/TBST and with 1.2 mM CaCl$_2$/TBS. Then, when the phages were enriched using the antigen-binding ability as an indicator, the beads added with 0.5 ml of 1 mg/ml trypsin were suspended at room temperature for 15 minutes, and then immediately separated using a magnetic stand to collect a phage solution. Alternatively, when the phages were enriched using the pH-dependent antigen-binding ability as an indicator, the beads added with 0.1 ml of 50 mM MES/1.2 mM CaCl$_{2/150}$ mM NaCl (pH 5.5) were suspended at room temperature, and then immediately separated using a magnetic stand to collect a phage solution. To eliminate the ability from phages displaying no Fab to infect *E. coli*, the pIII protein (helper phage-derived pIII protein) of phages displaying no Fab was cleaved by adding 5 μl of 100 mg/ml trypsin to the collected phage solution. The collected phages were added to 10 ml of *E. coli* strain ER2738 in a logarithmic growth phase (OD600 of 0.4-0.7). The *E. coli* was infected with the phages by culturing them while gently stirring at 37° C. for one hour. The infected *E. coli* was plated in a 225 mm×225 mm plate. Then, the phages were collected from the culture fluid of the plated *E. coli* to collect a phage library solution. The panning using the antigen-binding ability or the pH-dependent binding ability as an indicator was repeated twice.

(24-2) Assessment by Phage ELISA

Phage-containing culture supernatants were collected according to a conventional method (Methods Mol. Biol. (2002) 178, 133-145) from single colonies of *E. coli* obtained by the method described above.

To the phage-containing culture supernatants, BSA and CaCl$_2$ were added at a final concentration of 4% BSA and at a final calcium ion concentration of 1.2 mM. These phage-containing culture supernatants were subjected to ELISA by the following procedure. A StreptaWell 96 microtiter plate (Roche) was coated overnight with 100 μl of PBS containing the biotin-labeled antigen. After washing each well of the plate with PBST (PBS containing 0.1% Tween20) to remove the antigen, the wells were blocked with 250 μl of 4% BSA/TBS for one hour or more. After removing 4% BSA/TBS, the prepared culture supernatants were added to each well. The antibodies presented on the phages were allowed to bind to the antigens on each well by incubating the plate at 37° C. for one hour. Following wash with 1.2 mM CaCl$_2$/TBST, 1.2 mM CaCl$_2$/TBS (pH 7.6) or 1.2 mM CaCl$_2$/TBS (pH 5.5) was added to each well. The plate was incubated at 37° C. for 30 minutes. After washing with 1.2 mM CaCl$_2$/TBST (pH 7.6), HRP-coupled anti-M13 antibody (Amersham Pharmacia Biotech) diluted with TBS containing 4% BSA and 1.2 mM ionized calcium was added to each well. The plate was incubated for one hour. After washing with 1.2 mM CaCl$_2$/TBST, TMB single solution (ZYMED) was added to each well. The chromogenic reaction in the solution of each well was stopped by adding sulfuric acid, and then the absorbance at 450 nm was measured to assess the color development.

When enrichment was carried out using the antigen-binding ability as an indicator, phage ELISA following two rounds of panning showed that 17 of 96 clones were ELISA positive in an antigen-specific manner. Thus, clones were analyzed after three rounds of panning. Meanwhile, when enrichment was carried out using the pH-dependent antigen-binding ability as an indicator, phage ELISA following two rounds of panning showed that 70 of 94 clones were positive in ELISA. Thus, clones were analyzed after two rounds of panning.

The base sequences of genes amplified with specific primers were analyzed for the clones subjected to phage ELISA. The results of phage ELISA and sequence analysis are shown in Table 29 below.

TABLE 29

| LIBRARY ENRICHMENT INDEX | His LIBRARY 1 ANTIGEN-BINDING ABILITY | His LIBRARY 1 pH-DEPENDENT ANTIGEN-BINDING ABILITY |
| --- | --- | --- |
| NUMBER OF PANNING | 3 | 2 |
| NUMBER OF EXAMINED CLONES | 80 | 94 |
| ELISA-POSITIVE | 76 | 70 |
| TYPES OF ELISA-POSITIVE CLONE SEQUENCES | 30 | 67 |
| TYPES OF pH-DEPENDENT BINDING CLONE SEQUENCES | 22 | 47 |

By the same method, antibodies with pH-dependent antigen-binding ability were isolated from the naive human antibody phage display library. When enrichment was carried out using the antigen-binding ability as an indicator, 13 types of pH-dependent binding antibodies were isolated from 88 clones tested. Meanwhile, when enrichment was carried out using the pH-dependent antigen-binding ability as an indicator, 27 types of pH-dependent binding antibodies were isolated from 83 clones tested.

The result described above demonstrated that the variation of clones with pH-dependent antigen-binding ability isolated from the His library 1 was larger as compared to the naive human antibody phage display library.

(24-3) Expression and Purification of Antibodies

Clones assumed to have pH-dependent antigen-binding ability based on the result of phage ELISA were introduced into animal cell expression plasmids. Antibodies were expressed using the method described below. Cells of human fetal kidney cell-derived FreeStyle 293-F line (Invitrogen) were suspended in FreeStyle 293 Expression Medium (Invitrogen), and plated at a cell density of $1.33 \times 10^6$ cells/ml (3 ml) to each well of a 6-well plate. The prepared plasmids were introduced into the cells by a lipofection method. The cells were cultured in a $CO_2$ incubator (37° C., 8% $CO_2$, 90 rpm) for four days. By a method known to those skilled in the art, antibodies were purified using rProtein A Sepharose™ Fast Flow (Amersham Biosciences) from culture supernatants obtained as described above. The absorbance of solutions of purified antibodies was measured at 280 nm using a spectrophotometer. Antibody concentrations were calculated from the measured values by using the absorption coefficient determined by PACE method (Protein Science (1995) 4, 2411-2423).

(24-4) Assessment of Isolated Antibodies for their pH-Dependent Binding Ability to Human IL-6 Receptor Antibodies 6RpH #01 (heavy chain SEQ ID NO: 118; light chain SEQ ID NO: 119), 6RpH #02 (heavy chain SEQ ID NO: 120; light chain SEQ ID NO: 121), and 6RpH #03 (heavy chain SEQ ID NO: 122; light chain SEQ ID NO: 123) isolated as described in (24-3) were assessed for the pH dependency of their human IL-6 receptor-binding activity by analyzing the interaction between the antibodies and human IL-6 receptor using Biacore T100 (GE Healthcare). Tocilizumab (heavy chain SEQ ID NO: 60; light chain SEQ ID NO: 61) was used as a control antibody that does not have pH-dependent binding activity to human IL-6 receptor. The interaction for the antigen-antibody reaction was analyzed in solutions at pH 7.4 and pH 6.0, corresponding to a neutral pH and acidic pH conditions, respectively. An appropriate amount of Protein A/G (Invitrogen) was immobilized onto a Sensor chip CM5 (GE Healthcare) by an amino coupling method, and about 300 RU each of antibodies of interest were captured onto the chip. The two types of running buffers used were: 20 mM ACES/150 mM NaCl/0.05% (w/v) Tween20/1.2 mM $CaCl_2$ (pH 7.4); and 20 mM ACES/150 mM NaCl/0.05% (w/v) Tween20/1.2 mM $CaCl_2$ (pH 6.0). These buffers were each used to dilute human IL-6 receptor. All measurements were carried out at 37° C.

In the interaction analysis of the antigen-antibody reaction using tocilizumab as a control antibody, and antibodies 6RpH #01, 6RpH #02, and 6RpH #03, a diluted IL-6 receptor solution and a running buffer as a blank were injected at a flow rate of 5 μl/min for three minutes to allow IL-6 receptor to interact with antibodies tocilizumab, 6RpH #01, 6RpH #02, and 6RpH #03 captured onto the sensor chip. Then, 10 mM glycine-HCl (pH 1.5) was injected at a flow rate of 30 μl/min for 30 seconds to regenerate the sensor chip.

Figure 24:
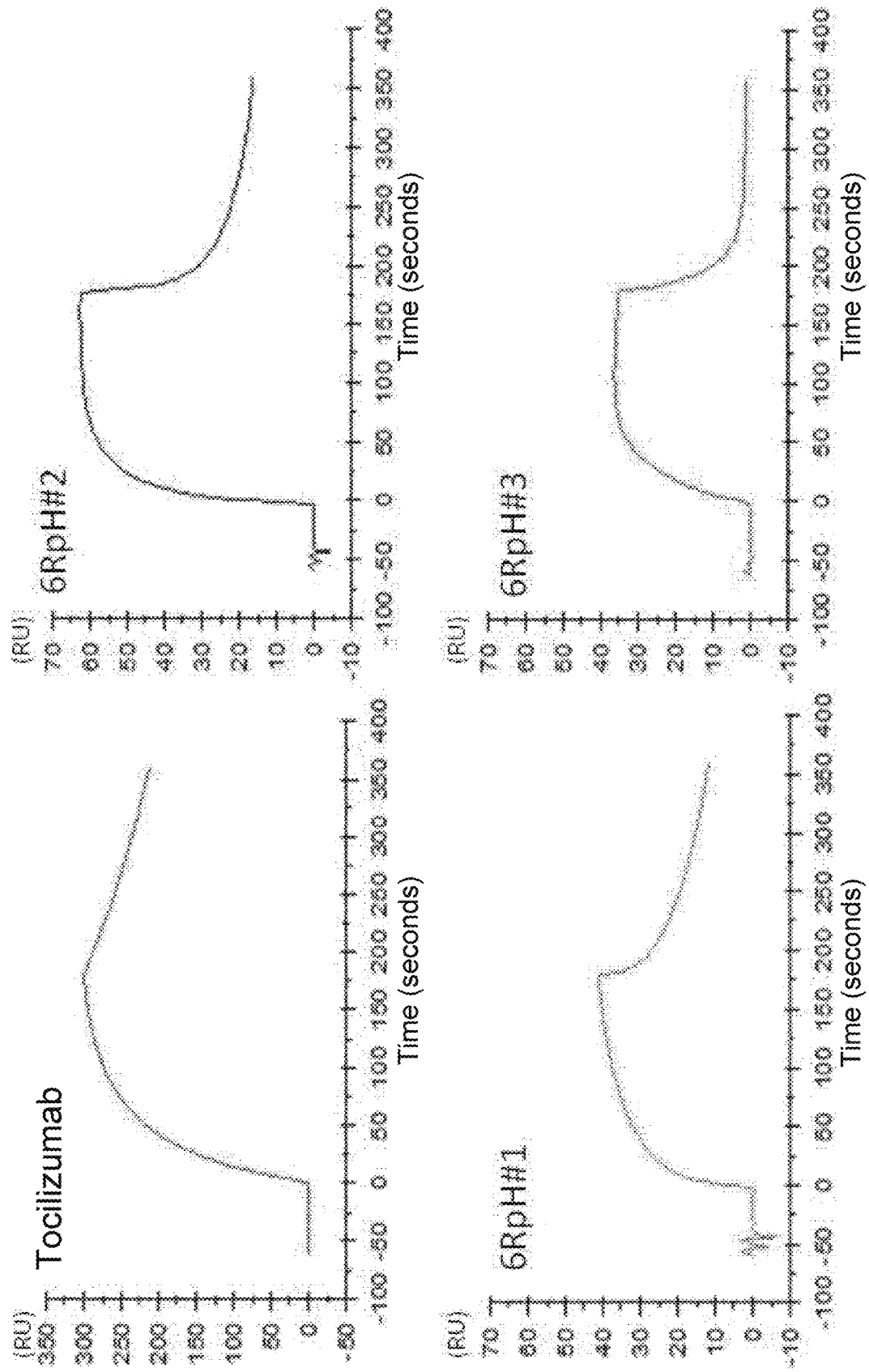
FIG. 24 shows sensorgrams for anti-IL-6R antibody (tocilizumab), antibody 6RpH #01, antibody 6RpH #02, and antibody 6RpH #03 at pH 7.4. The horizontal axis shows time, and the vertical axis shows RU value.
Figure 25:
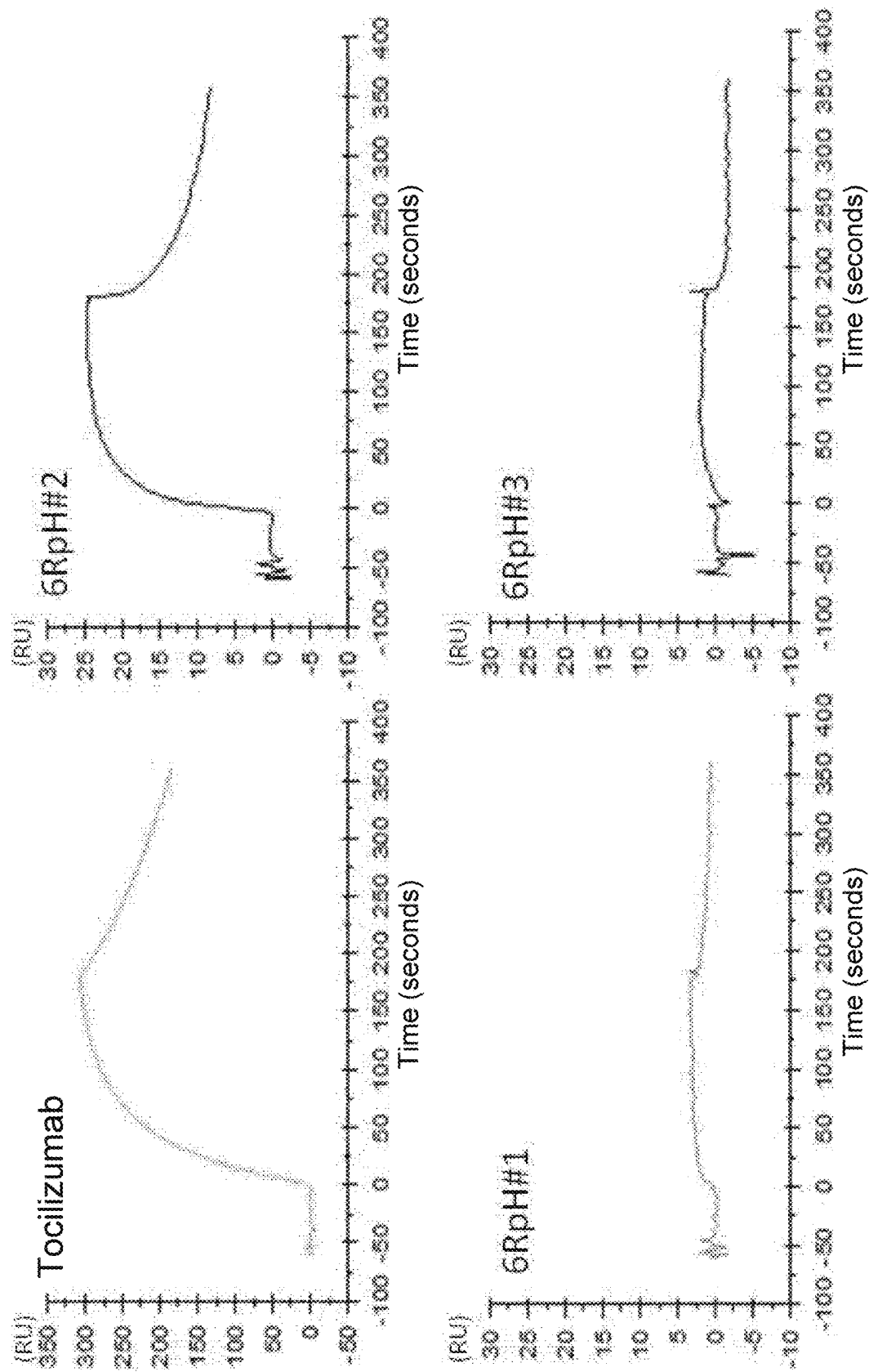
FIG. 25 shows sensorgrams for anti-IL-6R antibody (tocilizumab), antibody 6RpH #01, antibody 6RpH #02, and antibody 6RpH #03 at pH 6.0. The horizontal axis shows time, and the vertical axis shows RU value.

Sensorgrams at pH 7.4 obtained by the measurement using the method described above are shown in FIG. 24. Sensorgrams under the condition of pH 6.0 obtained by the same method are shown in FIG. 25.

The result described above shows that the IL-6 receptor-binding ability of antibodies 6RpH #01, 6RpH #02, and 6RpH #03 was significantly reduced when the buffer pH was shifted from pH 7.4 to pH 6.0.

(Reference Example 25) Production of Human IL-6 Receptor Knock-In Mice (25-1) Construction of a Knock-In Vector A bacterial artificial chromosome (BAC) clone into which a genomic region of mouse interleukin-6 gene (Il6ra) has been cloned was used. A DNA fragment in which the human interleukin-6 receptor gene coding sequence (GenBank #NM_000565_), hp7 sequence, poly A addition signal, loxP sequence, neomycin-resistance (neo) gene cassette, and loxP are serially linked was inserted into the target region of the mouse Il6ra gene on this BAC by homologous recombination using a Red/ET system (GeneBridges). In this case, insertion was carried out by matching the translation initiation site located in exon 1 of the mouse Il6ra gene on BAC with the translation initiation site of the human IL6R gene, and only 40 base pairs of the nucleotide sequence following the translation initiation site in exon 1 of the mouse Il6ra gene were deleted. A pkg gene promoter was added to neo, which is the drug-resistance gene, so that the neo gene is expressed in ES cells. However, the neo gene is predicted to possibly suppress the expression of the hIL6R gene introduced into the upstream region. Therefore, to enable later removal of the neo gene, the loxP sequence (ATAACTTCGTATAGCATACATTATACGAAGTTAT (SEQ ID NO: 131)) was placed on both sides of the neo gene. This produced a system where the neo gene situated between the loxP sequences will be removed by recombination when Cre acts on it. Next, to enable linearization of the knock-in vector, the restriction enzyme NotI recognition sequence (GCGGCCGC) was inserted together with the ampicillin resistance gene to the 5' upstream region of the mouse Il6ra gene on BAC.

(25-2) Introduction into ES Cells

The above-mentioned hIL6R knock-in vector was electroporated into ES cells (129SvEv mouse-derived cells), and after selective culturing with G418, drug-resistant clones were obtained. From these clones, homologous recombinants were screened by the PCR method. 60 μg of the knock-in vector was linearized with NotI, extracted with phenol/chloroform, precipitated with ethanol, and then dissolved in PBS.

To prepare PCR samples, ES cells to be used in the screening were cultured on a 96-well plate, washed twice using 200 μL of PBS per well, and then a cell lysis buffer having the following composition (5 μL of 10× LA buffer II (TAKARA LA for Taq), 5 μL of 5% NP-40, 4 μL of proteinase K (TAKARA) (20 mg/mL), and 36 μL of distilled water) was added thereto for treatment at 55° C. for two hours, followed by treatment at 95° C. for 15 minutes to inactivate proteinase K.

A total volume of 25 μL of a PCR reaction mixture was prepared by mixing 1 μL of the sample, 2.5 μL of 10× LA buffer II, 2.5 μL of 25 mM $MgCl_2$, 4 μL of dNTP (including 2.5 mM each of dATP, dCTP, dGTP, and dTTP), 0.2 μL each of the primers (50 μM each), 0.25 μL of LA Taq (TAKARA), and 14.35 μL of distilled water. The PCR conditions were: preheating at 94° C. for five minutes, 35 cycles of amplification consisting of 98° C. for ten seconds and 68° C. for 3 minutes 30 seconds, as well as heating at 68° C. for seven minutes.

Figure 32A:
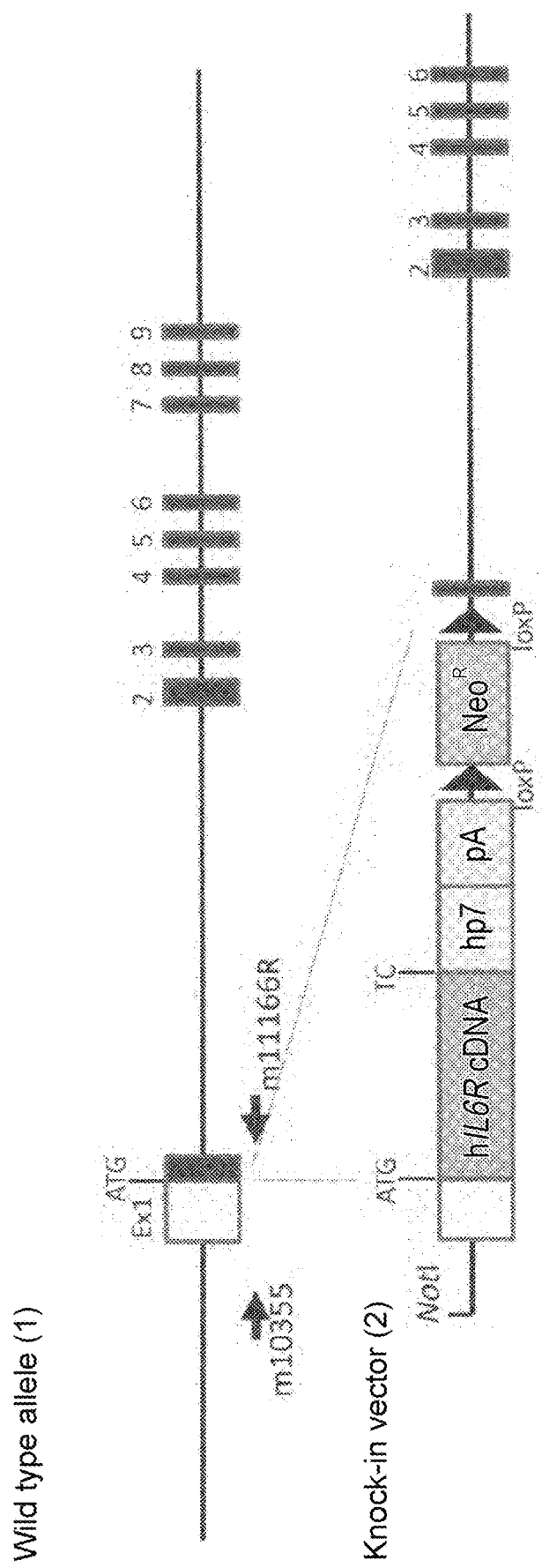
FIG. 32A is a schematic diagram showing the relationship between the genomic DNA structure of the mouse interleukin-6 receptor (Il6ra) gene (1) and the knock-in vector to be inserted (2). The knock-in vector has the full-length human interleukin-6-receptor (hIL6R) cDNA, the hp7 sequence, a poly-A addition signal, and a neomycin-resistance gene.

P6Ra1 (forward) 5'-ACAGGGCCTTAGACTCACAGC-3' (SEQ ID NO: 132) and hRLI6 11638R (reverse) 5'-AACTTGCTCCCGACACTACTGG-3' (SEQ ID NO: 133) were used for the primers. Primer P6Ra1 was placed in the mouse Il6ra genome region at the 5'-side further upstream of the homologous arm of the knock-in vector, and hRLI6 11638R was placed inside the hIL6R cDNA (see FIG. 32). In samples of ES cells that underwent homologous recombination, an approximately 2.2-kb band is amplified.

(3) Generation of Knock-In Mice

The homologous recombinant ES clones were suspended by trypsin treatment, and washed with the ES cell medium. Five IU of equine chorionic gonadotropin (eCG) and human chorionic gonadotropin (hCG) were administered intraperitoneally at 48-hour intervals to female C57BL/6J(B6) mice to perform superovulation treatment, and these female mice were crossed with male mice of the same lineage. The day when a plug was confirmed in a female mouse was regarded as day 0.5. On gestation day 2.5, the uterus and the oviduct were perfused, and embryos in the 8-cell stage to the morula stage were collected. The collected embryos were incubated overnight at 37° C., the embryos that developed into blastocysts were used as host embryos and 10 to 15 ES cells were injected therein. The injected embryos were transplanted into the uterus of pseudopregnant ICR-type recipient females on gestation day 2.5, and the offsprings were obtained 17 days later. Based on distinction by the coat color of the offspring obtained by injection of ES cells to the blastocysts, chimeric mice with mixed presence of the recombinant ES cells (wild-type color) and the host blastocyst-derived cells (black) were obtained. After maturation, the male chimeric mice were crossed with the B6-female mice, and transmission of the knock-in allele to the next generation mice was confirmed by the PCR method using the genomic DNA extracted from the tail of the next generation mice as the template. PCR was performed by the method used when screening for the above-mentioned homologous recombinant ES cells. As a result, individuals from which a 2.2-kb signal was detected were obtained, and the knock-in allele was confirmed to be transmitted to these individuals.

(4) Removal of the Neo Gene

The neo gene cassette was removed by microinjection of the recombinase Cre expression vector into the pronucleus of the fertilized egg obtained by propagation of individuals in which transmission of the knock-in allele was confirmed. That is, by transiently expressing Cre, recombination was induced between the two loxP sites placed in the knock-in allele, and the neo gene cassette was removed. The fertilized egg to which the Cre expression vector was microinjected was transferred to the oviducts of pseudopregnant ICR recipient females on gestation day 0.5 and the offsprings were born 19 days later. Removal of the neo gene cassette was confirmed by a PCR method using genomic DNA extracted from the tail collected after weaning of the offsprings.

The PCR reaction solution was composed of 1 μL of the sample, 12.5 μL of 2× GC buffer I, 4 μL of dNTP (including 2.5 mM each of dATP, dCTP, dGTP, and dTTP), 0.25 μL each of the primers (50 μM each), 0.25 μL of LA Taq (TAKARA), and 6.75 μL of distilled water, and upon mixing them, the total amount was set to 25 μL. The PCR conditions were: preheating at 94° C. for four minutes, 35 cycles of amplification consisting of 94° C. for 30 seconds, 62° C. for 30 seconds, and 72° C. for three minutes, as well as heating at 72° C. for seven minutes.

Figure 32B:
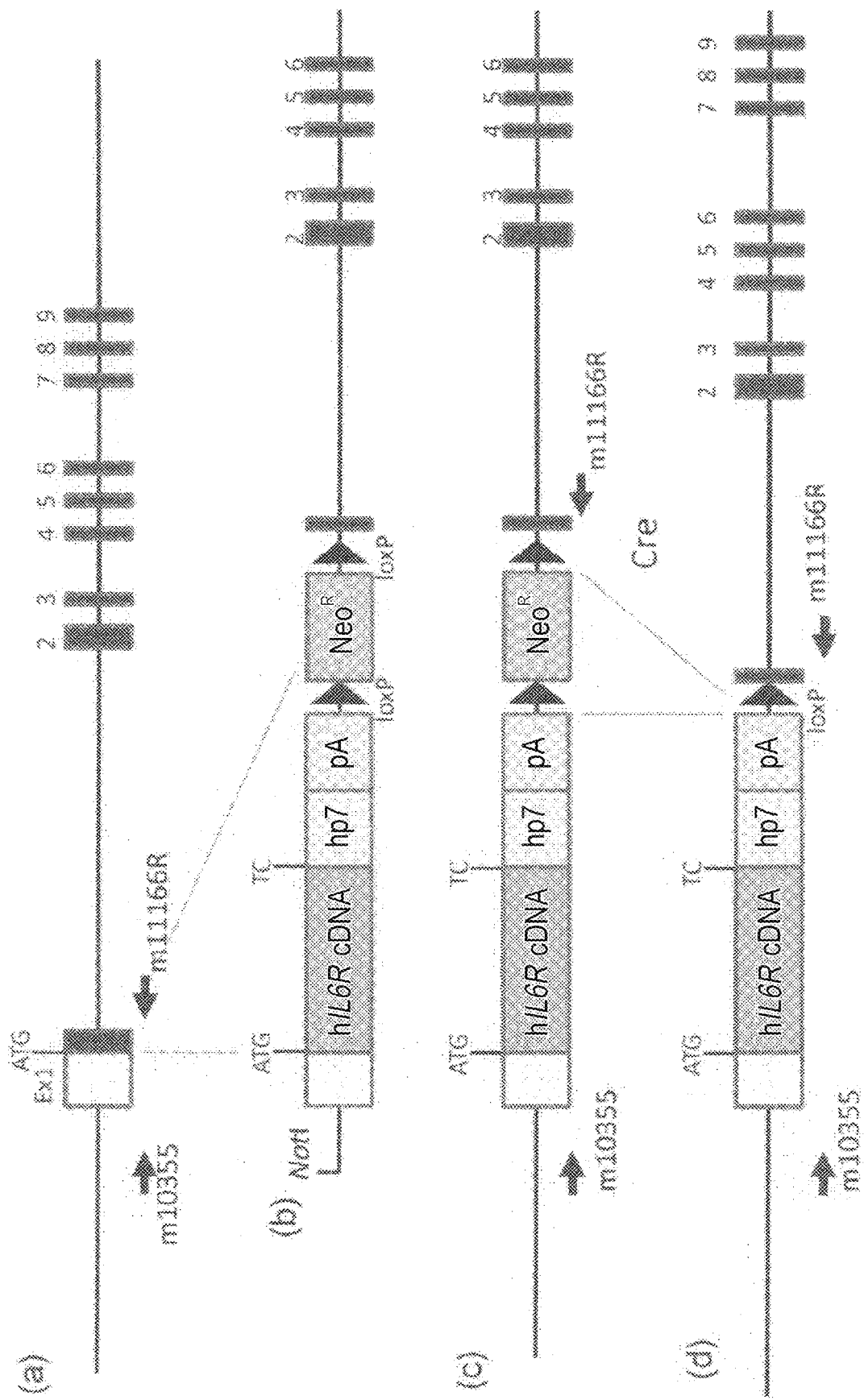
FIG. 32B is a schematic diagram showing how the genomic DNA of the mouse interleukin-6 receptor gene (a) and the knock-in vector (b) undergo homologous recombination to form a knock-in genomic DNA (c). Furthermore, it shows the process of completing the human interleukin-6 receptor gene knock-in allele (d) by allowing Cre recombinase to act on (c) to remove the neomycin-resistance gene cassette. The arrows in the figure indicate the positions for setting primers used for detecting the knocked-in human interleukin-6 receptor gene.
Figure 33:
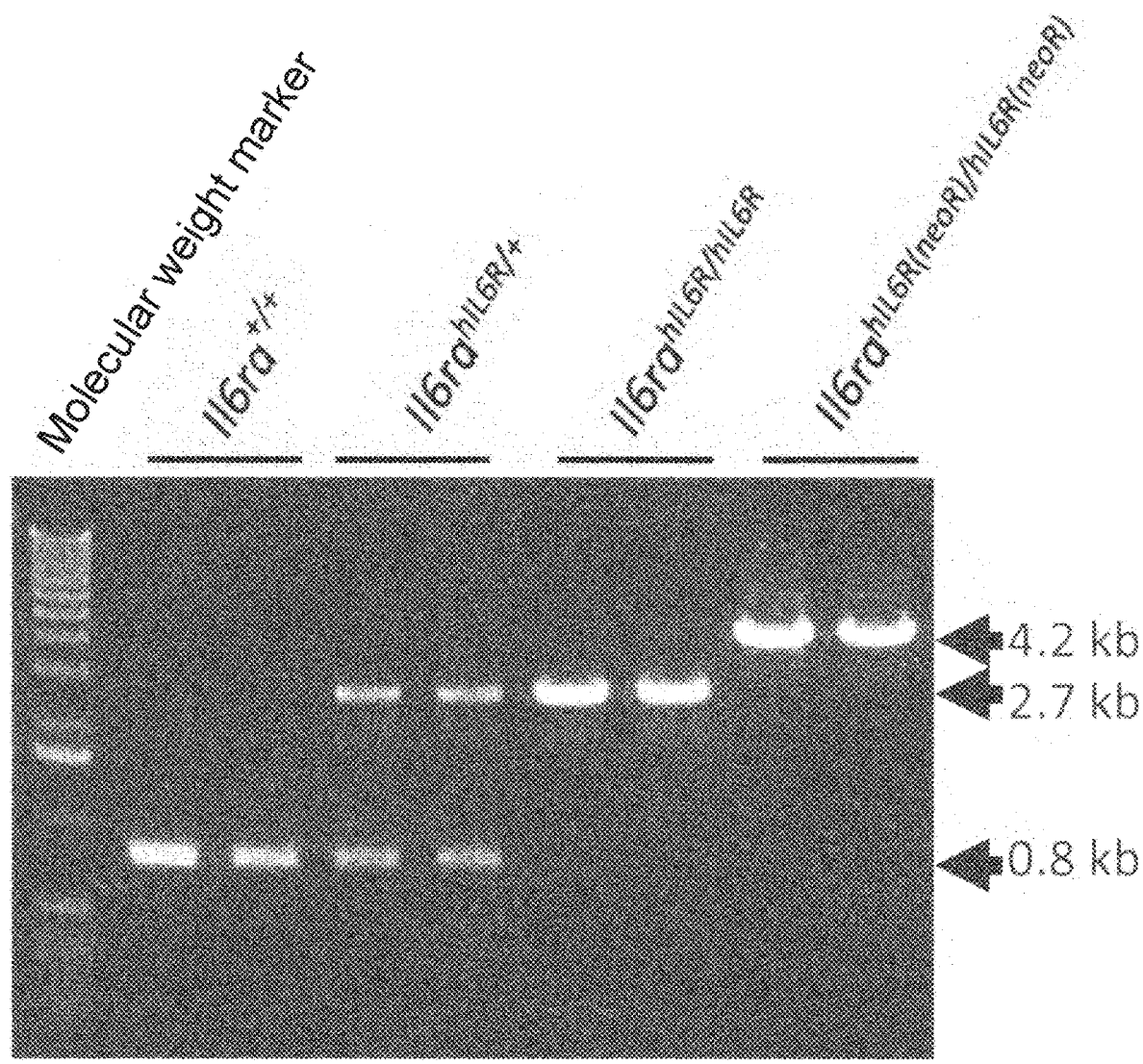
FIG. 33 shows a representative example of PCR which analyzed each genotype obtained in the process of establishing the human interleukin-6 receptor gene knock-in mice.

The positions where the primers were set are shown in FIG. 32B. mRLI6 10355 (5'-TCTGCAGTAGCCTT-CAAAGAGC-3' (SEQ ID NO: 134)) and mRLI6 11166R (5'-AACCAGACAGTGTCACATTCC-3' (SEQ ID NO: 135)) were used for the primers. In the samples from individuals before removal of the neo cassette, a 4.2-kb signal detected as an amplification product derived from the knock-in allele and a 0.8-kb signal derived from the wild-type allele were detected by PCR reaction, whereas in the samples from individuals whose neo cassette has been removed, an approximately 2.7-kb signal and a 0.8-kb signal derived from the wild-type allele were detected (FIG. 33).

Figure 34:
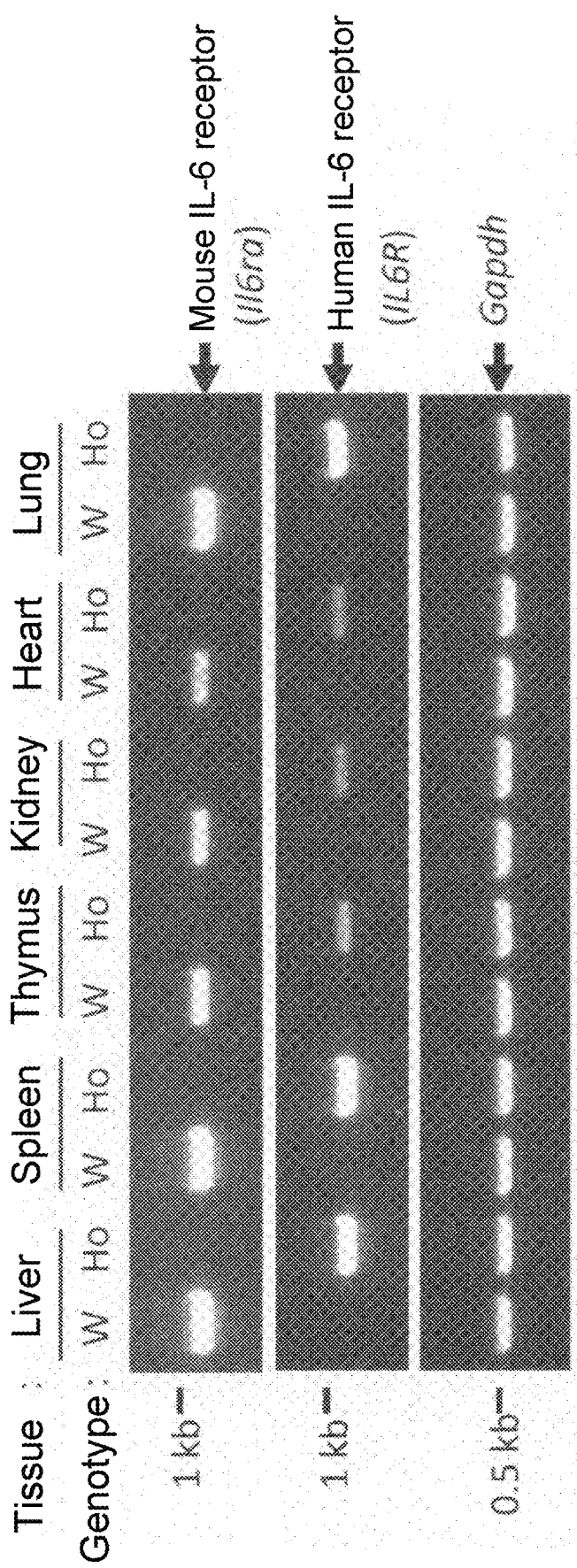
FIG. 34 shows the expression profile of the interleukin-6 receptor gene in the wild-type mouse and the human interleukin-6 receptor gene knock-in mouse.

(6) Confirmation of Human IL6R Expression and Mouse IL6ra Expression (6-1) Confirmation by the RT-PCR Method Using Tissue RNA Analyses of expression of human IL6R and mouse IL6ra were carried out by the RT-PCR method using tissue RNA of homozygous knock-in mice and wild-type mice. Tissue RNAs were prepared from the liver, spleen, thymus, kidney, heart and lung. Using 1 μg each of the tissue RNAs as templates, cDNAs were synthesized by performing a reverse transcription reaction using a SuperScript II First Strand cDNA Synthesis Kit (Invitrogen) and oligo dT (20) primer. Human IL6R and mouse IL6ra were detected by performing PCR using the synthesized cDNAs as templates. Human IL6R was detected using the combination of a forward primer 6RIK-s1 (5'-CCCGGCTGCGGAGCCGCTCTGC-3' (SEQ ID NO: 136)) set in the 5' untranslated region further upstream of the translation initiation site which is the insertion position of the hIL6R gene in the knock-in allele and a human IL6R-specific reverse primer RLI6-a1 (5'-ACAGTGATGCTGGAGGTCCTT-3' (SEQ ID NO: 137)). On the other hand, mouse IL6ra was detected by using the combination of the above-mentioned forward primer 6RIK-s1 and reverse primer 6RLIcA2 (5'-AGCAACACCGT-GAACTCCTTTG-3' (SEQ ID NO: 138)) which is specific to mouse IL6ra. The PCR reaction solution was composed of 12.5 μL of the sample, 12.5 μL of 2× GC buffer I, 4 μL of dNTP (including 2.5 mM each of dATP, dCTP, dGTP, and dTTP), 0.25 μL each of the primers (50 μM each), 0.25 μL of LA Taq (TAKARA), and 6.75 μL of distilled water, and upon mixing them, the total amount was set to 25 μL. The PCR conditions were: preheating at 94° C. for two minutes, 30 cycles of amplification consisting of 94° C. for 30 seconds, 62° C. for 30 seconds, and 72° C. for one minute, as well as heating at 72° C. for five minutes. While the amplification product of human IL6R is detected at 880 bp and the amplification product of mouse IL6ra is detected at 846 bp, only human IL6R was detected from each of the tissues of homozygous hIL6R knock-in mice, and mouse IL6ra was not detected. Meanwhile, human IL6R was not detected from each of the tissues of wild-type mice, and only mouse IL6ra was detected (FIG. 34). These results confirmed that the knock-in vector underwent homologous recombination as designed, giving mice that express human IL6R instead of mouse IL6ra.

(6-2) Measurement of Human IL-6R Concentration in the Plasma

Figure 35:
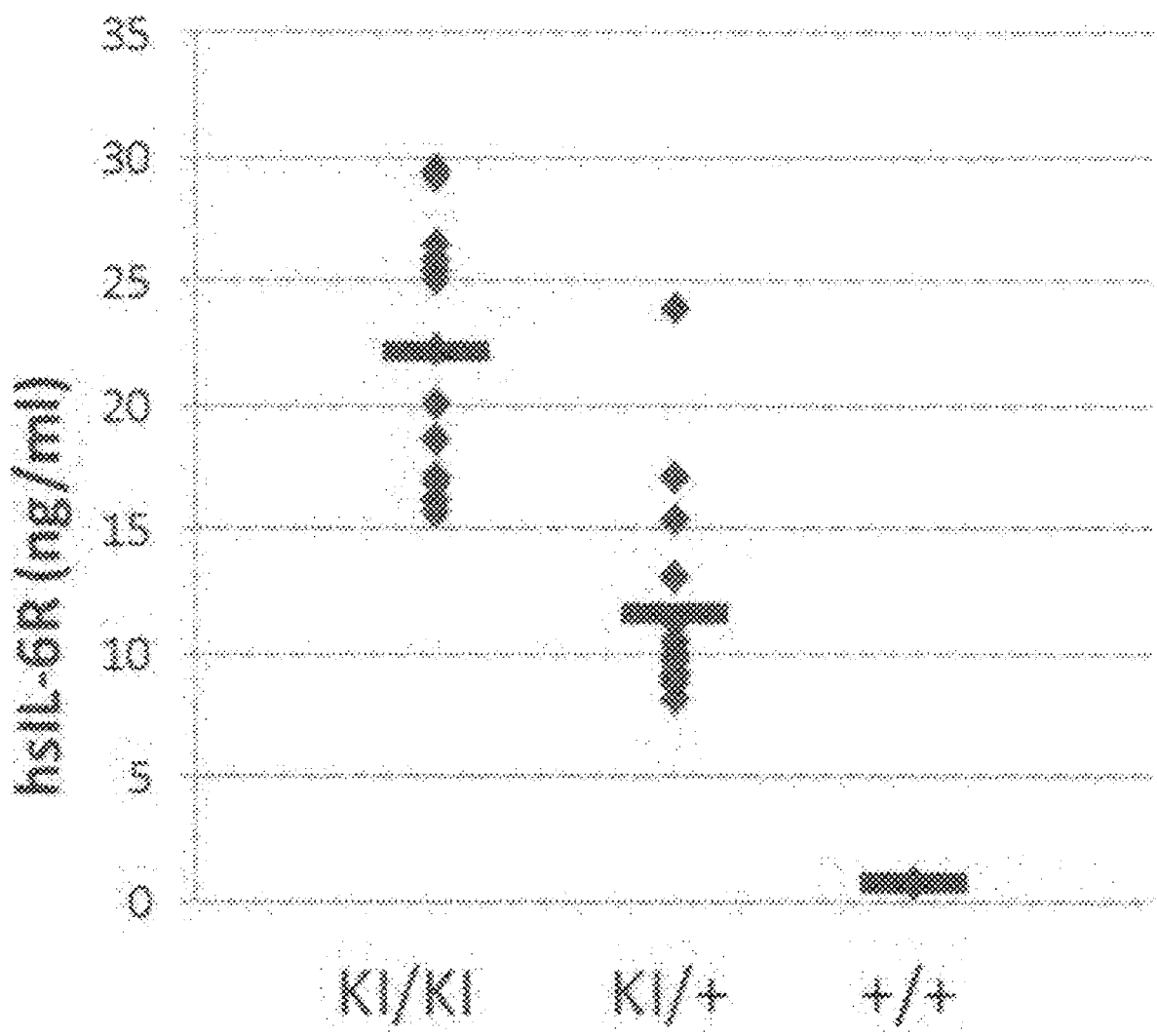
FIG. 35 is a graph showing the results of measuring the plasma concentration of soluble human interleukin-6 receptor (hsIL-6R) in wild-type mice and homozygous and heterozygous human interleukin-6 receptor gene knock-in mice. KI/KI, KI/+, and +/+ indicate the homozygous knock-in mice, heterozygous knock-in mice, and the wild-type, respectively.

Laparotomy was performed under isoflurane inhalation anesthesia, and the concentration of soluble human IL-6R in the plasma separated from the blood collected from the abdominal large vein was measured using a Quantikine Human IL-6sR Immunoassay Kit (R&D Systems). As a result, the concentration of soluble hIL-6R in plasma was 22.1±5.0 ng/mL for the homozygous knock-in mice, and 11.5±4.1 ng/mL for the heterozygous knock-in mice. Soluble hIL-6R was not detected in the plasma of wild-type mice (FIG. 35). The concentration in homozygous knock-in mice was equivalent to the concentration in blood reported for humans (Blood (2008) 112, 3959-3969).

(6-3) Confirmation of Species-Specific Ligand Reactivity

Figure 36:
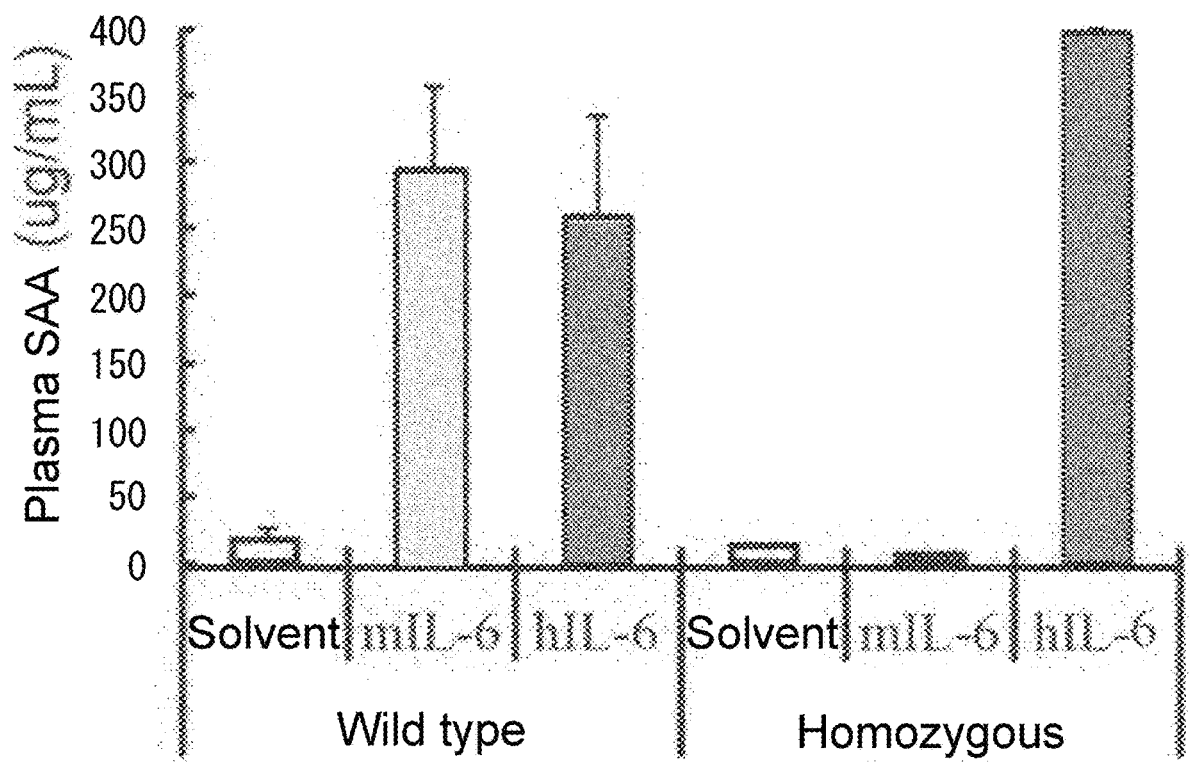
FIG. 36 is a graph showing the species-specific reactivity to interleukin-6 (ligand) in the wild-type mice and homozygous human interleukin-6 receptor gene knock-in mice.

Mouse IL-6 or human IL-6 were administered intraperitoneally to homozygous knock-in mice and wild-type mice at 4 μg per kg body weight, blood was collected six hours later, and the concentration of serum amyloid A (SAA) in the blood was quantified using an SAA ELISA Kit (Invitrogen). A solution produced by supplementing phosphate buffered saline solution (PBS) with mouse plasma so that it will become 0.5% was used as the solvent of IL-6 for administration. A control group to which only the solvent is administered was prepared. As a result, the homozygous knock-in mouse was responsive to human IL-6 only and the plasma SAA level increased, but it did not show any responsiveness to mouse IL-6 (FIG. 36). On the other hand, the wild-type mice were responsive to human IL-6 and mouse IL-6, and showed an increase in the plasma SAA level (FIG. 36). It is known that while mouse IL-6ra binds to mouse IL-6 as well as human IL-6, human IL-6R binds to human IL-6 but does not bind to mouse IL-6, and the results of this experiment were in accordance with this knowledge. Therefore, it was revealed that in the homozygous knock-in mice, mouse IL6ra is not expressed, and instead, human IL6R is expressed and is functioning, as designed.

Since the mRNA of the hIL6R gene transcribed by the knock-in allele of the present invention has a structure that will not be spliced out, it is not degraded by the NMD mechanism, but on the other hand, the expression level of genes that are not spliced out is known to become low. However, in the hIL6R knock-in mice of the present invention, the soluble hIL-6R concentration in the blood is the same as that in healthy individuals, and moreover, the mice are sufficiently responsive to the administered human IL-6 and SAA production was confirmed. This shows that the hp7 inserted together with the poly A addition signal contributed to the stabilization of the expression level of hIL6R which would normally have decreased because of its structure that is not spliced out.

The invention claimed is:

1. A method of producing a pharmaceutical composition that induces humoral immunity to a target antigen, the method comprising:
   identifying the amino acid sequence of a first antigen-binding molecule comprising
      (i) an antigen-binding domain comprising an antibody heavy chain variable region (VH) and an antibody light chain variable region (VL), wherein the antigen-binding domain binds to the target antigen with an antigen-binding activity that is higher at pH 7.4 than at pH 5.8, and the VL comprises a histidine at one or more of Kabat numbering positions 24, 27, 28, 31, 32, 34, 50, 51, 52, 53, 54, 55, 56, 89, 90, 91, 92, 93, 94, and 95A, and
      (ii) a first FcRn-binding domain;
   generating a DNA encoding a second antigen-binding molecule comprising the antigen-binding domain and a non-native human IgG1 Fc region comprising a second FcRn-binding domain, wherein the amino acid sequence of the second FcRn-binding domain differs from the amino acid sequence of the first FcRn-binding domain by substitution at one or more positions, wherein at least one of the substitutions is a set of one or more substitutions that matches the set of substitutions present in any one of the variants F10, F12, F14, F32, F34, F36, F38, F40, F47, F49, F50, F53, F54, F58, F59, F61, F69, F71, F73, F78, F80, F82, F84, F86, F88, F90, F92, F93, F95, F101, F103 to F108, F111, F113 to F116 listed in Tables 5-1 to 5-3, wherein all position numbers in Tables 5-1 to 5-3 are according to EU numbering, and wherein the second FcRn-binding domain's binding to a human FcRn receptor at pH 7.4 is greater than the binding of the first FcRn-binding domain to a human FcRn receptor at the same pH;
   expressing the DNA, thereby producing the second antigen-binding molecule;
   collecting the second antigen-binding molecule; and
   producing a pharmaceutical composition comprising the second antigen-binding molecule, wherein the pharmaceutical composition induces humoral immunity to the target antigen.

2. The method of claim 1, wherein the second antigen-binding molecule binds to and neutralizes the target antigen.

3. The method of claim 1, wherein the second antigen-binding molecule has cytotoxic activity against a cell expressing the target antigen.

4. The method of claim 1, wherein the non-native human IgG1 Fc region differs from a native human IgG1 Fc region at one or more positions, including one or more of the following EU numbering positions: 239, 252, 257, 286, 307, 308, 428, and 434.

5. The method of claim 1, wherein one or more of the following EU numbering positions in the non-native human IgG1 Fc region is occupied by the indicated amino acid:
Ala at position 257;
Pro at position 308;
Leu at position 428;
Tyr at position 434.

6. The method of claim 1, wherein the non-native human IgG1 Fc region's binding to a human Fcγ receptor is greater than a native human IgG1 Fc region's binding to the human Fcγ receptor, wherein the native human IgG1 Fc region comprises a fucose-containing sugar chain bound at EU numbering position 297.

7. The method of claim 6, wherein the human Fcγ receptor is FcγRIa, FcγRIIa(R), FcγRIIa(H), FcγRIIb, FcγRIIIa(V), or FcγRIIIa(F).

8. The method of claim 1, wherein the non-native human IgG1 Fc region differs from a native human IgG1 Fc region at one or more positions, including one or more of the following EU numbering positions: 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, 440.

9. The method of claim 6, wherein one or more of the following EU numbering positions in the non-native human IgG1 Fc region is occupied by the indicated amino acid:
either Lys or Tyr at position 221;
any one of Phe, Trp, Glu, and Tyr at position 222;
any one of Phe, Trp, Glu, and Lys at position 223;
any one of Phe, Trp, Glu, and Tyr at position 224;
any one of Glu, Lys, and Trp at position 225;
any one of Glu, Gly, Lys, and Tyr at position 227;
any one of Glu, Gly, Lys, and Tyr at position 228;
any one of Ala, Glu, Gly, and Tyr at position 230;
any one of Glu, Gly, Lys, Pro, and Tyr at position 231;
any one of Glu, Gly, Lys, and Tyr at position 232;
any one of Ala, Asp, Phe, Gly, His, Ile, Lys, Leu, Met, Asn, Gln, Arg, Ser, Thr, Val, Trp, and Tyr at position 233;
any one of Ala, Asp, Glu, Phe, Gly, His, Ile, Lys, Met, Asn, Pro, Gln, Arg, Ser, Thr, Val, Trp, and Tyr at position 234;
any one of Ala, Asp, Glu, Phe, Gly, His, Ile, Lys, Met, Asn, Pro, Gln, Arg, Ser, Thr, Val, Trp, and Tyr at position 235;
any one of Ala, Asp, Glu, Phe, His, Ile, Lys, Leu, Met, Asn, Pro, Gln, Arg, Ser, Thr, Val, Trp, and Tyr at position 236;
any one of Asp, Glu, Phe, His, Ile, Lys, Leu, Met, Asn, Pro, Gln, Arg, Ser, Thr, Val, Trp, and Tyr at position 237;
any one of Asp, Glu, Phe, Gly, His, Ile, Lys, Leu, Met, Asn, Gln, Arg, Ser, Thr, Val, Trp, and Tyr at position 238;
any one of Asp, Glu, Phe, Gly, His, Ile, Lys, Leu, Met, Asn, Pro, Gln, Arg, Thr, Val, Trp, and Tyr at position 239;
any one of Ala, Ile, Met, and Thr at position 240;
any one of Asp, Glu, Leu, Arg, Trp, and Tyr at position 241;
any one of Leu, Glu, Leu, Gln, Arg, Trp, and Tyr at position 243;
His at position 244;
Ala at position 245;
any one of Asp, Glu, His, and Tyr at position 246;
any one of Ala, Phe, Gly, His, Ile, Leu, Met, Thr, Val, and Tyr at position 247;
any one of Glu, His, Gln, and Tyr at position 249;
either Glu or Gln at position 250;
Phe at position 251;
any one of Phe, Met, and Tyr at position 254;
any one of Glu, Leu, and Tyr at position 255;
any one of Ala, Met, and Pro at position 256;
any one of Asp, Glu, His, Ser, and Tyr at position 258;
any one of Asp, Glu, His, and Tyr at position 260;
any one of Ala, Glu, Phe, Ile, and Thr at position 262;
any one of Ala, Ile, Met, and Thr at position 263;
any one of Asp, Glu, Phe, Gly, His, Ile, Lys, Leu, Met, Asn, Pro, Gln, Arg, Ser, Thr, Trp, and Tyr at position 264;
any one of Ala, Leu, Phe, Gly, His, Ile, Lys, Leu, Met, Asn, Pro, Gln, Arg, Ser, Thr, Val, Val, Trp, and Tyr at position 265;
any one of Ala, Ile, Met, and Thr at position 266;
any one of Asp, Glu, Phe, His, Ile, Lys, Leu, Met, Asn, Pro, Gln, Arg, Thr, Val, Trp, and Tyr at position 267;
any one of Asp, Glu, Phe, Gly, Ile, Lys, Leu, Met, Pro, Gln, Arg, Thr, Val, and Trp at position 268;
any one of Phe, Gly, His, Ile, Lys, Leu, Met, Asn, Pro, Arg, Ser, Thr, Val, Trp, and Tyr at position 269;
any one of Glu, Phe, Gly, His, Ile, Leu, Met, Pro, Gln, Arg, Ser, Thr, Trp, and Tyr at position 270;
any one of Ala, Asp, Glu, Phe, Gly, His, Ile, Lys, Leu, Met, Asn, Gln, Arg, Ser, Thr, Val, Trp, and Tyr at position 271;
any one of Asp, Phe, Gly, His, Ile, Lys, Leu, Met, Pro, Arg, Ser, Thr, Val, Trp, and Tyr at position 272;
either Phe or Ile at position 273;
any one of Asp, Glu, Phe, Gly, His, Ile, Leu, Met, Asn, Pro, Arg, Ser, Thr, Val, Trp, and Tyr at position 274;
either Leu or Trp at position 275;
any one of Asp, Glu, Phe, Gly, His, Ile, Leu, Met, Pro, Arg, Ser, Thr, Val, Trp, and Tyr at position 276;
any one of Asp, Glu, Gly, His, Ile, Lys, Leu, Met, Asn, Pro, Gln, Arg, Ser, Thr, Val, and Trp at position 278;
Ala at position 279;
any one of Ala, Gly, His, Lys, Leu, Pro, Gln, Trp, and Tyr at position 280;
any one of Asp, Lys, Pro, and Tyr at position 281;
any one of Glu, Gly, Lys, Pro, and Tyr at position 282;
any one of Ala, Gly, His, Ile, Lys, Leu, Met, Pro, Arg, and Tyr at position 283;
any one of Asp, Glu, Leu, Asn, Thr, and Tyr at position 284;
any one of Asp, Glu, Lys, Gln, Trp, and Tyr at position 285;
any one of Glu, Gly, Pro, and Tyr at position 286;
any one of Asn, Asp, Glu, and Tyr at position 288;

any one of Asp, Gly, His, Leu, Asn, Ser, Thr, Trp, and Tyr at position 290;
any one of Asp, Glu, Gly, His, Ile, Gln, and Thr at position 291;
any one of Ala, Asp, Glu, Pro, Thr, and Tyr at position 292;
any one of Phe, Gly, His, Ile, Leu, Met, Asn, Pro, Arg, Ser, Thr, Val, Trp, and Tyr at position 293;
any one of Phe, Gly, His, Ile, Lys, Leu, Met, Asn, Pro, Arg, Ser, Thr, Val, Trp, and Tyr at position 294;
any one of Asp, Glu, Phe, Gly, His, Ile, Lys, Met, Asn, Pro, Arg, Ser, Thr, Val, Trp, and Tyr at position 295;
any one of Ala, Asp, Glu, Gly, His, Ile, Lys, Leu, Met, Asn, Gln, Arg, Ser, Thr, and Val at position 296;
any one of Asp, Glu, Phe, Gly, His, Ile, Lys, Leu, Met, Pro, Gln, Arg, Ser, Thr, Val, Trp, and Tyr at position 297;
any one of Ala, Asp, Glu, Phe, His, Ile, Lys, Met, Asn, Gln, Arg, Thr, Val, Trp, and Tyr at position 298;
any one of Ala, Asp, Glu, Phe, Gly, His, Ile, Lys, Leu, Met, Asn, Pro, Gln, Arg, Ser, Val, Trp, and Tyr at position 299;
any one of Ala, Asp, Glu, Gly, His, Ile, Lys, Leu, Met, Asn, Pro, Gln, Arg, Ser, Thr, Val, and Trp at position 300;
any one of Asp, Glu, His, and Tyr at position 301;
Ile at position 302;
any one of Asp, Gly, and Tyr at position 303;
any one of Asp, His, Leu, Asn, and Thr at position 304;
any one of Glu, Ile, Thr, and Tyr at position 305;
any one of Ala, Asp, Asn, Thr, Val, and Tyr at position 311;
Phe at position 313;
Leu at position 315;
either Glu or Gln at position 317;
any one of His, Leu, Asn, Pro, Gln, Arg, Thr, Val, and Tyr at position 318;
any one of Asp, Phe, Gly, His, Ile, Leu, Asn, Pro, Ser, Thr, Val, Trp, and Tyr at position 320;
any one of Ala, Asp, Phe, Gly, His, Ile, Pro, Ser, Thr, Val, Trp, and Tyr at position 322;
Ile at position 323;
any one of Asp, Phe, Gly, His, Ile, Leu, Met, Pro, Arg, Thr, Val, Trp, and Tyr at position 324;
any one of Ala, Asp, Glu, Phe, Gly, His, Ile, Lys, Leu, Met, Pro, Gln, Arg, Ser, Thr, Val, Trp, and Tyr at position 325;
any one of Ala, Asp, Glu, Gly, Ile, Leu, Met, Asn, Pro, Gln, Ser, Thr, Val, Trp, and Tyr at position 326;
any one of Ala, Asp, Glu, Phe, Gly, His, Ile, Lys, Leu, Met, Asn, Pro, Arg, Thr, Val, Trp, and Tyr at position 327;
any one of Ala, Asp, Glu, Phe, Gly, His, Ile, Lys, Met, Asn, Pro, Gln, Arg, Ser, Thr, Val, Trp, and Tyr at position 328;
any one of Asp, Glu, Phe, Gly, His, Ile, Lys, Leu, Met, Asn, Gln, Arg, Ser, Thr, Val, Trp, and Tyr at position 329;
any one of Cys, Glu, Phe, Gly, His, Ile, Lys, Leu, Met, Asn, Pro, Arg, Ser, Thr, Val, Trp, and Tyr at position 330;
any one of Asp, Phe, His, Ile, Leu, Met, Gln, Arg, Thr, Val, Trp, and Tyr at position 331;
any one of Ala, Asp, Glu, Phe, Gly, His, Lys, Leu, Met, Asn, Pro, Gln, Arg, Ser, Thr, Val, Trp, and Tyr at position 332;
any one of Ala, Asp, Glu, Phe, Gly, His, Ile, Leu, Met, Pro, Ser, Thr, Val, and Tyr at position 333;
any one of Ala, Glu, Phe, Ile, Leu, Pro, and Thr at position 334;
any one of Asp, Phe, Gly, His, Ile, Leu, Met, Asn, Pro, Arg, Ser, Val, Trp, and Tyr at position 335;
any one of Glu, Lys, and Tyr at position 336;
any one of Glu, His, and Asn at position 337;
any one of Asp, Phe, Gly, Ile, Lys, Met, Asn, Gln, Arg, Ser, and Thr at position 339;
either Ala or Val at position 376;
either Gly or Lys at position 377;
Asp at position 378;
Asn at position 379;
any one of Ala, Asn, and Ser at position 380;
either Ala or Ile at position 382;
Glu at position 385;
Thr at position 392;
Leu at position 396;
Lys at position 421;
Asn at position 427;

either Phe or Leu at position 428;

Met at position 429;

Trp at position 434;

Ile at position 436;

any one of Gly, His, Ile, Leu, and Tyr at position 440.

10. The method of claim 6, wherein the percentage of the second antigen-binding molecule that has a fucose-deficient sugar chain bound at EU numbering position 297 in the pharmaceutical composition is higher than the percentage of a naturally-occurring IgG1 that has a fucose-deficient sugar chain bound at EU numbering position 297 in a composition of the naturally-occurring IgG1.

11. The method of claim 6, wherein the percentage of the second antigen-binding molecule that has a bisecting N-acetylglucosamine sugar chain bound at EU numbering position 297 in the pharmaceutical composition is higher than the percentage of a naturally-occurring IgG1 that has a bisecting N-acetylglucosamine sugar chain bound at EU numbering position 297 in a composition of the naturally-occurring IgG.

12. A method of producing a pharmaceutical composition that induces humoral immunity to a target antigen, the method comprising:

(a) identifying the amino acid sequence of a first antigen-binding molecule comprising a first FcRn-binding domain and an antigen-binding domain comprising a VH and a VL, wherein the antigen-binding domain binds to the target antigen, and the VL comprises a histidine at one or more of Kabat numbering positions 24, 27, 28, 31, 32, 34, 50, 51, 52, 53, 54, 55, 56, 89, 90, 91, 92, 93, 94, and 95A;

(b) testing the antigen-binding domain's antigen-binding activity at a first pH between pH 6.7-10.0 and at a second pH between pH 4.0-6.5, and determining that the antigen-binding activity is greater at the first pH than at the second pH;

(c) generating a DNA encoding a second antigen-binding molecule comprising the antigen-binding domain and a non-native human IgG1 Fc region comprising a second FcRn-binding domain that binds to a human FcRn receptor at pH 7.4, wherein the amino acid sequence of the second FcRn-binding domain differs from the amino acid sequence of the first FcRn-binding domain by substitution at one or more positions, wherein at least one of the substitutions is a set of one or more substitutions that matches the set of substitutions present in any one of variants F10, F12, F14, F25, F32, F34, F36, F38, F40, F47, F49, F50, F53, F54, F58, F59, F61, F69, F71, F73, F78, F80, F82, F84, F86, F88, F90, F92, F93, F95, F101, F103 to F108, F111, F113 to F116 listed in Tables 5-1 to 5-3; wherein all position numbers in Tables 5-1 to 5-3 are according to EU numbering, (d) culturing cells comprising the DNA, so that the cells express the second antigen-binding molecule;

(e) collecting the second antigen-binding molecule; and (f) producing a pharmaceutical composition comprising the second antigen-binding molecule, wherein the pharmaceutical composition induces humoral immunity to the target antigen.

13. The method of claim 12, wherein the second antigen-binding molecule is an antibody.

14. The method of claim 12, wherein the second antigen-binding molecule binds to and neutralizes the target antigen.

15. The method of claim 12, wherein the second antigen-binding molecule has cytotoxic activity against a cell expressing the target antigen.

16. The method of claim 12, wherein the non-native human IgG1 Fc region differs from a native human IgG Fc region at one or more of the following EU numbering positions: 257, 308, 428, 434.

17. The method of claim 12, wherein one or more of the following EU numbering positions in the non-native human IgG1 Fc region is occupied by the indicated amino acid:
   Ala at position 257;
   Pro at position 308;
   Leu at position 428;
   Tyr at position 434.

18. The method of claim 12, wherein the non-native human IgG1 Fc region's binding to a human Fcγ receptor is greater than a native human IgG Fc region's binding to the human Fcγ receptor, wherein the native human IgG Fc region comprises a fucose-containing sugar chain bound at EU numbering position 297.

19. The method of claim 18, wherein the human Fcγ receptor is FcγRIa, FcγRIIa(R), FcγRIIa(H), FcγRIIb, FcγRIIIa(V), or FcγRIIIa(F).

20. The method of claim 18, wherein one or more of the following EU numbering positions in the non-native human IgG1 Fc region is occupied by the indicated amino acid:
   either Lys or Tyr at position 221;
   any one of Phe, Trp, Glu, and Tyr at position 222;
   any one of Phe, Trp, Glu, and Lys at position 223;
   any one of Phe, Trp, Glu, and Tyr at position 224;
   any one of Glu, Lys, and Trp at position 225;
   any one of Glu, Gly, Lys, and Tyr at position 227;
   any one of Glu, Gly, Lys, and Tyr at position 228;
   any one of Ala, Glu, Gly, and Tyr at position 230;
   any one of Glu, Gly, Lys, Pro, and Tyr at position 231;
   any one of Glu, Gly, Lys, and Tyr at position 232;
   any one of Ala, Asp, Phe, Gly, His, Ile, Lys, Leu, Met, Asn, Gln, Arg, Ser, Thr, Val, Trp, and Tyr at position 233;
   any one of Ala, Asp, Glu, Phe, Gly, His, Ile, Lys, Met, Asn, Pro, Gln, Arg, Ser, Thr, Val, Trp, and Tyr at position 234;
   any one of Ala, Asp, Glu, Phe, Gly, His, Ile, Lys, Met, Asn, Pro, Gln, Arg, Ser, Thr, Val, Trp, and Tyr at position 235;
   any one of Ala, Asp, Glu, Phe, His, Ile, Lys, Leu, Met, Asn, Pro, Gln, Arg, Ser, Thr, Val, Trp, and Tyr at position 236;
   any one of Asp, Glu, Phe, His, Ile, Lys, Leu, Met, Asn, Pro, Gln, Arg, Ser, Thr, Val, Trp, and Tyr at position 237;
   any one of Asp, Glu, Phe, Gly, His, Ile, Lys, Leu, Met, Asn, Gln, Arg, Ser, Thr, Val, Trp, and Tyr at position 238;
   any one of Asp, Glu, Phe, Gly, His, Ile, Lys, Leu, Met, Asn, Pro, Gln, Arg, Thr, Val, Trp, and Tyr at position 239;
   any one of Ala, Ile, Met, and Thr at position 240;
   any one of Asp, Glu, Leu, Arg, Trp, and Tyr at position 241;
   any one of Leu, Glu, Leu, Gln, Arg, Trp, and Tyr at position 243;
   His at position 244;
   Ala at position 245;
   any one of Asp, Glu, His, and Tyr at position 246;
   any one of Ala, Phe, Gly, His, Ile, Leu, Met, Thr, Val, and Tyr at position 247;
   any one of Glu, His, Gln, and Tyr at position 249;
   either Glu or Gln at position 250;
   Phe at position 251;
   any one of Phe, Met, and Tyr at position 254;
   any one of Glu, Leu, and Tyr at position 255;
   any one of Ala, Met, and Pro at position 256;
   any one of Asp, Glu, His, Ser, and Tyr at position 258;
   any one of Asp, Glu, His, and Tyr at position 260;
   any one of Ala, Glu, Phe, Ile, and Thr at position 262;
   any one of Ala, Ile, Met, and Thr at position 263;
   any one of Asp, Glu, Phe, Gly, His, Ile, Lys, Leu, Met, Asn, Pro, Gln, Arg, Ser, Thr, Trp, and Tyr at position 264;
   any one of Ala, Leu, Phe, Gly, His, Ile, Lys, Leu, Met, Asn, Pro, Gln, Arg, Ser, Thr, Val, Val, Trp, and Tyr at position 265;
   any one of Ala, Ile, Met, and Thr at position 266;
   any one of Asp, Glu, Phe, His, Ile, Lys, Leu, Met, Asn, Pro, Gln, Arg, Thr, Val, Trp, and Tyr at position 267;
   any one of Asp, Glu, Phe, Gly, Ile, Lys, Leu, Met, Pro, Gln, Arg, Thr, Val, and Trp at position 268;
   any one of Phe, Gly, His, Ile, Lys, Leu, Met, Asn, Pro, Arg, Ser, Thr, Val, Trp, and Tyr at position 269;
   any one of Glu, Phe, Gly, His, Ile, Leu, Met, Pro, Gln, Arg, Ser, Thr, Trp, and Tyr at position 270;
   any one of Ala, Asp, Glu, Phe, Gly, His, Ile, Lys, Leu, Met, Asn, Gln, Arg, Ser, Thr, Val, Trp, and Tyr at position 271;
   any one of Asp, Phe, Gly, His, Ile, Lys, Leu, Met, Pro, Arg, Ser, Thr, Val, Trp, and Tyr at position 272;
   either Phe or Ile at position 273;
   any one of Asp, Glu, Phe, Gly, His, Ile, Leu, Met, Asn, Pro, Arg, Ser, Thr, Val, Trp, and Tyr at position 274;
   either Leu or Trp at position 275;
   any one of Asp, Glu, Phe, Gly, His, Ile, Leu, Met, Pro, Arg, Ser, Thr, Val, Trp, and Tyr at position 276;
   any one of Asp, Glu, Gly, His, Ile, Lys, Leu, Met, Asn, Pro, Gln, Arg, Ser, Thr, Val, and Trp at position 278;
   Ala at position 279;
   any one of Ala, Gly, His, Lys, Leu, Pro, Gln, Trp, and Tyr at position 280;
   any one of Asp, Lys, Pro, and Tyr at position 281;
   any one of Glu, Gly, Lys, Pro, and Tyr at position 282;
   any one of Ala, Gly, His, Ile, Lys, Leu, Met, Pro, Arg, and Tyr at position 283;
   any one of Asp, Glu, Leu, Asn, Thr, and Tyr at position 284;

any one of Asp, Glu, Lys, Gln, Trp, and Tyr at position 285;
any one of Glu, Gly, Pro, and Tyr at position 286;
any one of Asn, Asp, Glu, and Tyr at position 288;
any one of Asp, Gly, His, Leu, Asn, Ser, Thr, Trp, and Tyr at position 290;
any one of Asp, Glu, Gly, His, Ile, Gln, and Thr at position 291;
any one of Ala, Asp, Glu, Pro, Thr, and Tyr at position 292;
any one of Phe, Gly, His, Ile, Leu, Met, Asn, Pro, Arg, Ser, Thr, Val, Trp, and Tyr at position 293;
any one of Phe, Gly, His, Ile, Lys, Leu, Met, Asn, Pro, Arg, Ser, Thr, Val, Trp, and Tyr at position 294;
any one of Asp, Glu, Phe, Gly, His, Ile, Lys, Met, Asn, Pro, Arg, Ser, Thr, Val, Trp, and Tyr at position 295;
any one of Ala, Asp, Glu, Gly, His, Ile, Lys, Leu, Met, Asn, Gln, Arg, Ser, Thr, and Val at position 296;
any one of Asp, Glu, Phe, Gly, His, Ile, Lys, Leu, Met, Pro, Gln, Arg, Ser, Thr, Val, Trp, and Tyr at position 297;
any one of Ala, Asp, Glu, Phe, His, Ile, Lys, Met, Asn, Gln, Arg, Thr, Val, Trp, and Tyr at position 298;
any one of Ala, Asp, Glu, Phe, Gly, His, Ile, Lys, Leu, Met, Asn, Pro, Gln, Arg, Ser, Val, Trp, and Tyr at position 299;
any one of Ala, Asp, Glu, Gly, His, Ile, Lys, Leu, Met, Asn, Pro, Gln, Arg, Ser, Thr, Val, and Trp at position 300;
any one of Asp, Glu, His, and Tyr at position 301;
Ile at position 302;
any one of Asp, Gly, and Tyr at position 303;
any one of Asp, His, Leu, Asn, and Thr at position 304;
any one of Glu, Ile, Thr, and Tyr at position 305;
any one of Ala, Asp, Asn, Thr, Val, and Tyr at position 311;
Phe at position 313;
Leu at position 315;
either Glu or Gln at position 317;
any one of His, Leu, Asn, Pro, Gln, Arg, Thr, Val, and Tyr at position 318;
any one of Asp, Phe, Gly, His, Ile, Leu, Asn, Pro, Ser, Thr, Val, Trp, and Tyr at position 320;
any one of Ala, Asp, Phe, Gly, His, Ile, Pro, Ser, Thr, Val, Trp, and Tyr at position 322;
Ile at position 323;
any one of Asp, Phe, Gly, His, Ile, Leu, Met, Pro, Arg, Thr, Val, Trp, and Tyr at position 324;
any one of Ala, Asp, Glu, Phe, Gly, His, Ile, Lys, Leu, Met, Pro, Gln, Arg, Ser, Thr, Val, Trp, and Tyr at position 325;
any one of Ala, Asp, Glu, Gly, Ile, Leu, Met, Asn, Pro, Gln, Ser, Thr, Val, Trp, and Tyr at position 326;
any one of Ala, Asp, Glu, Phe, Gly, His, Ile, Lys, Leu, Met, Asn, Pro, Arg, Thr, Val, Trp, and Tyr at position 327;
any one of Ala, Asp, Glu, Phe, Gly, His, Ile, Lys, Met, Asn, Pro, Gln, Arg, Ser, Thr, Val, Trp, and Tyr at position 328;
any one of Asp, Glu, Phe, Gly, His, Ile, Lys, Leu, Met, Asn, Gln, Arg, Ser, Thr, Val, Trp, and Tyr at position 329;
any one of Cys, Glu, Phe, Gly, His, Ile, Lys, Leu, Met, Asn, Pro, Arg, Ser, Thr, Val, Trp, and Tyr at position 330;
any one of Asp, Phe, His, Ile, Leu, Met, Gln, Arg, Thr, Val, Trp, and Tyr at position 331;
any one of Ala, Asp, Glu, Phe, Gly, His, Lys, Leu, Met, Asn, Pro, Gln, Arg, Ser, Thr, Val, Trp, and Tyr at position 332;
any one of Ala, Asp, Glu, Phe, Gly, His, Ile, Leu, Met, Pro, Ser, Thr, Val, and Tyr at position 333;
any one of Ala, Glu, Phe, Ile, Leu, Pro, and Thr at position 334;
any one of Asp, Phe, Gly, His, Ile, Leu, Met, Asn, Pro, Arg, Ser, Val, Trp, and Tyr at position 335;
any one of Glu, Lys, and Tyr at position 336;
any one of Glu, His, and Asn at position 337;
any one of Asp, Phe, Gly, Ile, Lys, Met, Asn, Gln, Arg, Ser, and Thr at position 339;
either Ala or Val at position 376;
either Gly or Lys at position 377;
Asp at position 378;
Asn at position 379;
any one of Ala, Asn, and Ser at position 380;
either Ala or Ile at position 382;
Glu at position 385;
Thr at position 392;
Leu at position 396;
Lys at position 421;
Asn at position 427;
either Phe or Leu at position 428;
Met at position 429;
Trp at position 434;
Ile at position 436;
any one of Gly, His, Ile, Leu, and Tyr at position 440.

21. The method of claim 18, wherein the percentage of the second antigen-binding molecule that has a fucose-deficient sugar chain bound at EU numbering position 297 in the pharmaceutical composition is higher than the percentage of a naturally-occurring IgG that has a fucose-deficient sugar chain bound at EU numbering position 297 in a composition of the naturally-occurring IgG.

22. The method of claim 18, wherein the percentage of the second antigen-binding molecule that has a bisecting N-acetylglucosamine sugar chain bound at EU numbering position 297 in the pharmaceutical composition is higher than the percentage of a naturally-occurring IgG that has a bisecting N-acetylglucosamine sugar chain bound at EU numbering position 297 in a composition of the naturally-occurring IgG.

* * * * *

```
SEQUENCE LISTING

<160> NUMBER OF SEQ ID NOS: 138

<210> SEQ ID NO 1
<211> LENGTH: 468
<212> TYPE: PRT
<213> ORGANISM: Homo sapiens

<400> SEQUENCE: 1

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220
```

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
            245                 250                 255

Tyr Arg Ala Glu Arg Ser Lys Thr Phe Thr Thr Trp Met Val Lys Asp
        260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465

<210> SEQ ID NO 2
<211> LENGTH: 1407
<212> TYPE: DNA
<213> ORGANISM: Homo sapiens

<400> SEQUENCE: 2
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccggaag acaatgccac tgttcactgg     180
gtgctcagga agccggctgc aggctcccac ccagcagat gggctggcat gggaaggagg     240
ctgctgctga ggtcggtgca gctccacgac tctggaaact attcatgcta ccgggccggc     300
cgcccagctg ggactgtgca cttgctggtg gatgttcccc ccgaggagcc ccagctctcc     360
tgcttccgga agagcccct cagcaatgtt gtttgtgagt ggggtcctcg gagcaccccca     420 tccctgacga caaaggctgt gctcttggtg aggaagtttc agaacagtcc ggccgaagac     480
ttccaggagc cgtgccagta ttcccaggag tcccagaagt ctcctgcca gttagcagtc     540 ccggagggag acagctcttt ctacatagtg tccatgtgcg tcgccagtag tgtcgggagc     600
aagttcagca aaactcaaac ctttcagggt tgtggaatct tgcagcctga tccgcctgcc     660

```
aacatcacag tcactgccgt ggccagaaac ccccgctggc tcagtgtcac ctggcaagac   720
ccccactcct ggaactcatc tttctacaga ctacggtttg agctcagata tcgggctgaa   780
cggtcaaaga cattcacaac atggatggtc aaggacctcc agcatcactg tgtcatccac   840
gacgcctgga gcggcctgag gcacgtggtg cagcttcgtg cccaggagga gttcgggcaa   900
ggcgagtgga gcgagtggag cccggaggcc atgggcacgc cttggacaga atccaggagt   960
cctccagctg agaacgaggt gtccaccccc atgcaggcac ttactactaa taaagacgat  1020
gataatattc tcttcagaga ttctgcaaat gcgacaagcc tcccagtgca agattcttct  1080
tcagtaccac tgcccacatt cctggttgct ggagggagcc tggccttcgg aacgctcctc  1140
tgcattgcca ttgttctgag gttcaagaag acgtggaagc tgcgggctct gaaggaaggc  1200
aagacaagca tgcatccgcc gtactctttg gggcagctgg tcccggagag gcctcgaccc  1260
accccagtgc ttgttcctct catctcccca ccggtgtccc ccagcagcct ggggtctgac  1320
aatacctcga ccacaaccg accagatgcc aggaccccac ggagccctta tgacatcagc  1380
aatacagact acttcttccc cagatag                                      1407
```

<210> SEQ ID NO 3
<211> LENGTH: 19
<212> TYPE: PRT
<213> ORGANISM: Artificial sequence
<220> FEATURE:
<223> OTHER INFORMATION: An artificially synthesized peptide sequence

<400> SEQUENCE: 3

Met Gly Trp Ser Cys Ile Ile Leu Phe Leu Val Ala Thr Ala Thr Gly
1               5                   10                  15

Val His Ser

<210> SEQ ID NO 4
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 4

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 5
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 6
<211> LENGTH: 112
<212> TYPE: PRT
<213> ORGANISM: Artificial sequence
<220> FEATURE:
<223> OTHER INFORMATION: An artificially synthesized peptide sequence

<400> SEQUENCE: 6

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110

<210> SEQ ID NO 7
<211> LENGTH: 107
```

```
<212> TYPE: PRT
<213> ORGANISM: Artificial sequence
<220> FEATURE:
<223> OTHER INFORMATION: An artificially synthesized peptide sequence

<400> SEQUENCE: 7

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 8
<211> LENGTH: 112
<212> TYPE: PRT
<213> ORGANISM: Artificial sequence
<220> FEATURE:
<223> OTHER INFORMATION: An artificially synthesized peptide sequence

<400> SEQUENCE: 8

Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
50                  55                  60

Pro Asp Arg Phe Ser Ala Ser Gly Ser Gly Thr Glu Phe Thr Leu Thr
65                  70                  75                  80

Ile Ser Asp Leu Gln Ala Glu Asp Ala Ala Val Tyr Tyr Cys Gln Gln
                85                  90                  95

Tyr Tyr Arg Ala Pro Ser Phe Gly Gln Gly Thr Lys Leu Gln Ile Lys
            100                 105                 110

<210> SEQ ID NO 9
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
```

```
            50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                     85                  90                  95
Ala Arg Asp Asp Pro Gly Gly Gly Glu Tyr Tyr Phe Asp Tyr Trp Gly
                100                 105                 110
Gln Gly Thr Leu Val Thr Val Ser Ser Ala Ser Thr Lys Gly Pro Ser
             115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro

<210> SEQ ID NO 10
<211> LENGTH: 126
```

```
<212> TYPE: PRT
<213> ORGANISM: Artificial sequence
<220> FEATURE:
<223> OTHER INFORMATION: An artificially synthesized peptide sequence

<400> SEQUENCE: 10
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

```
<210> SEQ ID NO 11
<211> LENGTH: 330
<212> TYPE: PRT
<213> ORGANISM: Homo sapiens

<400> SEQUENCE: 11
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 13
<211> LENGTH: 377
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 14
<211> LENGTH: 327
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
```

```
                290                 295                 300
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 365
<212> TYPE: PRT
<213> ORGANISM: Homo sapiens

<400> SEQUENCE: 15

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
                20                  25                  30

His Leu Thr Ala Val Ser Ser Pro Ala Pro Gly Thr Pro Ala Phe Trp
            35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
                100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
                180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
        210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
                260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
        290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335
```

```
Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
            355                 360                 365

<210> SEQ ID NO 16
<211> LENGTH: 119
<212> TYPE: PRT
<213> ORGANISM: Homo sapiens

<400> SEQUENCE: 16

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 17
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 18
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
```

```
                    85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 19
<211> LENGTH: 1125
<212> TYPE: DNA
<213> ORGANISM: Homo sapiens

<400> SEQUENCE: 19
atgtggttct tgacaactct gctcctttgg gttccagttg atgggcaagt ggacaccaca      60
aaggcagtga tcactttgca gcctccatgg gtcagcgtgt ccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg aaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg agggaatct ggtcaccctg agctgtgaaa caaagttgct cttgcagagg     660
cctggttttgc agctttactt ctccttctac atgggcagca agaccctgcg aggcaggaac     720
acatcctctg aataccaaat actaactgct agaagagaag actctggggtt atactggtgc     780
gaggctgcca cagaggatgg aaatgtcctt aagcgcagcc ctgagttgga gcttcaagtg     840
cttggcctcc agttaccaac tcctgtctgg tttcatgtcc ttttctatct ggcagtggga     900
ataatgttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggccca cgtag                    1125

<210> SEQ ID NO 20
<211> LENGTH: 374
<212> TYPE: PRT
<213> ORGANISM: Homo sapiens

<400> SEQUENCE: 20
```

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
                100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
        130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
        290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
                355                 360                 365

Glu Pro Gln Gly Ala Thr
        370
```

<210> SEQ ID NO 21
<211> LENGTH: 951
<212> TYPE: DNA
<213> ORGANISM: Homo sapiens

<400> SEQUENCE: 21

```
atgactatgg agacccaaat gtctcagaat gtatgtccca gaaacctgtg ctgcttcaa      60
ccattgacag ttttgctgct gctggcttct gcagacagtc aagctgctcc cccaaaggct    120
gtgctgaaac ttgagccccc gtggatcaac gtgctccagg aggactctgt gactctgaca    180
tgccagggg ctcgcagccc tgagagcgac tccattcagt ggttccacaa tgggaatctc     240
attcccaccc acacgcagcc cagctacagg ttcaaggcca acaacaatga cagcggggag    300
tacacgtgcc agactggcca gaccagcctc agcgaccctg tgcatctgac tgtgctttcc    360
gaatggctgg tgctccagac ccctcacctg gagttccagg agggagaaac catcatgctg    420
aggtgccaca gctggaagga caagcctctg gtcaaggtca cattcttcca gaatggaaaa    480
tcccagaaat ctcccatttt ggatcccacc ttctccatcc cacaagcaaa ccacagtcac    540
agtggtgatt accactgcac aggaaacata ggctacacgc tgttctcatc caagcctgtg    600
accatcactg tccaagtgcc agcatgggc agctcttcac caatgggggt cattgtggct     660
gtggtcattg cgactgctgt agcagccatt gttgctgctg tagtggcctt gatctactgc    720
aggaaaaagc ggatttcagc caattccact gatcctgtga aggctgccca atttgagcca    780
cctggacgtc aaatgattgc catcagaaag agacaacttg aagaaccaa caatgactat     840
gaaacagctg acggcggcta catgactctg aacccaggg cacctactga cgatgataaa     900
aacatctacc tgactcttcc tcccaacgac catgtcaaca gtaataacta a              951
```

<210> SEQ ID NO 22
<211> LENGTH: 316
<212> TYPE: PRT
<213> ORGANISM: Homo sapiens

<400> SEQUENCE: 22

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
```

```
            195                 200                 205
Met Gly Ser Ser Ser Pro Met Gly Val Ile Val Ala Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala
                245                 250                 255

Gln Phe Glu Pro Pro Gly Arg Gln Met Ile Ala Ile Arg Lys Arg Gln
                260                 265                 270

Leu Glu Glu Thr Asn Asn Asp Tyr Glu Thr Ala Asp Gly Gly Tyr Met
                275                 280                 285

Thr Leu Asn Pro Arg Ala Pro Thr Asp Asp Asp Lys Asn Ile Tyr Leu
            290                 295                 300

Thr Leu Pro Pro Asn Asp His Val Asn Ser Asn Asn
305                 310                 315
```

<210> SEQ ID NO 23
<211> LENGTH: 876
<212> TYPE: DNA
<213> ORGANISM: Homo sapiens

<400> SEQUENCE: 23

```
atgggaatcc tgtcattctt acctgtcctt gccactgaga gtgactgggc tgactgcaag     60
tccccccagc cttggggtca tatgcttctg tggacagctg tgctattcct ggctcctgtt    120
gctgggacac ctgcagctcc cccaaaggct gtgctgaaac tcgagcccca gtggatcaac    180
gtgctccagg aggactctgt gactctgaca tgccggggga ctcacagccc tgagagcgac    240
tccattcagt ggttccacaa tgggaatctc attcccaccc acacgcagcc cagctacagg    300
ttcaaggcca acaacaatga cagcggggag tacacgtgcc agactggcca gaccagcctc    360
agcgaccctg tgcatctgac tgtgctttct gagtggctgg tgctccagac ccctcacctg    420
gagttccagg agggagaaac catcgtgctg aggtgccaca gctggaagga caagcctctg    480
gtcaaggtca cattcttcca gaatggaaaa tccaagaaat tttcccgttc ggatcccaac    540
ttctccatcc acaagcaaa ccacagtcac agtggtgatt accactgcac aggaaacata    600
ggctacacgc tgtactcatc caagcctgtg accatcactg tccaagctcc cagctcttca    660
ccgatgggga tcattgtggc tgtggtcact gggattgctg tagcggccat gttgctgct     720
gtagtggcct tgatctactg caggaaaaag cggatttcag ccaatcccac taatcctgat    780
gaggctgaca agttggggc tgagaacaca atcacctatt cacttctcat gcacccggat    840
gctctggaag agcctgatga ccagaaccgt atttag                              876
```

<210> SEQ ID NO 24
<211> LENGTH: 291
<212> TYPE: PRT
<213> ORGANISM: Homo sapiens

<400> SEQUENCE: 24

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
```

```
            50                  55                  60
Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asp Ser Gly Glu Tyr Thr
            100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
            130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
                180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Ser Pro Met Gly Ile
210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
            275                 280                 285

Asn Arg Ile
    290

<210> SEQ ID NO 25
<211> LENGTH: 765
<212> TYPE: DNA
<213> ORGANISM: Homo sapiens

<400> SEQUENCE: 25
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gttgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga tggcaaagg caggaagtat tttcatcata attctgactt ctacattcca   480
aaagccacac tcaaagacag cggctcctac ttctgcaggg ggcttgttgg gagtaaaaat   540
gtgtcttcag agactgtgaa catcaccatc actcaaggtt tgtcagtgtc aaccatctca   600
tcattctttc cacctgggta ccaagtctct ttctgcttgg tgatggtact ccttttttgca   660
gtggacacag gactatattt ctctgtgaag acaaacattg aagctcaac aagagactgg   720
```
aaggaccata aatttaaatg gagaaaggac cctcaagaca aatga    765

<210> SEQ ID NO 26
<211> LENGTH: 254
<212> TYPE: PRT
<213> ORGANISM: Homo sapiens

<400> SEQUENCE: 26

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 27
<211> LENGTH: 702
<212> TYPE: DNA
<213> ORGANISM: Homo sapiens

<400> SEQUENCE: 27
atgtggcagc tgctcctccc aactgctctg ctacttctag tttcagctgg catgcggact    60
gaagatctcc caaaggctgt ggtgttcctg agcctcaat ggtacagcgt gcttgagaag    120
gacagtgtga ctctgaagtg ccaggggagcc tactcccctg aggacaattc cacacagtgg    180
tttcacaatg agagcctcat ctcaagccag gcctcgagct acttcattga cgctgccaca    240
gtcaacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420

```
tatttacaga atggcaaaga caggaagtat tttcatcata attctgactt ccacattcca    480
aaagccacac tcaaagatag cggctcctac ttctgcaggg ggcttgttgg gagtaaaaat    540
gtgtcttcag agactgtgaa catcaccatc actcaaggtt tggcagtgtc aaccatctca    600
tcattctctc cacctgggta ccaagtctct ttctgcttgg tgatggtact ccttttttgca   660 gtggacacag gactatattt ctctgtgaag acaaacattt ga                       702
```

```
<210> SEQ ID NO 28
<211> LENGTH: 233
<212> TYPE: PRT
<213> ORGANISM: Homo sapiens

<400> SEQUENCE: 28
```

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

```
<210> SEQ ID NO 29
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 29
```

Gly Gly Gly Ser
1

```
<210> SEQ ID NO 30
```

```
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 30

Ser Gly Gly Gly
1

<210> SEQ ID NO 31
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 31

Gly Gly Gly Gly Ser
1               5

<210> SEQ ID NO 32
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 32

Ser Gly Gly Gly Gly
1               5

<210> SEQ ID NO 33
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 33

Gly Gly Gly Gly Gly Ser
1               5

<210> SEQ ID NO 34
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 34

Ser Gly Gly Gly Gly Gly
1               5

<210> SEQ ID NO 35
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 35

Gly Gly Gly Gly Gly Gly Ser
1               5

<210> SEQ ID NO 36
<211> LENGTH: 7
```

```
<212> TYPE: PRT
<213> ORGANISM: Artificial sequence
<220> FEATURE:
<223> OTHER INFORMATION: An artificially synthesized peptide sequence

<400> SEQUENCE: 36

Ser Gly Gly Gly Gly Gly
1               5

<210> SEQ ID NO 37
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 38
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 39
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 39

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
                20                  25                  30

Leu Asn Trp Tyr Gln Gln Lys Pro Gly Lys Ala Pro Glu Leu Leu Ile
                35                  40                  45

Tyr Tyr Gly Ser Glu Leu His Ser Gly Val Pro Ser Arg Phe Ser Gly
            50                  55                  60

Ser Gly Ser Gly Thr Asp Phe Thr Phe Thr Ile Ser Ser Leu Glu Ala
```

```
            65                  70                  75                  80
        Glu Asp Ala Ala Thr Tyr Tyr Cys Gln Gln Gly Asn Ser Leu Pro Tyr
                        85                  90                  95
        Thr Phe Gly Gln Gly Thr Lys Val Glu Ile Glu Arg Thr Val Ala Ala
                        100                 105                 110
        Pro Ser Val Phe Ile Phe Pro Pro Ser Asp Glu Gln Leu Lys Ser Gly
                        115                 120                 125
        Thr Ala Ser Val Val Cys Leu Leu Asn Asn Phe Tyr Pro Arg Glu Ala
                    130                 135                 140
        Lys Val Gln Trp Lys Val Asp Asn Ala Leu Gln Ser Gly Asn Ser Gln
        145                 150                 155                 160
        Glu Ser Val Thr Glu Gln Asp Ser Lys Asp Ser Thr Tyr Ser Leu Ser
                        165                 170                 175
        Ser Thr Leu Thr Leu Ser Lys Ala Asp Tyr Glu Lys His Lys Val Tyr
                        180                 185                 190
        Ala Cys Glu Val Thr His Gln Gly Leu Ser Ser Pro Val Thr Lys Ser
                    195                 200                 205
        Phe Asn Arg Gly Glu Cys
            210

<210> SEQ ID NO 40
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 40

Asp Ile Gln Met Thr Gln Ser Pro Ser Ser Leu Ser Ala Ser Val Gly
        1               5                   10                  15
        Asp Ser Val Thr Ile Thr Cys Gln Ala Ser Thr Asp Ile Ser Ser His
                        20                  25                  30
        Leu Asn Trp Tyr Gln Gln Lys Pro Gly Lys Ala Pro Glu Leu Leu Ile
                    35                  40                  45
        Tyr Tyr Gly Ser His Leu Leu Ser Gly Val Pro Ser Arg Phe Ser Gly
            50                  55                  60
        Ser Gly Ser Gly Thr Asp Phe Thr Phe Thr Ile Ser Ser Leu Glu Ala
        65                  70                  75                  80
        Glu Asp Ala Ala Thr Tyr Tyr Cys Gly Gln Gly Asn Arg Leu Pro Tyr
                        85                  90                  95
        Thr Phe Gly Gln Gly Thr Lys Val Glu Ile Glu Arg Thr Val Ala Ala
                        100                 105                 110
        Pro Ser Val Phe Ile Phe Pro Pro Ser Asp Glu Gln Leu Lys Ser Gly
                        115                 120                 125
        Thr Ala Ser Val Val Cys Leu Leu Asn Asn Phe Tyr Pro Arg Glu Ala
                    130                 135                 140
        Lys Val Gln Trp Lys Val Asp Asn Ala Leu Gln Ser Gly Asn Ser Gln
        145                 150                 155                 160
        Glu Ser Val Thr Glu Gln Asp Ser Lys Asp Ser Thr Tyr Ser Leu Ser
                        165                 170                 175
        Ser Thr Leu Thr Leu Ser Lys Ala Asp Tyr Glu Lys His Lys Val Tyr
                        180                 185                 190
        Ala Cys Glu Val Thr His Gln Gly Leu Ser Ser Pro Val Thr Lys Ser
                    195                 200                 205
        Phe Asn Arg Gly Glu Cys
```

<210> SEQ ID NO 41
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 41

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Ala Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                  355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
                420                 425                 430

Ala Leu His Tyr His Tyr Thr Gln Lys Ser Leu Ser Leu Ser Pro
            435                 440                 445

<210> SEQ ID NO 42
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Ala Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
        290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Tyr His Tyr Thr Gln Lys Ser Leu Ser Leu Ser Pro
                435                 440                 445

<210> SEQ ID NO 43
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 43

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105

<210> SEQ ID NO 44
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 45
<211> LENGTH: 445
<212> TYPE: PRT
<213> ORGANISM: Artificial sequence
<220> FEATURE:
<223> OTHER INFORMATION: An artificially synthesized peptide sequence

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

```
Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445

<210> SEQ ID NO 46
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Thr Leu Tyr Asp Phe Trp Ser Gly Tyr Tyr Ser Tyr
            100                 105                 110

Asp Ala Phe Asp Ile Trp Gly Gln Gly Thr Met Val Thr Val Ser Ser
        115                 120                 125

<210> SEQ ID NO 47
<211> LENGTH: 122
<212> TYPE: PRT
<213> ORGANISM: Artificial sequence
<220> FEATURE:
<223> OTHER INFORMATION: An artificially synthesized peptide sequence

<400> SEQUENCE: 47

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Leu Asp Thr Gly Pro Tyr Tyr Tyr Gly Met Asp Val Trp
            100                 105                 110

Gly Gln Gly Thr Met Val Thr Val Ser Ser
            115                 120

<210> SEQ ID NO 48
<211> LENGTH: 124
<212> TYPE: PRT
<213> ORGANISM: Artificial sequence
<220> FEATURE:
<223> OTHER INFORMATION: An artificially synthesized peptide sequence

<400> SEQUENCE: 48

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Gly Met Asp
            100                 105                 110

Val Trp Gly Gln Gly Thr Met Val Thr Val Ser Ser
            115                 120

<210> SEQ ID NO 49
<211> LENGTH: 119
<212> TYPE: PRT
<213> ORGANISM: Artificial sequence
<220> FEATURE:
<223> OTHER INFORMATION: An artificially synthesized peptide sequence

<400> SEQUENCE: 49

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys

```
                85                  90                  95
Ala Arg His Arg Ala Gly Asp Leu Gly Gly Asp Tyr Trp Gly Gln Gly
                100                 105                 110

Thr Leu Val Thr Val Ser Ser
        115

<210> SEQ ID NO 50
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 50

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 51

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45
```

Gln Glu Ala Thr Thr Leu Val Pro Gly Ile Ser Pro Arg Phe Ser Gly
      50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 52
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 52

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Glu Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 53
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 53

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Tyr Glu Ala Thr Thr Leu Val Pro Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Asp Asn Phe Pro Tyr
                 85                  90                  95

Thr Phe Gly Gln Gly Thr Lys Val Glu Ile Lys
            100                 105
```

<210> SEQ ID NO 55
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 55

```
Asp Ile Val Met Thr Gln Ser Pro Leu Ser Leu Pro Val Thr Pro Gly
  1               5                  10                  15

Glu Pro Ala Ser Ile Ser Cys Lys Ala Ser Gln Asp Ile Asp Asp Asp
                 20                  25                  30

Met Asn Trp Tyr Leu Gln Lys Pro Gly Gln Ser Pro Gln Leu Leu Ile
             35                  40                  45

Tyr Glu Ala Thr Thr Leu Val Pro Gly Val Pro Asp Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Leu Gln His Asp Asn Phe Pro Tyr
                 85                  90                  95

Thr Phe Gly Gln Gly Thr Lys Leu Glu Ile Lys
            100                 105
```

<210> SEQ ID NO 56
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 56

```
Glu Ile Val Leu Thr Gln Ser Pro Gly Thr Leu Ser Leu Ser Pro Gly
  1               5                  10                  15

Glu Arg Ala Thr Leu Ser Cys Lys Ala Ser Gln Asp Ile Asp Asp Asp
                 20                  25                  30

Met Asn Trp Tyr Gln Gln Lys Pro Gly Gln Ala Pro Arg Leu Leu Ile
             35                  40                  45

Tyr Glu Ala Thr Thr Leu Val Pro Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Leu Gln His Asp Asn Phe Pro Tyr
                 85                  90                  95

Thr Phe Gly Gln Gly Thr Lys Val Glu Ile Lys
            100                 105
```

<210> SEQ ID NO 57
<211> LENGTH: 107
<212> TYPE: PRT
<213> ORGANISM: Artificial sequence
<220> FEATURE:
<223> OTHER INFORMATION: An artificially synthesized peptide sequence

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Ile Asp Asp
            20                  25                  30

Met Asn Trp Tyr Gln Gln Lys Pro Gly Gln Pro Pro Lys Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln His Asp Asn Phe Pro Tyr
                85                  90                  95

Thr Phe Gly Gln Gly Thr Lys Leu Glu Ile Lys
            100                 105

<210> SEQ ID NO 58
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 58

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 214

```
<212> TYPE: PRT
<213> ORGANISM: Artificial sequence
<220> FEATURE:
<223> OTHER INFORMATION: An artificially synthesized peptide sequence

<400> SEQUENCE: 59
```

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 60
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 60
```

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 61
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 61

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 62
<211> LENGTH: 214
<212> TYPE: PRT
<213> ORGANISM: Artificial sequence

```
<220> FEATURE:
<223> OTHER INFORMATION: An artificially synthesized peptide sequence

<400> SEQUENCE: 62

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 63
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 63

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 64
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 64

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
                20                  25                  30

Met Asn Trp Tyr Gln Gln Lys Pro Gly Glu Ala Ala Ile Phe Ile Ile
            35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 65
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 65

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Ala Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 66
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp Asp
                20                  25                  30

Leu Asn Trp Tyr Gln Gln Lys Pro Gly Lys Ala Pro Lys Leu Leu Ile
            35                  40                  45

Tyr Glu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 456
<212> TYPE: PRT
<213> ORGANISM: Artificial sequence
<220> FEATURE:
<223> OTHER INFORMATION: An artificially synthesized peptide sequence

<400> SEQUENCE: 68
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Pro Pro Tyr Ser Ser Ser Tyr Tyr Tyr Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
    195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
    275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Tyr Thr Leu Pro Pro Ser Arg Asp Glu
    355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415
```

```
Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro
    450                 455

<210> SEQ ID NO 69
<211> LENGTH: 452
<212> TYPE: PRT
<213> ORGANISM: Artificial sequence
<220> FEATURE:
<223> OTHER INFORMATION: An artificially synthesized peptide sequence

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Ile Gln Leu Trp Leu Arg Pro Ser Tyr Phe Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

-continued

```
Leu Asn Gly Lys Glu Tyr Lys Cys Lys Val Ser Asn Lys Ala Leu Pro
            325                 330                 335
Ala Pro Ile Glu Lys Thr Ile Ser Lys Ala Lys Gly Gln Pro Arg Glu
        340                 345                 350
Pro Gln Val Tyr Thr Leu Pro Pro Ser Arg Asp Glu Leu Thr Lys Asn
            355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
            405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro
        450

<210> SEQ ID NO 70
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 70

Gln Val Gln Leu Gln Glu Ser Gly Pro Gly Leu Val Lys Pro Trp Glu
1               5                   10                  15
Thr Leu Ser Leu Thr Cys Thr Val Ala Gly Asp Ser Ile Lys Tyr Ser
            20                  25                  30
Ser Asp Tyr Trp Gly Trp Val Arg Gln Ser Pro Gly Lys Gly Leu Glu
        35                  40                  45
Trp Ile Gly Ser Ser Tyr Leu Ser Gly Thr Thr Gln Tyr Asn Pro Ser
    50                  55                  60
Leu Lys Ser Arg Val Thr Met Ser Val Asp Thr Ser Lys Asn Gln Phe
65                  70                  75                  80
Ser Leu Arg Leu Ser Ser Val Thr Ala Ala Asp Thr Ala Val Tyr Tyr
                85                  90                  95
Cys Ala Arg His Arg Gly Pro Thr Gly Val Asp Gln Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 71
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 71

Glu Val Gln Leu Val Gln Ser Gly Gly Gly Leu Val Gln Pro Gly Arg
1               5                   10                  15

Ser Leu Thr Leu Ser Cys Val Gly Tyr Gly Phe Thr Phe His Glu Asn
            20                  25                  30

Asp Met His Trp Leu Arg Gln Pro Leu Gly Lys Gly Leu Glu Trp Val
        35                  40                  45

Ser His Ile Gly Trp Asn Asn Asn Arg Val Ala Tyr Ala Asp Ser Val
    50                  55                  60

Lys Gly Arg Phe Ala Val Ser Arg Asp Asn Ala Lys Asn Ser Leu Phe
65                  70                  75                  80

Leu His Met Asn Ser Leu Arg Pro Asp Asp Thr Ala Leu Tyr Tyr Cys
                85                  90                  95

Ala Lys Asp Leu Gly Asn Pro Ile Tyr Asp Val Phe Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 72
<211> LENGTH: 452
<212> TYPE: PRT
<213> ORGANISM: Artificial sequence
<220> FEATURE:
<223> OTHER INFORMATION: An artificially synthesized peptide sequence

<400> SEQUENCE: 72

Gln Pro Ala Leu Ala Gln Met Gln Leu Val Glu Ser Gly Gly Gly Leu
1               5                   10                  15

Val Gln Pro Gly Arg Ser Leu Arg Leu Ser Cys Ala Ala Ser Gly Phe
            20                  25                  30

Thr Phe Asp Asp Tyr Ala Met His Trp Val Arg Gln Ala Pro Gly Lys
            35                  40                  45

Gly Leu Glu Trp Val Ser Gly Ile Ser Trp Asn Ser Gly Ser Ile Gly
```

```
                50                  55                  60
Tyr Ala Asp Ser Val Lys Gly Arg Phe Thr Ile Ser Arg Asp Asn Ala
 65                  70                  75                  80

Lys Asn Ser Leu Tyr Leu Gln Met Asn Ser Leu Arg Ala Glu Asp Thr
                 85                  90                  95

Ala Leu Tyr Tyr Cys Ala Arg Glu Gly Val Leu Gly Asp Ala Phe Asp
                100                 105                 110

Ile Trp Gly Gln Gly Thr Met Val Thr Val Ser Ser Ala Ser Thr Lys
                115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro
450

<210> SEQ ID NO 73
```

```
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 73

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Val Arg Ser Gly Ser Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380
```

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
            450

<210> SEQ ID NO 74
<211> LENGTH: 450
<212> TYPE: PRT
<213> ORGANISM: Artificial sequence
<220> FEATURE:
<223> OTHER INFORMATION: An artificially synthesized peptide sequence

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ile Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Lys Asp Pro Arg Val Trp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro
    450

<210> SEQ ID NO 75
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 75

Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Val Leu Ala Ile Ala Asn Tyr Ala Gln Lys Phe
    50                  55                  60
Gln Gly Arg Val Thr Ile Thr Ala Asp Lys Ser Thr His Thr Ala Tyr
65                  70                  75                  80
Met Glu Leu Ser Ser Leu Arg Ser Gly Asp Thr Ala Val Tyr Tyr Cys
                85                  90                  95
Ala Arg Asp Ser Gly Tyr Ser Ala Gly Tyr Gly Gly Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 76
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 76

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Lys Thr Tyr
            20                  25                  30

Trp Met Asn Trp Val Arg Gln Ala Pro Gly Lys Gly Leu Glu Trp Val
        35                  40                  45

Ala Asn Ile Arg Ala Asp Gly Gly Gln Met Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Ile Ser Leu Arg Pro Glu Asp Thr Ala Leu Tyr Tyr Cys
                85                  90                  95

```
Ala Arg Asp Pro Phe Ala Ser Gly Gly Leu Asp Gln Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 77
<211> LENGTH: 450
<212> TYPE: PRT
<213> ORGANISM: Artificial sequence
<220> FEATURE:
<223> OTHER INFORMATION: An artificially synthesized peptide sequence

<400> SEQUENCE: 77

Glu Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Ser Tyr
             20                  25                  30

Gly Met Glu Trp Val Arg Gln Ala Pro Gly Lys Gly Leu Glu Trp Val
         35                  40                  45

Ala Leu Ile Ser His Asp Gly Asn Asn Lys Tyr Tyr Ala Asp Ser Val
 50                  55                  60

Glu Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Val Arg Tyr Phe Asp Ser Tyr Gly Met Asp Val Trp
            100                 105                 110

Gly His Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
```

```
                  435                 440                 445
Ser Pro
    450

<210> SEQ ID NO 78
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 78

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Phe
            20                  25                  30

Trp Ile Asn Trp Val Arg Gln Met Pro Gly Lys Gly Leu Glu Trp Met
        35                  40                  45

Gly Asn Ile Asp Pro Ser Asp Ser Tyr Thr Asn Tyr Ser Pro Ser Phe
    50                  55                  60

Gln Gly His Val Ala Ile Ser Ala Asp Lys Ser Ile Ser Thr Ala Tyr
65                  70                  75                  80

Leu His Trp Asn Ser Leu Lys Ala Ser Asp Thr Ala Met Tyr Tyr Cys
                85                  90                  95

Ala Arg His Arg Tyr Leu Gly Gln Leu Ala Pro Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
            340                 345                 350
Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro

<210> SEQ ID NO 79
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Ala Trp Tyr Gln Gln Lys Pro Gly Lys Ala Pro Lys Leu Leu Ile
            35                  40                  45

Tyr Glu Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 214
<212> TYPE: PRT
<213> ORGANISM: Artificial sequence
```

```
<220> FEATURE:
<223> OTHER INFORMATION: An artificially synthesized peptide sequence

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Gly Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 214
<212> TYPE: PRT
<213> ORGANISM: Artificial sequence
<220> FEATURE:
<223> OTHER INFORMATION: An artificially synthesized peptide sequence
```

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 84
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 85
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Ala Trp Tyr Gln Gln Lys Pro Gly Lys Ala Pro Lys Leu Leu Ile
            35                  40                  45

Tyr His Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 86
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 86
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Ala Trp Tyr Gln Gln Lys Pro Gly Lys Ala Pro Lys Leu Leu Ile
        35                  40                  45

Tyr His Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asp Asn Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Arg Asp Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 88
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asp Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 89
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 89

Asp Ile Gln Met Thr Gln Ser Pro Ser Ser Leu Ser Ala Ser Val Gly

```
              1               5                  10                 15
Asp Arg Val Thr Ile Thr Cys Arg Ala Ser Gln Ser Ile Glu Asp Asp
                20                 25                 30

Leu Ala Trp Tyr Gln Gln Lys Pro Gly Lys Ala Pro Lys Leu Leu Ile
            35                 40                 45

Tyr Glu Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln His Asp Asn Tyr Pro Tyr
                85                 90                 95

Thr Phe Gly Gln Gly Thr Lys Val Glu Ile Lys Arg Thr Val Ala Ala
            100                105                110

Pro Ser Val Phe Ile Phe Pro Pro Ser Asp Glu Gln Leu Lys Ser Gly
        115                120                125

Thr Ala Ser Val Val Cys Leu Leu Asn Asn Phe Tyr Pro Arg Glu Ala
130                135                140

Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
        195                200                205

Phe Asn Arg Gly Glu Cys
        210

<210> SEQ ID NO 90
<211> LENGTH: 455
<212> TYPE: PRT
<213> ORGANISM: Artificial sequence
<220> FEATURE:
<223> OTHER INFORMATION: An artificially synthesized peptide sequence

<400> SEQUENCE: 90

Gln Val Gln Leu Val Gln Ser Gly Ala Glu Val Lys Lys Pro Gly Ser
1               5                  10                 15

Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
            35                 40                 45

Gly Gly Ile Ile Pro Ile Phe Gly Thr Ala Asn Tyr Ala Gln Lys Phe
        50                 55                 60

Gln Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Ala Ala Phe Leu Glu Trp Pro Ile Trp Gly Ser Glu Tyr Phe
            100                105                110

Gln His Trp Gly Gln Gly Thr Leu Val Thr Val Ser Ser Ala Ser Thr
        115                120                125

Lys Gly Pro Ser Val Phe Pro Leu Ala Pro Ser Ser Lys Ser Thr Ser
130                135                140

Gly Gly Thr Ala Ala Leu Gly Cys Leu Val Lys Asp Tyr Phe Pro Glu
```

```
                        145                 150                 155                 160
                Pro Val Thr Val Ser Trp Asn Ser Gly Ala Leu Thr Ser Gly Val His
                                    165                 170                 175

Thr Phe Pro Ala Val Leu Gln Ser Ser Gly Leu Tyr Ser Leu Ser Ser
                                    180                 185                 190

Val Val Thr Val Pro Ser Ser Leu Gly Thr Gln Thr Tyr Ile Cys
                                    195                 200                 205

Asn Val Asn His Lys Pro Ser Asn Thr Lys Val Asp Lys Lys Val Glu
                                    210                 215                 220

Pro Lys Ser Cys Asp Lys Thr His Thr Cys Pro Pro Cys Pro Ala Pro
                225                 230                 235                 240

Glu Leu Leu Gly Gly Pro Ser Val Phe Leu Phe Pro Pro Lys Pro Lys
                                    245                 250                 255

Asp Thr Leu Met Ile Ser Arg Thr Pro Glu Val Thr Cys Val Val Val
                                    260                 265                 270

Asp Val Ser His Glu Asp Pro Glu Val Lys Phe Asn Trp Tyr Val Asp
                                    275                 280                 285

Gly Val Glu Val His Asn Ala Lys Thr Lys Pro Arg Glu Glu Gln Tyr
                                    290                 295                 300

Asn Ser Thr Tyr Arg Val Val Ser Val Leu Thr Val Leu His Gln Asp
                305                 310                 315                 320

Trp Leu Asn Gly Lys Glu Tyr Lys Cys Lys Val Ser Asn Lys Ala Leu
                                    325                 330                 335

Pro Ala Pro Ile Glu Lys Thr Ile Ser Lys Ala Lys Gly Gln Pro Arg
                                    340                 345                 350

Glu Pro Gln Val Tyr Thr Leu Pro Pro Ser Arg Asp Glu Leu Thr Lys
                                    355                 360                 365

Asn Gln Val Ser Leu Thr Cys Leu Val Lys Gly Phe Tyr Pro Ser Asp
                                    370                 375                 380

Ile Ala Val Glu Trp Glu Ser Asn Gly Gln Pro Glu Asn Asn Tyr Lys
                385                 390                 395                 400

Thr Thr Pro Pro Val Leu Asp Ser Asp Gly Ser Phe Phe Leu Tyr Ser
                                    405                 410                 415

Lys Leu Thr Val Asp Lys Ser Arg Trp Gln Gln Gly Asn Val Phe Ser
                                    420                 425                 430

Cys Ser Val Met His Glu Ala Leu His Asn His Tyr Thr Gln Lys Ser
                                    435                 440                 445

Leu Ser Leu Ser Pro Gly Lys
                    450                 455

<210> SEQ ID NO 91
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Ala Trp Tyr Gln Gln Lys Pro Gly Lys Ala Pro Lys Leu Leu Ile
            35                  40                  45

Tyr His Ala Ser Ser Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Asp Ser Tyr Pro Leu
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 92
<211> LENGTH: 453
<212> TYPE: PRT
<213> ORGANISM: Artificial sequence
<220> FEATURE:
<223> OTHER INFORMATION: An artificially synthesized peptide sequence

<400> SEQUENCE: 92

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Ala Thr Tyr Tyr Tyr Asp Ser Ser Ala Pro Ala Phe Asp Ile
                100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
```

```
                   195                 200                 205
Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450

<210> SEQ ID NO 93
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Ala Trp Tyr Gln Gln Lys Pro Gly Lys Ala Pro Lys Leu Leu Ile
                35                  40                  45

Tyr Glu Ala Ser Thr Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asp Ser Pro Leu
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 94
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 94

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Ser Gly Phe Asn Trp Gly Asn Tyr Ala Phe Asp
            100                 105                 110

Ile Trp Gly Gln Gly Phe Ser Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
```

```
                245                 250                 255
Thr Leu Met Ile Ser Arg Thr Pro Glu Val Thr Cys Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 95
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 96
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 96

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 97
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 98
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 99
<211> LENGTH: 217
<212> TYPE: PRT
<213> ORGANISM: Artificial sequence
<220> FEATURE:
<223> OTHER INFORMATION: An artificially synthesized peptide sequence

<400> SEQUENCE: 99

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
        35                  40                  45

Leu Ile Ser His Asn Thr His Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 100
<211> LENGTH: 455
<212> TYPE: PRT
<213> ORGANISM: Artificial sequence
<220> FEATURE:
```

-continued

<223> OTHER INFORMATION: An artificially synthesized peptide sequence

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

```
Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 101
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 101

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30
```

```
Gln Ala Trp Ser Trp Val Arg Gln Pro Pro Gly Glu Gly Leu Glu Trp
            35                  40                  45
Ile Gly Tyr Ile Ser Tyr Ser Gly Ile Thr Asn Tyr Asn Pro Ser Leu
 50                  55                  60
Lys Gly Arg Val Thr Ile Ser Arg Asp Thr Ser Lys Asn Gln Phe Ser
 65                  70                  75                  80
Leu Lys Leu Ser Ser Val Thr Ala Ala Asp Thr Ala Ala Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

Lys

<210> SEQ ID NO 103
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 103

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 104
<211> LENGTH: 213
<212> TYPE: PRT
<213> ORGANISM: Artificial sequence
<220> FEATURE:
<223> OTHER INFORMATION: An artificially synthesized peptide sequence

<400> SEQUENCE: 104

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Ala Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 105
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

```
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
450

<210> SEQ ID NO 106
<211> LENGTH: 443
<212> TYPE: PRT
<213> ORGANISM: Artificial sequence
<220> FEATURE:
<223> OTHER INFORMATION: An artificially synthesized peptide sequence

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125
```

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 107
<211> LENGTH: 219
<212> TYPE: PRT
<213> ORGANISM: Artificial sequence
<220> FEATURE:
<223> OTHER INFORMATION: An artificially synthesized peptide sequence

<400> SEQUENCE: 107

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 108
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Ala Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
                100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

```
Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro
    450

<210> SEQ ID NO 109
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Ala Ala Pro Tyr Tyr Tyr Asp Ser Ser Gly Tyr Thr Asp Ala
                100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro
    450

<210> SEQ ID NO 110
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 110

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Ala Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
```

```
                420                 425                 430
Ser Cys Ser Val Met His Glu Ala Leu His Asn His Tyr Thr Gln Lys
            435                 440                 445

Ser Leu Ser Leu Ser Pro
        450

<210> SEQ ID NO 111
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Ala Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

```
                        325                 330                 335
Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro
            450

<210> SEQ ID NO 112
<211> LENGTH: 454
<212> TYPE: PRT
<213> ORGANISM: Artificial sequence
<220> FEATURE:
<223> OTHER INFORMATION: An artificially synthesized peptide sequence

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Ala Pro Tyr Tyr Asp Ser Ser Gly Tyr Thr Asp Ala
            100                 105                 110

Phe Ala Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Val
    210                 215                 220

Glu Pro Lys Ser Cys Asp Lys Thr His Thr Cys Pro Pro Cys Pro Ala
```

```
                225                 230                 235                 240
Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro
        450

<210> SEQ ID NO 113
<211> LENGTH: 213
<212> TYPE: PRT
<213> ORGANISM: Artificial sequence
<220> FEATURE:
<223> OTHER INFORMATION: An artificially synthesized peptide sequence

<400> SEQUENCE: 113

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Ala Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

-continued

```
                130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 114
<211> LENGTH: 213
<212> TYPE: PRT
<213> ORGANISM: Artificial sequence
<220> FEATURE:
<223> OTHER INFORMATION: An artificially synthesized peptide sequence

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ala Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 115
<211> LENGTH: 453
<212> TYPE: PRT
<213> ORGANISM: Artificial sequence
<220> FEATURE:
<223> OTHER INFORMATION: An artificially synthesized peptide sequence

<400> SEQUENCE: 115
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
                100                 105                 110

Asp Ile Trp Gly Gln Gly Thr Met Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
```

```
                    420                 425                 430
Cys Ser Val Met His Glu Ala Leu His Trp His Tyr Thr Gln Lys Ser
        435                 440                 445
Leu Ser Leu Ser Pro
    450

<210> SEQ ID NO 116
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Trp His Tyr Thr Gln Lys Ser Leu Ser Leu Ser
                435                 440                 445

Pro

<210> SEQ ID NO 117
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
                35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Trp His Tyr Thr Gln Lys Ser Leu Ser Leu Ser Pro
            435                 440                 445

<210> SEQ ID NO 118
<211> LENGTH: 458
<212> TYPE: PRT
<213> ORGANISM: Artificial sequence
<220> FEATURE:
<223> OTHER INFORMATION: An artificially synthesized peptide sequence

<400> SEQUENCE: 118

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ile Tyr Cys Ser Ser Thr Ser Cys Tyr Glu Pro Pro
            100                 105                 110

Tyr Tyr Tyr Tyr Met Asp Val Trp Gly Lys Gly Thr Met Val Thr Val
            115                 120                 125

Ser Ser Ala Ser Thr Lys Gly Pro Ser Val Phe Pro Leu Ala Pro Ser
            130                 135                 140

Ser Lys Ser Thr Ser Gly Gly Thr Ala Ala Leu Gly Cys Leu Val Lys
145                 150                 155                 160
```

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro
    450                 455

<210> SEQ ID NO 119
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Ala Trp Tyr Gln Gln Lys Pro Gly Lys Ala Pro Lys Leu Leu Ile
        35                  40                  45

Tyr Ala Ala Ser His Leu Gln Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Asn Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 120

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Met Ile Asn Gly Val Trp Glu Gly Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 121
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Ser His
            20                  25                  30

Leu Asn Trp Tyr Gln Gln Lys Pro Gly Lys Ala Pro Lys Leu Leu Ile
        35                  40                  45

Tyr His Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Gly Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 122
<211> LENGTH: 451
<212> TYPE: PRT
<213> ORGANISM: Artificial sequence
<220> FEATURE:
<223> OTHER INFORMATION: An artificially synthesized peptide sequence

<400> SEQUENCE: 122

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ile Trp Val Arg Gln Ala Pro Gly Lys Gly Leu Glu Trp Val
        35                  40                  45

Gly Arg Ile Lys Ser Lys Val Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asp Ser Leu Lys Thr Glu Asp Thr Ala Val Tyr
                85                  90                  95

Tyr Cys Val Ala Asp Val Pro Ala Ser Asn Pro Tyr Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 123
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser His
            20                  25                  30

Leu Asn Trp Tyr Gln Gln Lys Pro Gly Lys Ala Pro Lys Leu Leu Ile
        35                  40                  45

Tyr Asp Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 124
<211> LENGTH: 443
<212> TYPE: PRT
<213> ORGANISM: Artificial sequence
<220> FEATURE:
<223> OTHER INFORMATION: An artificially synthesized peptide sequence

<400> SEQUENCE: 124

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Tyr Ile Thr Leu Glu Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320
```

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu Lys Phe His His
            420                 425                 430

Thr Glu Lys Ser Leu Ser His Ser Pro Gly Lys
        435                 440

<210> SEQ ID NO 125
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 125

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 126

<211> LENGTH: 443
<212> TYPE: PRT
<213> ORGANISM: Artificial sequence
<220> FEATURE:
<223> OTHER INFORMATION: An artificially synthesized peptide sequence

<400> SEQUENCE: 126

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380
```

```
Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 127
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 127

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 128
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 128

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

-continued

```
            20                  25                  30
His Ala Trp Ser Trp Val Arg Gln Pro Pro Gly Glu Gly Leu Glu Trp
         35                  40                  45
Ile Gly Phe Ile Ser Tyr Ser Gly Ile Thr Asn Tyr Asn Pro Ser Leu
         50                  55                  60
Gln Gly Arg Val Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ser Leu Ala Arg Thr Thr Ala Met Asp Tyr Trp Gly Glu Gly
                100                 105                 110
Thr Leu Val Thr Val Ser Ser Ala Lys Thr Thr Ala Pro Ser Val Tyr
                115                 120                 125
Pro Leu Ala Pro Val Cys Gly Asp Thr Thr Gly Ser Ser Val Thr Leu
                130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Thr Ser Ser
                180                 185                 190
Thr Trp Pro Ser Gln Ser Ile Thr Cys Asn Val Ala His Pro Ala Ser
                195                 200                 205
Ser Thr Lys Val Asp Lys Lys Ile Glu Pro Arg Gly Pro Thr Ile Lys
                210                 215                 220
Pro Cys Pro Pro Cys Lys Cys Pro Ala Pro Asn Leu Leu Gly Gly Pro
225                 230                 235                 240
Ser Val Phe Ile Phe Pro Pro Lys Ile Lys Asp Val Leu Met Ile Ser
                245                 250                 255
Leu Ser Pro Ile Val Thr Cys Val Val Val Asp Val Ser Glu Asp Asp
                260                 265                 270
Pro Asp Val Gln Ile Ser Trp Phe Val Asn Asn Val Glu Val His Thr
                275                 280                 285
Ala Gln Thr Gln Thr His Arg Glu Asp Tyr Asn Ser Thr Leu Arg Val
                290                 295                 300
Val Ser Ala Leu Pro Ile Gln His Gln Asp Trp Met Ser Gly Lys Glu
305                 310                 315                 320
Phe Lys Cys Lys Val Asn Asn Lys Asp Leu Pro Ala Pro Ile Glu Arg
                325                 330                 335
Thr Ile Ser Lys Pro Lys Gly Ser Val Arg Ala Pro Gln Val Tyr Val
                340                 345                 350
Leu Pro Pro Pro Glu Glu Glu Met Thr Lys Lys Gln Val Thr Leu Thr
                355                 360                 365
Cys Met Val Thr Asp Phe Met Pro Glu Asp Ile Tyr Val Glu Trp Thr
                370                 375                 380
Asn Asn Gly Lys Thr Glu Leu Asn Tyr Lys Asn Thr Glu Pro Val Leu
385                 390                 395                 400
Asp Ser Asp Gly Ser Tyr Phe Met Tyr Ser Lys Leu Arg Val Glu Lys
                405                 410                 415
Lys Asn Trp Val Glu Arg Asn Ser Tyr Ser Cys Ser Val Val His Glu
                420                 425                 430
Gly Leu His Asn His His Thr Thr Lys Ser Phe Ser Arg Thr Pro Gly
                435                 440                 445
```

Lys

<210> SEQ ID NO 129
<211> LENGTH: 443
<212> TYPE: PRT
<213> ORGANISM: Artificial sequence
<220> FEATURE:
<223> OTHER INFORMATION: An artificially synthesized peptide sequence

<400> SEQUENCE: 129

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Tyr Ile Thr Leu Glu Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350
```

```
Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu Lys Phe His His
            420                 425                 430

Thr Glu Lys Ser Leu Ser His Ser Pro Gly Lys
            435                 440

<210> SEQ ID NO 130
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 130

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Asp Val Phe Ile Phe Pro Pro Lys Ile Lys Asp Val Leu Tyr Ile Ser
                245                 250                 255

Leu Glu Pro Ile Val Thr Cys Val Val Asp Val Ser Glu Asp Asp
            260                 265                 270
```

-continued

```
Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Asp Asp Tyr Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu Lys Phe His His Thr Thr Lys Ser Phe Ser Arg Thr Pro Gly
        435                 440                 445

Lys

<210> SEQ ID NO 131
<211> LENGTH: 34
<212> TYPE: DNA
<213> ORGANISM: Artificial sequence
<220> FEATURE:
<223> OTHER INFORMATION: An artificially synthesized peptide sequence

<400> SEQUENCE: 131
ataacttcgt atagcataca ttatacgaag ttat                                 34

<210> SEQ ID NO 132
<211> LENGTH: 21
<212> TYPE: DNA
<213> ORGANISM: Artificial sequence
<220> FEATURE:
<223> OTHER INFORMATION: An artificially synthesized peptide sequence

<400> SEQUENCE: 132
acagggcctt agactcacag c                                               21

<210> SEQ ID NO 133
<211> LENGTH: 22
<212> TYPE: DNA
<213> ORGANISM: Artificial sequence
<220> FEATURE:
<223> OTHER INFORMATION: An artificially synthesized peptide sequence

<400> SEQUENCE: 133
aacttgctcc cgacactact gg                                              22

<210> SEQ ID NO 134
<211> LENGTH: 22
<212> TYPE: DNA
<213> ORGANISM: Artificial sequence
<220> FEATURE:
<223> OTHER INFORMATION: An artificially synthesized peptide sequence
```

<400> SEQUENCE: 134
tctgcagtag ccttcaaaga gc    22

<210> SEQ ID NO 135
<211> LENGTH: 21
<212> TYPE: DNA
<213> ORGANISM: Artificial sequence
<220> FEATURE:
<223> OTHER INFORMATION: An artificially synthesized peptide sequence

<400> SEQUENCE: 135
aaccagacag tgtcacattc c    21

<210> SEQ ID NO 136
<211> LENGTH: 22
<212> TYPE: DNA
<213> ORGANISM: Artificial sequence
<220> FEATURE:
<223> OTHER INFORMATION: An artificially synthesized peptide sequence

<400> SEQUENCE: 136
cccggctgcg gagccgctct gc    22

<210> SEQ ID NO 137
<211> LENGTH: 21
<212> TYPE: DNA
<213> ORGANISM: Artificial sequence
<220> FEATURE:
<223> OTHER INFORMATION: An artificially synthesized peptide sequence

<400> SEQUENCE: 137
acagtgatgc tggaggtcct t    21

<210> SEQ ID NO 138
<211> LENGTH: 22
<212> TYPE: DNA
<213> ORGANISM: Artificial sequence
<220> FEATURE:
<223> OTHER INFORMATION: An artificially synthesized peptide sequence

<400> SEQUENCE: 138
agcaacaccg tgaactcctt tg    22